United States Patent
Tsantrizos et al.

(10) Patent No.: US 7,879,851 B2
(45) Date of Patent: *Feb. 1, 2011

(54) VIRAL POLYMERASE INHIBITORS

(75) Inventors: Youla S. Tsantrizos, Montreal (CA);
Catherine Chabot, Terrebonne (CA);
Pierre Beaulieu, Rosemere (CA);
Christian Brochu, Blainville (CA);
Martin Poirier, Blainville (CA);
Timothy A. Stammers, Rosemere (CA);
Bounkham Thavonekham, Longueuil (CA); Jean Rancourt, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 5 days.

This patent is subject to a terminal disclaimer.

(21) Appl. No.: 12/372,533

(22) Filed: Feb. 17, 2009

(65) Prior Publication Data

US 2009/0170859 A1  Jul. 2, 2009

Related U.S. Application Data

(63) Continuation of application No. 11/062,305, filed on Feb. 18, 2005, now Pat. No. 7,582,770.

(60) Provisional application No. 60/546,213, filed on Feb. 20, 2004.

(51) Int. Cl.
| | |
|---|---|
| A61K 31/5377 | (2006.01) |
| A61K 31/4439 | (2006.01) |
| A61K 31/4184 | (2006.01) |
| C07D 413/14 | (2006.01) |
| C07D 401/14 | (2006.01) |
| C07D 235/04 | (2006.01) |

(52) U.S. Cl. ............ 514/234.5; 514/256; 514/339; 514/394; 546/273.4; 544/139; 544/333; 548/305.1

(58) Field of Classification Search ......... 514/234.5, 514/256, 339, 394; 544/139, 333; 546/273.4; 548/305.1
See application file for complete search history.

(56) References Cited

U.S. PATENT DOCUMENTS

| | | |
|---|---|---|
| 3,565,912 A | 2/1971 | Szmuszkovicz |
| 4,003,908 A | 1/1977 | Denzel et al. |
| 4,146,725 A | 3/1979 | Meyer et al. |
| 4,250,317 A | 2/1981 | Meyer et al. |
| 4,252,803 A | 2/1981 | Webb |
| 4,264,325 A | 4/1981 | Meyer et al. |
| 4,360,679 A | 11/1982 | Meyer et al. |
| 4,384,121 A | 5/1983 | Meyer et al. |
| 4,432,886 A | 2/1984 | Meyer et al. |
| 4,433,975 A | 2/1984 | Meyer et al. |
| 4,590,200 A | 5/1986 | Cross et al. |
| 4,740,519 A | 4/1988 | Shroot et al. |
| 4,859,684 A | 8/1989 | Raeymaekers et al. |
| 4,898,863 A | 2/1990 | Brown et al. |
| 4,920,140 A | 4/1990 | Shroot et al. |
| 5,059,621 A | 10/1991 | Shroot et al. |
| 5,216,003 A | 6/1993 | Vazquez |
| 5,410,061 A | 4/1995 | Gilmore et al. |
| 5,482,956 A | 1/1996 | Lunkenheimer et al. |
| 5,527,819 A | 6/1996 | Williams et al. |
| 5,817,689 A | 10/1998 | Kato et al. |
| 5,866,594 A | 2/1999 | Endo et al. |
| 5,912,260 A | 6/1999 | Kalindjian et al. |
| 5,932,743 A | 8/1999 | Collini et al. |
| 6,063,806 A | 5/2000 | Kamiya et al. |
| 6,069,156 A | 5/2000 | Oku et al. |
| 6,169,107 B1 | 1/2001 | Kitano et al. |
| 6,184,238 B1 | 2/2001 | Takano et al. |
| 6,228,868 B1 | 5/2001 | Gwaltney et al. |
| 6,358,992 B1 | 3/2002 | Pamukcu et al. |
| 6,399,644 B1 | 6/2002 | Wexler et al. |
| 6,448,281 B1 | 9/2002 | Beaulieu et al. |
| 6,455,525 B1 | 9/2002 | Singh et al. |
| 6,479,508 B1 | 11/2002 | Beaulieu et al. |
| 6,579,882 B2 | 6/2003 | Stewart et al. |
| 6,770,643 B2 | 8/2004 | Cox et al. |
| 6,770,666 B2 | 8/2004 | Hashimoto et al. |
| 6,794,404 B2 | 9/2004 | Beaulieu et al. |
| 6,841,566 B2 | 1/2005 | Beaulieu et al. |
| 6,897,207 B2 | 5/2005 | Cox et al. |

(Continued)

FOREIGN PATENT DOCUMENTS

CA          1111695 A          11/1981

(Continued)

OTHER PUBLICATIONS 13-0127-ISR PCT/CA2005/000208; Mail date of ISR Jun. 13, 2005.

(Continued)

*Primary Examiner*—Kamal A Saeed
*Assistant Examiner*—Samantha L Shterengarts
(74) *Attorney, Agent, or Firm*—Michael P. Morris; Philip I. Datlow

(57) ABSTRACT

An enantiomer, diastereoisomer or tautomer of a compound, represented by formula I:

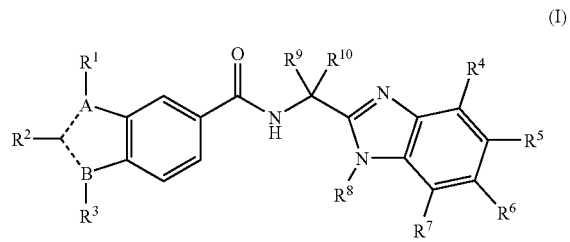

wherein A, B, $R^1$, $R^2$, $R^3$, $R^4$, $R^5$, $R^6$, $R^7$, $R^8$, $R^9$, and $R^{10}$ are as defined herein, or a salt or ester thereof, as an inhibitor of HCV NS5B polymerase.

15 Claims, No Drawings

U.S. PATENT DOCUMENTS

| | | |
|---|---|---|
| 7,098,231 B2 | 8/2006 | Poupart et al. |
| 7,112,600 B1 | 9/2006 | Hashimoto et al. |
| 7,141,574 B2 | 11/2006 | Beaulieu et al. |
| 7,157,486 B2 | 1/2007 | Beaulieu et al. |
| 7,223,785 B2 | 5/2007 | Beaulieu et al. |
| 7,241,801 B2 | 7/2007 | Beaulieu et al. |
| 7,323,470 B2 | 1/2008 | Poupart |
| 7,332,614 B2 | 2/2008 | Khodabocus |
| 2001/0039286 A1 | 11/2001 | Dinnell et al. |
| 2002/0173527 A1 | 11/2002 | Astles |
| 2003/0050320 A1 | 3/2003 | Hashimoto et al. |
| 2003/0108862 A1 | 6/2003 | Kukolj et al. |
| 2004/0082635 A1 | 4/2004 | Hashimoto et al. |
| 2004/0097438 A1 | 5/2004 | Hashimoto et al. |
| 2004/0110126 A1 | 6/2004 | Kukolj et al. |
| 2004/0171833 A1 | 9/2004 | Buchwald et al. |
| 2004/0224955 A1 | 11/2004 | Beaulieu et al. |
| 2005/0032875 A1 | 2/2005 | Wolleb et al. |
| 2005/0209465 A1 | 9/2005 | Li et al. |
| 2005/0222236 A1 | 10/2005 | Tsantrizos et al. |
| 2006/0160798 A1 | 7/2006 | Beaulieu et al. |
| 2006/0183752 A1 | 8/2006 | Khodabocus et al. |
| 2006/0293306 A1 | 12/2006 | Beaulieu et al. |
| 2007/0142380 A1 | 6/2007 | Beaulieu et al. |
| 2007/0249629 A1 | 10/2007 | Beaulieu et al. |
| 2008/0119490 A1 | 5/2008 | Poupart |

FOREIGN PATENT DOCUMENTS

| | | |
|---|---|---|
| CA | 2067112 A1 | 2/1992 |
| CA | 2150812 | 6/1994 |
| CA | 2158996 A1 | 10/1994 |
| CA | 2143040 | 8/1995 |
| CA | 2124169 A1 | 11/1995 |
| CA | 2164394 | 6/1996 |
| CA | 2223585 A1 | 12/1996 |
| CA | 2241186 | 7/1997 |
| CA | 2389165 A1 | 5/2001 |
| CA | 2363274 A1 | 7/2001 |
| CA | 2412718 A1 | 1/2002 |
| CA | 2448737 A1 | 1/2003 |
| CA | 2449180 A1 | 2/2003 |
| CH | 511873 | 10/1971 |
| DE | 2641060 A1 | 3/1978 |
| DE | 3522230 A1 | 1/1987 |
| DE | 19507913 A1 | 9/1996 |
| EP | 0010063 A2 | 4/1980 |
| EP | 0011824 A1 | 6/1980 |
| EP | 0012291 A1 | 6/1980 |
| EP | 0014411 A1 | 8/1980 |
| EP | 0050957 A1 | 10/1981 |
| EP | 0073663 A2 | 8/1982 |
| EP | 0209707 A2 | 1/1987 |
| EP | 0242167 A2 | 10/1987 |
| EP | 0318084 A2 | 5/1989 |
| EP | 0353606 A2 | 2/1990 |
| EP | 0429240 A1 | 5/1991 |
| EP | 0439356 A1 | 7/1991 |
| EP | 0459334 A1 | 12/1991 |
| EP | 539117 A1 | 4/1993 |
| EP | 0546713 A1 | 6/1993 |
| EP | 0549175 A1 | 6/1993 |
| EP | 0563910 A1 | 10/1993 |
| EP | 0583665 A2 | 2/1994 |
| EP | 0607439 A1 | 7/1994 |
| EP | 0615159 A1 | 9/1994 |
| EP | 0750226 A1 | 12/1996 |
| EP | 0987250 A1 | 3/2000 |
| EP | 1142880 A1 | 10/2001 |
| EP | 1162196 A1 | 12/2001 |
| EP | 1256628 A2 | 11/2002 |
| FR | 1604809 | 5/1972 |
| FR | 2291749 | 6/1976 |
| GB | 1094903 | 12/1967 |
| GB | 1186504 | 4/1970 |
| GB | 1436089 | 5/1976 |
| GB | 1509527 | 5/1978 |
| GB | 2118552 A | 4/1983 |
| GB | 2164648 A | 3/1986 |
| GB | 2197320 A | 5/1988 |
| GB | 2203420 A | 10/1988 |
| JP | 60149502 A | 8/1985 |
| JP | 61085360 A | 6/1986 |
| JP | 3156444 | 7/1991 |
| JP | 5239036 | 9/1993 |
| JP | 6161064 | 6/1994 |
| JP | 6186703 | 7/1994 |
| JP | 6186705 | 7/1994 |
| JP | 6186706 | 7/1994 |
| JP | 6194794 | 7/1994 |
| JP | 6239841 | 8/1994 |
| JP | 6297858 | 10/1994 |
| JP | 7140604 | 6/1995 |
| JP | 7228530 | 8/1995 |
| JP | 9124632 A | 5/1997 |
| JP | 9328678 | 12/1997 |
| JP | 10067682 | 3/1998 |
| JP | 10114654 | 5/1998 |
| JP | 10204059 | 8/1998 |
| JP | 10265478 A2 | 10/1998 |
| JP | 11021693 A2 | 1/1999 |
| JP | 11177218 | 7/1999 |
| JP | 3100165 B2 | 10/2000 |
| JP | 2001122855 A | 5/2001 |
| WO | 91/16313 A1 | 10/1991 |
| WO | 92/10097 A1 | 6/1992 |
| WO | 93/06828 A1 | 4/1993 |
| WO | 94/11349 A1 | 5/1994 |
| WO | 95/07263 A1 | 3/1995 |
| WO | 96/16938 A1 | 6/1996 |
| WO | 96/32379 A1 | 10/1996 |
| WO | 96/39391 A1 | 12/1996 |
| WO | 97/12613 A1 | 4/1997 |
| WO | 97/44319 A1 | 11/1997 |
| WO | 97/48697 A1 | 12/1997 |
| WO | 98/01436 A1 | 1/1998 |
| WO | 98/08847 A1 | 3/1998 |
| WO | 98/29408 A1 | 7/1998 |
| WO | 98/37069 A1 | 8/1998 |
| WO | 98/37079 A1 | 8/1998 |
| WO | 99/28297 A1 | 6/1999 |
| WO | 99/29660 A1 | 6/1999 |
| WO | 99/29661 A1 | 6/1999 |
| WO | 99/61020 A1 | 12/1999 |
| WO | 99/65886 A1 | 12/1999 |
| WO | 00/06529 A1 | 2/2000 |
| WO | 00/06556 | 2/2000 |
| WO | 00/06566 A1 | 2/2000 |
| WO | 00/10573 A1 | 3/2000 |
| WO | 00/13708 A1 | 3/2000 |
| WO | 00/18231 A1 | 4/2000 |
| WO | 00/26202 A1 | 5/2000 |
| WO | 00/27846 A2 | 5/2000 |
| WO | 01/30744 A1 | 3/2001 |
| WO | 01/32653 A1 | 5/2001 |
| WO | 01/47883 A1 | 7/2001 |
| WO | 01/47922 A2 | 7/2001 |
| WO | 01/51487 | 7/2001 |
| WO | 01/85172 A1 | 11/2001 |
| WO | 01/87885 A1 | 11/2001 |
| WO | 01/90121 A2 | 11/2001 |
| WO | 02/04425 A2 | 1/2002 |
| WO | 02/06246 A1 | 1/2002 |
| WO | 02/057287 A2 | 7/2002 |

| | | |
|---|---|---|
| WO | 02/057425 A2 | 7/2002 |
| WO | 02/059118 A1 | 8/2002 |
| WO | 02/069903 A2 | 9/2002 |
| WO | 02/00846 A1 | 12/2002 |
| WO | 02/098424 A1 | 12/2002 |
| WO | 02/100851 A2 | 12/2002 |
| WO | 03/000254 A1 | 1/2003 |
| WO | 03/007945 A1 | 1/2003 |
| WO | 03/010140 A2 | 2/2003 |
| WO | 03/010141 A2 | 2/2003 |
| WO | 03/014377 A2 | 2/2003 |
| WO | 03/018555 A1 | 3/2003 |
| WO | 2005/012288 A1 | 3/2003 |
| WO | 03/026587 A2 | 4/2003 |
| WO | 03/040112 A1 | 5/2003 |
| WO | 03/101993 A1 | 12/2003 |
| WO | 2004/005286 A2 | 1/2004 |
| WO | 2004/065367 A1 | 5/2004 |
| WO | 2004/064925 A1 | 8/2004 |
| WO | 2004/087714 A1 | 10/2004 |
| WO | 2005/014543 A1 | 2/2005 |

OTHER PUBLICATIONS 13-0121-ISR/PCT/CA2004/000017.

Afdhal, N, O'Brien C, Godofsky E, et al. Valpicitabine (NM283), alone or with PEG-interferon, compared to PEG interferon/ribavirin (PEGIFN/RBV) retreatment in patients with HCV-1 infection and prior non-response to PEBIFN/RBV: One-year results. Presented at the 42nd annual EASL meeting, Apr. 11-15, 2007, Barcelona, Spain.

Amat, Mercedes, et al, "An Efficient Synthesis of 2-(2-Pyridyl)indoles by Palladium (0)-catalyzed heteroarylation", Tetrahedron Letters, vol. 34, No. 31, 1993, p. 5005.

Baba et al.; "A Novel Stereospecific Alkenyl'Alkenyl Cross-Coupling by a Palladium or Nickel-Catalyzed Reaction of Alkenylalanes with Alkenyl Halides" J. Am. Chem. Soc., 1976, 98, 6729-6731.

Beaulieu et al. "Non-nucleoside inhibitors of the hepatitis C virus NS5B polymerase: discovery and preliminary SAR of benzimidazole derivatives." Bioorganic and Medicinal Chemistry Letters, 14 (2004) 119-124.

Beaulieu, P.L. et al; "Therapies for Hepatitis C Infection: Targeting the Non-Structural Proteins of HCV"; Curr. Med. Chem.-Anti-Infective Agents, 2002, vol. 1, No. 2, pp. 1-14.

Behrens, S.E.; Tomei, L.; DeFraancesco, R.; "Identification and properties of the RNA-dependent RNA polymerase of hepatitis C virus;" 1996; *EMBO J.* 15: p. 12-22.

Danieli, B. et al. "Application of the PD-catalyzed hetroarylation to the synthesis of 5-(indol2'-yl)pyridin-2-one and 5-(indol-2'yl) pyran-2-one" Tetrahedron, vol. 54, No. 46, 1998, p. 14081.

Deutsch, M. et al; "Old and emerging therapies in chronic hepatitis C: an update;" 2008, J. of Viral Hepatitis, 15, p. 2-11.

Erhardt et al, "Safety, Pharmacokinetics and Antiviral effects of Boehringer Ingelheim BILB 1941, a Novel HCV RNA Polymerase, After 5 days Oral treatment in Patients with Chronic Hepatitis C", Poster from EASL 42nd Mtg. of Euruopean Association for the Study of Liver Diseases, Barcelona, Spain Apr. 11-15, 2007.

Fuerstner, A. et al; "Titanium-Induced Zipper Reactions"; Angewandte Chemie, International Edition in English (1995), 34(6),pp. 678-681 (XP-002233857).

Hishmat, O. H., et al; "Synthesis of Pharmacologically Active Indoles"; Bolletino Chimico Farmaceutico (1999), 183(6), pp. 259-266 (XP-002233311).

Hoofnagle, J.H.; 1997; Hepatology 26: 15S-20S.

Hulme, C., et al; "The Synthesis And Biological Evaluation Of A Novel Series Of Indole PDE4 Inhibitors I"; Bioorganic & Medicinal Chemistry Letters 8 (1998), pp. 1867-1872 (XP-002233861).

Ishiyama, T., Murata, M., Miyaura, N.; "Palladium(0)-Catalyzed Cross-Coupling Reaction of Alkoxydiboron with Haloarenes: A Direct Procedure for Arylboronic Esters;" *J. Org. Chem.* 1995, 60, 7508.

Kolykhalov, A.A. et al,"Hepatitis C Virus-Encoded Enzymatic Activities and Conserved RNA Elements in the 3' nontranslated Region are Essential for Virus Replication in Vivo", J. Virology, 2000, 74(4): 2046-2051.

Lauer, G. and Walker, B., "Hepatitis C Virus Infection," N. Engl. J. Med., vol. 345(1), pp. 41-52 (Jul. 2001), at p. 46, col. 1, lines 23-25.

Lemon, S.H.; Honda, M.; "Internal Ribosome Entry Sites within the RNA Genomes of Hepatitis C Virus and Other Flaviviruses;" 1997; *Semin. Virol.* 8: 274-288.

Levin, Jules, "Safety, Pharmacokinetics and Antiviral effects of Boehringer Ingelheim BILB 1941, a Novel HCV RNA Polymerase, After 5 days Oral treatment in Patients with Chronic Hepatitis C", www.natap.org/2007/EASL/EASL_48.htm EASL 42nd Mtg. of Euruopean Association for the Study of Liver Diseases, Barcelona, Spain Apr. 11-15, 2007.

Lindsay, K.L.; "Therapy of Hepatitis C: Overview;" 1997; *Hepatology* 26: 71S-77S.

Lohmann, V. et al, "Replication of Subgenomic Hepatitis C Virus RNAs in a Hepatoma Cell Line" Science, 1999, 285: 110-113.

Lohmann, V.; Köerner, F.; Herian, U.; Bartenschlager, R.; 1997; J. Virol. 71: 8416-8428.

Mayer et al, "Solid-Phase Synthesis of Benzimidazoles"; Tetrahedron Letters 39 (1998) 6655-6658.

Merlic, C.A. et al. "Benzannulation reactions of Fischer carbene compleses for the synthesis of indolocarbozoles" Tetrahedron, vol. 57, No. 24, p. 5199-5212, 2001.

Miller, J.A. et al, "Preparation of Unsymmetrical Biaryls via Ni-or Pd-Catalyzed Coupling of Aryl chlorides with Arylzincs". Tetrandron Letters, vol. 39 (36), 1998, pp. 6441-6444.

Minato, Akio et al, "Palladium-Phosphine Complex Catalyzed Cross-Coupling Reaction of 1-Methyl-2-pyrrolyl-magnesium Bromide and -zinc chloride with organic halides" Tetrahedron Letters, vol. 22, No. 52, 1981 p. 5319.

Miyaura, N. et al. "Palladium Catalyzed Cross-Coupling Reactions of Organoboron Compounds", Chem. Rev. 1995, vol. 95, pp. 2457-2483.

Murata, M.; Oyama, T.; Watanabe, S., Masuda, Y. "Palladium-Catalyzed Borylation of Aryl Halides or Triflates with Dialkoxyborne: A Novel and Facile Synthetic Route to Arylboronates;" *J. Org. Chem.* 2000, 65, 164.

Negishi, S. Baba, "Novel Stereoselective Alkenyl-Aryl Coupling via Nickel-catalysed Reaction of Alkenylalanes with Aryl Halides;" *J. Chem. Soc. Chem. Communications*, 1976, 596-597.

Perandones, F. et al; Synthesis of imidazol[4,5-b]pyridines from aminoimidazolecarbaldehydes, J. heterocyc. Chem. vol. 34, pp. 107-112, 1997.

Reed, K.E.; Rice, C.M.; "Overview of Hepatitis C Virus Genome Structure, Polyprotein Processing, and Protein Properties;" 1999; *Curr. Top. Microbiol. Immunol.* 242: pp. 55-84.

Reichard, O. et al, "Therapy of Hepatitis C: Alpha Interferon and Ribavirin;" 1997 Hepatology 26; pp. 108S-111S.

Rice, C.M.; 1996; "Flaviviridae: the viruses and their replication"; pp. 931-960 in *Fields Virology;* Fields, B.N.; Knipe, D.M.; Howley, P.M. (eds.); Lippincott-Raven Publishers, Philadelphia, PA.

Rorrer, L.C. et al. "Convenient New Route to Tetradentate and Pentadentate Macrocyclic Tetraamide Ligands", Organic Letters, 1999, vol. 1, No. 8, pp. 1157-1159.

Roth, H. J., et al; "Synthesis of Indole and Carbazole Derivatives By Condensation of Alpha-hydroxyketones and Aromatic Amines"; Archiv der Pharmazie and Berichte der Deutschen Pharmazeutischen Gesellschaft (1972), 305(3), pp. 159-171 (XP-002233858).

Sakamoto, T., et al, "Indolylzinc Iodides by Oxidative addition of activ zinc to Iodoindoles" Tetrahedron Letters, vol. 34, No. 37, 1993, p. 5955.

Stanforth, S.P. "Catalytic Cross-coupling Reactions in Biaryl Synthesis" Tetrahedron, vol. 54(3-4), 1998, pp. 263-303.

Watanabe, T. et al, "Synthesis of sterically hindered blaryis via the palladium-catalyzed cross-coupling reaction of aryliboronic acids of their esters with haloarenes" SYNLETT, vol. 3, p. 207-210, 1992.

Wu et al; "One-pot' nitro reduction-cyclisation solid phase route to benzimidazoles"; Tetrahedron Letters 41 (2000) 9871-9874.

Youngdale, G. A. et al; "Synthesis and Antiinflammatory Activity of 5-Substituted 2,3-bis(p-methoxyphenyl)indoles"; J Med Chem (1969) 12, pp. 948-949 (XP-002233859).

Zhang, H-C., et al: "Efficient synthesis of 3-substituted 2-arylindoles via Suzuki coupling reactions in the solid phase"; Tetrahedron Letters, 42, 2001, pp. 4751-4754.

Translation of Claims only for PCT Application WO 03/000254 (Hashimoto/Japan Tabacco Patent US 2004/082635 and CA2423800).

Hashimoto, et al., WO 2001047883; CA 135:76874,2001.

Takehide, N. et al; "Benzo-Heterocyclic Derivative"; Patent Abstracts of Japan; Publication No. 09124632 A; May 13, 1997.

CAS Registry No. 214150-93-3 Registry Copyright 2001 ACS.
CAS Registry No. 214150-90-0 Registry Copyright 2001 ACS.
CAS Registry No. 115577-24-7 Registry Copyright 2001 ACS.
CAS Registry No. 66630-73-7 Registry Copyright 2001 ACS.
CAS Registry No. 66315-52-4 Registry Copyright 2001 ACS.
CAS Registry No. 66315-51-3 Registry Copyright 2001 ACS.
CAS Registry No. 66315-47-7 Registry Copyright 2001 ACS.
Chemical Abstract for DE 2642877: CA1977:453062.
Chemical Abstract for EP50957: CA1982:509865.
Chemical Abstract for EP73663: CA 1983:505247.
Chemical Abstract for WO 2000006556 A1: CA2000:98534.
Chemical Abstract for WO 2000026202 A1: CA2000:314687.
Chemical Abstract for WO 2000027846 A2: CA2000:335410.
Chemical Abstract for WO 2001/047883: CA2001:489367.
Chemical Abstract for WO 2001/087885: CA2001:851160.
Chemical Abstract for WO 9632379: CA 1996:746234.
Chemical Abstract for WO 9808847 A1: CA1998163594.
Chemical Abstract for WO 9829408 A1: CA1998:485053.
CA Abstract, CA 123: 33085, 1995.
CA Abstract, CA 126: 305540, 1997.
Chemical Abstract: CA 128:275074 for JP 10-067682.
Chemical Abstract: CA 129:45274 for JP 10 114654.
Chemical Abstract: CA 134:340435 for JP 2001 122855.
Chemical Abstract: CA 1968:418961.
Chemical Abstract: CA 1969:68209.
Chemical Abstract: CA 1986:514976.
Chemical Abstract: CA 1987:458985.
Chemical Abstract: CA 1990:234572.
Chemical Abstract: CA 384846-70-2.
U.S. Appl. No. 10/180,558, Filed on Jun. 26, 2002.

VIRAL POLYMERASE INHIBITORS

RELATED APPLICATIONS

This application is a continuation of U.S. application Ser. No. 11/062,305 dated Feb. 18, 2005 now U.S. Pat. No. 7,582,770 which claims benefit to U.S. provisional application No. 60/546,213, filed Feb. 20, 2004.

TECHNICAL FIELD OF THE INVENTION

The invention relates to inhibitors of RNA dependent RNA polymerases, particularly those viral polymerases within the Flaviviridae family, more particularly to HCV polymerase.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Virol.* 74: 2046-2051). HCV is not easily cleared by the hosts' immunological defenses; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S-20S). There are an estimated 170 million HCV carriers world-wide, and HCV-associated end-stage liver disease is now the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection.

Currently, the only approved therapy for patients chronically infected with HCV is treatment with interferon or a combination of interferon and ribavirin. Recently, pegylated versions of interferon (peginterferon alpha-2a (Pegasys™, Roche) and peginterferon alpha-2b (PEG-Intron™, Schering)) have been approved for marketing in some countries for treatment of chronic hepatitis C infection, both alone and in combination with ribavirin. However, it has been reported that these therapies achieve a sustained response in fewer than 60% of cases.

HCV belongs to the family Flaviviridae, genus hepacivirus, which comprises three genera of small enveloped positive-strand RNA viruses (Rice, C. M.; 1996; "*Flaviviridae*: the viruses and their replication"; pp. 931-960 in *Fields Virology*; Fields, B. N.; Knipe, D. M.; Howley, P. M. (eds.); Lippincott-Raven Publishers, Philadelphia Pa.). The 9.6 kb genome of HCV consists of a long open reading frame (ORF) flanked by 5' and 3' non-translated regions (NTR's). The HCV 5' NTR is 341 nucleotides in length and functions as an internal ribosome entry site for cap-independent translation initiation (Lemon, S. H.; Honda, M.; 1997; *Semin. Virol.* 8: 274-288). The HCV polyprotein is cleaved co- and post-translationally into at least 10 individual polypeptides (Reed, K. E.; Rice, C. M.; 1999; *Curr. Top. Microbiol. Immunol.* 242: 55-84). The structural proteins result from signal peptidases in the N-terminal portion of the polyprotein. Two viral proteases mediate downstream cleavages to produce non-structural (NS) proteins that function as components of the HCV RNA replicase. The NS2-3 protease spans the C-terminal half of the NS2 and the N-terminal one-third of NS3 and catalyses cis cleavage of the NS2/3 site. The same portion of NS3 also encodes the catalytic domain of the NS3-4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12-22; and Lohmann, V.; Korner, F.; Herian, U.; Bartenschlager, R.; 1997; *J. Virol.* 71: 8416-8428). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051).

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics.

WO 01/47883, WO 02/04425, WO 03/000254, WO 03/007945, WO 03/010140, WO 03/026587, WO 03/101993, WO 04/005286, WO 2004/064925, WO 2004/065367 and WO 2004/087714 report inhibitors of NS5B proposed for treatment of HCV.

Indole inhibitors of the NS5B polymerase of HCV are disclosed in WO 03/010141. However, the inhibitors of the invention differ from those disclosed in WO 03/010141 in that they exhibit unexpectedly good activity in a cell-based HCV RNA replication assay.

SUMMARY OF THE INVENTION

The present invention provides a novel series of compounds having good to very good inhibitory activity against HCV polymerase and/or unexpectedly good activity in a cell-based HCV RNA replication assay.

Further objects of this invention arise for the one skilled in the art from the following description and the examples.

In a first aspect of the invention, there is provided a compound, represented by formula I, or an enantiomer, diastereoisomer or tautomer thereof, including a salt or ester thereof:

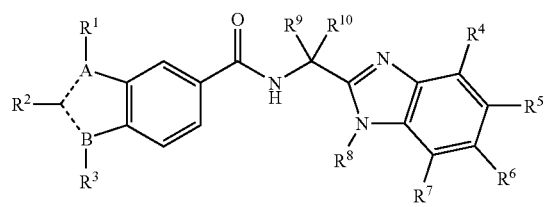

wherein:

either A or B is N and the other B or A is C, wherein ---- between two C-atoms represents a double bond and ---- between a C-atom and a N-atom represents a single bond;

$R^1$ is H or $(C_{1-6})$alkyl;

$R^2$ is selected from halogen, cyano, $(C_{1-6})$alkyl, $(C_{2-6})$alkenyl, $(C_{2-6})$alkynyl, $(C_{3-7})$cycloalkyl, aryl and Het; said aryl and Het being optionally substituted with $R^{21}$;

wherein $R^{21}$ is one, two or three substituents each independently selected from —OH, —CN, —N($R^{N2}$)$R^{N1}$, halogen, ($C_{1-6}$)alkyl, ($C_{1-6}$)alkoxy, ($C_{1-6}$)alkylthio, Het and —CO—N($R^{N2}$)$R^{N1}$;
  wherein said ($C_{1-6}$)alkyl, ($C_{1-6}$)alkoxy and ($C_{1-6}$)alkylthio are each optionally substituted with one, two or three halogen atoms;

$R^3$ is ($C_{5-6}$)cycloalkyl, optionally substituted with from one to four halogen atoms;

$R^4$ and $R^7$ are each independently selected from H, ($C_{1-6}$)alkyl, ($C_{1-6}$)alkoxy, ($C_{1-6}$)alkylthio, —NH$_2$, —NH($C_{1-6}$)alkyl, —N(($C_{1-6}$)alkyl)$_2$ and halogen;

One of $R^5$ and $R^6$ is selected from COOH, —CO—N($R^{N2}$)$R^{N1}$, aryl, Het and ($C_{2-6}$)alkenyl, wherein aryl, Het, ($C_{2-6}$)alkenyl and $R^{N1}$ or any heterocycle formed between $R^{N2}$ and $R^{N1}$ are each optionally substituted with $R^{50}$;
  wherein $R^{50}$ is one, two or three substituents each independently selected from ($C_{1-6}$)alkyl, —COOH, —OH, oxo, —N($R^{N2}$)$R^{N1}$, —CO—N($R^{N2}$)$R^{N1}$ and halogen wherein the ($C_{1-6}$)alkyl is optionally substituted with aryl or —N($R^{N2}$)$R^{N1}$;

and the other of $R^5$ and $R^6$ is selected from H, ($C_{1-6}$)alkyl, ($C_{1-6}$)alkoxy, ($C_{1-6}$)alkylthio, and N($R^{N2}$)$R^{N1}$;

$R^8$ is ($C_{1-6}$)alkyl, ($C_{3-7}$)cycloalkyl or ($C_{3-7}$)cycloalkyl-($C_{1-6}$)alkyl-;
  wherein said alkyl, cycloalkyl and cycloalkyl-alkyl are each optionally substituted with one, two or three substituents each independently selected from halogen, ($C_{1-6}$)alkoxy and ($C_{1-6}$)alkylthio;

$R^9$ and $R^{10}$ are each independently selected from ($C_{1-6}$)alkyl; or $R^9$ and $R^{10}$ are linked, together with the C atom to which they are attached, to form ($C_{3-7}$)cycloalkyl, ($C_{5-7}$)cycloalkenyl or a 4-, 5- or 6-membered heterocycle having from 1 to 3 heteroatoms each independently selected from O, N, and S;
  wherein said cycloalkyl, cycloalkenyl or heterocycle is in each case optionally substituted with ($C_{1-4}$)alkyl;

$R^{N1}$ is selected from H, ($C_{1-6}$)alkyl, ($C_{3-7}$)cycloalkyl, ($C_{3-7}$)cycloalkyl-($C_{1-6}$)alkyl-, —CO—($C_{1-6}$)alkyl, —CO—O—($C_{1-6}$)alkyl and Het;
  wherein the alkyl and cycloalkyl portions of each of said ($C_{1-6}$)alkyl, ($C_{3-7}$)cycloalkyl, ($C_{3-7}$)cycloalkyl-($C_{1-6}$)alkyl-, —CO—($C_{1-6}$)alkyl and —CO—O—($C_{1-6}$)alkyl are each optionally substituted with one, two or three substituents each independently selected from halogen, ($C_{1-6}$)alkoxy and ($C_{1-6}$)alkylthio; and $R^{N2}$ is H or ($C_{1-6}$)alkyl, or $R^{N2}$ and $R^{N1}$ may be linked, together with the N atom to which they are attached, to form a 4-, 5-, 6- or 7-membered saturated, unsaturated or aromatic N-containing heterocycle or a 8-, 9-, 10- or 11-membered N-containing saturated, unsaturated or aromatic heterobicycle, each optionally having additionally from 1 to 3 heteroatoms each independently selected from O, N, and S;
  wherein the heterocycle or heterobicycle formed by $R^{N2}$ and $R^{N1}$ is optionally substituted with one, two or three substituents each independently selected from halogen, ($C_{1-6}$)alkyl, ($C_{1-6}$)alkoxy and ($C_{1-6}$)alkylthio;

wherein Het is defined as a 4-, 5-, 6- or 7-membered heterocycle having 1 to 4 heteroatoms each independently selected from O, N and S, which may be saturated, unsaturated or aromatic, or a 8-, 9-, 10- or 11-membered heterobicycle having 1 to 5 heteroatoms wherever possible, each independently selected from O, N and S, which may be saturated, unsaturated or aromatic.

Included within the scope of this invention are compounds of the formula (I) as described hereinbefore, to which at least one of a "detectable label", an "affinity tag" and a "photoreactive group" is linked.

The compounds according to this invention generally show an inhibitory activity against HCV polymerase. In particular compounds according to this invention inhibit RNA synthesis by the RNA dependent RNA polymerase of HCV, especially of the enzyme NS5B encoded by HCV. Furthermore, compounds according to this invention show an unexpectedly good activity in a cell-based HCV RNA replication assay. A further advantage of compounds provided by this invention is their low to very low or even non-significant activity against other polymerases.

In a second aspect of the invention, there is provided a use of a compound of formula I according to this invention, or a pharmaceutically acceptable salt or ester thereof, or a composition thereof, as an HCV polymerase inhibitor, preferably as an inhibitor of RNA dependent RNA polymerase activity of the enzyme NS5B, encoded by HCV.

In a third aspect of the invention, there is provided a use of a compound of the formula I according to this invention, or a pharmaceutically acceptable salt or ester thereof, or a composition thereof, as an inhibitor of HCV replication.

In a fourth aspect of the invention, there is provided a use of a compound of the formula I according to this invention, or a pharmaceutically acceptable salt or ester thereof, or a composition thereof, for the treatment or prevention of HCV infection in a mammal.

In a fifth aspect of the invention, there is provided a method of inhibiting the RNA-dependent RNA polymerase activity of the enzyme NS5B, encoded by HCV, comprising exposing the enzyme NS5B to an effective amount of a compound of formula I under conditions where the RNA-dependent RNA polymerase activity of the enzyme NS5B is inhibited.

In a sixth aspect of the invention, there is provided a method of inhibiting HCV replication, comprising exposing a cell infected with HCV to an effective amount of a compound of formula I under conditions where replication of HCV is inhibited.

In a seventh aspect of the invention, there is provided a method of treating or preventing HCV infection in a mammal, comprising administering to the mammal an effective amount of a compound of formula I according to this invention, or a pharmaceutically acceptable salt or ester thereof, or a composition thereof.

In a eighth aspect of the invention, there is provided a method of treating or preventing HCV infection in a mammal, comprising administering to the mammal an effective amount of a compound of formula I, or a pharmaceutically acceptable salt or ester thereof, or a composition thereof, in combination with at least one other antiviral agent.

In a ninth aspect of the invention, there is provided a pharmaceutical composition for the treatment or prevention of HCV infection, comprising an effective amount of a compound of formula I according to this invention, or a pharmaceutically acceptable salt or ester thereof, and a pharmaceutically acceptable carrier.

According to a specific embodiment, the pharmaceutical composition of this invention additionally comprises a therapeutically effective amount of one or more antiviral agents. Examples of antiviral agents include, but are not limited to, ribavirin and amantadine.

According to a further specific embodiment, the pharmaceutical composition of this invention additionally comprises at least one other anti-HCV agent as an antiviral agent.

According to a more specific embodiment, the pharmaceutical composition of this invention comprises an additional immunomodulatory agent as an other anti-HCV agent. Examples of additional immunomodulatory agents include but are not limited to, α-, β-, δ-γ-, τ- and ω-interferons and pegylated forms thereof.

According to another more specific embodiment, the pharmaceutical composition of this invention additionally comprises at least one other inhibitor of HCV polymerase as an other anti-HCV agent.

According to another more specific embodiment, the pharmaceutical composition of this invention additionally comprises at least one inhibitor of HCV NS3 protease as an other anti-HCV agent.

According to yet another more specific embodiment, the pharmaceutical composition of this invention additionally comprises at least one inhibitor of another target in the HCV life cycle as an other anti-HCV agent. Examples of such inhibitors of other targets include, but are not limited to, agents that inhibit a target selected from HCV helicase, HCV NS2/3 protease and HCV IRES and agents that interfere with the function of other viral targets including but not limited to an NS5A protein.

In an tenth aspect of the invention, there is provided a use of a compound of formula I according to this invention, or of a pharmaceutically acceptable salt or ester thereof, or a composition thereof, for the manufacture of a medicament for the treatment and/or the prevention of a Flaviviridae viral infection, preferably an HCV infection.

An eleventh aspect of this invention refers to an article of manufacture comprising a composition effective to treat or prevent an HCV infection or to inhibit the NS5B polymerase of HCV and packaging material comprising a label which indicates that the composition can be used to treat infection by the hepatitis C virus, wherein said composition comprises a compound of formula (I) according to this invention or a pharmaceutically acceptable salt or ester thereof.

DETAILED DESCRIPTION OF THE INVENTION

Definitions

The following definitions apply unless otherwise noted:

As used herein, the term "$(C_{1-n})$alkyl", wherein n is an integer, either alone or in combination with another radical, is intended to mean acyclic straight or branched chain alkyl radicals containing 1 to n carbon atoms respectively. Examples of such radicals include, but are not limited to, methyl, ethyl, n-propyl, 1-methylethyl (iso-propyl), n-butyl, 1-methylpropyl, 2-methylpropyl, 1,1-dimethylethyl (tert-butyl), n-pentyl, etc. In the following, the term Me denotes a methyl group.

If an alkyl group is substituted by halogen, it is preferably mono-, di- or trisubstituted with fluorine or monosubstituted by chlorine or bromine.

As used herein, the term "$(C_{2-n})$alkenyl", wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, 1-butenyl, etc. The cis and trans isomers, and mixtures thereof, of the $(C_{2-n})$alkenyl radical are encompassed by the term. A $(C_{2-n})$alkenyl radical may be substituted on any of the carbon atoms thereof which would otherwise bear a hydrogen atom.

As used herein, the term "$(C_{2-n})$alkynyl", wherein n is an integer, either alone or in combination with another radical, means an acyclic, straight or branched chain radical containing from 2 to n carbon atoms, at least two of which are linked by a triple bond. Examples of such radicals include, but are not limited to, ethynyl, 1-propynyl, 2-propynyl, and 1-butynyl. A $(C_{2-n})$alkynyl radical may be substituted on any of the carbon atoms thereof which would otherwise bear a hydrogen atom.

As used herein, the term "$(C_{3-n})$cycloalkyl", wherein n is an integer, either alone or in combination with another radical, means a cycloalkyl radical containing from three to n carbon atoms. Examples of such radicals include, but are not limited to, cyclopropyl, cyclobutyl, cyclopentyl, cyclohexyl and cycloheptyl.

As used herein, the term "$(C_{5-n})$cycloalkenyl", wherein n is an integer, either alone or in combination with another radical, means an unsaturated cyclic radical containing five to n carbon atoms. Examples include, but are not limited to, cyclopentenyl and cyclohexenyl.

As used herein the term "$(C_{3-m})$cycloalkyl-$(C_{1-n})$alkyl-", wherein n and m are integers, either alone or in combination with another radical, means a branched or straight chain alkyl radical having 1 to n carbon atoms to which a cycloalkyl radical containing from three to m carbon atoms is covalently bonded. Examples of $(C_{3-7})$cycloalkyl-$(C_{1-6})$alkyl-include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl, 2-cyclohexylethyl, etc.

As used herein, the term "protecting group" defines protecting groups that can be used during synthetic transformation, examples of which are listed in Greene, "Protective Groups in Organic Chemistry", John Wiley & Sons, New York (1981) and "The Peptides: Analysis, Synthesis, Biology", Vol. 3, Academic Press, New York (1981).

A carboxyl group is usually protected as an ester that can be cleaved to give the carboxylic acid. Protecting groups that can be used include, but are not limited to,: 1) alkyl esters such as methyl, ethyl, trimethylsilylethyl and tert-butyl, 2) aralkyl esters such as benzyl and substituted benzyl, or 3) esters that can be cleaved by mild base treatment or mild reductive means such as trichloroethyl and phenacyl esters.

As used herein, the term "aryl" either alone or in combination with another radical means a 6- or 10-membered aryl, i.e. an aromatic radical containing six or ten carbon atoms. Examples include, but are not limited to, phenyl, 1-naphthyl or 2-naphthyl.

As used herein, the term "Het" defines a 4-, 5-, 6- or 7-membered heterocycle having 1 to 4 heteroatoms each independently selected from O, N and S, which may be saturated, unsaturated or aromatic, or a 8-, 9-, 10- or 11-membered heterobicycle having 1 to 5 heteroatoms wherever possible, each independently selected from O, N and S, which may be saturated, unsaturated or aromatic, unless specified otherwise.

As used herein the term "heteroatom" means O, S or N.

As used herein, the term "heterocycle", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Examples of such heterocycles include, but are not limited to, azetidine, pyrrolidine, tetrahydrofuran, thiazolidine, pyrrole, thiophene, hydantoin, diazepine, 1H-imidazole, isoxazole, thiazole, tetrazole, piperidine, piperazine, homopiperidine, homo-piperazine, 1,4-dioxane, 4-morpholine, 4-thiomorpholine, pyridine, pyridine-N-oxide or pyrimidine, or the following heterocycles:

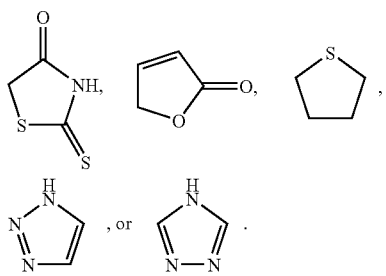

As used herein, the term "9- or 10-membered heterobicycle" or "heterobicycle" either alone or in combination with another radical, means a heterocycle as defined above fused to one or more other cycle, be it a heterocycle or any other cycle. Examples of such heterobicycles include, but are not limited to, indole, benzimidazole, thiazolo[4,5-b]-pyridine, quinoline, or coumarin, or the following:

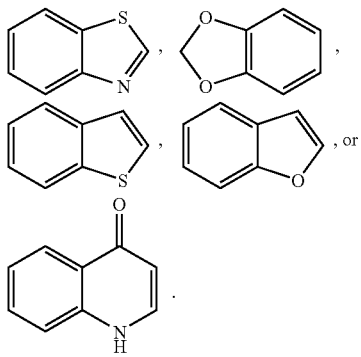

As used herein, the term "halo" or "halogen" means a halogen atom and includes fluorine, chlorine, bromine and iodine.

As used herein, the term "OH" refers to a hydroxyl group. It is well known to one skilled in the art that hydroxyl groups may be substituted by functional group equivalents. Examples of such functional group equivalents that are contemplated by this invention include, but are not limited to, ethers, sulfhydryls, thioethers and primary, secondary or tertiary amines.

As used herein, the term "SH" refers to a sulfhydryl group. It is intended within the scope of the present invention that, whenever a "SH" or "SR" group is present, it can also be substituted by any other appropriate oxidation state such as SOR, $SO_2R$, or $SO_3R$.

As used herein, the term "$(C_{1-n})$alkoxy" refers to an oxygen atom further bonded to an $(C_{1-n})$alkyl radical. Examples of $(C_{1-6})$alkoxy include, but are not limited to, methoxy ($CH_3O-$), ethoxy ($CH_3CH_2O-$), n-propoxy ($CH_3CH_2CH_2O-$), 1-methylethoxy (iso-propoxy; $(CH_3)_2CHO-$), 1,1-dimethylethoxy (tert-butoxy; $(CH_3)_3CO-$), etc. When a $(C_{1-n})$alkoxy group is substituted, it is understood to be substituted on the $(C_{1-n})$alkyl portion thereof.

As used herein, the term "$(C_{1-n})$alkylthio" refers to a sulfur atom further bonded to an $(C_{1-n})$alkyl radical. Examples of $(C_{1-6})$alkylthio include, but are not limited to, methylthio ($CH_3S-$), ethylthio ($CH_3CH_2S-$), n-propylthio ($CH_3CH_2CH_2S-$), 1-methylethylthio (iso-propylthio; $(CH_3)_2CHS-$), 1,1-dimethylethylthio (tert-butylthio $(CH_3)_3CS-$), etc. When a $(C_{1-n})$alkylthio group is substituted, it is understood to be substituted on the $(C_{1-n})$alkyl portion thereof.

The term "oxo" as used herein means an oxygen atom attached to a carbon atom as a substituent by a double bond (=O).

It is intended that when the term "substituted" is applied in conjunction with a radical having more than one moiety such as $(C_{3-7})$cycloalkyl-$(C_{1-6})$alkyl-, such substitution applies to both moieties i.e. either or both of the alkyl and cycloalkyl moieties can be substituted with the defined substituents.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, imides, boronic acids, phosphonic acids, sulfonic acids, tetrazoles, triazoles, N-acylsulfonyldiamides ($RCONHSO_2NR_2$), and N-acylsulfonamides ($RCONHSO_2R$).

As used herein, the term "functional group equivalent" is intended to mean an element or group or a substituted derivative thereof, that is replaceable by another element or group that has similar electronic, hybridization or bonding properties.

The following signs ---- and ⁓ are used interchangeably in subformulas to indicate the bond, or in the case of a spirocyclic group the atom, which is bonded to the rest of the molecule as defined.

As used herein, the term "detectable label" means any group that may be linked to the polymerase or to a compound of the present invention such that when the compound is associated with the polymerase target, such label allows recognition either directly or indirectly of the compound such that it can be detected, measured and quantified. Examples of such "labels" are intended to include, but are not limited to, fluorescent labels, chemiluminescent labels, colorimetric labels, enzymatic markers, radioactive isotopes and affinity tags such as biotin. Such labels are attached to the compound or to the polymerase by well known methods.

As used herein, the term "affinity tag" means a ligand (that may be linked to the polymerase or to a compound of the present invention) whose strong affinity for a receptor can be used to extract from a solution the entity to which the ligand is attached. Examples of such ligands include, but are not limited to, biotin or a derivative thereof, a histidine polypeptide, a polyarginine, an amylose sugar moiety or a defined epitope recognizable by a specific antibody. Such affinity tags are attached to the compound or to the polymerase by well-known methods.

As used herein, the term "photoreactive group" means a group that is transformed, upon activation by light, from an inert group to a reactive species, such as a free radical. Such a group may be used as, for example, a photoaffinity label. Examples of such groups include, but are not limited to, benzophenones, azides, and the like.

The term "salt thereof" means any acid and/or base addition salt of a compound according to the invention; preferably a pharmaceutically acceptable salt thereof.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Examples of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "ester thereof" means any ester of a compound in which any of the carboxyl functions of the molecule is replaced by an alkoxycarbonyl function, including but not limited to pharmaceutically acceptable esters thereof.

The term "pharmaceutically acceptable ester" as used herein, either alone or in combination with another substituent, means esters of the compound of formula (I) in which any of the carboxyl functions of the molecule, but preferably the carboxy terminus, is replaced by an alkoxycarbonyl function:

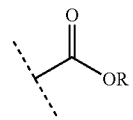

in which the R moiety of the ester is selected from alkyl (e.g. methyl, ethyl, n-propyl, tert-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $(C_{1-4})$alkyl or $(C_{1-4})$alkoxy. Other suitable esters can be found in Design of prodrugs, Bundgaard, H. Ed. Elsevier (1985). Such pharmaceutically acceptable esters are usually hydrolyzed in vivo when injected in a mammal and transformed into the acid form of the compound of formula (I). With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Antiviral agents include, but are not limited to, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, other inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, but are not limited to, class I interferons (such as α-, β-, δ- and ω interferons, τ-interferons, consensus interferons and asialo-interferons), class II interferons (such as γ-interferons) and pegylated forms thereof.

The term "inhibitor of HCV NS3 protease" as used herein means an agent (compound or biological) that is effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 02/060926, US 2002/0177725, WO 03/053349, WO 03/062265, WO 03/064416, WO 03/064455, WO 03/064456, WO 03/099316, WO 03/099274, WO 2004/032827, WO 2004/037855, WO 2004/043339, WO 2004/072243, WO 2004/093798, WO 2004/094452, WO 2004/101602, WO 2004/101605, WO 2004/103996, the Boehringer Ingelheim clinical candidate identified as BILN 2061 and the Vertex clinical candidate identified as VX-950.

The term "other inhibitor of HCV polymerase" as used herein means an agent (compound or biological) that is effective to inhibit the function of HCV polymerase in a mammal, whereby this agent has a structure different from the compounds according to this invention and preferably binds to a site of the HCV polymerase different from the site targeted by the compounds according to this invention. Other inhibitors of HCV polymerase include non-nucleosides, for example, those compounds described in: WO 2004/087714 (IRBM), WO 04/005286 (Gilead), WO 04/002977 (Pharmacia), WO 04/002944 (Pharmacia), WO 04/002940 (Pharmacia), WO 03/101993 (Neogenesis), WO 03/099824 (Wyeth), WO 03/099275 (Wyeth), WO 03/099801 (GSK)), WO 03/097646 (GSK), WO 03/095441 (Pfizer), WO 03/090674 (Viropharma), WO 03/084953 (B&C Biopharm), WO 03/082265 (Fujisawa), WO 03/082848 (Pfizer), WO 03/062211 (Merck), WO 03/059356 (GSK), EP 1321463 (Shire), WO 03/040112 (Rigel), WO 03/037893 (GSK), WO 03/037894 (GSK), WO 03/037262 (GSK), WO 03/037895 (GSK), WO 03/026587 (BMS), WO 03/002518 (Dong Wha), WO 03/000254 (Japan Tobacco), WO 02/100846 A1 (Shire), WO 02/100851 A2 (Shire), WO 02/098424 A1 (GSK), WO 02/079187 (Dong Wha), WO 03/02/20497 (Shionogi), WO 02/06246 (Merck), WO 01/47883 (Japan Tobacco), WO 01/85172 A1 (GSK), WO 01/85720 (GSK), WO 01/77091 (Tularik), WO 00/18231 (Viropharma), WO 00/13708 (Viropharma), WO 01/10573 (Viropharma) WO 00/06529 (Merck), EP 1 256 628 A2 (Agouron), WO 02/04425 (Boehringer Ingelheim) WO 03/007945 (Boehringer Ingelheim), WO 03/010140 (Boehringer Ingelheim), WO 03/010141 (Boehringer Ingelheim), WO 2004/064925 (Boehringer Ingelheim) and WO 2004/065367 (Boehringer Ingelheim). Furthermore other inhibitors of HCV polymerase also include nucleoside analogs, for example, those compounds described in: WO 04/007512 (Merck/Isis), WO 04/003000 (Idenix), WO 04/002999 (Idenix), WO 04/0002422 (Idenix), WO 04/003138 (Merck), WO 03/105770 (Merck), WO 03/105770 (Merck), WO 03/093290 (Genelabs), WO 03/087298 (Biocryst), WO 03/062256 (Ribapharm), WO 03/062255 (Ribapharm), WO 03/061385 (Ribapharm), WO 03/026675 (Idenix), WO 03/026589 (Idenix), WO 03/020222 (Merck), WO 03/000713 (Glaxo), WO 02/100415 (Hoffmann-La Roche), WO 02/1094289 (Hoffmann-La Roche), WO 02/051425 (Mitsubishi), WO 02/18404 (Hoffmann-La Roche), WO 02/069903 (Biocryst Pharmaceuticals Inc.), WO 02/057287 (Merck/Isis), WO 02/057425 (Merck/Isis), WO 01/90121 (Idenix), WO 01/60315 (Shire) and WO 01/32153 (Shire).

The term "inhibitor of another target in the HCV life cycle" as used herein means an agent (compound or biological) that is effective to inhibit the formation and/or replication of HCV in a mammal other than by inhibiting the RNA dependent RNA polymerase of HCV. This includes agents that interfere with either host or HCV viral mechanisms necessary for the formation and/or replication of HCV in a mammal. Inhibitors of another target in the HCV life cycle include, but are not limited to, agents that inhibit a target selected from a HCV helicase, HCV NS2/3 protease and HCV IRES and agents that interfere with the function of other viral targets including but not limited to an NS5A protein.

The term "HIV inhibitor" as used herein means an agent (compound or biological) that is effective to inhibit the formation and/or replication of HIV in a mammal. This includes agents that interfere with either host or viral mechanisms necessary for the formation and/or replication of HIV in a mammal. HIV inhibitors include, but are not limited to, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include, but are not limited to, Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include agents that inhibit HBV viral DNA polymerase or HBV vaccines. Specific examples of HBV inhibitors include, but are not limited to, Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include, but are not limited to, α-, β-, δ-, ω-interferons, τ-interferons, consensus interferons, asialo-interferons and pegylated forms thereof.

The term "class II interferon" as used herein means an interferon selected from a group of interferons that all bind to receptor type II. Examples of class II interferons include, but are not limited to, γ-interferons and pegylated forms thereof.

As discussed above, combination therapy is contemplated wherein a compound of formula (I), or a pharmaceutically acceptable salt or ester thereof, is co-administered with at least one additional agent selected from: an antiviral agent, an immunomodulatory agent, an inhibitor of HCV NS3 protease, another inhibitor of HCV polymerase, an inhibitor of another target in the HCV life cycle, an HIV inhibitor, an HAV inhibitor and an HBV inhibitor. Examples of such agents are provided in the Definitions section above. Specific preferred examples of such agents are listed below:

antiviral agents: ribavirin or amantadine;
 immunomodulatory agents: class I interferons, class II
  interferons or pegylated forms thereof;
 HCV NS3 protease inhibitors;
 other inhibitors of the HCV polymerase: nucleoside or
  non-nucleoside inhibitors;
 an inhibitor of another target in the HCV life cycle that
  inhibits a target selected from: NS3 helicase, HCV
  NS2/3 protease and internal ribosome entry site (IRES)
  or an agent that interferes with the function of an NS5A
  protein;

HIV inhibitors: nucleoside inhibitors, non-nucleoside inhibitors, protease inhibitors, fusion inhibitors or integrase inhibitors; or HBV inhibitors: agents that inhibit HBV viral DNA polymerase or an agent that is an HBV vaccine.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt or ester thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood.

Preferred Embodiments

Unless stated otherwise, all groups and substituents, including but not limited to $R^1$, $R^2$, $R^3$, $R^4$, $R^5$, $R^6$, $R^7$, $R^8$, $R^9$, $R^{10}$, $R^{21}$, $R^5$, $R^{N1}$, $R^{N2}$, A, B, and Het, have the definitions as defined hereinbefore and hereinafter. In the following, the preferred embodiments, groups and substituents according to this invention are described.

Core:

This invention comprises compounds of the formula Ia:

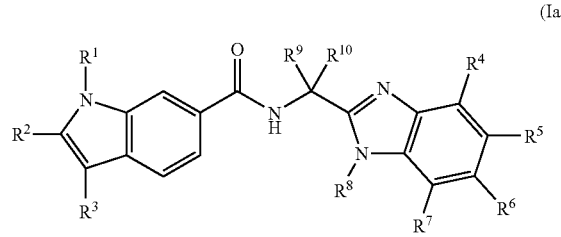

(Ia)

Alternatively, this invention comprises compounds of the formula Ib:

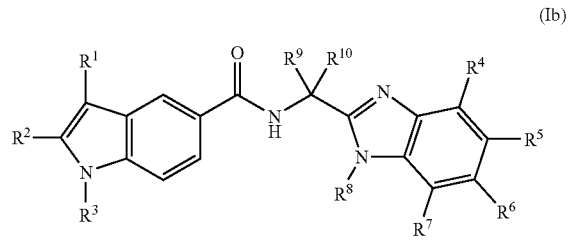

(Ib)

$R^1$:

According to a preferred embodiment of this invention $R^1$ is selected from the group consisting of H, methyl and ethyl.

More preferably, $R^1$ is methyl.

$R^2$:

Preferably $R^2$ is selected from halogen, cyano, $(C_{1-4})$alkyl, $(C_{2-4})$alkenyl, $(C_{2-4})$alkynyl, $(C_{3-6})$cycloalkyl, phenyl and Het selected from the group of formulas:

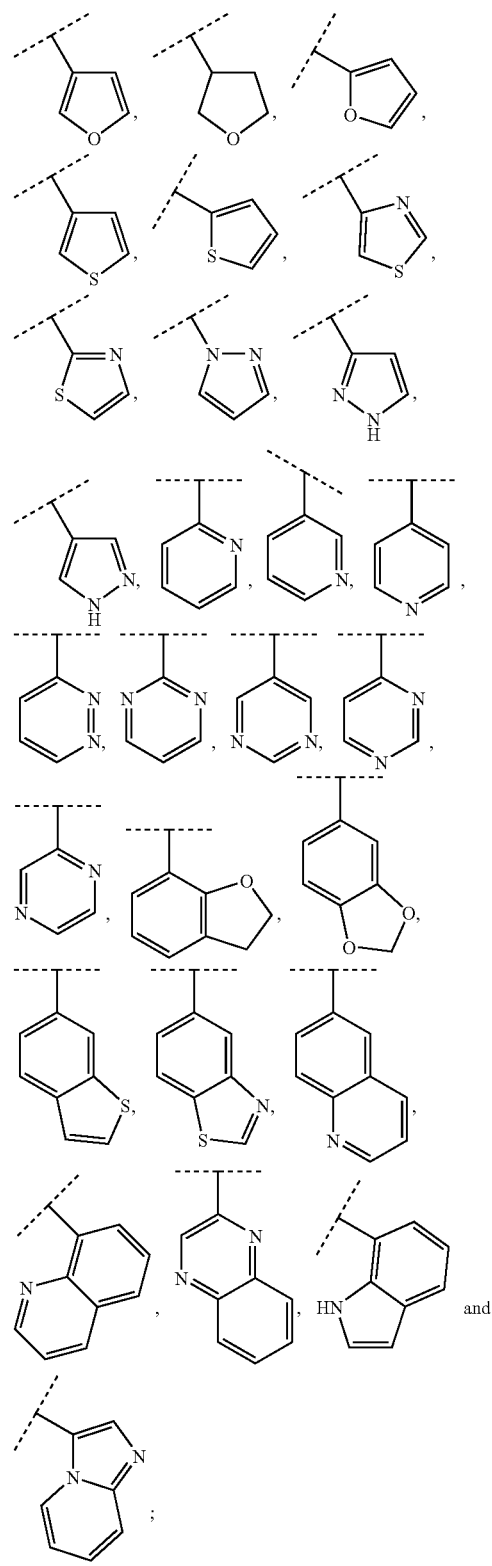

wherein said phenyl and Het are unsubstituted or substituted with $R^{21}$ wherein $R^{21}$ is as defined herein.

More preferably, $R^2$ is selected from Br, Cl, cyano, methyl, ethyl, propyl, 1-methylethyl, ethenyl, 1-methylethenyl, ethynyl, cyclopropyl, phenyl and Het selected from the group of formulas:

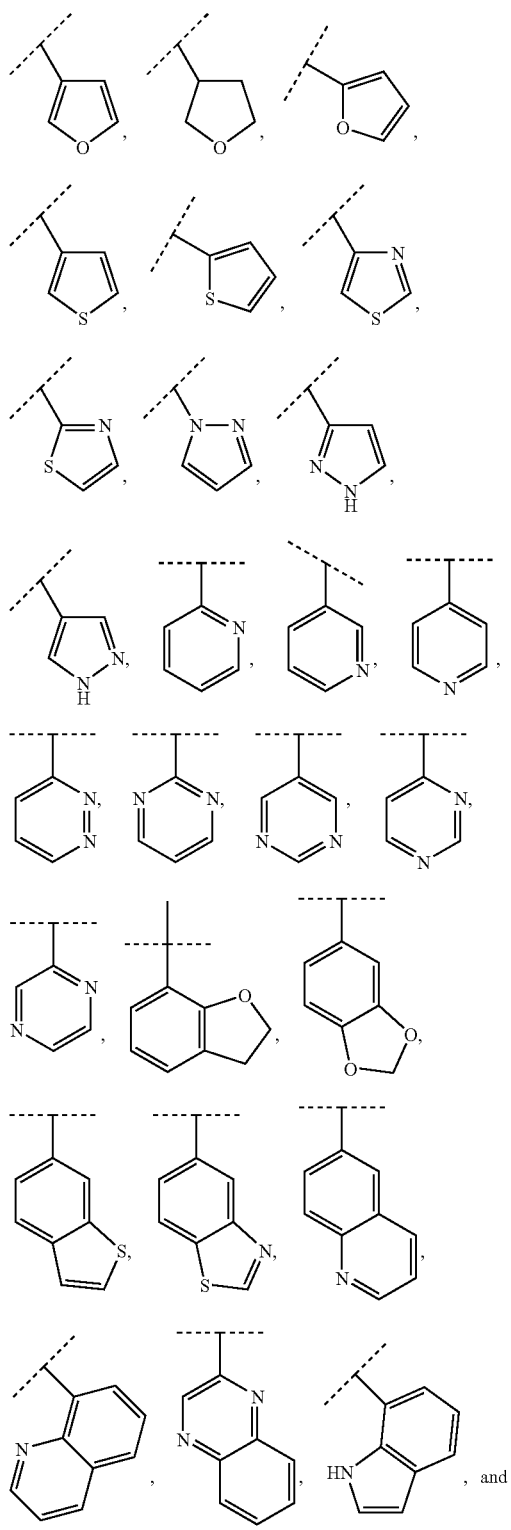

-continued

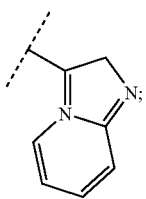

wherein said phenyl and Het are unsubstituted or substituted with $R^{21}$, wherein $R^{21}$ is as defined herein.

$R^{21}$:

Preferably, $R^{21}$ is 1, 2 or 3 substituents each independently selected from:
- 1 to 3 substituents each independently selected from halogen; and
- 1 to 2 substituents each independently selected from:
  a) hydroxy, $(C_{1-4})$alkyl or $(C_{1-4})$alkoxy; wherein said alkyl and alkoxy are each optionally substituted with one, two or three halogen atoms;
  b) —$NR^{N2}R^{N1}$ wherein
     $R^{N1}$ is selected from H, $(C_{1-3})$alkyl, —CO—$(C_{1-3})$alkyl, —CO—O—$(C_{1-3})$alkyl and Het; wherein the alkyl portions of each of said $(C_{1-3})$alkyl, —CO—$(C_{1-3})$alkyl, and —CO—O—$(C_{1-3})$alkyl are optionally substituted with one, two or three substituents selected from halogen and $(C_{1-6})$alkoxy; and wherein said Het is a 5- or 6-membered monocyclic saturated, unsaturated or aromatic heterocycle having 1 or 2 heteroatoms, each independently selected from N, O, and S; and
     $R^{N2}$ is H or $(C_{1-3})$alkyl;
  c) —$CONR^{N2}R^{N1}$ wherein $R^{N2}$ and $R^{N1}$ are each independently selected from H and $(C_{1-3})$alkyl; and
  d) Het, wherein said Het is a 5- or 6-membered monocyclic heterocycle having 1, 2 or 3 heteroatoms, each independently selected from N, O and S.

More preferably, $R^{21}$ is 1, 2 or 3 substituents each independently selected from:
- 1 to 2 substituents each independently selected from fluorine, chlorine and bromine; and
- 1 to 2 substituents each independently selected from:
  a) hydroxy, methyl, ethyl, propyl, 1-methylethyl, methoxy, ethoxy, propoxy or 1-methylethoxy; wherein said methyl, ethyl, propyl, 1-methylethyl, methoxy, ethoxy, propoxy and 1-methylethoxy are each optionally substituted with one, two or three halogen atoms;
  b) —$N(CH_3)_2$ or —$NHR^{N1}$ wherein
     $R^{N1}$ is selected from H, methyl, ethyl, propyl, 1-methylethyl, —CO—$CH_3$, 2-pyridyl, 3-pyridyl and 4-pyridyl; wherein said methyl, ethyl, propyl and 1-methylethyl are each optionally substituted with one, two or three substituents selected from halogen and $(C_{1-3})$alkoxy;
  c) —$CONH_2$; and
  d) 3-pyridyl, 4-pyridyl, 5-pyrimidinyl, 2-furyl, 1-pyrrolyl and 1-morpholino.

Therefore preferably, $R^2$ is selected from Br, Cl, cyano, methyl, ethyl, propyl, 1-methylethyl, cyclopropyl, ethenyl, 1-methylethenyl, ethynyl,

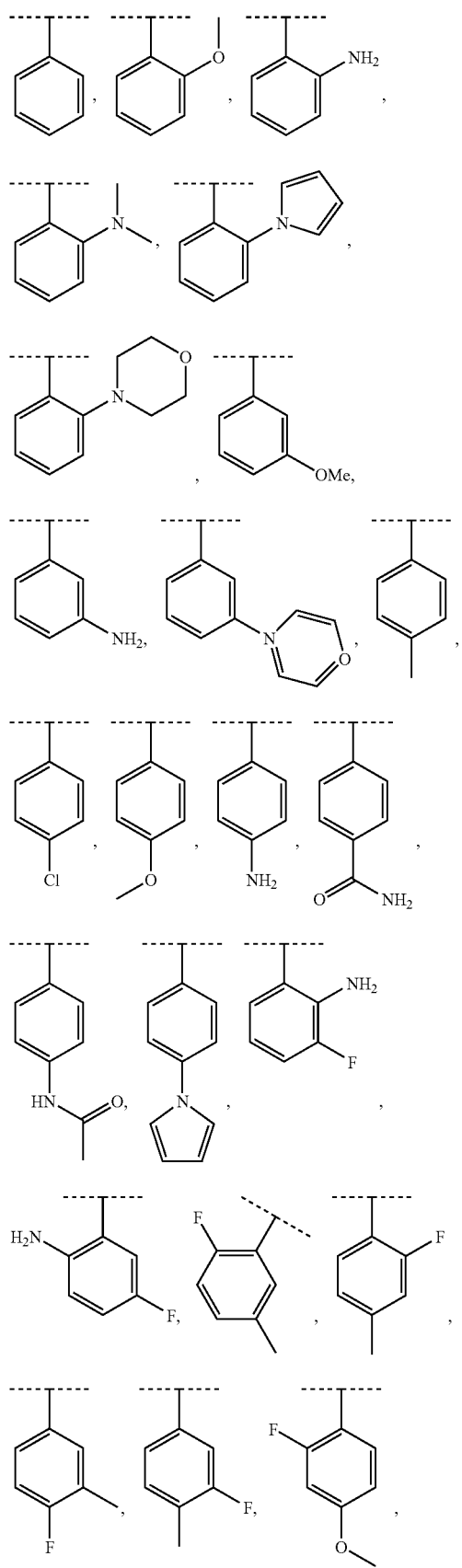
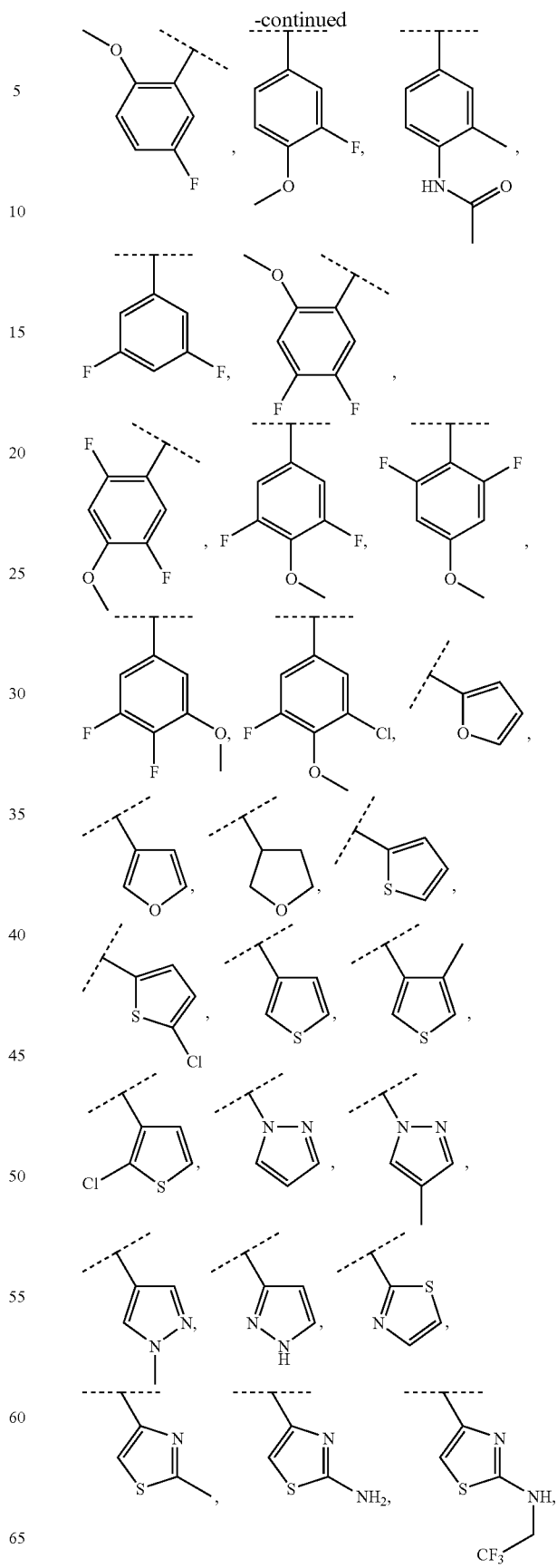

-continued
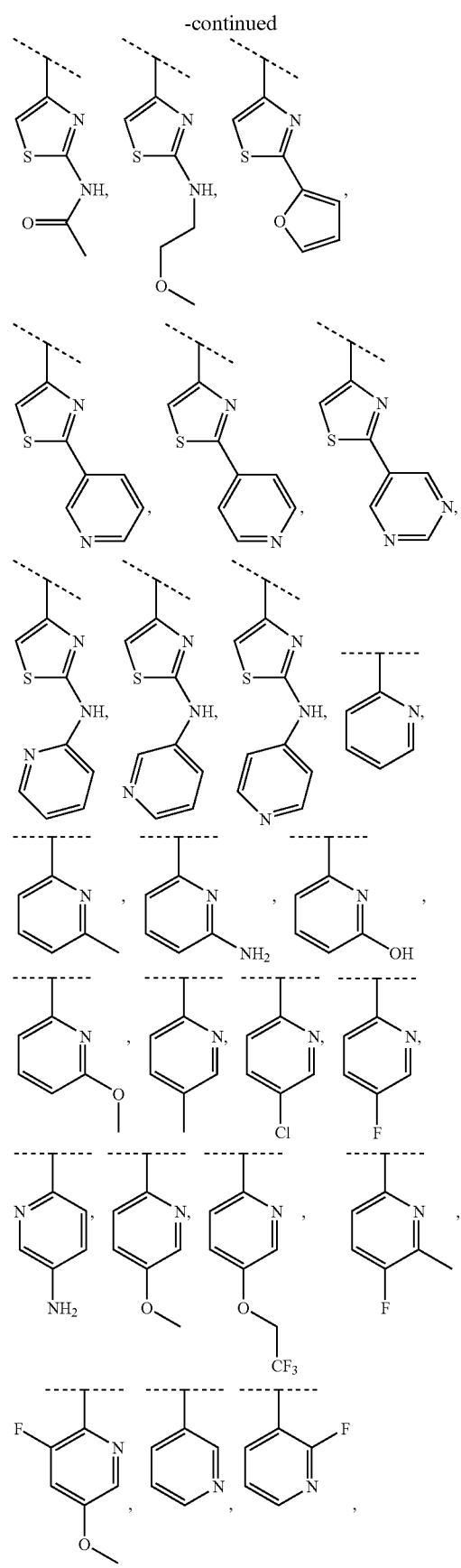
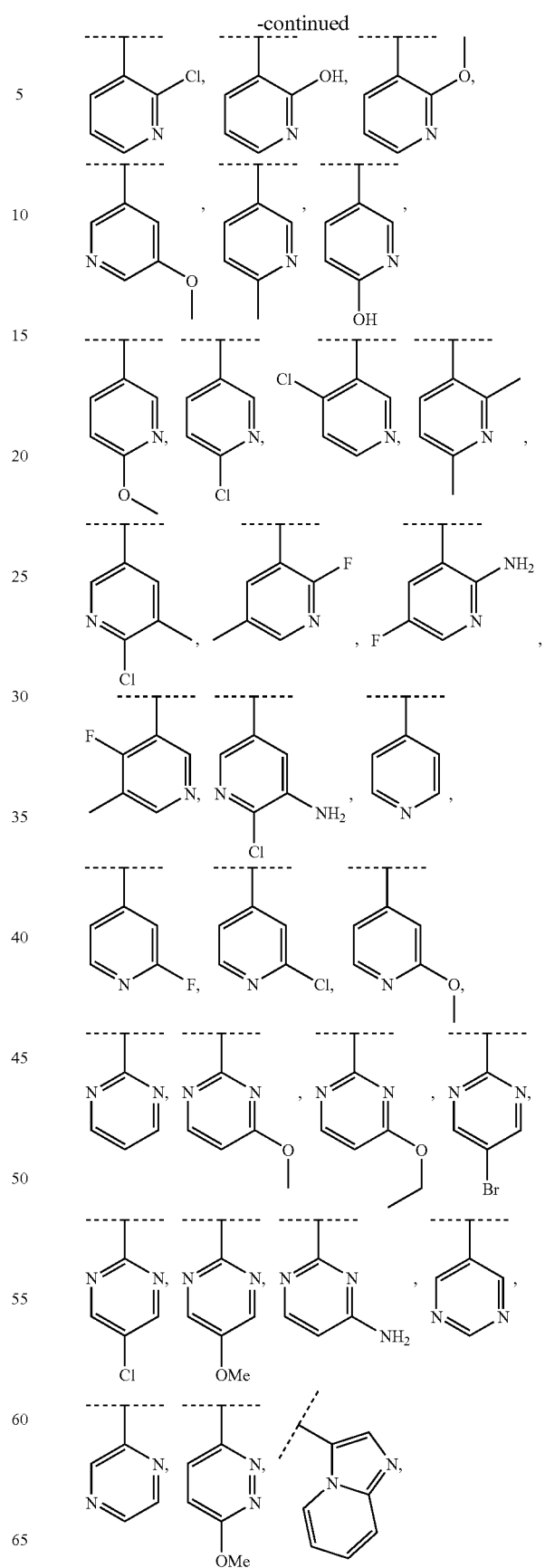

-continued
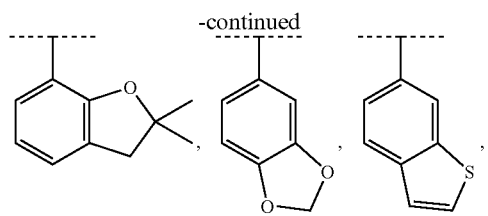
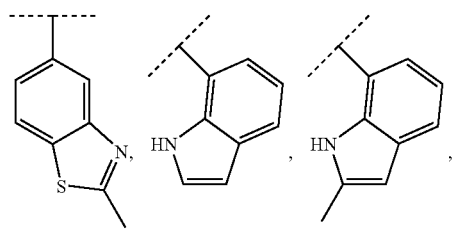
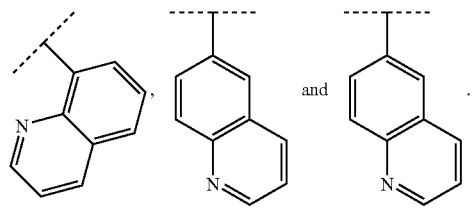
More preferably, R² is selected from cyclopropyl, ethenyl, 1-methylethenyl,
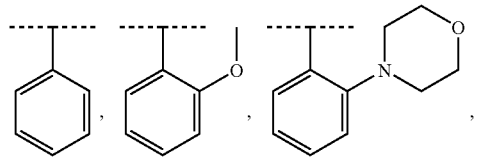
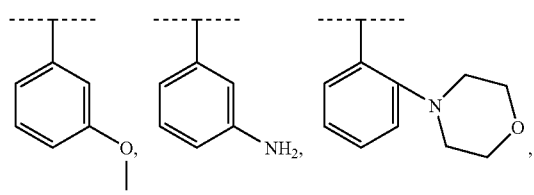
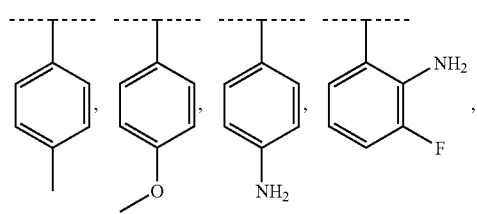
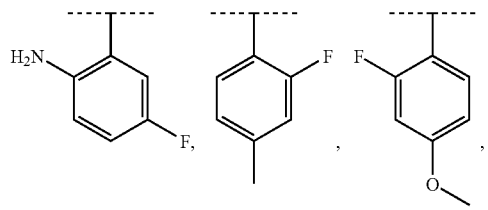
-continued
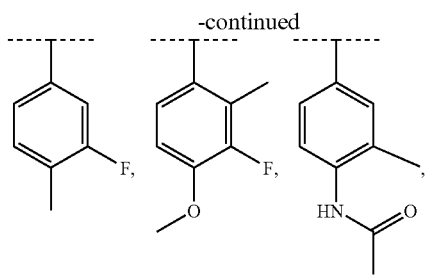
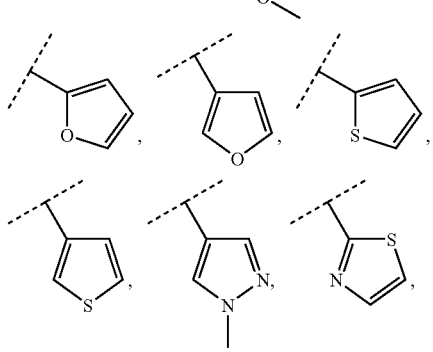
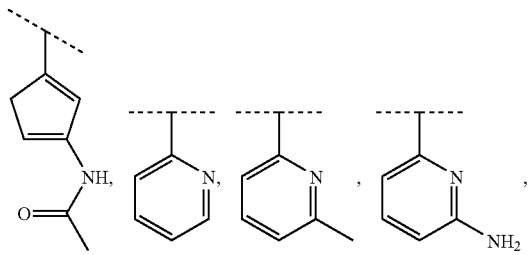
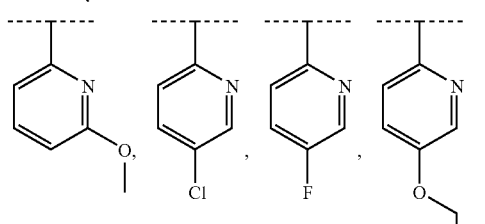
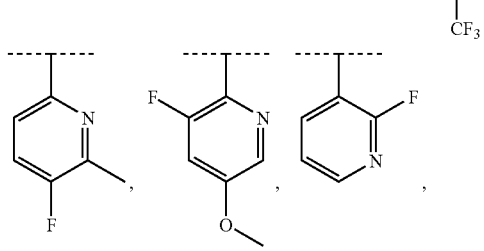
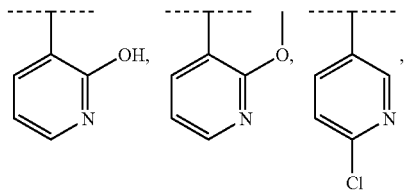

-continued

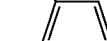

Even more preferably, R² is selected from:

Most preferably, R² is selected from:

R³:
Preferably, R³ is cyclopentyl, or cyclohexyl, each being optionally substituted with one or two fluorine atoms.
More preferably, R³ is cyclopentyl or cyclohexyl.

R⁴ and R⁷:
Preferably R⁴ is H or halogen and R⁷ is H.
More preferably, R⁴ is H or Cl and R⁷ is H.
Most preferably, R⁴ and R⁷ are both H.

R⁵ and R⁶:
Preferably, one of R⁵ and R⁶ is selected from:
a) (C$_{2-4}$)alkenyl substituted with COOH or CONHR$^{N1}$ wherein R$^{N1}$ is selected from H and (C$_{1-3}$)alkyl, said alkenyl being optionally further substituted with one or two substituents each independently selected from (C$_{1-3}$)alkyl and halogen;
b) phenyl or Het, each being optionally substituted with one or two substituents each independently selected from:
 i. —OH, oxo, COOH;
 ii. (C$_{1-3}$)alkyl optionally substituted with phenyl or —N(R$^{N2}$)R$^{N1}$, wherein R$^{N1}$ and R$^{N2}$ are each independently selected from H and (C$_{1-3}$)alkyl or R$^{N1}$ and R$^{N2}$ are linked, together with the N atom to which they are attached, to form a 5- or 6-membered monocyclic, saturated, unsaturated or aromatic N-containing heterocycle, optionally having additionally one or two heteroatoms each independently selected from N, O and S; and
 iii. —N(R$^{N2}$)R$^{N1}$; wherein R$^{N1}$ is selected from H, (C$_{1-3}$) alkyl and —CO(C$_{1-3}$)alkyl and R$^{N2}$ is H or (C$_{1-3}$)alkyl;
 wherein Het is a 5- or 6-membered monocyclic saturated, unsaturated or aromatic heterocycle having from 1 to 3 heteroatoms, each independently selected from O, N and S; and
c) COOH;
and the other of R⁵ and R⁶ is selected from H, NHR$^{N1}$, (C$_{1-3}$)alkyl, and (C$_{1-3}$)alkoxy,
wherein R$^{N1}$ is selected from H and —CO—O—(C$_{1-6}$) alkyl.
More preferably, one of R⁵ and R⁶ is selected from:
a) (C$_{2-4}$)alkenyl substituted with COOH or —CONH$_2$, and optionally further substituted with one or two substituents selected from (C$_{1-3}$)alkyl and halogen; and
b) phenyl or Het, each being optionally substituted with one or two substituents each independently selected from:
 i. —OH, oxo, COOH;
 ii. (C$_{1-3}$)alkyl optionally substituted with phenyl, —N(CH$_3$)$_2$, or

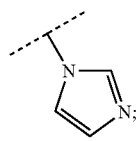

and iii. —NH₂, —N(CH₃)₂ and —NHCOCH₃;
wherein Het is selected from the formulas:

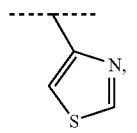 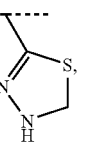 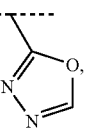 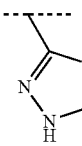

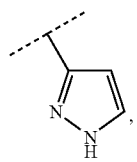 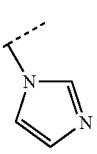 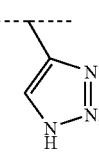

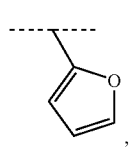 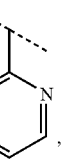 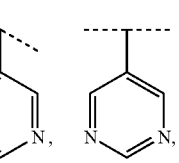

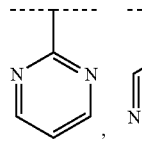, 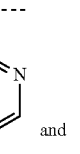 and 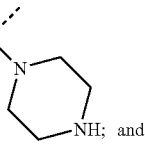

c) COOH;

and the other of $R^5$ and $R^6$ is selected from H, methyl, methoxy, ethoxy, —NH₂ and —NHCO—OCH(CH₃)₂.

Even more preferably, one of $R^5$ and $R^6$ is selected from:

a) —CH═CH—COOH or —CH═CH—CONH₂, each optionally substituted with one or two substituents selected from methyl, ethyl and fluoro; and b) phenyl optionally substituted with NH₂ or Het optionally substituted with one or two substituents each independently selected from:

i. —OH, oxo, COOH;

ii. methyl or ethyl, each optionally substituted with phenyl, —N(CH₃)₂, or

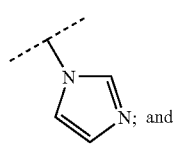

iii. —NH₂, —N(CH₃)₂ and —NHCOCH₃;

wherein Het is selected from the formulas:

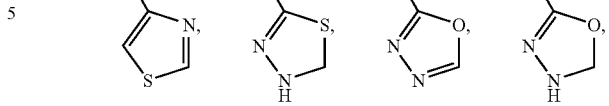

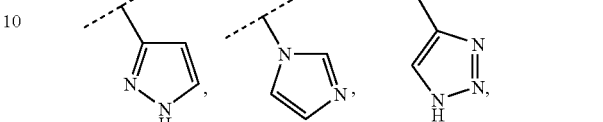

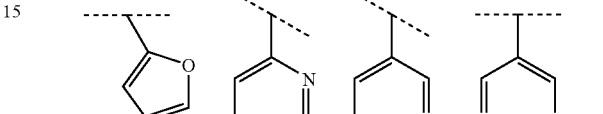

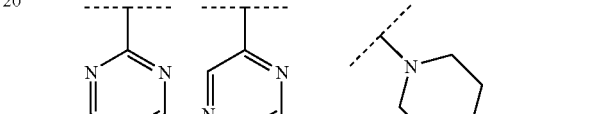

c) COOH;

and the other of $R^5$ and $R^6$ is selected from H, methyl, methoxy, ethoxy, —NH₂ and —NHCO—OCH(CH₃)₂.

Yet more preferably, one of $R^5$ and $R^6$ is selected from —COOH,

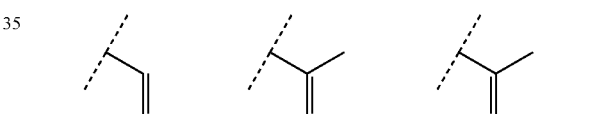

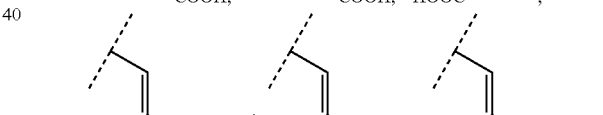

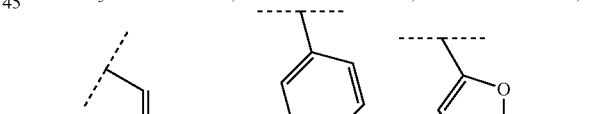

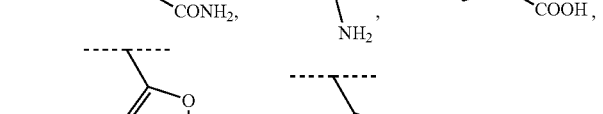

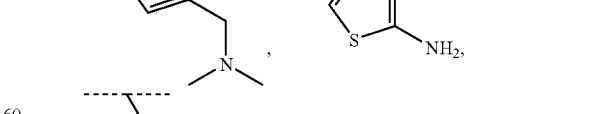

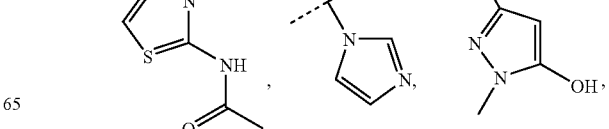

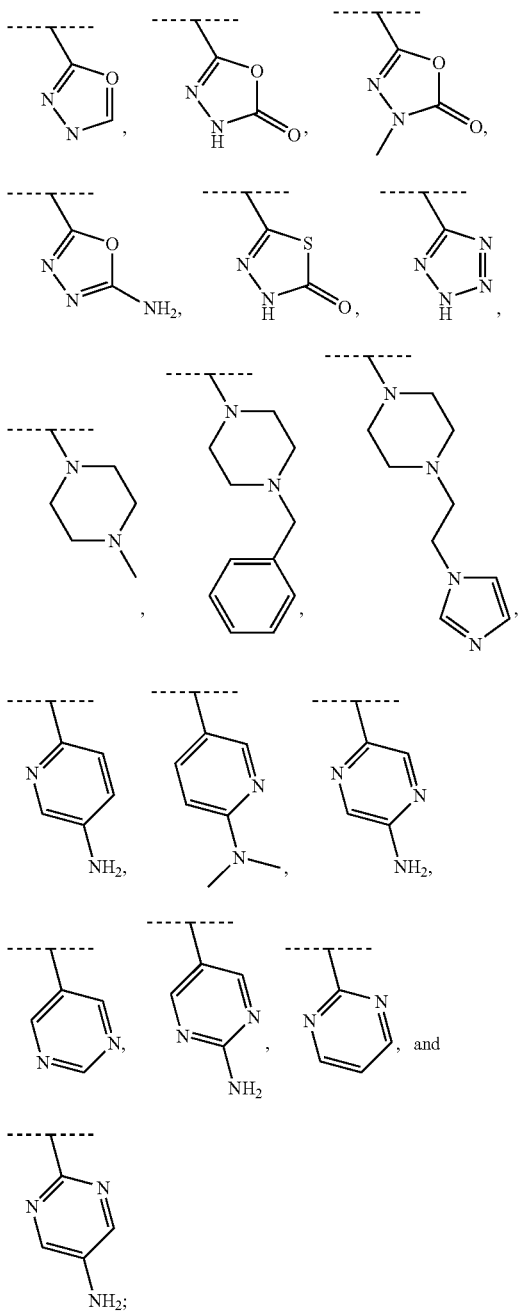

and the other of R⁵ and R⁶ is selected from H, methyl, methoxy, ethoxy, —NH₂ and —NHCO—OCH(CH₃)₂.

Most preferably, one of R⁵ and R⁶ is

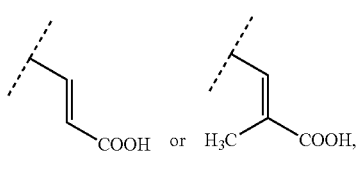

and the other of R⁵ and R⁶ is H.

Alternatively most preferably, one of $R^5$ and $R^6$ is selected from:

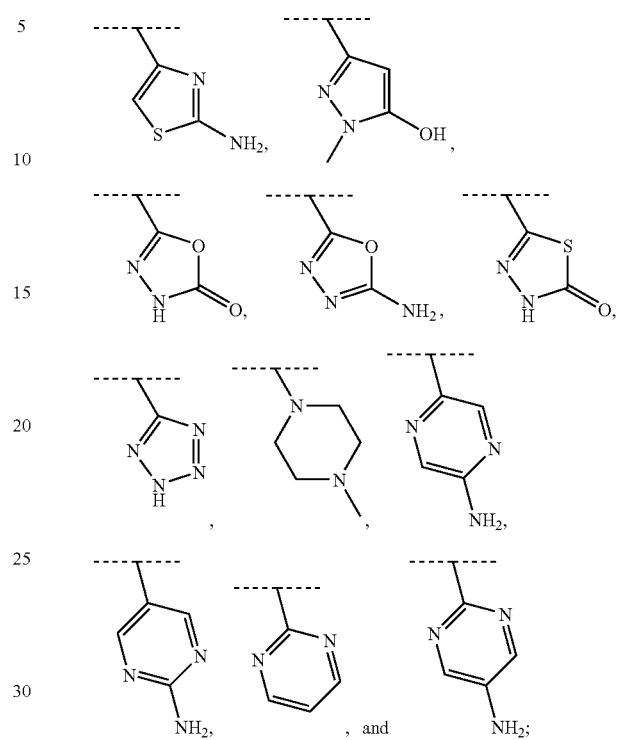

and the other of R⁵ and R⁶ is H.

R⁸:

Preferably, $R^8$ is selected from $(C_{1-5})$alkyl, $(C_{4-6})$cycloalkyl, and $(C_{3-4})$cycloalkyl-$(C_{1-3})$alkyl, wherein the $(C_{1-5})$alkyl is optionally substituted with $(C_{1-3})$alkoxy or from one to three fluoro atoms.

More preferably, R⁸ is selected from methyl, ethyl, propyl, 1-methylethyl, 2-methylpropyl, 3-methylbutyl, cyclobutyl, cyclopropylmethyl, 2-fluoroethyl, 2,2,2-trifluoroethyl and 2-methoxyethyl.

Most preferably R⁸ is methyl.

R⁹ and R¹⁰:

Preferably, $R^9$ and $R^{10}$ are each independently selected from $(C_{1-3})$alkyl or $R^9$ and $R^{10}$ are linked, together with the C atom to which they are attached, to form $(C_{3-6})$cycloalkyl, $(C_{5-6})$cycloalkenyl or a 5- or 6-membered monocyclic heterocycle having from 1 to 2 heteroatoms each independently selected from O and N; wherein said cycloalkyl, cycloalkenyl or heterocycle is each optionally substituted with $(C_{1-4})$alkyl.

More preferably, the group

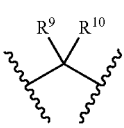

is selected from:

[structures shown]

Even more preferably, the group $R^9$ $R^{10}$ [structure]

is selected from:

[structures shown]

Most preferably, the group $R^9$ $R^{10}$ [structure], is [structure].

Encompassed within the scope of the present invention are compounds of formula I:

(I)

[structure of formula I with substituents $R^1$, $R^2$, $R^3$, A, B, $R^9$, $R^{10}$, $R^4$, $R^5$, $R^6$, $R^7$, $R^8$]

wherein:

either A or B is N and the other B or A is C, wherein ---- between two C-atoms represents a double bond and ---- between a C-atom and a N-atom represents a single bond;

$R^1$ is H or ($C_{1-6}$)alkyl;

$R^2$ is halogen, aryl or Het; said aryl and Het being optionally substituted with $R^{21}$;
  wherein $R^{21}$ is one, two or three substituents each independently selected from —OH, —CN, —N($R^{N2}$)$R^{N1}$, halogen, ($C_{1-6}$)alkyl, ($C_{1-6}$)alkoxy, ($C_{1-6}$)alkylthio, Het and —CO—N($R^{N2}$)$R^{N1}$;
    wherein said alkyl, alkoxy and alkylthio are each optionally substituted with one, two or three halogen atoms;

$R^3$ is ($C_{5-6}$)cycloalkyl, optionally substituted with from one to four halogen atoms;

$R^4$ and $R^7$ are each independently selected from H, ($C_{1-6}$)alkyl, ($C_{1-6}$)alkoxy, ($C_{1-6}$)alkylthio, —NH$_2$, —NH($C_{1-6}$)alkyl, —N(($C_{1-6}$)alkyl)$_2$ and halogen;

one of $R^5$ and $R^6$ is selected from COOH, —CO—N($R^{N2}$)$R^{N1}$, Het and ($C_{2-6}$)alkenyl, wherein Het, ($C_{2-6}$)alkenyl and $R^{N1}$ or any heterocycle formed between $R^{N2}$ and $R^{N1}$ are each optionally substituted with $R^{50}$;
  wherein $R^{50}$ is one, two or three substituents each independently selected from ($C_{1-6}$)alkyl, —COOH, —N($R^{N2}$)$R^{N1}$, —CO—N($R^{N2}$)$R^{N1}$ and halogen;

and the other of $R^5$ and $R^6$ is selected from H, ($C_{1-6}$)alkyl, ($C_{1-6}$)alkoxy, ($C_{1-6}$)alkylthio, and N($R^{N2}$)$R^{N1}$;

$R^8$ is ($C_{1-6}$)alkyl, ($C_{3-7}$)cycloalkyl or ($C_{3-7}$)cycloalkyl-($C_{1-6}$)alkyl-;
  wherein said alkyl, cycloalkyl and cycloalkyl-alkyl are each optionally substituted with one, two or three substituents each independently selected from halogen, ($C_{1-6}$)alkoxy and ($C_{1-6}$)alkylthio;

$R^9$ and $R^{10}$ are each independently selected from ($C_{1-6}$)alkyl; or $R^9$ and $R^{10}$ are linked together with the C atom to which they are attached, to form ($C_{3-7}$)cycloalkyl, ($C_{5-7}$)cycloalkenyl or a 4-, 5- or 6-membered heterocycle having from 1 to 3 heteroatoms each independently selected from 0 N, and S;
  wherein said cycloalkyl, cycloalkenyl or heterocycle are each optionally substituted with ($C_{1-4}$)alkyl;

$R^{N1}$ is selected from H, ($C_{1-6}$)alkyl, ($C_{3-7}$)cycloalkyl, ($C_{3-7}$)cycloalkyl-($C_{1-6}$)alkyl-, —CO—($C_{1-6}$)alkyl, —CO—O—($C_{1-6}$)alkyl and Het;
  wherein all of said alkyl and cycloalkyl is optionally substituted with one, two or three substituents each independently selected from halogen, ($C_{1-6}$)alkoxy and ($C_{1-6}$)alkylthio; and $R^{N2}$ is H or ($C_{1-6}$)alkyl, or $R^{N2}$ and $R^{N1}$ may be linked, together with the N atom to which they are attached, to form a 4-, 5-, 6- or 7-membered saturated or unsaturated N-containing heterocycle or a 8-, 9-, 10- or 11-membered N-containing heterobicycle, each having additionally from 1 to 3 heteroatoms each independently selected from O, N, and S;
  wherein the heterocycle or heterobicycle formed by $R^{N2}$ and $R^{N1}$ is optionally substituted with one, two or three substituents each independently selected from halogen, ($C_{1-6}$)alkyl, ($C_{1-6}$)alkoxy and ($C_{1-6}$)alkylthio;

wherein Het is defined as a 4-, 5-, 6- or 7-membered heterocycle having 1 to 4 heteroatoms each independently selected from O, N and S, which may be saturated, unsaturated or aromatic, or a 8-, 9-, 10- or 11-membered heterobicycle having 1 to 5 heteroatoms wherever possible, each independently selected from O, N and S, which may be saturated, unsaturated or aromatic;

or a salt thereof.

Also encompassed within the scope of the present invention are compounds of formula I, in particular of the formula Ia or Ib, wherein:

$R^1$ is selected from the group consisting of H, methyl and ethyl;

$R^2$ is selected from halogen, cyano, $(C_{1-4})$alkyl, $(C_{2-4})$alkenyl, $(C_{2-4})$alkynyl, $(C_{3-6})$cycloalkyl, phenyl and Het selected from the group of formulas:

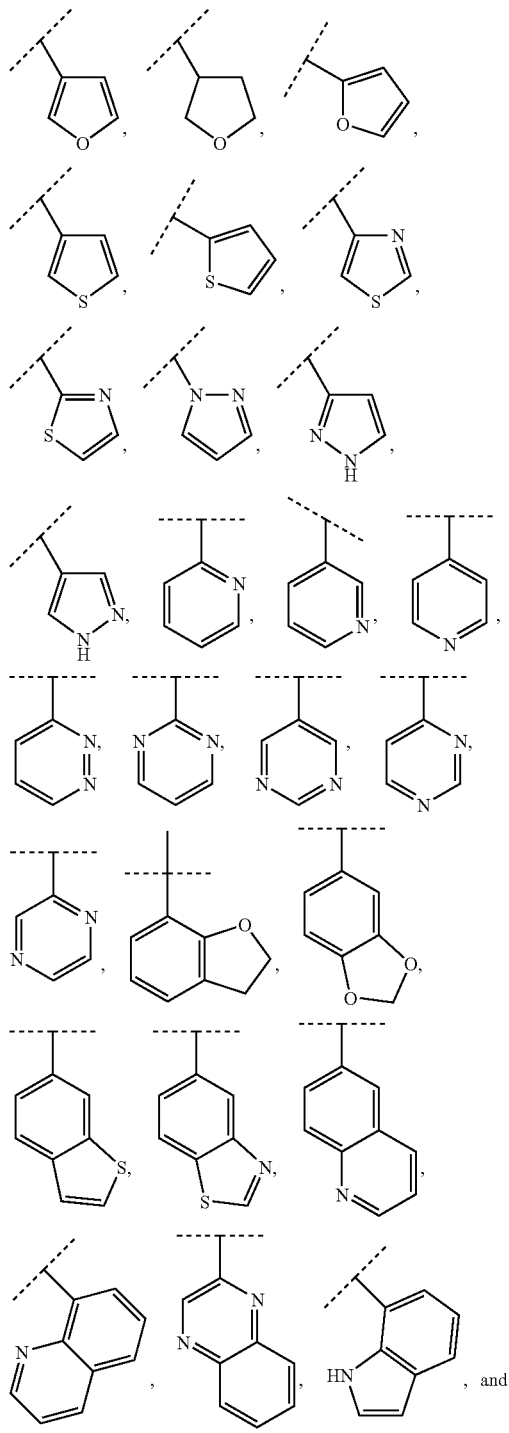

-continued

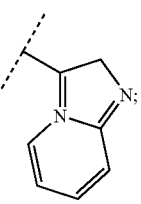

wherein said phenyl and Het are unsubstituted or substituted with $R^{21}$ wherein R is 1, 2 or 3 substituents each independently selected from:
- 1, 2 or 3 substituents each independently selected from halogen; and
- 1 or 2 substituents each independently selected from:
  a) hydroxy, $(C_{1-4})$alkyl or $(C_{1-4})$alkoxy; wherein said alkyl and alkoxy are each optionally substituted with one, two or three halogen atoms;
  b) —$NR^{N2}R^{N1}$ wherein
     $R^{N1}$ is selected from H, $(C_{1-3})$alkyl, —CO—$(C_{1-3})$alkyl, —CO—O—$(C_{1-3})$alkyl and Het;
     wherein the alkyl portions of each of said $(C_{1-3})$alkyl, —CO—$(C_{1-3})$alkyl, and —CO—O—$(C_{1-3})$alkyl are optionally substituted with one, two or three substituents selected from halogen and $(C_{1-6})$alkoxy; and wherein said Het is a 5- or 6-membered monocyclic saturated, unsaturated or aromatic heterocycle having 1 or 2 heteroatoms, each independently selected from N, O and S; and
     $R^{N2}$ is H or $(C_{1-3})$alkyl;
  c) —$CONR^{N2}R^{N1}$ wherein $R^{N2}$ and $R^{N1}$ are each independently selected from H and $(C_{1-3})$alkyl; and
  d) Het, wherein said Het is a 5- or 6-membered monocyclic heterocycle having 1, 2 or 3 heteroatoms, each independently selected from N, O and S;

$R^3$ is cyclopentyl or cyclohexyl, each optionally substituted with one to four fluorine atoms;
$R^4$ is H or halogen and $R^7$ is H;

one of $R^5$ and $R^6$ is selected from:
  a) $(C_{2-4})$alkenyl substituted with COOH or $CONHR^{N1}$ wherein $R^{N1}$ is selected from H and $(C_{1-3})$alkyl, said alkenyl being optionally further substituted with one or two substituents each independently selected from $(C_{1-3})$alkyl and halogen;
  b) phenyl or Het, each being optionally substituted with one or two substituents each independently selected from:
     i. —OH, oxo, COOH;
     ii. $(C_{1-3})$alkyl optionally substituted with phenyl or —$N(R^{N2})R^{N1}$, wherein $R^{N1}$ and $R^{N2}$ are each independently selected from H and $(C_{1-3})$alkyl or $R^{N1}$ and $R^{N2}$ are linked, together with the N atom to which they are attached, to form a 5- or 6-membered monocyclic, saturated, unsaturated or aromatic N-containing heterocycle, optionally having additionally one or two heteroatoms each independently selected from N, O and S; and
     iii. —$N(R^{N2})R^{N1}$; wherein $R^{N1}$ is selected from H, $(C_{1-3})$alkyl and —$CO(C_{1-3})$alkyl and $R^{N2}$ is H or $(C_{1-3})$alkyl;
     wherein Het is a 5- or 6-membered monocyclic saturated, unsaturated or aromatic heterocycle having from 1 to 3 heteroatoms, each independently selected from 0 N and S; and
  c) COOH;

and the other of $R^5$ and $R^6$ is selected from H, $NHR^{N1}$, $(C_{1-3})$alkyl, and $(C_{1-3})$alkoxy, wherein $R^{N1}$ is selected from H and —CO—O—$(C_{1-6})$alkyl;

$R^8$ is selected from $(C_{1-5})$alkyl, $(C_{4-6})$cycloalkyl, and $(C_{3-4})$cycloalkyl-$(C_{1-3})$alkyl, wherein the $(C_{1-5})$alkyl is optionally substituted with $(C_{1-3})$alkoxy or from one to three fluoro atoms; and $R^9$ and $R^{10}$ are each independently selected from $(C_{1-3})$alkyl or $R^9$ and $R^{10}$ are linked, together with the C atom to which they are attached, to form $(C_{3-6})$cycloalkyl, $(C_{5-6})$cycloalkenyl or a 5- or 6-membered heterocycle having from 1 to 2 heteroatoms selected from O and N; wherein said cycloalkyl, cycloalkenyl or heterocycle is optionally substituted with $(C_{1-4})$alkyl.

More preferably, $R^1$ is selected from the group consisting of H, methyl and ethyl;

$R^2$ is selected from Br, Cl, cyano, methyl, ethyl, propyl, 1-methylethyl, ethenyl, 1-methylethenyl, ethynyl, cyclopropyl, phenyl and Het selected from the group of formulas:

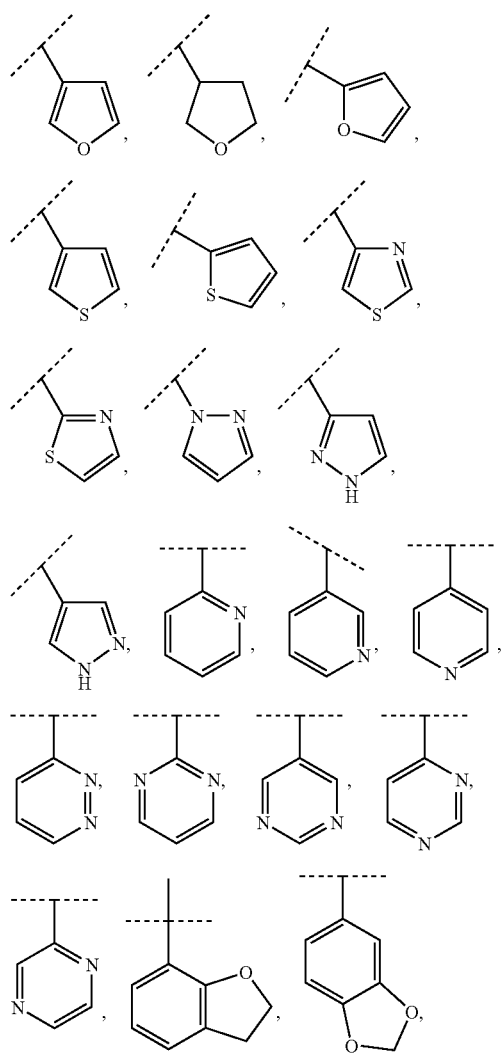

-continued

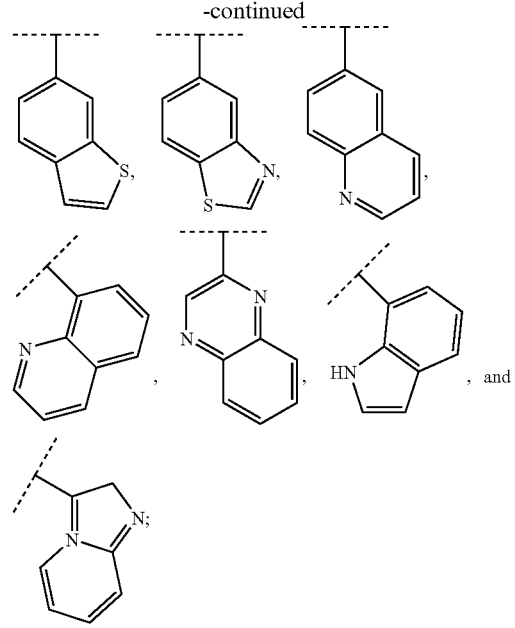

wherein said phenyl and Het are unsubstituted or substituted with $R^{21}$ wherein $R^{21}$ is 1, 2 or 3 substituents each independently selected from:
- 1 to 2 substituents each independently selected from fluorine; chlorine and bromine; and
- 1 to 2 substituents each independently selected from:

a) hydroxy, methyl, ethyl, propyl, 1-methylethyl, methoxy, ethoxy, propoxy or 1-methylethoxy; wherein said methyl, ethyl, propyl, 1-methylethyl, methoxy, ethoxy, propoxy and 1-methylethoxy are each optionally substituted with one, two or three halogen atoms;

b) —N(CH$_3$)$_2$ or —NHR$^{N1}$ wherein
$R^{N1}$ is selected from H, methyl, ethyl, propyl, 1-methylethyl, —CO—CH$_3$, 2-pyridyl, 3-pyridyl and 4-pyridyl; wherein said methyl, ethyl, propyl and 1-methylethyl are each optionally substituted with one, two or three substituents selected from halogen and $(C_{1-3})$alkoxy;

c) —CONH$_2$; and d) 3-pyridyl, 4-pyridyl, 5-pyrimidinyl, 2-furyl, 1-pyrrolyl and 1-morpholino;

$R^3$ is cyclopentyl or cyclohexyl, each optionally substituted with one or two fluorine atoms;

$R^4$ is H or halogen and $R^7$ is H;

one of $R^5$ and $R^6$ is selected from:

a) $(C_{2-4})$alkenyl substituted with COOH or —CONH$_2$, and optionally further substituted with one or two substituents selected from $(C_{1-3})$alkyl and halogen; and b) phenyl or Het, each being optionally substituted with one or two substituents each independently selected from:
   i. —OH, oxo, COOH;
   ii. $(C_{1-3})$alkyl optionally substituted with phenyl, —N(CH$_3$)$_2$, or
   iii. —NH$_2$, —N(CH$_3$)$_2$ and —NHCOCH$_3$;

wherein Het is selected from the formulas:

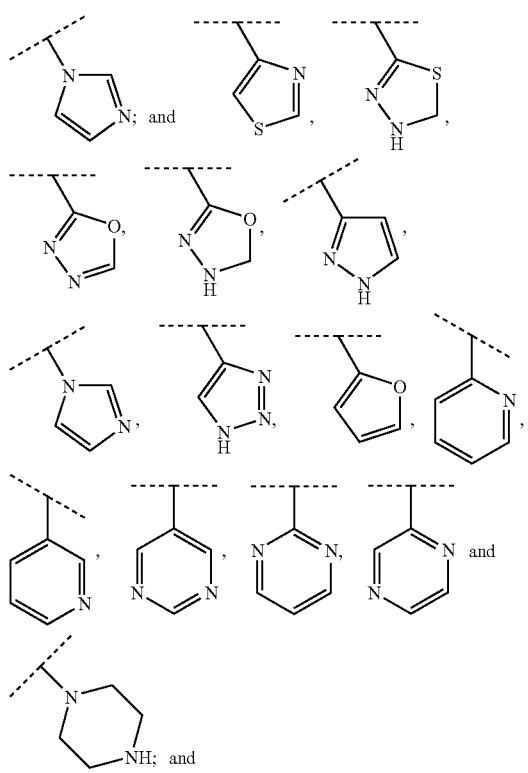

c) COOH;

and the other of $R^5$ and $R^6$ is selected from H, methyl, methoxy, ethoxy, —$NH_2$ and —NHCO—OCH($CH_3$)$_2$;

$R^8$ is selected from methyl, ethyl, propyl, 1-methylethyl, 2-methylpropyl, 3-methylbutyl, cyclobutyl, cyclopropylmethyl, 2-fluoroethyl, 2,2,2-trifluoroethyl and 2-methoxyethyl; and the group

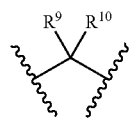

is selected from:

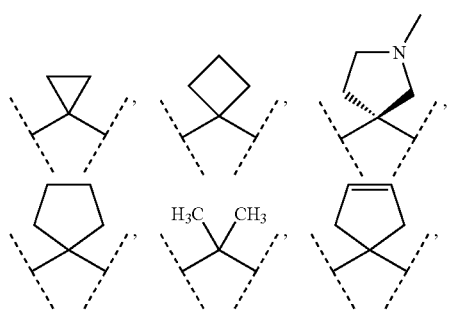

-continued

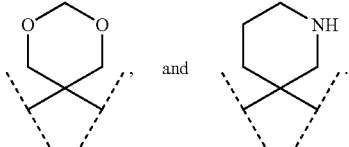

Even more preferably $R^1$ is selected from the group consisting of H, methyl and ethyl;

$R^2$ is selected from Br, Cl, cyano, methyl, ethyl, propyl, 1-methylethyl, ethenyl, 1-methylethenyl, ethynyl, cyclopropyl, phenyl and Het selected from the group of formulas:

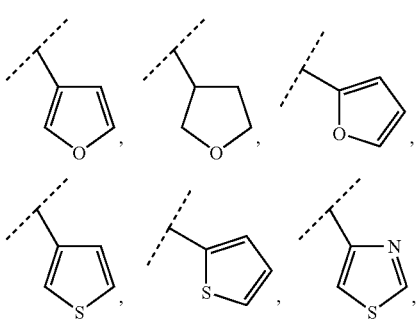

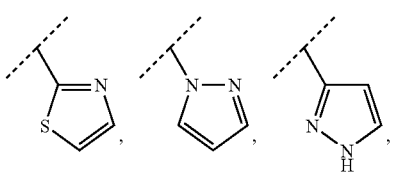

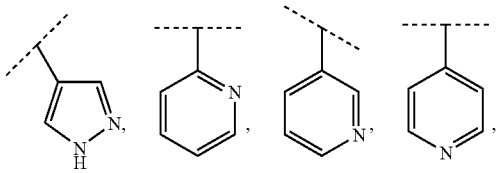

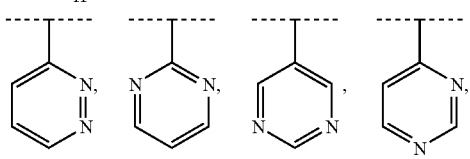

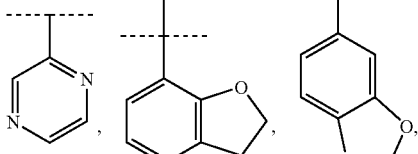

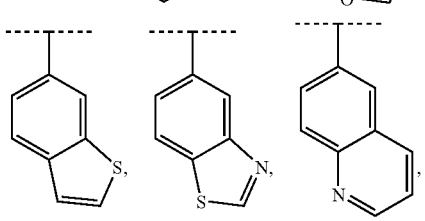

-continued

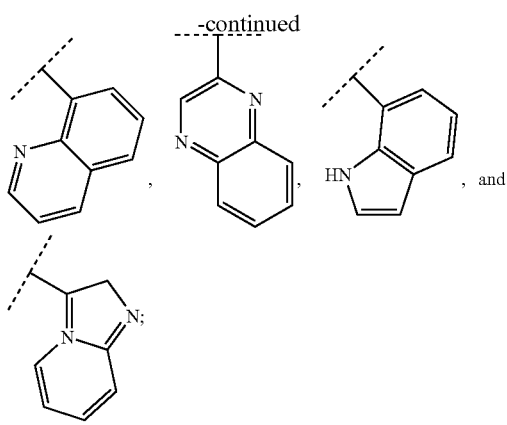
, and wherein said phenyl and Het are unsubstituted or substituted with $R^{21}$ wherein $R^{21}$ is 1, 2 or 3 substituents each independently selected from:
- 1 to 2 substituents each independently selected from fluorine; chlorine and bromine; and
- 1 to 2 substituents each independently selected from:
a) hydroxy, methyl, ethyl, propyl, 1-methylethyl, methoxy, ethoxy, propoxy or 1-methylethoxy; wherein said methyl, ethyl, propyl, 1-methylethyl, methoxy, ethoxy, propoxy and 1-methylethoxy are each optionally substituted with one, two or three halogen atoms;
b) —N(CH$_3$)$_2$ or —NHR$^{N1}$ wherein
  R$^{N1}$ is selected from H, methyl, ethyl, propyl, 1-methylethyl, —CO—CH$_3$, 2-pyridyl, 3-pyridyl and 4-pyridyl;
  wherein said methyl, ethyl, propyl and 1-methylethyl are each optionally substituted with one, two or three substituents selected from halogen and (C$_{1-3}$)alkoxy;
c) —CONH$_2$; and
d) 3-pyridyl, 4-pyridyl, 5-pyrimidinyl, 2-furyl, 1-pyrrolyl and 1-morpholino;

$R^3$ is cyclopentyl or cyclohexyl, each optionally substituted with one or two fluorine atoms;

$R^4$ is H or Cl and $R^7$ is H;

one of $R^5$ and $R^6$ is selected from:
a) —CH=CH—COOH or —CH=CH—CONH$_2$, each optionally substituted with one or two substituents selected from methyl, ethyl and fluoro; and
b) phenyl optionally substituted with NH$_2$ or
  Het optionally substituted with one or two substituents each independently selected from:
  i. —OH, oxo, COOH;
  ii. methyl or ethyl, each optionally substituted with phenyl, —N(CH$_3$)$_2$, or

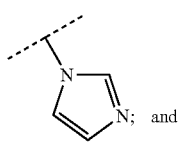
; and iii. —NH$_2$, —N(CH$_3$)$_2$ and —NHCOCH$_3$;

wherein Het is selected from the formulas:

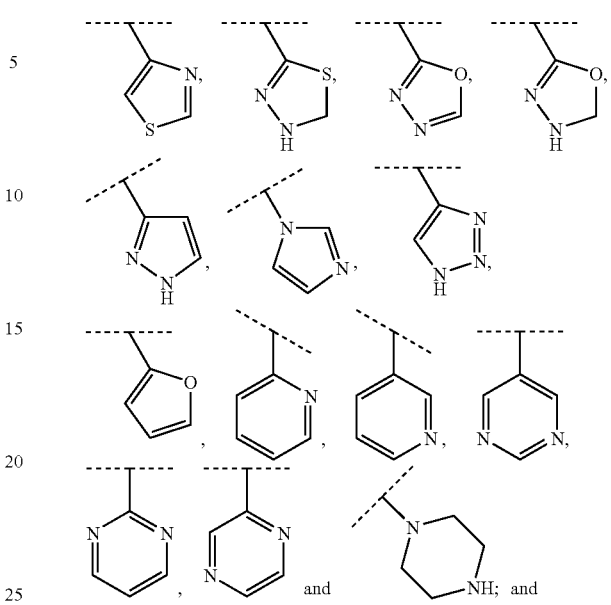
and c) COOH;
and the other of $R^5$ and $R^6$ is selected from H, methyl, methoxy, ethoxy, —NH$_2$ and —NHCO—OCH(CH$_3$)$_2$;
$R^8$ is selected from methyl, ethyl, propyl, 1-methylethyl, 2-methylpropyl, 3-methylbutyl, cyclobutyl, cyclopropylmethyl, 2-fluoroethyl, 2,2,2-trifluoroethyl and 2-methoxyethyl; and
the group

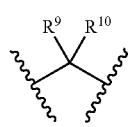

is selected from:

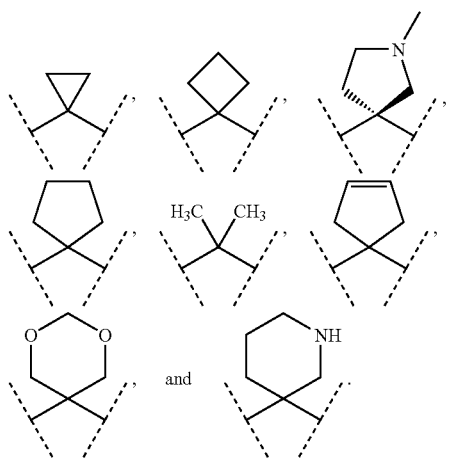

Most preferably,
$R^1$ is methyl;

R² is selected from:

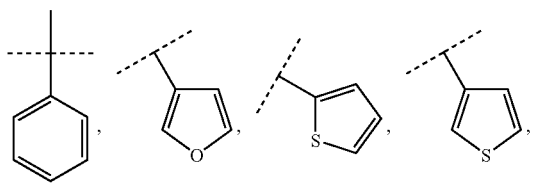

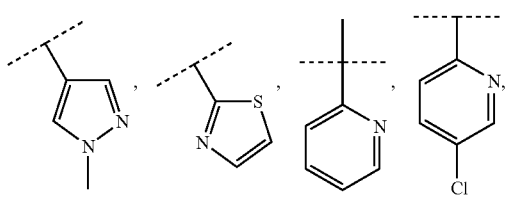

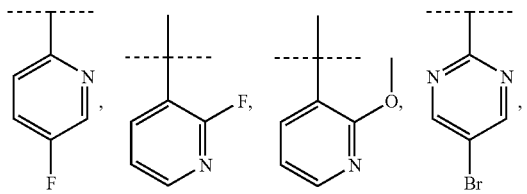

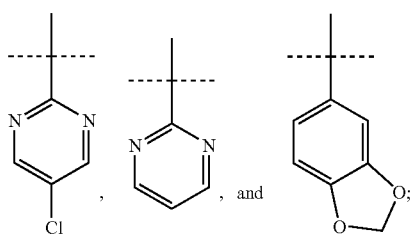

R³ is cyclopentyl or cyclohexyl;
R⁴ and R⁷ are both H;
one of R⁵ and R⁶ is

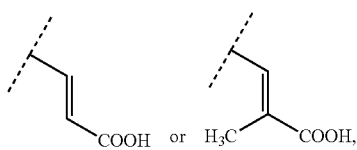

and the other of R⁵ and R⁶ is H;
R⁸ is methyl; and
the group

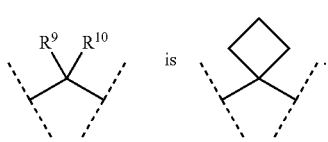 is

Alternatively most preferably,
R¹ is methyl;

R² is selected from:

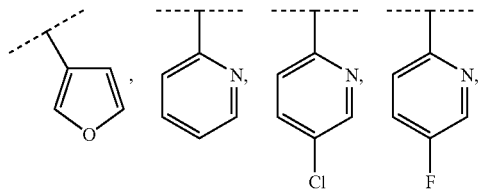

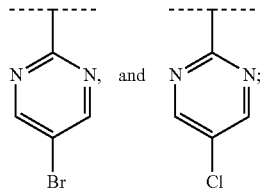 and

R³ is cyclopentyl or cyclohexyl;
R⁴ and R⁷ are both H;
one of R⁵ and R⁶ is

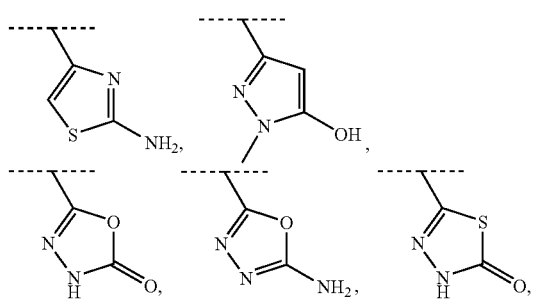

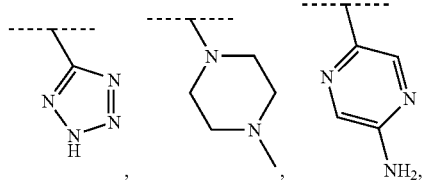

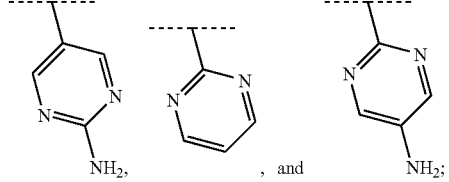

and the other of R⁵ and R⁶ is H;
R⁸ is methyl; and
the group

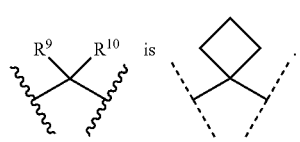 is

Included within the scope of this invention is each single compound of formula I as presented in Tables 1 to 4.

Polymerase Activity

The ability of the compounds of formula (I) to inhibit RNA synthesis by the RNA dependent RNA polymerase of HCV can be demonstrated by any assay capable of measuring HCV RNA dependent RNA polymerase activity. A suitable assay is described in the examples.

Specificity for RNA Dependent RNA Polymerase Activity

To demonstrate that the compounds of the invention act by specific inhibition of HCV polymerase, the compounds may be tested for inhibitory activity in an assay measuring the activity of an RNA-dependent RNA polymerase other than HCV polymerase or in a DNA dependent RNA polymerase assay.

Cell-Based HCV RNA Replication Activity

The ability of the compounds of the invention to inhibit the replication of HCV RNA in cells may be demonstrated by testing the compounds for inhibitory activity in a cell-based HCV RNA replication assay. A suitable assay is described in the examples.

When a compound of formula (I), or one of its therapeutically acceptable salts, is employed as an antiviral agent, it can be administered orally, topically or systemically to mammals, including, but not limited to, humans, cattle, pig, dogs, cats, rabbits or mice, in a vehicle comprising one or more pharmaceutically acceptable carriers, the proportion of which is determined by the solubility and chemical nature of the compound, chosen route of administration and standard biological practice.

For oral administration, the compound or a therapeutically acceptable salt thereof can be formulated in unit dosage forms such as capsules or tablets each containing a predetermined amount of the active ingredient, ranging from about 1 to about 500 mg, in a pharmaceutically acceptable carrier.

For topical administration, the compound can be formulated in pharmaceutically accepted vehicles containing about 0.1 to about 5 percent, preferably about 0.5 to about 5 percent, of the active agent. Such formulations can be in the form of a solution, cream or lotion.

For systemic administration, the compound of formula (I) can be administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers which may be used for the above noted formulations are described in pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula I is most desirably administered at a concentration level that will generally afford antivirally effective results without causing any harmful or deleterious side effects.

For oral administration, the compound or a therapeutically acceptable salt can be administered in the range of about 0.01 to about 200 mg per kilogram of body weight per day, with a preferred range of about 0.05 to about 100 mg per kilogram.

For systemic administration, the compound of formula (I) can be administered at a dosage of about 0.01 mg to about 100 mg per kilogram of body weight per day, although the aforementioned variations will occur. A dosage level that is in the range of from about 0.05 mg to about 50 mg per kilogram of body weight per day is most desirably employed in order to achieve effective results.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV polymerase or to treat or prevent HCV virus infection. Such treatment may also be achieved using the compounds of this invention in combination with agents which include, but are not limited to: immunomodulatory agents, including but not limited to $\alpha$-, $\beta$-, $\delta$-$\gamma$-, $\tau$- and $\omega$-interferons or pegylated forms thereof; other antiviral agents such as ribavirin, amantadine; other inhibitors of HCV NS5B polymerase; inhibitors of other targets in the HCV life cycle, which include but are not limited to, agents that inhibit a target including, but not limited to, a HCV helicase, HCV NS2/3 protease, HCV NS3 protease and HCV IRES and agents that interfere with the function of other viral targets including but not limited to an NS5A protein; or combinations thereof. The additional agents may be combined with the compounds of this invention to create a single dosage form. Alternatively these additional agents may be separately administered to a mammal as part of a multiple dosage form.

Methodology and Synthesis

The synthesis of compounds according to this invention is preferably accomplished following the general procedure outlined in Scheme 1 below.

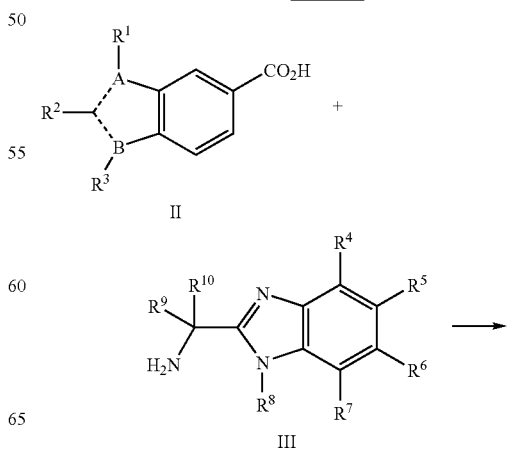

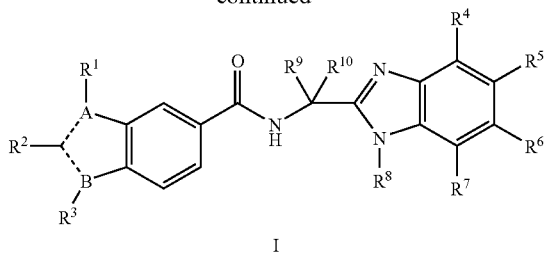

I

Compounds of formula I, wherein $R^1$, $R^2$, $R^3$, $R^4$, $R^5$, $R^6$, $R^7$, $R^8$, $R^9$ and $R^{10}$ are defined as hereinbefore, are preferably prepared by coupling carboxylic acids of general formula II with amines of general formula II, as illustrated in Scheme 1 above, using carboxyl-activating reagents well known by those skilled in the art. Such reagents include, but are not limited to, TBTU, HATU, BOP, BrOP, EDAC, DCC, isobutyl chloroformate and the like. Alternatively, carboxylic acids of general formula II may be converted to the corresponding acid chlorides using standard reagents, then coupled with amine derivatives of the general formula III. In the cases where either $R^5$ or $R^6$ contain an ester-protected carboxylic acid moiety, a saponification reaction is carried out (using protocols well known by those skilled in the art) to obtain the final inhibitor product as the free carboxylic acid.

Intermediate carboxylic acids of formula II may be prepared by procedures described in WO 03/010141, or by procedures described in the examples below. Intermediate amines of formula III may be prepared according to the general procedures outlined in Schemes 2 and 3 below.

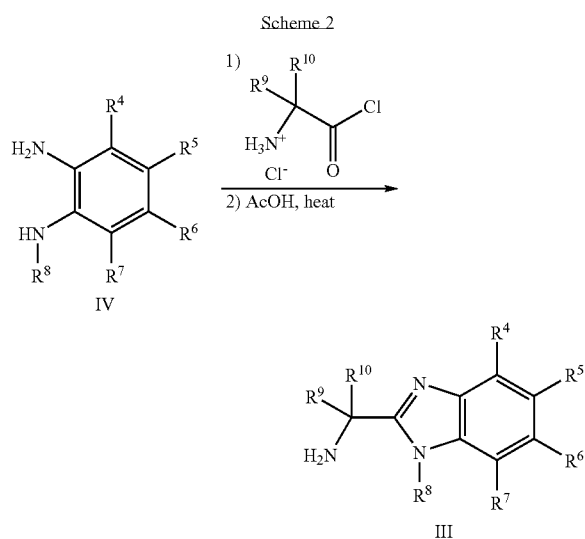

Amine intermediates of general formula III in Scheme 1 may be prepared from the corresponding diamine precursors of general formula IV by coupling with the appropriate α,α-disubstituted amino acid chloride hydrochlorides. Preparation of the appropriate α,α-disubstituted amino acid chloride hydrochlorides from the corresponding α,α-disubstituted amino acids may be carried out as described in WO 03/007945 or WO 03/010141, or by using the procedure, or an adaptation thereof, described by E. S. Uffelman et al. (*Org. Lett.* 1999, 1, 1157). The amide intermediate formed in the coupling reaction is then cyclized by heating with acetic acid, to provide amine intermediates of general formula III.

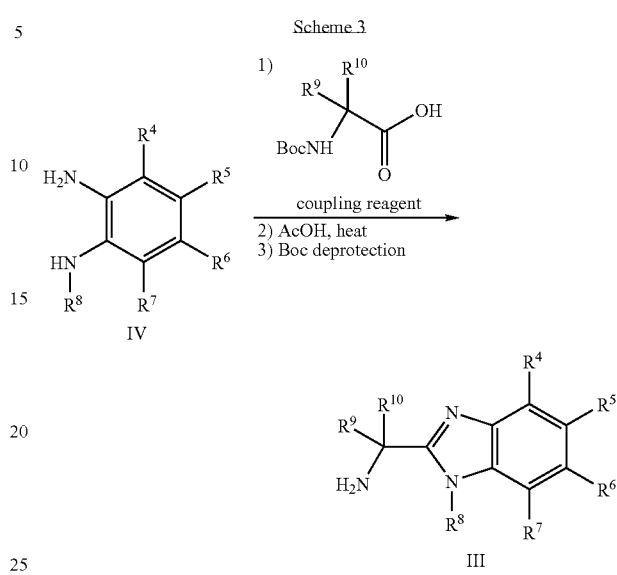

Alternatively, amine intermediates of general formula III in Scheme 1 may be prepared from the corresponding diamine precursors of general formula IV by coupling with the appropriate Boc-protected α,α-disubstituted amino acid as illustrated in Scheme 3, using coupling reagents well known to one skilled in the art, such as TBTU, HATU, BOP, BrOP, EDAC, DCC, isobutyl chloroformate and the like. Appropriate Boc-protected α,α-disubstituted amino acids may be prepared from the free α,α-disubstituted amino acids, using standard conditions well known to one skilled in the art, such as reaction with $Boc_2O$ (di-tert-butyldicarbonate) in the presence of a tertiary amine such as triethylamine, and the like. The amide intermediate formed in the coupling reaction is then cyclized by heating with acetic acid. Deprotection of the Boc group to provide the amine intermediate of general formula III in Scheme 1 is carried out using standard reagents well known to one skilled in the art. Such reagents include, but are not limited to, trifluoroacetic acid, a solution of HCl in dioxane and the like.

Preparation of the diamine precursors of general formula IV in Schemes 2 and 3 is preferably carried out by applying the procedures as outlined in the examples, including any adaptation of these procedures, and/or applying additional synthetic steps known to the person skilled in the art.

Amine intermediates of general formula III in Scheme 1 wherein one of $R^5$ and $R^6$ is —CH=C($R^{50a}$)—COOR, wherein $R^{50a}$ is selected from H, ($C_{1-6}$)alkyl and halogen and wherein R is, for example, methyl or ethyl, may be prepared from the corresponding amine intermediates of general formula III, or suitably protected derivatives thereof, wherein one of $R^5$ and $R^6$ is —COOR, wherein R is, for example, methyl or ethyl, by applying the procedures of Scheme 4 below. While Scheme 4 specifically illustrates the preparation of amine intermediates of general formula III wherein $R^5$ is —CH=C($R^{50a}$)—COOR, it is understood by the person skilled in the art that when $R^6$ is —COOR, the illustrated procedures, or adaptations thereof, will result in a product wherein $R^6$ is —CH=C($R^{50a}$)—COOR. Also, it is understood by the person skilled in the art that the procedures of Scheme 4, or adaptations thereof, may also be used when converting a diamine precursor of general formula IV in Schemes 2 and 3 above, or a suitably protected derivative thereof, or a suitable intermediate in its preparation, wherein one of $R^5$ and $R^6$ is —COOR, to a diamine precursor of general formula IV, or a suitably protected derivative thereof, or a suitable intermediate in its preparation wherein one of $R^5$ and $R^6$ is —CH=C($R^{50a}$)—COOR, wherein $R^{50a}$ and R defined as hereinbefore.

of amine intermediates of general formula III wherein $R^5$ is —C($R^{50}$)=CH—COOR, it is understood by the person skilled in the art that when $R^6$ is —CHO, the illustrated procedures, or adaptations thereof, will result in a product wherein $R^6$ is —C($R^{50}$)=CH—COOR. Also, it is understood by the person skilled in the art that the procedures of Scheme 5, or adaptations thereof, may also be used when converting a diamine precursor of general formula IV in Schemes 2 and 3

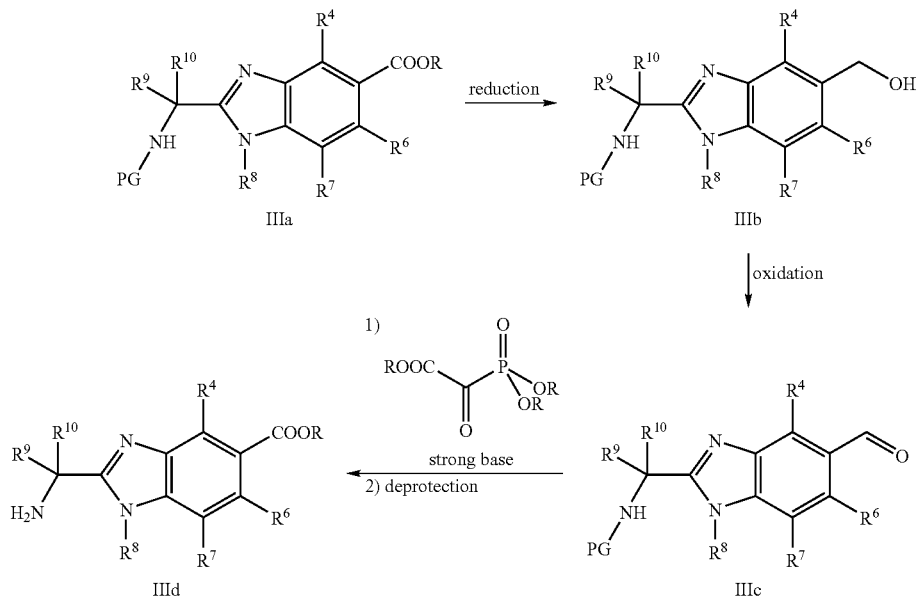

A suitably protected amine intermediate of general formula IIIa in scheme 4 above may be converted to an alcohol intermediate of general formula IIIb by treatment with a suitable reducing agent such as DIBAL-H and the like. Suitable protecting groups (PG) include, but are not limited to, carbamate protecting groups, such as Boc (tert-butyloxycarbonyl) and the like. Preparation of protected amine intermediates of general formula IIIa from amine intermediates of general formula III in Scheme 1 above may be carried out by standard procedures well-known to one skilled in the art.

The alcohol intermediate IIIb may be converted to the aldehyde intermediate IIIc, using standard oxidizing agents well-known to one skilled in the art, such as 1,1,1-tris(acetyloxy-1,1-dihydro-1,2-benziodoxol-3-(1H)-one (also known as Dess-Martin periodinane) and the like.

The aldehyde intermediate IIIc may be converted to an amine intermediate of general formula IIId using a standard Horner-Emmons procedure, or related procedures such as Wittig procedures or the like, well known to a person skilled in the art, followed by deprotection of the PG group using well-known standard procedures. In the case where the PG group is Boc, such procedures include, but are not limited to, treatment with acidic conditions such as trifluoroacetic acid, HCl dissolved in dioxane and the like.

Amine intermediates of general formula III in Scheme 1 wherein one of $R^5$ and $R^6$ is —C($R^{50}$)=CH—COOR, wherein $R^{50}$ is $(C_{1-6})$alkyl and wherein R is, for example, methyl or ethyl, may be prepared from intermediate IIIc in Scheme 4 above by applying the procedures of Scheme 5 below. While Scheme 5 specifically illustrates the preparation above, or a suitably protected derivative thereof, or a suitable intermediate in its preparation, wherein one of $R^5$ and $R^6$ is —CHO, to a diamine precursor of general formula IV, or a suitably protected derivative thereof, or a suitable intermediate in its preparation wherein one of $R^5$ and $R^6$ is —C($R^{50}$)=CH—COOR, wherein $R^{50}$ and R defined as hereinbefore.

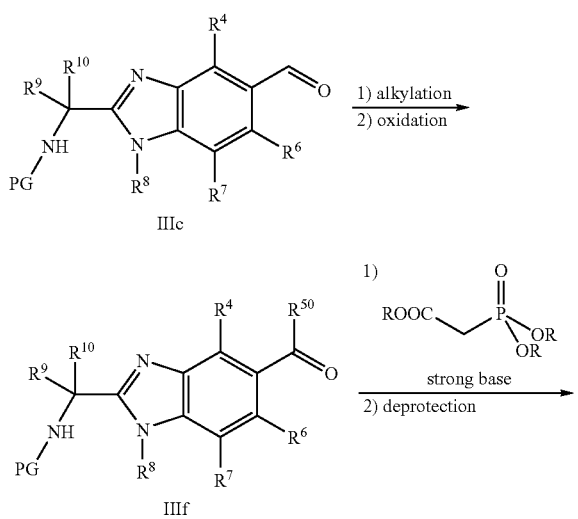

-continued

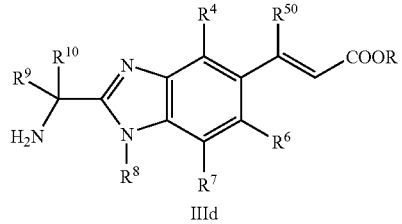

IIId

The aldehyde intermediate IIIc (from Scheme 4) may be converted to a ketone of general formula IIIf by alkylation with a suitable nucleophilic alkylating agent, well known to those skilled in the art, such as an alkyl lithium or the like, followed by oxidation of the intermediate secondary alcohol to the ketone, using oxidizing agents well known to one skilled in the art, such as 1,1,1-tris(acetyloxy)-1,1-dihydro-1,2-benziodoxol-3-(1H)-one (also known as Dess-Martin periodinane) and the like. The ketone IIIf may then be converted to an amine intermediate of general formula IIId using a standard Horner-Emmons procedure, or related procedures such as Wittig procedures or the like, well known to a person skilled in the art, followed by deprotection of the PG group using well-known standard procedures. In the case where the PG group is Boc, such procedures include, but are not limited to, treatment with acidic conditions such as trifluoroacetic acid, HCl dissolved in dioxane and the like.

Alternatively, amine intermediates of general formula III in Scheme 1 wherein one of $R^5$ and $R^6$ is —CH═C($R^{50a}$)—COOR, wherein $R^{50a}$ is selected from H, ($C_{1-6}$)alkyl and halogen and wherein R is ($C_{1-6}$)alkyl, may be prepared from the corresponding amine intermediates of general formula III, or suitably protected derivatives thereof, wherein one of $R^5$ and $R^6$ is X, wherein X is a leaving group such as a halogen atom, a sulfonate ester, and the like, by applying the typical conditions of the Heck reaction, as presented in Scheme 6 and further described in the examples below. While Scheme 6 specifically illustrates the preparation of amine intermediates of general formula III wherein $R^5$ is —CH═C($R^{50a}$)—COOR, it is understood by the person skilled in the art that when $R^6$ is X, the illustrated procedures, or adaptations thereof, will result in a product wherein $R^6$ is —CH═C($R^{50a}$)—COOR. Also, it is understood by the person skilled in the art that the procedures of Scheme 6, or adaptations thereof, may also be used when converting a diamine precursor of general formula IV in Schemes 2 and 3 above, or a suitably protected derivative thereof, or a suitable intermediate in its preparation, wherein one of $R^5$ and $R^6$ is X, to a diamine precursor of general formula IV, or a suitably protected derivative thereof, or a suitable intermediate in its preparation wherein one of $R^5$ and $R^6$ is —CH═C($R^{50a}$)—COOR, wherein $R^{50a}$ and R defined as hereinbefore.

Scheme 6

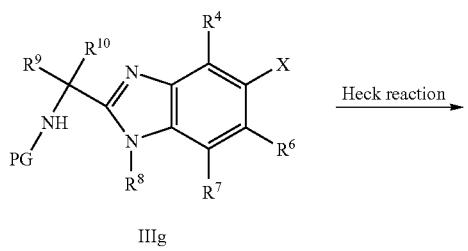

IIIg

-continued

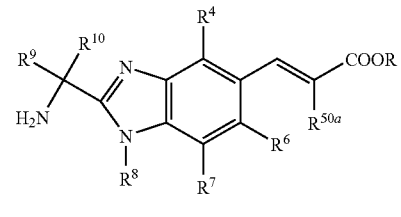

IIId

EXAMPLES

The present invention is illustrated in further detail by the following non-limiting examples. As is well known by a person skilled in the art, reactions are performed in a nitrogen or argon atmosphere where necessary to protect reaction components from air or moisture. Temperatures are given in degrees Celsius. Flash chromatography is performed on silica gel. Solution percentages or ratios express a volume to volume relationship, unless stated otherwise. Mass spectral analyses are recorded using electrospray mass spectrometry. Analytical HPLC was carried out under standard conditions using a Combiscreen ODS-AQ C18 reverse phase column, YMC, 50×4.6 mm i.d., 5 μM, 120 Å at 220 nM, elution with a linear gradient as described in the following table (Solvent A is 0.1% TFA in $H_2O$; solvent B is 0.1% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Hereinbefore and hereinafter the following abbreviations or symbols are used:

AcOH: acetic acid;

$Ac_2O$: acetic anhydride;

BOC or Boc: tert-butyloxycarbonyl;

BOP: benzotriazole-1-yloxy-tris(dimethylamino)phosphonium hexafluorophosphate;

BroP: Bromo tris(dimethylamino)phosphonium hexafluorophosphate;

Bu: butyl;

CPS: counts per second;

DAST: (diethylamino)sulfur trifluoride;

dba: dibenzylideneacetone;

DCC: 1,3-Dicyclohexyl carbodiimide;

DCM: dichloromethane;

DCMA: dicyclohexylmethylamine;

DIBAL-H: di-iso-butylaluminum hydride

DMEM: Dulbecco's Modified Earle Medium;

DMF: N,N-dimethylformamide;

DMSO: dimethylsulfoxide;

EC$_{50}$: 50% effective concentration;

EDAC: see EDC;

EDC: 1-(3-dimethylaminopropyl)-3-ethyl carbodiimide hydrochloride;

ES$^-$: electro spray (negative ionization);

ES$^+$: electro spray (positive ionization);

Et: ethyl;

Et$_2$O: diethyl ether;

EtOAc: ethyl acetate;

EtOH: ethanol;

FBS: fetal bovine serum

Fmoc: 9-fluorenylmethoxycarbonyl

HATU: O-(7-azabenzotriazol-1-yl)-N,N N',N'-tetramethyluronium hexafluorophosphate;

HBTU: O-Benzotriazol-1-yl-N,N,N',N'-tetramethyluronium hexafluorophosphate;

HOAT: 1-hydroxy-7-azabenzotriazole;

HOBt: 1-Hydroxybenzotriazole;

HPLC: high performance liquid chromatography;

$^i$Pr or i-Pr: iso-propyl

Me: methyl;

PBS: phosphate buffer saline;

Ph: phenyl;

PG: protecting group;

PVDF: polyvinylidene fluoride;

RT: room temperature (approximately 25° C.);

TBME: tert-butylmethyl ether;

TBTU: 2-(1H-benzotriazol-1-yl)-N,N N',N'-tetramethyluronium tetrafluoroborate;

tBu: tert.-butyl;

Tf: trifluoromethylsulfonyl;

TfO: trifluoromethylsulfonate;

TFA: trifluoroacetic acid;

THF: tetrahydrofuran;

TLC: thin layer chromatography;

TMS: trimethylsilyl;

Troc: trichloroethoxycarbonyl.

Example 1

3-(3,3-Difluorocyclopentyl)-1-methyl-1H-indole-6-carboxylic acid methyl ester

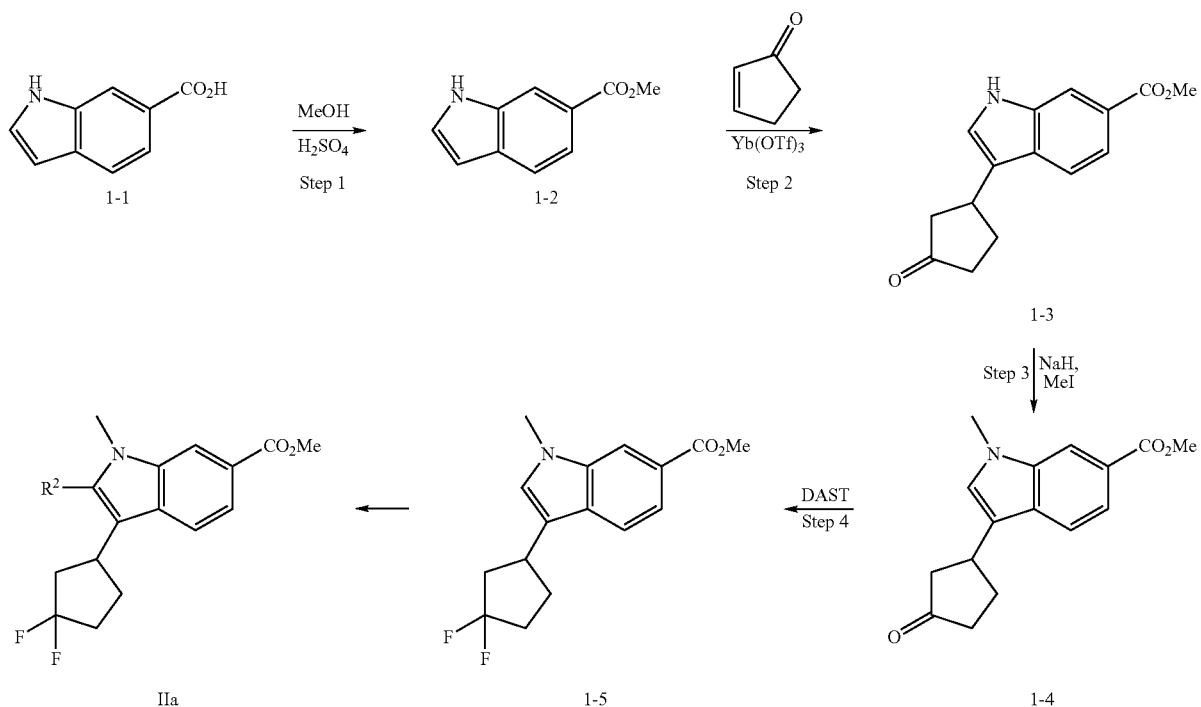

MeCN: acetonitrile;

MeOH: methanol;

MS (ES): electrospray mass spectrometry;

NMR: nuclear magnetic resonance spectroscopy;

Step 1:

Indole-6-carboxylic acid 1-1 (5.0 g, 31.0 mmol) was dissolved in MeOH (100 mL), a catalytic amount of H$_2$SO$_4$ (1.0 mL) was added and the reaction mixture was stirred at reflux for 16 h. A small amount of solid K$_2$CO$_3$ was added, in order to neutralize the excess H₂SO₄, and stirring was continued at RT for 1 h. The reaction mixture was concentrated under vacuum to remove the MeOH, diluted with saturated aqueous NaHCO₃ (~50 mL) and extracted with EtOAc (~200 mL). The organic layer was washed with brine (100 mL), dried over anhydrous MgSO₄ and concentrated to dryness. The resulting residue was purified by flash column chromatography, using 30% EtOAc in hexane as the eluent, to obtain the pure methyl ester 1-2 (4.78 g, 88% yield).

Step 2:

The methyl ester 1-2 from step 1 (3.31 g, 18.9 mmol) was dissolved in MeCN (50 mL) and a catalytic amount of Yb(OTf)₃ (586 mg, 0.95 mmol) was added. 2-Cyclopenten-1-one (7.76 mL, 94.5 mmol) was added and the reaction mixture was stirred at reflux for 16 h. The MeCN solvent was removed under vacuum, the residue was re-dissolved in EtOAc (~200 mL) and extracted with aqueous saturated NaHCO₃ (~100 mL), H₂O (50 mL) and brine (50 mL). The organic layer was dried over anhydrous MgSO₄ and concentrated to dryness under vacuum. After purification of the residue by flash column chromatography, using 40% EtOAc in hexane as the solvent gradient, the desired cyclopentanone adduct 1-3 was isolated as isolated as a beige-colored powder (3.4 g, 70% yield).

Step 3:

To a solution of the cyclopentanone adduct intermediate 1-3 from step 2 (3.81 g, 14.8 mmol) in anhydrous DMF (150 mL) at 0° C., NaH (60% dispersion in oil, 770 mg, 19.2 mmol) was added slowly. The reaction mixture was stirred at 0° C. for 5 min, then MeI (1.2 mL, 19.2 mmol) was added dropwise and stirring was continued at 0° C. for 3 h. The mixture was allowed to warm-up to RT and was quenched by the addition of aqueous saturated NH₄Cl (200 mL). The mixture was extracted with EtOAc (2×500 mL) and the organic layer was washed with aqueous saturated NH₄Cl (2×200 mL) H₂O (200 mL) and brine (200 mL). The combined organic layers were dried over anhydrous MgSO₄, evaporated to dryness and the residue was purified by flash column chromatography (using 30% EtOAc in hexane as the eluent) to isolate the N-methylindole intermediate 1-4 as a beige solid (3.1 g, 77% yield).

Step 4:

In a sealed tube, the N-methylindole intermediate 1-4 from step 3 (1.4 g, 5.16 mmol) and DAST (2.7 mL, 20.6 mmol) were dissolved in CH₂Cl₂ (50 mL) and stirred at reflux for 3 days. The mixture was poured slowly into aqueous saturated NaHCO₃ (~50 mL) and once the evolution of CO₂ had stopped, the mixture was extracted with CH₂Cl₂ (2×100 mL). The combined organic layers were washed with brine (50 mL), dried over anhydrous MgSO₄ and concentrated to dryness. The residue was purified by flash column chromatography (using a solvent gradient from 10% to 20% EtOAc in hexane) to isolate 3-(3,3-difluorocyclopentyl)-1-methyl-1H-indole-6-carboxylic acid methyl ester 1-5 (750 mg, 50% yield).

3-(3,3-Difluorocyclopentyl)-1-methyl-1H-indole-6-carboxylic acid methyl ester 1-5 is converted to carboxylic acid intermediates of formula IIa, wherein R² is defined as hereinbefore, using procedures described in WO 03/010141. These intermediates may be converted to compounds of general formula I using procedures illustrated in Scheme 1 above and described in WO 03/010141.

Example 2

(E)-3-(3-Amino-4-methylaminophenyl)acrylic acid methyl ester

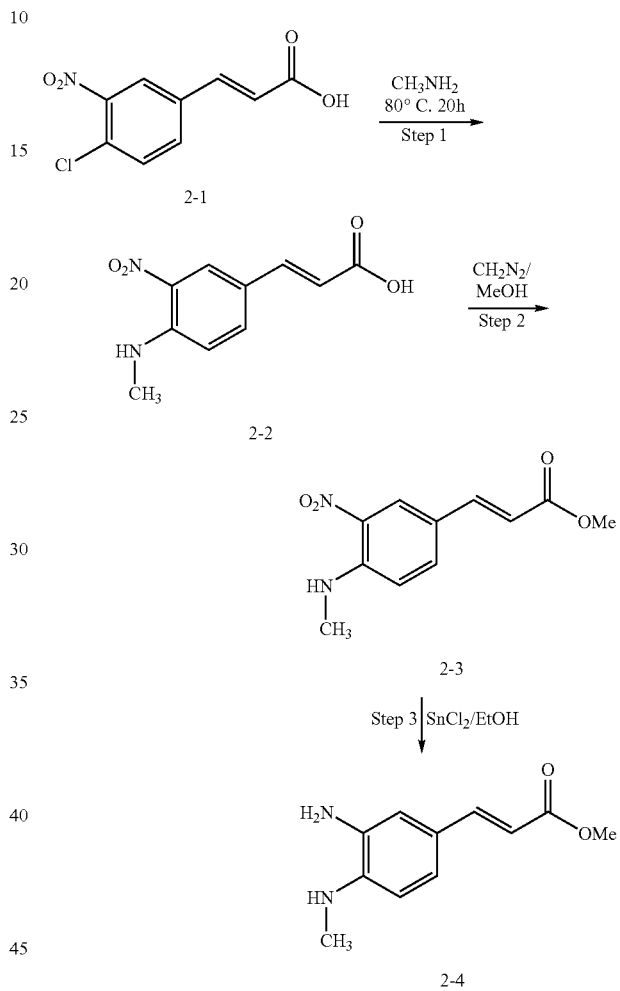

Step 1:

A mixture of 4-chloro-3-nitrocinnamic acid 2-1 (500 mg, 2.2 mmol) and a solution of methylamine in THF (2M, 8 mL, 16 mmol) were heated in a sealed tube at 80° C. for 20 hours. The mixture was then cooled to room temperature and concentrated to an orange solid 2-2 that was used in the following step without further purification.

It will be apparent to the person skilled in the art that other diamine intermediates of general formula IV in Schemes 2 and 3 above, where R⁸ is other than methyl, may be prepared by replacing methylamine (CH₃NH₂) in step 1 above with the appropriate R⁸—NH₂.

Step 2:

The crude 4-methylamino-3-nitrocinnamic acid intermediate 2-2 from step 1 (488 mg, 2.2 mmol) was dissolved in methanol (20 mL) and an ether solution of diazomethane was added until HPLC analysis indicated complete conversion of the acid to the methyl ester. The solution was concentrated to dryness to obtain 540 mg of the methyl ester 2-3 as an orange solid which was used in step 3 without further purification.

Step 3:

The crude methyl ester 2-3 from step 2 (540 mg, ~2.2 mmol) and SnCl₂ dihydrate (2.25 g, 10 mmol) were dissolved in ethanol (20 mL) and the mixture was stirred at 80° C. for 4 hours. After that period, the mixture was cooled to room temperature and was slowly added to aqueous solution of saturated NaHCO₃. The reaction mixture was extracted with ethyl acetate (100 mL), the organic layer was dried over anhydrous MgSO₄ and the solvent was removed under reduced pressure. The residue was purified by flash column chromatography, using a gradient of hexane in ethyl acetate (from 50% to 30%) to give (E)-3-(3-amino-4-methylaminophenyl)acrylic acid methyl ester 2-4 as a yellow solid (245 mg).

Example 3

(E)-3-[2-(1-Aminocyclobutyl)-1-methyl-1H-benzoimidazol-5-yl]acrylic acid methyl ester

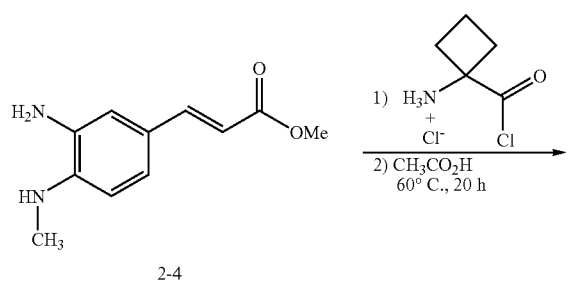

2-4

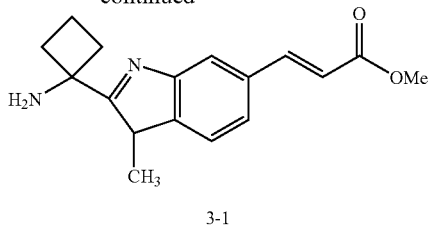

3-1

(E)-3-(3-Amino-4-methylaminophenyl)acrylic acid methyl ester 2-4 from Example 2 (40 mg, 0.194 mmol) was suspended in CH₂Cl₂ (3 mL) and 1-aminocyclobutanecarboxylic acid chloride hydrochloride, prepared from 1-aminocyclobutanecarboxylic acid following an adaptation of the procedure described by E. S. Uffelman et al. (*Org. Lett.* 1999, 1, 1157), (31 mg, 0.18 mmol) was added. The reaction mixture was stirred at room temperature for 2 hours and then concentrated to obtain a white solid. The solid was then dissolved in acetic acid (5 mL) and heated to 60° C. for 20 hours. The reaction crude was diluted with aqueous saturated NaHCO₃, extracted with CH₂Cl₂ (2×50 mL) and brine, the organic layer was dried over anhydrous MgSO₄ and the solvent was removed under reduced pressure to give (E)-3-[2-(1-aminocyclobutyl)-1-methyl-1H-benzoimidazol-5-yl] acrylic acid methyl ester 3-1 as a light brown foam (53 mg).

Example 4

(E)-3-(2-{1-[(3-Cyclopentyl-1-methyl-2-pyridin-2-yl-1H-indole-6-carbonyl)amino]cyclobutyl}-1-methyl-1H-benzoimidazol-5-yl)acrylic Acid

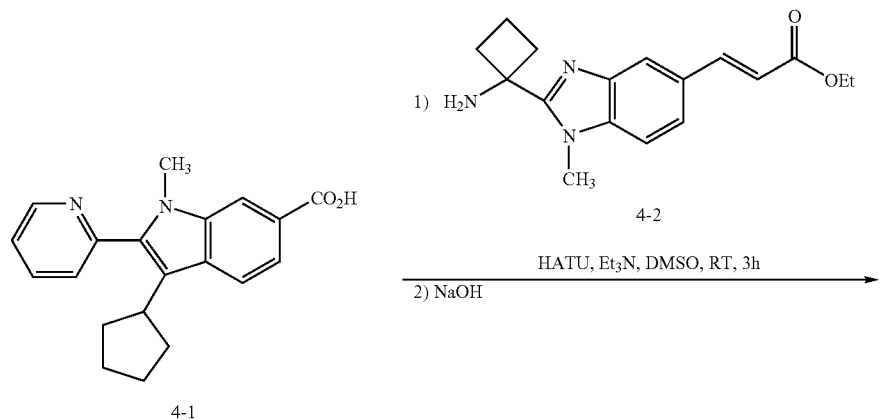

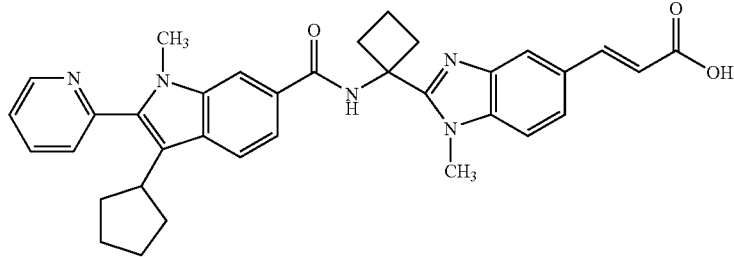

4-3

A solution of 3-cyclopentyl-1-methyl-2-pyridin-2-yl-1H-indole-6-carboxylic acid 4-1, prepared using procedures described in WO 03/010141 (31.1 mg, 0.97 mmol), (E)-3-[2-(1-aminocyclobutyl)-1-methyl-1H-benzoimidazol-5-yl]acrylic acid methyl ester 4-2, prepared from the ethyl ester analogue of compound 2-4, using an analogous procedure to that described in Example 3 (27.7 mg, 0.97 mmol), HATU (47.9 mg, 0.126 mmol) and Et$_3$N (58 µL, 0.42 mmol) in DMSO (2 mL) was stirred at RT for 3 h. After that period, NaOH (280 µL, 2.5N) was added and the reaction mixture was stirred at RT for 16 h. The reaction mixture was neutralized with the addition of a few drops of acetic acid, and purified on a reversed phase C$_{18}$, semi-preparative HPLC column (using a solvent gradient from 5% to 100% MeCN in H$_2$O (all solvents contain 0.1% trifluoroacetic acid)) to isolate the final inhibitor (E)-3-(2-{1-[(3-cyclopentyl-1-methyl-2-pyridin-2-yl-1H-indole-6-carbonyl)amino]cyclobutyl}-1-methyl-1H-benzoimidazol-5-yl)acrylic acid 4-3 (compound 4001, Table 4) as a white amorphous solid in >95% homogeneity (45 mg, 78% yield).

$^1$H NMR (400 MHz, DMSO): δ 1.48-1.58 (m, 2H), 1.75-1.85 (m, 6H), 1.85-1.95 (m, 1H), 2.05-2.15 (m, 1H), 2.69-2.76 (m, 2H), 2.98-3.10 (m, 3H), 3.63 (s, 3H), 3.82 (s, 3H), 6.59 (d, J=16 Hz, 1H), 7.42 (dd, J=0.8 & 5.7 Hz, 1H), 7.51 (d, J=7.7 Hz, 1H), 7.53 (d, J=8.5 Hz, 1H), 7.65 (d, J=8.5 Hz, 1H), 7.71 (d, J=8.4 Hz, 1H), 7.76 (d, J=16 Hz, 1H), 7.82 (d, J=8.4 Hz, 1H), 7.92 (ddd, J=1.6 & 7.8 Hz, 1H), 8.01 (s, 1H), 8.04 (s, 1H), 8.73 (d, J=4.1 Hz, 1H), 9.45 (s, 1H).

Example 5

3-Cyclopentyl-1-methyl-2-pyrazin-2-yl-1H-indole-6-carboxylic acid {1-[5-((E)-2-carbamoylethenyl)-1-methyl-1H-benzimidazol-2-yl]cyclobutyl}amide

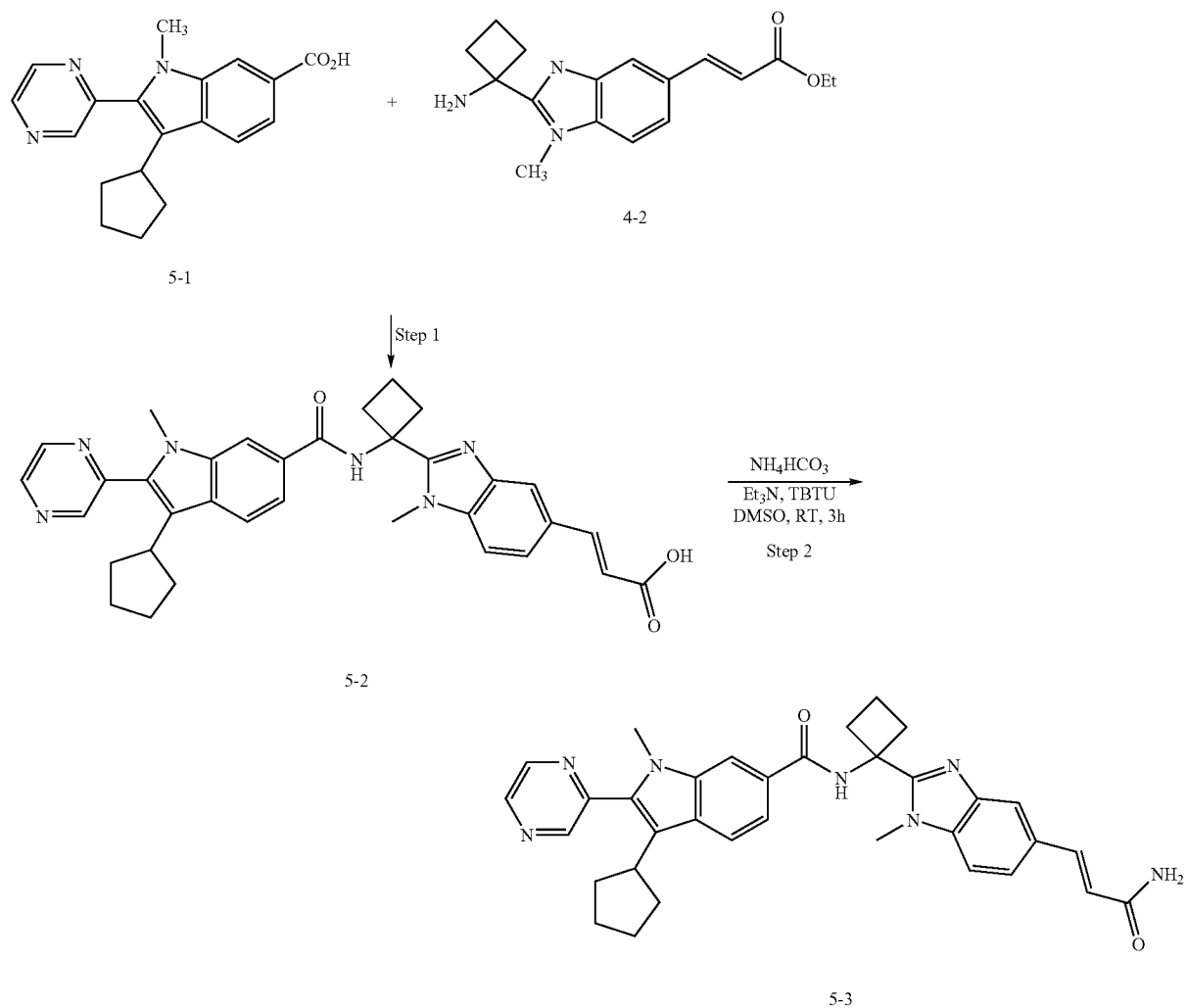

Step 1:

3-cyclopentyl-1-methyl-2-pyrazin-2-yl-1H-indole-6-carboxylic acid 5-1 (prepared using procedures described in WO 03/010141) and (E)-3-[2-(1-aminocyclobutyl)-1-methyl-1H-benzimidazol-5-yl]acrylic acid ethyl ester 4-2 were coupled, followed by saponification of the ethyl ester, using analogous procedures to those described in Example 4 to give (E)-3-(2-{1-[(3-Cyclopentyl-1-methyl-2-pyrazin-2-yl-1H-indole-6-carbonyl)amino]cyclobutyl}-1-methyl-1H-benzimidazol-5-yl)acrylic acid 5-2 (compound 4003, Table 4).

$^1$H NMR (400 MHz, DMSO-d$_6$): δ 1.50-1.58 (m, 2H), 1.78-1.20 (m, 7H), 2.05-2.15 (m, 1H), 2.65-2.75 (m, 2H), 2.97-3.10 (m, 3H), 3.66 (s, 3H), 3.81 (s, 3H), 6.57 (d, J=16.0 Hz, 1H), 7.55 (dd, J=1.0 & 8.4 Hz, 1H), 7.68 (2d, J=8.4 Hz, 2H), 7.75 (d, J=16.0 Hz, 1H), 7.78 (d, J=11.0 Hz, 1H), 8.00 (s, 1H), 8.07 (s, 1H), 8.68 (d, J=2.3 Hz, 1H), 8.78 (d, J=1.2 Hz, 1H), 8.82 (dd, J=0.8 & 2.2 Hz, 1H), 9.44 (brs, 1H).

1H), 7.68 (dd, J=1.0 & 8.4 Hz, 1H), 7.80 (d, J=8.4 Hz, 1H), 7.90 (s, 1H), 8.20 (s, 1H), 8.80 (d, J=2.5 Hz, 1H), 8.91 (d, J=1.2 Hz, 1H), 8.95 (dd, J=2.1 & 3.7 Hz, 1H), 9.23 (s, 1H).

Example 6

4-Amino-2-methyl-5-(methylamino)benzoic acid methyl ester

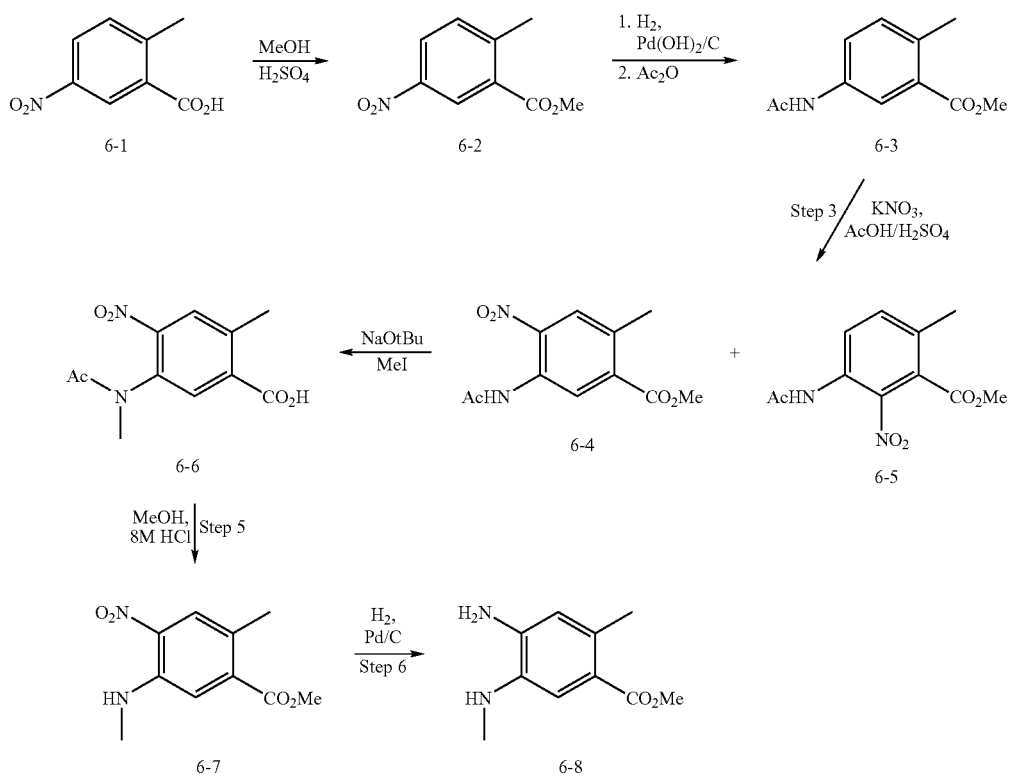

Step 2:

A solution of (E)-3-(2-{1-[(3-cyclopentyl-1-methyl-2-pyrazin-2-yl-1H-indole-6-carbonyl)amino]cyclobutyl}-1-methyl-1H-benzimidazol-5-yl)acrylic acid 5-2 (compound 4003, Table 4; 60 mg, 0.087 mmol), TBTU (68 mg, 0.18 mmol), ammonium hydrogen carbonate (20 mg, 0.26 mmol) and Et$_3$N (36 μL, 0.26 mmol) in DMSO (3 mL) was stirred at RT for 3 h. The reaction mixture was neutralized with the addition of a few drops of acetic acid, and purified on a reversed phase C$_{18}$, semi-preparative HPLC column (using a solvent gradient from 5% to 100% MeCN in H$_2$O (all solvents contain 0.1% trifluoroacetic acid)) to isolate the inhibitor 3-cyclopentyl-1-methyl-2-pyrazin-2-yl-1H-indole-6-carboxylic acid {1-[5-((E)-2-carbamoylethenyl)-1-methyl-1H-benzoimidazol-2-yl]cyclobutyl}amide 5-3 (compound 1005, Table 1) as a pale yellow amorphous solid in >95% homogeneity (17 mg, 34% yield).

$^1$H NMR (400 MHz, DMSO-d$_6$): δ 1.65-1.75 (m, 2H), 1.92-2.15 (m, 8H), 2.73-2.82 (m, 2H), 3.04-3.10 (m, 2H), 3.15-3.25 (m, 1H), 3.79 (s, 3H), 3.81 (s, 3H), 6.65 (d, J=15.8 Hz, 1H), 7.06 (brs, 1H), 7.53 (brs, 3H), 7.61 (d, J=15.7 Hz, Step 1:

A solution of 2-methyl-5-nitrobenzoic acid 6-1 (10.0 g, 55.2 mmol) in MeOH (200 mL) and H$_2$SO$_4$ (1.0 mL) was heated to reflux while stirring for ~3 days. The solvent was evaporated under vacuum and the residue was re-dissolved in EtOAc (~200 mL), washed with cold H$_2$O (~50 mL), cold saturated aqueous NaHCO$_3$ (~50 mL) and cold brine (~50 mL). The organic layer was then dried over anhydrous MgSO$_4$ and concentrated to dryness to give the methyl ester 6-2 as a white solid, which was used without purification in step 2.

Step 2:

To a solution of the crude methyl ester 6-2 from step 1 (~55.2 mmol) in MeOH (200 mL), Pearlman's catalyst (20% palladium hydroxide on carbon, 1.0 g) was added and the mixture was stirred under an atmosphere of H$_2$ for 20 h at RT. The mixture was filtered through Celite and concentrated to dryness. The residue was re-dissolved in THF (200 mL), Ac$_2$O (6.2 mL, 66 mmol) was added and the solution was stirred at RT for 3 h. The reaction mixture was concentrated to dryness under vacuum and the residue was re-dissolved in minimum volume of t-Bu methyl ether (~150 mL). The ether suspension was stirred at RT for 1 h before hexane (~100 mL) was added to precipitate the desired acetylated intermediate as a white solid. The solid was washed with hexane and dried to give the acetylated compound 6-3 in high purity (10.1 g, 88% yield).

Step 3:

A solution of the acetylated ester 6-3 from step 2 (8.42 g, 40.6 mmol) and potassium nitrate (5.0 g, 50 mmol) in AcOH: $H_2SO_4$ (1:1 ratio, 200 mL) was stirred at RT for 2 h and at 40° C. for a further two hours. The crude reaction mixture was then poured slowly on ice (~1 L) and mixed for 20 min. The precipitate formed was filtered and washed several times with $H_2O$ to give a mixture of mainly two products, the desired 4-nitro isomer 6-4 and the undesired 6-nitro isomer 6-5 (1:2 ratio) which were separated after flash column chromatography using 30% EtOAc in hexane as the eluent. The pure 4-nitro isomer 6-4 was isolated as a yellow solid (2.05 g, 20% yield).

Step 4:

The 4-nitro Intermediate 6-4 from step 3 (2.05 g, 8.13 mmol) was dissolved in THF (50 mL) and the solution was cooled to 0° C. before MeI (2.51 mL, 40.6 mmol) and t-BuONa (4.46 g, 46.4 mmol) were added slowly. The reaction mixture was stirred at RT for 15 h, $H_2O$ (~50 mL) was added and the aqueous mixture was washed with t-butyl methyl ether (~20 mL). The aqueous layer was acidified to pH 3 with 1N HCl and then extracted with EtOAc (~100 mL). The organic layer was washed with brine (~50 mL), dried over anhydrous $MgSO_4$ and concentrated to dryness to give the N-methylated compound 6-6 as a gummy foam which was used directly in step 5 without purification.

It will be apparent to the person skilled in the art that other diamine intermediates of general formula IV in Schemes 2 and 3 above, wherein $R^8$ is other than methyl, may be prepared by replacing methyl iodide ($CH_3I$) in step 4 above with the appropriate $R^8$—X, wherein X is a leaving group such as Cl, Br, I, methanesulfonate (mesylate), p-toluenesulfonate (tosylate), trifluoromethanesulfonate (triflate), and the like.

Step 5:

A solution of the methylated derivative 6-6 from step 4 (~8 mmol) in MeOH (10 mL) and HCl (8N, 15 mL) was stirred at 70° C. for 20 h. The solvent was evaporated under vacuum and the residue was partitioned between saturated aqueous $NaHCO_3$ (20 mL) and EtOAc (50 mL). The organic layer was washed with brine, dried over anhydrous $MgSO_4$ and concentrated to give the methyl ester 6-7 as an orange solid (1.54 g), which was used in step 6 without purification.

Step 6:

A solution of the crude methyl ester 6-7 from step 5 (1.54 g, 6.7 mmol) in MeOH (30 mL) was treated under catalytic hydrogenation conditions using Pd/C (10%, 150 mg) under an atmosphere of $H_2$ at RT for 2 h. The reaction mixture was filtered through Celite and concentrated to give 4-amino-2-methyl-5-(methylamino)benzoic acid methyl ester 6-8 as a purple solid (1.33 g) which was sufficiently pure (confirmed by NMR) to be used without further purification.

Example 7

2-(1-tert-Butoxycarbonylaminocyclobutyl)-3,6-dimethyl-3H-benzoimidazole-5-carboxylic acid methyl ester

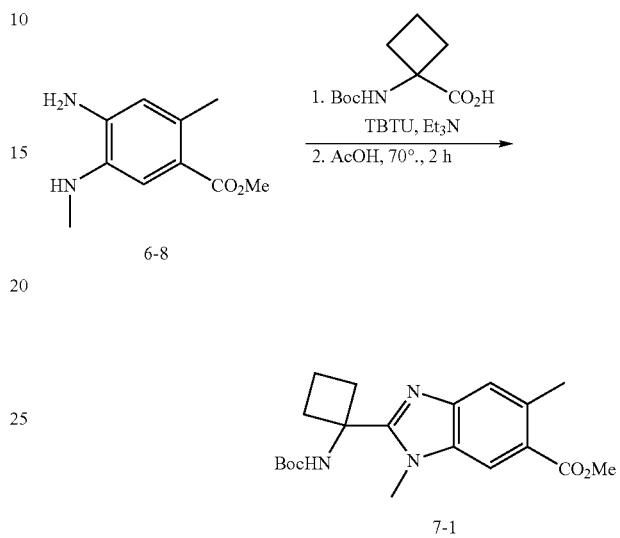

1-((1,1-Dimethylethoxycarbonyl)amino)cyclobutanecarboxylic acid (1.40 g, 6.5 mmol) was dissolved in $CH_2Cl_2$ (45 mL) and reacted with TBTU in the presence of $Et_3N$ for a period of 30 min to pre-activate the acid. A solution of 4-amino-2-methyl-5-(methylamino)benzoic acid methyl ester 6-8 from Example 6 (1.33 g, 6.85 mmol) in $CH_2Cl_2$ (10 mL) was added slowly over a period of 30 min and stirring of the reaction mixture was continued for 20 h. The reaction mixture was concentrated to dryness, and the residue was re-dissolved in AcOH (10.0 mL) and stirred at 70° C. for 2 h to achieve cyclization of the benzimidazole ring. The reaction mixture was concentrated to dryness and the residue was dissolved in EtOAc (~250 mL), extracted with aqueous saturated $NaHCO_3$ (2×100 mL) and brine (100 mL). The organic layer was dried over anhydrous $MgSO_4$ and evaporated to dryness. The residue was purified by flash column chromatography (using a solvent gradient from 40% to 50% EtOAc in hexane) to obtain the pure 2-(1-tert-butoxycarbonylaminocyclobutyl)-3,6-dimethyl-3H-benzoimidazole-5-carboxylic acid methyl ester 7-1 as a beige solid (1.41 g, 55% yield) and recover some of the unreacted diamino starting material.

2-(1-tert-Butoxycarbonylaminocyclobutyl)-3,6-dimethyl-3H-benzoimidazole-5-carboxylic acid methyl ester 7-1 may be converted to an amine intermediate of general formula III in Scheme 1 using standard reagents well known to one skilled in the art. Such reagents include, but are not limited to, trifluoroacetic acid, a solution of HCl in dioxane, and the like. The corresponding amine intermediate of general formula III in Scheme 1 may be further elaborated to inhibitors of general formula I in Scheme 1 using the procedure of Example 4.

Example 8

(E)-3-[2-(1-Amino-cyclobutyl)-3,6-dimethyl-3H-benzoimidazol-5-yl]-2-methyl-acrylic acid ethyl ester

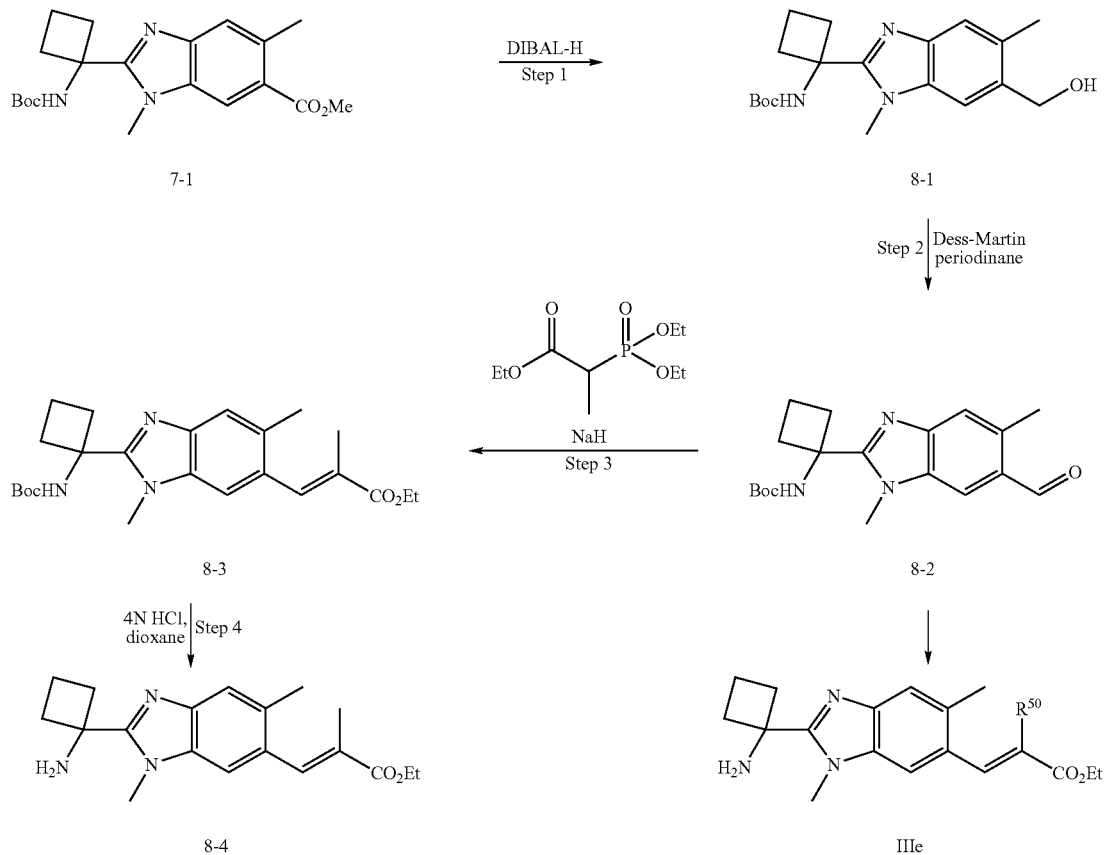

Step 1:

2-(1-tert-Butoxycarbonylaminocyclobutyl)-3,6-dimethyl-3H-benzoimidazole-5-carboxylic acid methyl ester 7-1 from Example 7 (1.41 g, 3.8 mmol) was dissolved in THF (40 mL) and the solution was cooled to 0° C. A solution of DIBAL-H (18 mL, 1M in THF, 18 mmol) was added slowly and the reaction mixture was stirred at 0° C. for 1 h and then at 50° C. for 4 h. The reaction mixture was cooled to RT, a solution of potassium sodium tartrate (1M, 50 mL) was added very slowly and stirring was continued for 1 h at RT. The solution was concentrated under vacuum in order to remove most of the THF and the extracted with EtOAc (~200 mL). The organic layer was washed with saturated aqueous NaHCO$_3$ (50 mL) and brine (50 mL), dried over anhydrous MgSO$_4$ and concentrated to dryness. The residue was purified by flash column chromatography, using a solvent gradient from 50% EtOAc in hexane to pure EtOAc and then to 3% MeOH in EtOAc, to obtain the pure alcohol 8-1 as a yellow solid (1.09 g, 84% yield).

Step 2:

A solution of the alcohol 8-1 from step 1 (1.09 g, 3.16 mmol) and Dess-Martin periodinane (1.70 g, 4.0 mmol) in CH$_2$Cl$_2$ (40 mL) was stirred at RT for 2 h. The solvent was evaporated under vacuum and the residue was purified by flash column chromatography, using EtOAc:hexane (1:1 ratio), to obtain the pure aldehyde 8-2 (605 mg, 56% yield).

Step 3:

A solution of triethyl-2-phosphonopropionate (0.228 mL, 1.06 mmol) in THF (5.4 mL) was cooled to 0° C. and NaH (42.5 mg, 60% in oil, 1.06 mmol) was added. The mixture was stirred at 0° C. for 30 min before a solution of the aldehyde 8-2 from step 2 (300 mg in 3 mL of THF, 0.874 mmol) was slowly added and stirring was continued at RT for 20 h. The mixture was diluted with EtOAc (~100 mL) and washed with saturated aqueous NaHCO$_3$ (2×30 mL) and brine (30 mL). The organic layer was dried over anhydrous MgSO$_4$, and concentrated to a brown residue which was subsequently purified by flash column chromatography, using a solvent gradient from 40% to 60% EtOAc in hexane, to give the N-Boc-protected ester 8-3 as a yellow foam (85 mg, 23% yield).

Step 4:

Hydrolysis of the Boc protecting group was achieved quantitatively by adding 4N HCl in dioxane (2 mL) and stirring the solution at RT for 1 h. After evaporation of the solvent under vacuum, (E)-3-[2-(1-aminocyclobutyl)-3,6-dimethyl-3H-benzoimidazol-5-yl]-2-methylacrylic acid ethyl ester 8-4 was isolated pure as a yellow solid (79 mg).

It will be apparent to the person skilled in the art that the triethyl-2-phosphonopropionate used in step 3 of this procedure can be replaced by appropriately substituted derivatives to prepare analogues of the general formula IIIe in the scheme above, wherein $R^{50}$ is defined as hereinbefore. In addition, methyl esters can also be prepared in an analogous fashion using the appropriate reagent. Compound 8-4 and its analogues of general formula IIIe above may be further elaborated to inhibitors of general formula I in Scheme 1 using the procedure of Example 4.

Example 9

3-Fluoro-4-nitrobenzaldehyde

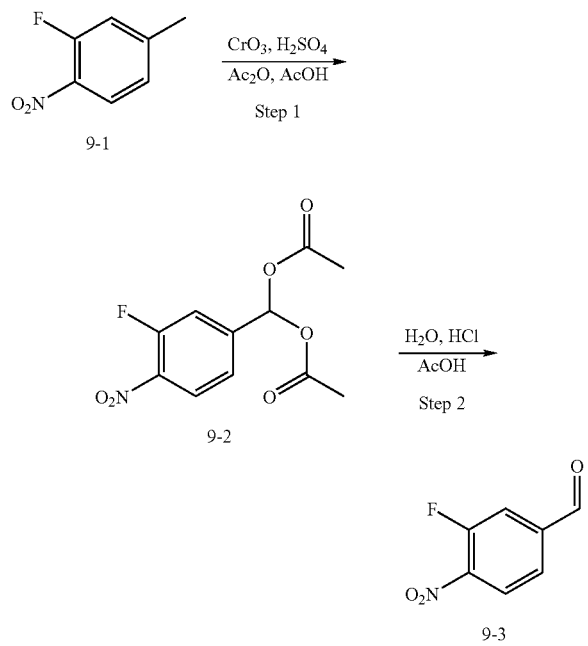

Step 1:

A two-necked flask (equipped with an internal thermometer) was charged with glacial AcOH (252 mL), acetic anhydride (252.0 mL) and 2-fluoro-4-methyl-1-nitrobenzene 9-1 (25.0 g, 161 mmol) at −10° C. To the cooled solution, concentrated sulfuric acid (40 mL) was added drop-wise over a period of 5 min, followed by the very slow addition of chromium (VI) oxide (45 g, 450 mmol); the rate of addition must be very slow (~1.5 h) in order to maintain the temperature below 10° C. Upon addition of the $CrO_3$, the clear colorless solution becomes amber and finally dark brown at the end of the addition. After completion of the addition, the reaction was stirred for an additional 45 min (HPLC analysis indicated ~70% completion of the reaction). The tar-like partial suspension was poured on ice (1.6 L), and the resulting slush was diluted with $H_2O$ up to a total of 3 L, at which point the product began to precipitate. After filtration, the beige solid was washed with cold $H_2O$ to obtain a white solid. The solid was then suspended in cold 2% $NaHCO_3$ (250 mL), filtered and washed again with cold $H_2O$ to give the diacetate 9-2 (22 g, containing some of the unreacted starting material) as a white solid which was used as such in step 2.

Step 2:

In a screw-cap vial, the diacetate 9-2 from step 1 (1.0 g, 3.7 mmol) was dissolved in glacial acetic acid (10.0 mL), followed by addition of $H_2O$ (1.0 mL) and concentrated HCl (1.0 mL). The resulting partially soluble mixture was heated at 115° C. for 45 min. Most of the solvents were removed under vacuum to give a gummy residue, the remaining acid and $H_2O$ was azeotroped twice with $CH_2Cl_2$-hexane to give the desired semi-pure 3-fluoro-4-nitrobenzaldehyde 9-3 as a yellow solid (600 mg). This compound was further purified by flash column chromatography (using 20% EtOAc in hexanes as the eluent) to remove small amounts of unreacted 2-fluoro-4-methyl-1-nitrobenzene 9-1 (~35% overall yield).

Example 10

(E)-3-(4-Amino-3-(methylamino)phenyl)acrylic Acid Ethyl Ester

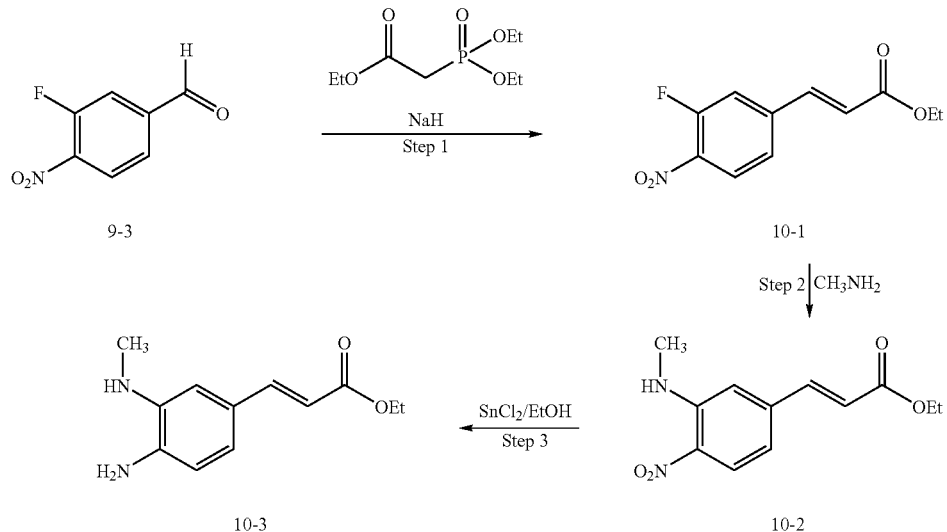

Step 1:

To a solution of triethyl phosphonoacetate (1.37 mL, 6.90 mmol) in THF (13 mL) at 0° C., NaH (60% dispersion in oil, 314 mg, 7.84 mmol) was added and the mixture was stirred for 30 min. After that period, 3-fluoro-4-nitrobenzaldehyde 9-3 from Example 9 (1.06 g, 6.27 mmol) was added and stirring was continued at RT for 16 h. The reaction was quenched by the addition of $H_2O$ (20 mL) and the product was extracted into EtOAc (2×100 mL). The combined organic layers were washed with brine, dried over anhydrous $MgSO_4$ and concentrated to give the cinnamate ester 10-1 as a light orange solid which was used in step 2 without purification.

It will be apparent to the person skilled in the art that analogues bearing various substituents on the cinnamate double bond may be prepared by replacing the triethyl phosphonoacetate used in this procedure with appropriately substituted derivatives or by replacing the aldehyde 9-3 with an appropriate ketone. In addition, cinnamate methyl esters can also be prepared in an analogous fashion using the appropriate reagent.

Step 2:

The cinnamate ester 10-1 from step 1 (~6.27 mmol) and methylamine (2M in THF, 6.3 mL, 12.5 mmol) were dissolved in DMSO (6 mL) and the reaction mixture was stirred at RT for 2 h. After that period, the mixture was diluted with EtOAc (100 mL) and the organic layer was washed with $H_2O$ (3×30 mL) and brine (50 mL), dried over anhydrous $MgSO_4$ and concentrated to give the crude methylamino intermediate 10-2 as an orange solid. This product was used in step 3 without purification.

It will be apparent to the person skilled in the art that other diamine intermediates of general formula IV in Schemes 2 and 3 above, where $R^8$ is other than methyl, may be prepared by replacing methylamine ($CH_3NH_2$) in step 2 above with the appropriate $R^8$—$NH_2$.

Step 3:

The 3-methylamino-4-nitrocinnamate ester 10-2 from step 2 (2-2, ~150 mg) and $SnCl_2$ dihydrate (950 mg, 4.2 mmol) were dissolved in ethanol (10 mL) and the mixture was stirred at 80° C. for 20 hours. The mixture was cooled to room temperature and concentrated to dryness. The residue was dissolved in ethyl acetate (100 mL) and was slowly added to an aqueous solution of saturated $NaHCO_3$ and stirred for 30 min. The organic layer was then extracted with ice cold brine, dried over anhydrous $MgSO_4$ and the solvent was removed under reduced pressure. The residue was purified by flash column chromatography (using a gradient from 70% to 60% of hexane in ethyl acetate) to give (E)-3-(4-amino-3-(methylamino)phenyl)acrylic acid ethyl ester 10-3 as a yellow solid (100 mg).

(E)-3-(4-Amino-3-(methylamino)phenyl)acrylic acid ethyl ester may be converted into amine derivatives of general formula III in Scheme 1 following the procedures of Examples 3 or 7, and further elaborated to inhibitors of general formula I in Scheme 1 using the procedure of Example 4.

Example 11

5-Amino-2-methyl-4-methylaminobenzoic acid methyl ester

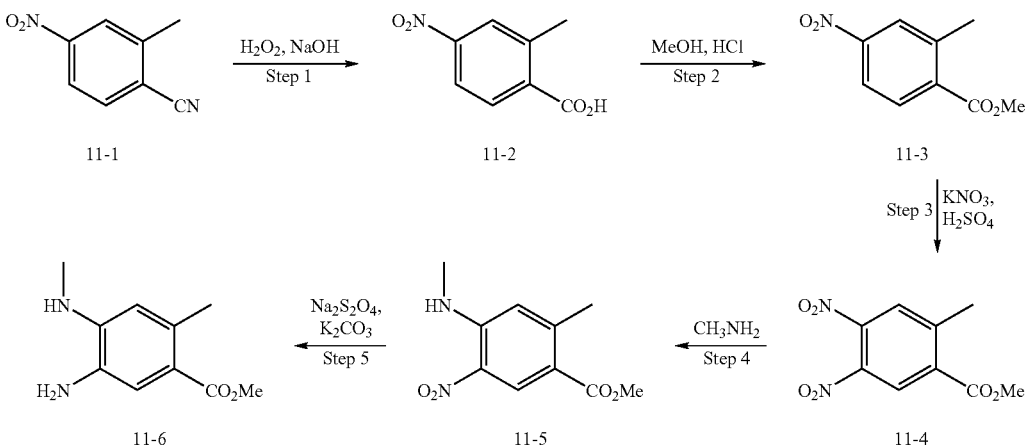

Step 1:

A solution of 2-methyl-4-nitrobenzonitrile 11-1 (2.53 g, 15.6 mmol) in aqueous NaOH (10%, 31.0 mL) and aqueous $H_2O_2$ (10%, 16 mL) was stirred at reflux for 2.5 h. The water circulation in the cooling condenser was halted for 5-10 min (to allow removal of the dissolved ammonia), and then the water flow was restored and reflux continued for an additional 1.5 h. The reaction mixture was cooled to RT, HCl (concentrated) was added drop-by-drop until the pH was ~3, at which point the carboxylic acid 11-2 precipitated as an orange-color solid (3.60 g). The carboxylic acid was used in step 2 without purification.

Step 2:

A solution of the acid 11-2 from step 1 (3.60 g, 15.6 mmol) in MeOH (30 mL) and HCl (4N HCl in dioxane, 2.0 mL) was heated to reflux for 48 h. The solvent was evaporated to dryness under vacuum and the residue obtained was re-dissolved in EtOAc (200 mL). The solution was washed with aqueous saturated $NaHCO_3$ (100 mL) and brine (100 mL), dried over anhydrous $MgSO_4$ and evaporated to dryness to give the ester intermediate 11-3 as a yellow-colored solid (2.38 g). This material was used in step 3 without purification.

Step 3:

To a solution of the ester 11-3 from step 2 (1.27 g, 6.5 mmol) in $H_2SO_4$ (conc., 13.0 mL), pre-cooled to 0° C., $KNO_3$ (760 mg, 7.5 mmol) was added very slowly. After a few min of stirring, the ice bath was removed and the reaction mixture was stirred at RT for 20 h. The reaction mixture was then poured slowly on ice (~50 mL) and stirred until the ice had melted, and the desired dinitro product 11-4 was precipitated and filtered (~1.55 g of light yellow and slightly wet solid). The compound was used as such in step 4.

Step 4:

To a solution of the dinitro intermediate 11-4 from step 3 (1.55 g, 6.45 mmol) in THF (15.0 mL) at 0° C., a solution of methylamine (2M in THF, 15.2 mL, 32.3 mmol) was added, the ice-bath was removed and the reaction mixture was stirred at RT for 1.5 h. The solution was concentrated to remove some of the THF and then diluted with EtOAc (~100 mL). The organic layer was washed with $H_2O$ (~50 mL) and brine (~50 mL), dried over anhydrous $MgSO_4$ and concentrated to give the methylamino intermediate 11-5 as an orange solid (1.26 g). The compound was used in step 5 without further purification.

It will be apparent to the person skilled in the art that other diamine intermediates of general formula IV in Schemes 2 and 3 above, where $R^8$ is other than methyl, may be prepared by replacing methylamine ($CH_3NH_2$) in step 4 above with the appropriate $R^8$—$NH_2$.

Step 5:

To a solution of the methylamino derivative 11-5 from step 4 (1.25 g, 5.58 mmol) in EtOH—$H_2O$ (110 mL, 1:1 ratio), $K_2CO_3$ (4.62 g, 33.5 mmol) and $Na_2S_2O_4$ were added and the mixture was stirred at RT for 3 h. More $H_2O$ (~30 mL) was added and the mixture was concentrated under vacuum to remove most of the EtOH. The reaction mixture was then diluted with EtOAc (~200 mL) and the organic layer was separated and extracted with brine. The organic layer was dried over anhydrous $MgSO_4$ and concentrated under vacuum to give 5-amino-2-methyl-4-(methylamino)benzoic acid methyl ester 11-6 (927 mg, 86% yield) as a brown-colored solid.

Compound 11-6 may be converted into the corresponding amine intermediates of general formula III in Scheme 1, wherein $R^6$ is $CH_3$ and $R^5$ is —$COOCH_3$, following the procedures of Examples 3 or 7. These amine intermediates may be further converted into amine intermediates of general formula III in Scheme 1, wherein $R^6$ is $CH_3$ and $R^5$ is —CH=C($R^{50}$)—COOR, by following the procedure of Example 8. All these amine intermediates of general formula III in Scheme 1 may be further elaborated to inhibitors of general formula I in Scheme 1 using the procedure of Example 4.

Example 12

(E)-3-(5-Amino-2-ethoxy-4-(methylamino)phenyl) acrylic acid methyl ester

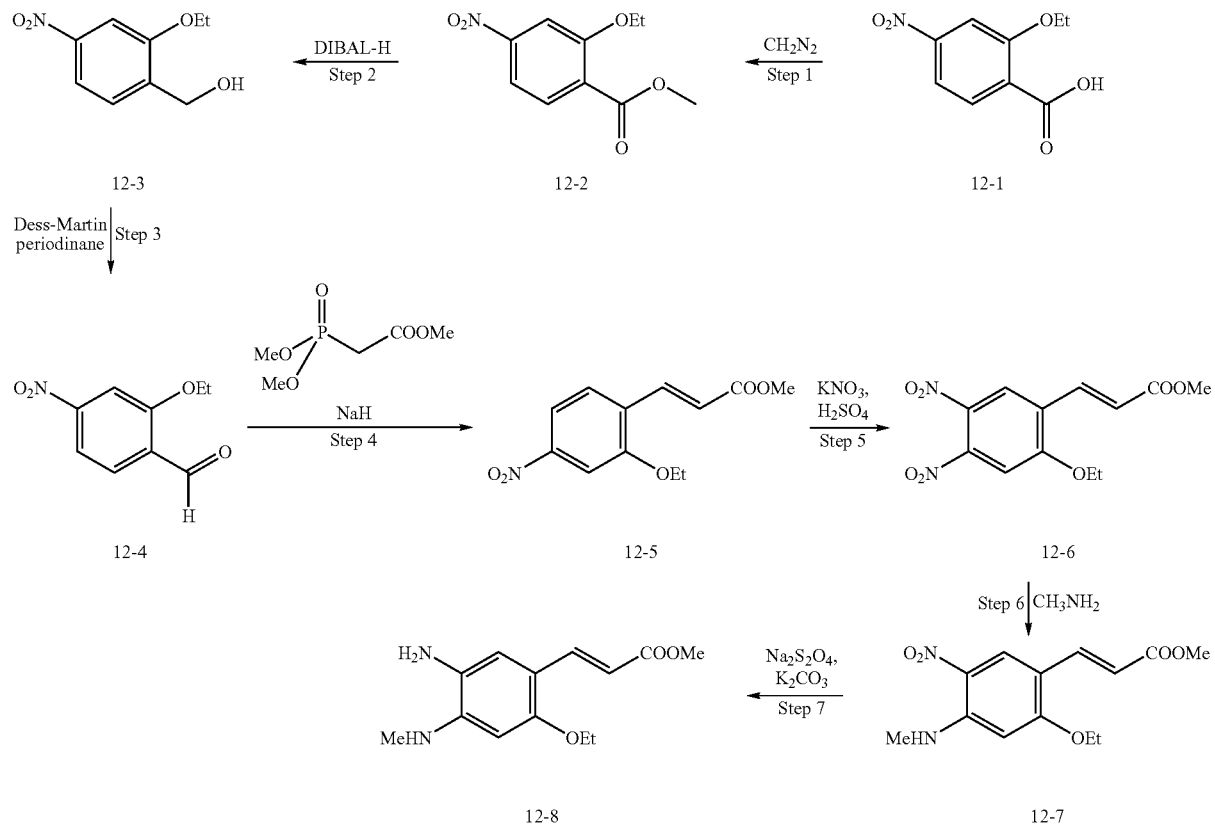

Step 1:

2-Ethoxy-4-nitrobenzoic acid 12-1 (1.56 g; 7.38 mmol) was dissolved in methanol (15 mL) and the resulting solution stirred at 0° C. A solution of diazomethane in ethyl ether was slowly added until the yellow color persisted and was stirred for a further 20 min. The solvents were evaporated to afford the methyl ester 12-2 as a pale yellow solid (1.66 g, quant.) which was used in step 2 without further purification.

Step 2:

The ester 12-2 from step 1 (1.60 g; 7.10 mmol) was dissolved in dry toluene and the solution cooled to −78° C. under a nitrogen atmosphere. A solution of diisobutylaluminum hydride in tetrahydrofuran (1M; 8 mL; 8 mmol) was added and the reaction mixture allowed to warm to ambient temperature. Two additional portions of DIBAL-H were added in this way (7 and 10 mL) after 1 h and a further 1.5 h. 0.5 h after the last addition, the reaction was cooled to 0° C. and 1N HCl (25 mL) was slowly added and the mixture stirred vigorously for 0.5 h. The organic solvents were then evaporated and the aqueous residue was extracted with ethyl acetate (2×50 mL) and washed with water (50 mL) and brine (50 mL). The combined extracts were then dried over $MgSO_4$ and evaporated to afford the alcohol 12-3 as a pale yellow, fibrous solid (1.40 g; quant.) which was used as such in step 3.

Step 3:

A turbid solution of 1,1,1-tris(acetyloxy-1,1-dihydro-1,2-benziodoxol-3-(1H)-one (Dess-Martin periodinane) (2.32 g; 5.47 mmol) in dichloromethane (40 mL+5 mL rinse) was added to a stirred solution of the alcohol 12-3 from step 2 (0.98 g; 4.97 mmol) in DCM (40 mL) and the reaction stirred at ambient temperature under a nitrogen atmosphere. After 4 h, saturated $NaHCO_3$/10% $Na_2S_2O_3$ (1:1, 160 mL) was added and the mixture stirred vigorously until the phases were clear (ca. 0.5 h). The organic phase was separated and the aqueous phase was extracted with dichloromethane (50 mL) and washed with saturated $NaHCO_3$ (2×150 mL). The combined organic phases were then dried over $MgSO_4$ and evaporated to yield the aldehyde 12-4 as a pale yellow solid (960 mg; 99%) which was used as such in step 4.

Step 4:

Sodium hydride (95% dry powder; 158 mg; 6.25 mmol) was suspended in anhydrous THF (10 mL) and trimethyl phosphonoacetate (0.945 mL; 5.84 mmol) added dropwise at 0° C. under a nitrogen atmosphere resulting in a solid white mass which could not be stirred. A solution of the aldehyde 12-4 from step 3 (950 mg; 4.87 mmol) in THF (7 mL+3 mL rinse) was then added dropwise resulting in a yellow colour and slow dissolution of the white solid mass. After the addition, the reaction was allowed to warm to ambient temperature. After 15 h, the cloudy reaction mixture was evaporated to a pale yellow solid which was extracted with ethyl acetate (2×50 mL) and washed with saturated $NaHCO_3$ (3×75 mL). The combined extracts were dried over $MgSO_4$ and evaporated to afford the cinnamate ester 12-5 as pale yellow solid (1.212 g; 99%) which was used in step 5 without further purification.

It will be apparent to the person skilled in the art that the trimethyl phosphonoacetate used in this procedure can be replaced by appropriately substituted derivatives to prepare analogues bearing various substituents on the cinnamate double bond.

Step 5:

The 4-nitro-2-ethoxycinnamate 12-5 from step 4 (303 mg, 1.206 mmol), was dissolved in concentrated sulfuric acid (3 mL) and the solution cooled to 0° C. Potassium nitrate (128 mg, 1.27 mmol) was added and the mixture stirred for 3.5 h at room temperature. After completion, the reaction mixture was poured over ice and the precipitated solid was collected by filtration. The crude product 12-6 was washed with water, dried under vacuum and used without purification in step 6 (390 mg).

Step 6:

The dinitro derivative 12-6 from step 5 (390 mg) was dissolved in THF (3 mL) and methylamine in THF (3.02 mL of a 2M solution in THF) was added. After stirring for 30 min, volatiles were removed under reduced pressure and the orange solid 12-7 used as such in step 7.

It will be apparent to the person skilled in the art that other diamine intermediates of general formula IV in Schemes 2 and 3 above, where $R^8$ is other than methyl, may be prepared by replacing methylamine ($CH_3NH_2$) in step 6 above with the appropriate $R^8$—$NH_2$.

Step 7:

The nitro arene 12-7 from step 6 was suspended in a mixture of EtOH (12 mL) and water (12 mL) and $K_2CO_3$ (1.00 g, 6 equivalents) was added followed by sodium hydrosulfite (1.26 g, 6 equivalents). The mixture was stirred for 4 h at room temperature and EtOH was removed under reduced pressure. The residue was extracted with EtOAc and the organic phase washed with brine and dried ($MgSO_4$). Removal of the solvent and purification of the residue by flash chromatography (50 to 75% EtOAc in hexane) gave (E)-3-(5-amino-2-ethoxy-4-(methylamino)phenyl)acrylic acid methyl ester 12-8 (162 mg).

(E)-3-(5-Amino-2-ethoxy-4-(methylamino)phenyl) acrylic acid methyl ester 12-8 may be converted to amine intermediates of general formula III in Example 1 using the procedures described in Examples 3 or 7 and further elaborated to inhibitors of general formula I in Scheme 1 using the procedure of Example 4.

It will also be apparent to one skilled in the art that inhibitors of general formula I in Scheme I wherein $R^6$ is —$OCH_3$ and $R^5$ is —CH=C($R^{50}$)—COOR may be prepared using the procedure of Example 12 but starting from a precursor identical to compound 12-1, except wherein the ethoxy group has been replaced with a methoxy group.

Example 13

4-Amino-2-methoxy-5-(methylamino)benzoic acid methyl ester

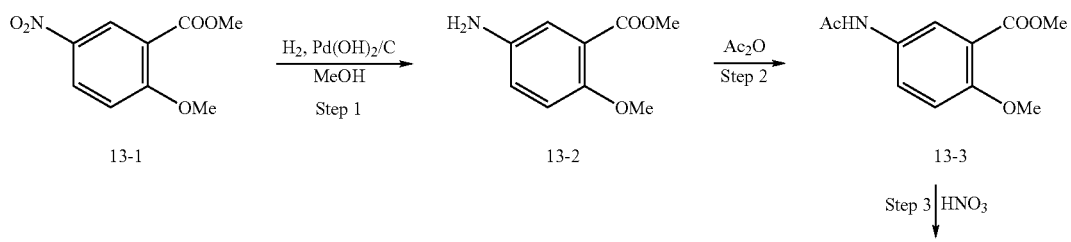

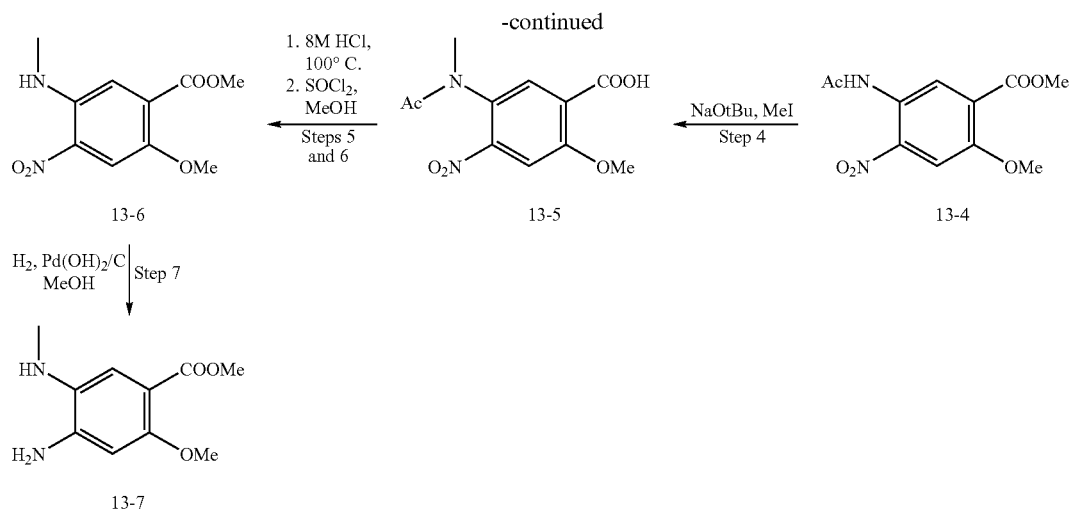

Step 1:

Methyl 2-methoxy-5-nitrobenzoate 13-1 (6.21 g, 29.4 mmol) was suspended in MeOH (100 mL) and 20% Pd(OH)$_2$/C (500 mg) was added. The mixture was stirred under a hydrogen atmosphere (1 atm) for 18 h. The catalyst was removed by filtration and the solvent evaporated under reduced pressure to give a residue of compound 13-2 (5.256 g), which was used as such in step 2.

Step 2:

The aniline 13-2 from step 1 (5.23 g) was dissolved in THF (50 mL) and acetic anhydride (2.984 g) was added. The mixture was stirred overnight at room temperature. The white suspension was concentrated under reduced pressure to a white paste, tert-butylmethyl ether (TBME, 20 mL) was added and while stirring, hexane (100 mL) was added slowly. The suspension was then stirred for an additional 2 h and the solid collected by filtration. The product 13-3 was washed with hexane and dried in air (6.372 g).

Step 3:

90% Nitric acid (9 mL) was diluted with water (9 mL) and cooled to 0° C. The anilide 13-3 from step 2 (5.905 g) was added in one portion and the mixture stirred for 30 min in the ice-water bath. The reaction mixture was then added dropwise to ice-water (700 mL) and the precipitated yellow solid was collected by filtration, washed with water and dried in air. The orange solid (5.907 g) was shown by $^1$H NMR to consist of a 2:1 mixture of compounds. Extraction of the aqueous filtrate from above with EtOAc gave an additional 1 g of material that was combined with the first crop and purified by flash chromatography on silica gel using 015% EtOAc in CHCl$_3$ as eluent. An orange solid 13-4 (4.11 g) was obtained (one isomer).

Step 4:

The nitroanilide 13-4 from step 3 (3.580 g) was dissolved in THF (50 mL) and the solution cooled in ice. Iodomethane (4.155 mL, 66.7 mmol, 5 equivalents) and sodium tert-butoxide (6.414 g, 66.7 mmol, 5 equivalents) were added in two portions at a 3.5 h interval. Stirring at room temperature was continued for an additional 20 h after the second addition. THF was evaporated under reduced pressure and water (100 mL) was added. The deep red solution was washed with TBME (100 mL). The aqueous phase was acidified with conc. HCl and extracted with EtOAc (2×100 mL). The combined organic extracts were dried and concentrated to give compound 13-5 as a dark red powder (3.78 g) that was used directly in step 5.

It will be apparent to the person skilled in the art that other diamine intermediates of general formula IV in Schemes 2 and 3 above, wherein R$^8$ is other than methyl, may be prepared by replacing methyl iodide (CH$_3$I) in step 4 above with the appropriate R$^8$—X, wherein X is a leaving group such as Cl, Br, I, methanesulfonate (mesylate), p-toluenesulfonate (tosylate), trifluoromethanesulfonate (triflate), and the like.

Step 5:

The free carboxylic acid 13-5 from step 4 (3.75 g) was suspended in 8M HCl (100 mL) and the mixture stirred at 100° C. for 8 h. After cooling to room temperature, volatiles were evaporated under vacuum and the residue was co-evaporated 3 times with MeOH.

Step 6:

The residue from step 5 was suspended again in MeOH (100 mL) and cooled in ice-water. Thionyl chloride (5.10 mL, 5 equivalents) was added dropwise and the suspension stirred at 65° C. for 4 h. Volatiles were removed under reduced pressure and the residue 13-6 co-evaporated twice with MeOH (100 mL) and then toluene (2×100 mL).

Step 7:

The residue 13-6 from step 6 was then dissolved in MeOH (200 mL), 20% Pd(OH)$_2$/C (500 mg) was added and the mixture stirred overnight under 1 atm of hydrogen gas. The catalyst was then removed by filtration and the solution evaporated to dryness. The residue was dissolved in EtOAc and the solution washed with aqueous NaHCO$_3$ and dried (MgSO$_4$). Removal of solvents gave a solid that was suspended in TBME (50 mL) and heated to 60° C. for 30 min. An equal volume of hexane was then slowly added to the hot solution and the precipitated 4-amino-2-methoxy-5-(methylamino)benzoic acid methyl ester 13-7 was collected by filtration, washed with TBME-hexane and dried (2.00 g).

4-Amino-2-methoxy-5-(methylamino)benzoic acid methyl ester 13-7 may be converted into the corresponding amine intermediates of general formula III in Scheme 1 following the procedures of Examples 3 or 7. These amine intermediates may be further converted into amine intermediates of general formula III in Scheme 1, wherein $R^5$ is —$OCH_3$ and $R^6$ is —CH=C($R^{50}$)—COOR, by following the procedure of Example 8. All these amine intermediates of general formula III in Scheme 1 may be further elaborated to inhibitors of general formula I in Scheme 1 using the procedure of Example 4.

It will be apparent to one skilled in the art that the procedure of Example 13 may be applied to compound 12-2 from Example 12, or to its analogue wherein the ethoxy group has been replaced by a methoxy group, to produce diamine precursors of general formula IV in Scheme 2 or 3, wherein $R^6$ is $OCH_3$ or OEt. Such diamine precursors may also be converted to amine intermediates of general formula III in Scheme 1 following the procedures of Examples 3 or 7, and further elaborated to inhibitors of general formula I in Scheme 1, using the procedure of Example 4.

Example 14

$N^2$-Methyl-4-(1H-[1,2,3]triazol-4-yl)benzene-1,2-diamine

It will be apparent to the person skilled in the art that other diamine intermediates of general formula IV in Schemes 2 and 3 above, where $R^8$ is other than methyl, may be prepared by replacing methylamine ($CH_3NH_2$) in step 1 above with the appropriate $R^8$—$NH_2$.

Step 2:

A solution of n-BuLi (2.5 M in THF, 14.4 mL, 36.0 mmol) in anhydrous THF (60 mL) was added slowly to a solution of TMS-diazomethane (10% in hexane, 18 mL, 36.0 mmol) at −78° C. The mixture was stirred at −78° C. for 30 min, before a solution of the methylamino intermediate 14-1 from step 1 (2.16 g, 12.0 mmol, dissolved in 2 mL THF) was added slowly. The reaction mixture was stirred at −78° C. for 1 h, and then allowed to warm up to RT and to stir for an additional 3 h before quenching by addition of $H_2O$. The crude mixture was partitioned between saturated aqueous $NaHCO_3$ (30 mL) and EtOAc (60 mL), the aqueous layer was extracted again with EtOAc (2×60 mL) and the combined organic layers were washed with brine, dried over anhydrous $MgSO_4$ and concentrated to dryness. The residue was purified by flash column

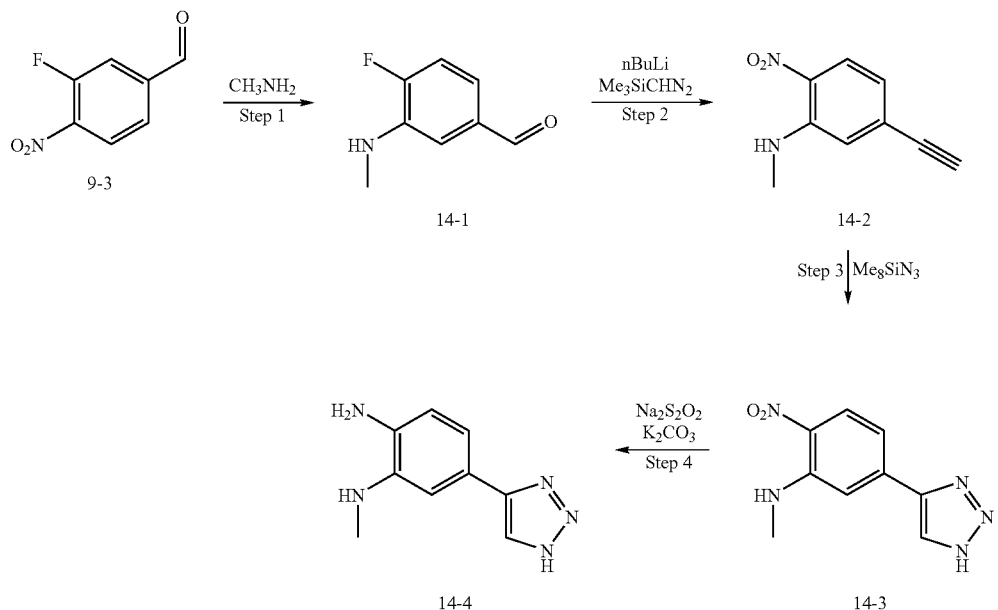

chromatography (using 20% EtOAc in hexane as the eluent) to give the desired alkyne 14-2 as a light brown solid (445 mg, ~21% yield).

Step 3:

In a thick-walled pressure tube, the alkyne 14-2 from step 2 (260 mg, 1.48 mmol) was dissolved in dry DMSO (6.0 mL) and TMS-azide (0.392 mL, 2.96 mmol) was added. The reaction was heated to 140° C. for 2 h, then cooled and extracted with EtOAc (50 mL) and washed with brine (2×50 mL). The organic layer was dried over anhydrous $MgSO_4$ and evaporated to obtain the crude triazole 14-3 as a yellow-brown solid which was used in step 4 without further purification.

Step 1:

3-Fluoro-4-nitrobenzaldehyde 9-3 from Example 9 (2.0 g, 11.8 mmol) was dissolved in THF (30 mL) and excess methylamine (2M in THF, ~21 mL, 42 mmol) was added. The reaction mixture was stirred at RT until complete conversion was confirmed by HPLC (~2-3 h). The turbid solution was then evaporated to an orange solid which was extracted with ethyl acetate (2×50 mL) and washed with 1 N HCl (shaken until the deep burgundy colour dissipated; 100 mL), water (100 mL) and brine (60 mL). The combined extracts were dried over anhydrous $MgSO_4$ and evaporated to give the methylamino intermediate 14-1 as an orange powder which was used in step 2 without any purification.

Step 4:

The crude triazole intermediate 14-3 from step 3 (~1.10 mmol) was dissolved in EtOH (10 mL) and H$_2$O (6 mL) which resulted in some precipitation of the starting material, K$_2$CO$_3$ (0.91 g, 6.58 mmol) and sodium hydrosulfite (1.15 g, 6.58 mmol) were added and the reaction mixture was stirred for 2 h at RT. The reaction mixture was then extracted with EtOAc (50 mL), the organic layer was washed with H$_2$O (50 mL) and brine (30 mL), dried over anhydrous MgSO$_4$ and evaporated to a brown gum which contained N$^2$-methyl-4-(1H-[1,2,3]triazol-4-yl)benzene-1,2-diamine 14-4 (amongst other minor products).

The crude N$^2$-methyl-4-(1H-[1,2,3]triazol-4-yl)benzene-1,2-diamine may be converted, without further purification, into the corresponding amine intermediates of general formula III in Scheme 1 following the procedures of Examples 3 or 7, and further elaborated to inhibitors of general formula I in Scheme 1, using the procedure of Example 4.

Example 15

N$^2$-Methyl-4-(4-methylpiperazin-1-yl)benzene-1,2-diamine

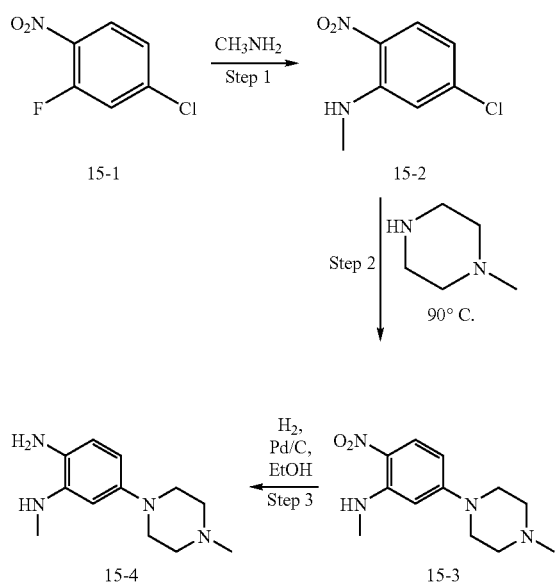

Step 1:

To a solution of 4-chloro-2-fluoro-1-nitrobenzene 15-1 (1.18 g, 6.72 mmol) in DMSO (7 mL), a solution of methylamine (2M in THF, 13.6 mL, 26.9 mmol) was added and the reaction mixture was stirred at RT for 24 h. The solution was diluted with EtOAc (~300 mL), the organic layer was washed with H$_2$O (3×50 mL) and brine (50 mL), dried over anhydrous MgSO$_4$ and concentrated under vacuum to give the methylamino derivative 15-2 as a yellow solid (1.19 g). The crude material was used in step 2 without purification.

It will be apparent to the person skilled in the art that other diamine intermediates of general formula IV in Schemes 2 and 3 above, where R$^8$ is other than methyl, may be prepared by replacing methylamine (CH$_3$NH$_2$) in step 1 above with the appropriate R$^8$—NH$_2$.

Step 2:

A mixture of the methylamino derivative 15-2 from step 1 (105 mg, 0.56 mmol) and N-methylpiperazine (0.5 mL) was heated to 90° C. while stirring for 3 h and then at RT for an additional 15 h. The reaction mixture was diluted with EtOAc (~50 mL) and the organic layer was washed with H$_2$O (3×10 mL) and brine (20 mL), dried over anhydrous MgSO$_4$ and concentrated under vacuum to give the piperazine derivative 15-3 as a yellow solid (140 mg) which was used in step 3 without purification.

One skilled in the art will readily see that piperazine derivatives bearing other substituents may be readily used in place of N-methylpiperazine in Step 2 above to prepare intermediates leading to other compounds of formula (I).

Step 3:

To a solution of the piperazine derivative 15-3 from step 2 (140 mg) in EtOH (6 mL), Pd/C (10%, 25 mg) was added and the mixture was stirred under an atmosphere of H$_2$ at RT for 15 h. The reaction mixture was filtered and the solvent evaporated to give a fairly pure sample of the desired product, N$^2$-methyl-4-(4-methylpiperazin-1-yl)benzene-1,2-diamine 15-4, as a purple colored oil (133 mg).

N$^2$-Methyl-4-(4-methylpiperazin-1-yl)benzene-1,2-diamine 15-4 was converted, without further purification, into the corresponding amine intermediates of general formula III in Scheme 1 following the procedures of Examples 3 or 7, and further elaborated to inhibitors of general formula I in Scheme 1, using the procedure of Example 4.

Example 16

4-Imidazol-1-yl-N$^2$-methylbenzene-1,2-diamine

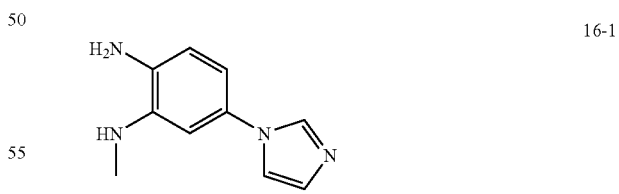

4-Imidazol-1-yl-N$^2$-methylbenzene-1,2-diamine 16-1 was prepared using the procedure of Example 15, except that imidazole was used instead of N-methylpiperazine in step 2. 4-Imidazol-1-yl-N$^2$-methylbenzene-1,2-diamine 16-1 may be converted into the corresponding amine intermediates of general formula III in Scheme 1 following the procedures of Examples 3 or 7, and further elaborated to inhibitors of general formula I in Scheme 1, using the procedure of Example 4.

Example 17

4-(2-Aminothiazol-4-yl)-N$^1$-methylbenzene-1,2-diamine

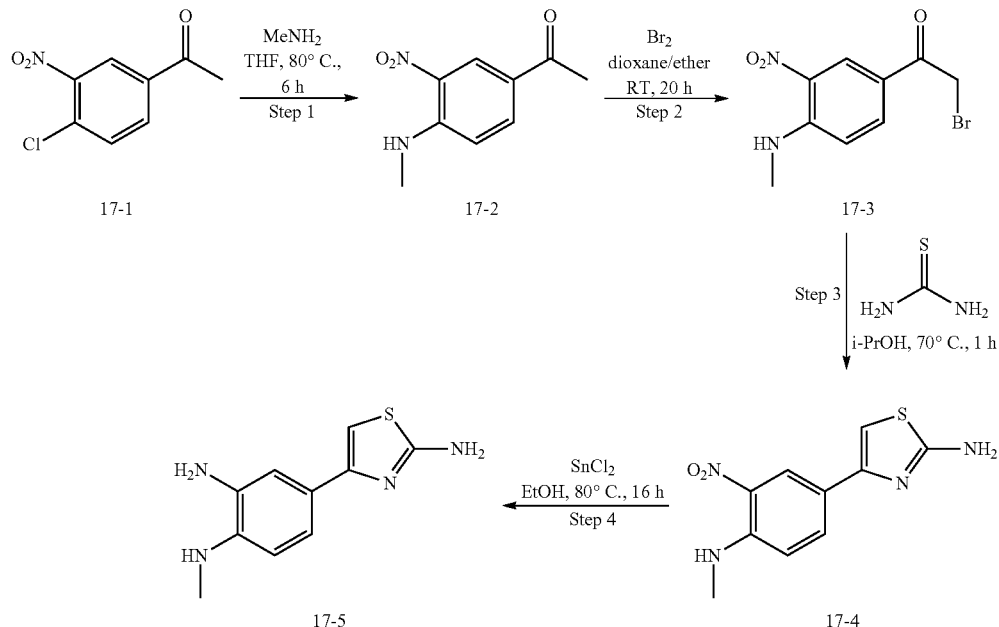

Step 1:

A mixture of 4-chloro-3-nitroacetophenone 17-1 (3.00 g, 15.0 mmol) and methylamine (15.0 mL, 2M in THF, 30.0 mmol) were placed in a sealed pressure tube and stirred at 80° C. for 6 h and at RT for 20 h. The reaction mixture was concentrated to dryness and the residue was purified by flash column chromatography (using 20-30% hexane in EtOAc) to isolate the desired pure product 17-2 as an orange solid (980 mg, 34% yield).

It will be apparent to the person skilled in the art that other diamine intermediates of general formula IV in Schemes 2 and 3 above, where R$^8$ is other than methyl, may be prepared by replacing methylamine (CH$_3$NH$_2$) in step 1 above with the appropriate R$^8$—NH$_2$.

Step 2:

To a solution of the 4-methylamino-3-nitroacetophenone intermediate 17-2 from step 1 (700 mg, 3.6 mmol) in dioxane:ether (10 mL, 1:1 ratio), Br$_2$ (0.20 mL, 3.96 mmol) was added slowly and the reaction mixture was stirred at RT for 20 h. The reaction mixture was concentrated to dryness and the residue was re-dissolved in EtOAc (200 mL). The solution was washed with saturated aqueous NaHCO$_3$ (2×100 mL) and brine (100 mL), dried over anhydrous MgSO$_4$ and concentrated to dryness to give the crude bromoketone intermediate 17-3 (1.0 g) which was used in step 3 without purification.

Step 3:

A solution of the bromoketone intermediate 17-3 from step 2 (1.0 g) and thiourea (548 mg, 7.2 mmol) in i-PrOH (30 mL) was stirred at 70° C. for 1 h. The mixture was cooled to RT, and the precipitate formed was filtered, washed with diethyl ether and dried to give the desired aminothiazole intermediate 17-4 as an orange solid (~1.0 g). This compound was used in step 4 without purification.

Step 4:

A solution of the nitro intermediate 17-4 from step 3 (500 mg, ~2 mmol) and SnCl$_2$ dihydrate (2.25 g, 10 mmol) in EtOH (15 mL) was stirred at 80° C. for 16 h. The mixture was poured slowly on NaHCO$_3$ and stirred vigorously for 30 min. The mixture was extracted with CH$_2$Cl$_2$ (2×200 mL) and the combined organic layers were dried over anhydrous Na$_2$SO$_4$ and concentrated to dryness. The residue was purified by flash column chromatography (using a solvent gradient from 30% hexane in EtOAc to 100% EtOAc and then to 3% MeOH in EtOAc) to recover some unreacted starting material and the pure diamine product, 4-(2-aminothiazol-4-yl)-N$^1$-methylbenzene-1,2-diamine 17-5, (167 mg, 38% yield).

4-(2-Aminothiazol-4-yl)-N$^1$-methylbenzene-1,2-diamine 17-5 was converted into the corresponding amine intermediates of general formula III in Scheme 1 following the procedures of Examples 3 or 7, and further elaborated to inhibitors of general formula I in Scheme 1, using the procedure of Example 4.

The free amino moiety of the aminothiazole substituent of an inhibitor of general formula I in Scheme 1, or a suitable intermediate in its preparation, may be alkylated by using procedures well known to those skilled in the art, or acetylated by using procedures well known to those skilled in the art, such as treatment with acetic anhydride, acetyl chloride, or the like. Alternatively, replacing thiourea in step 3 above with a suitably N-substituted thiourea will give intermediates wherein the free amino moiety has been substituted.

Example 18
4-Amino-2-(9H-fluoren-9-ylmethoxycarbony-lamino)-5-(methylamino)benzoic acid methyl ester
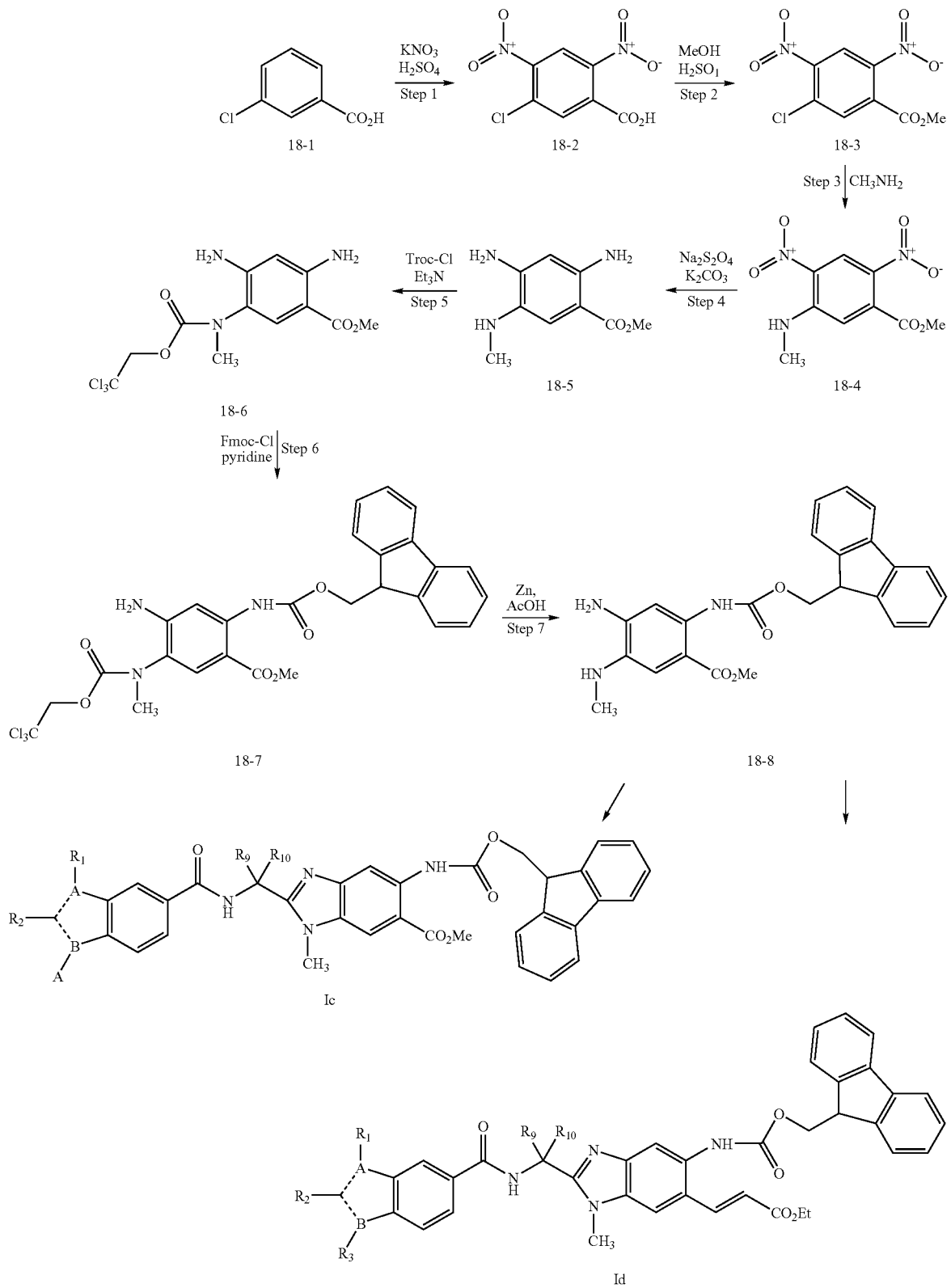

Step 1:

To a solution of m-chlorobenzoic acid 18-1 (12.5 g, 79.8 mmol) in sulfuric acid (100 mL) at 40° C., potassium nitrate (approximately half of the total amount; 22.0 g, 218 mmol) was added slowly, portion-wise, with stirring, (temperature maintained below 70° C.). The solution was then heated slowly to 105° C., the remaining $KNO_3$ was slowly added (temperature maintained below 110° C.), and finally the solution was heated to 130° C. for 15 min, allowed to cool back to RT, and poured on ice (~500 mL). The yellow solid formed was filtered, washed with water (50 mL), air dried for 2 h to yield 13.25 g (67%) of a 2:1 mixture of the desired product 18-2 and an unknown side-product. The mixture was used as such in step 2.

Step 2:

The crude dinitro carboxylic acid 18-2 (~13 g) from step 1 was dissolved in methanol (100 mL) and sulfuric acid (13.0 mL) was added very slowly as the reaction is very exothermic. The reaction mixture was stirred at reflux for 18 h. The solution was poured on ice (~500 mL), and the product was extracted with EtOAc (2×100 mL). The organic layers were washed with 5% aqueous $NaHCO_3$ (3×100 mL), dried over anhydrous $MgSO_4$ and evaporated to give the desired dinitro methyl ester intermediate 18-3 (9.54 g, 69% yield).

Step 3:

To a solution of the above dinitro arylchloride 18-3 (9.5 g, 36.5 mmol) in DMF (20 mL) at 0°, methylamine (2M in THF, 39.2 mL, 74.7 mmol) was added with stirring. After a few minutes a crystalline solid was formed, the suspension was allowed to warm-up to RT and stirring was continued for 2 h. The reaction mixture was partitioned between $H_2O$ (200 mL) and EtOAc (100 mL). The organic solution was washed with 5% aqueous $NaHCO_3$ (100 mL), brine (3×100 mL), dried over anhydrous $MgSO_4$ and the solvent was evaporated to dryness to give the desired product 18-4 as a yellow-orange solid (7.09 g, 76% yield).

It will be apparent to the person skilled in the art that other diamine intermediates of general formula IV in Schemes 2 and 3 above, where $R^8$ is other than methyl, may be prepared by replacing methylamine ($CH_3NH_2$) in step 3 above with the appropriate $R^8$—$NH_2$.

Step 4:

To a EtOH/$H_2O$ (100 mL, 1:1 ratio) suspension of the above dinitro aniline intermediate 18-4, $K_2CO_3$ (10.3 g, 74.5 mmol) was added with vigourous stirring, followed by the portion-wise addition of sodium hydrosulfite (13.0 g, 74.5 mmol). The yellow suspension turned blood red then black, became more homogeneous (slightly exothermic), then biphasic and a white precipitate was formed. After 30 minutes of stirring at RT, the EtOH was partly evaporated and the residue was diluted with $H_2O$ (100 mL). The reaction mixture was extracted with EtOAc (2×75 mL), the combined organic layers were dried over anhydrous $MgSO_4$ and evaporated to yield a black amorphous solid 18-5 (1.26 g, 55%) which was used as such in step 5.

Step 5:

To a stirred, ice cold solution of the above trianiline 18-5 (400 mg, 2.05 mmol) in acetonitrile (5 mL) under nitrogen, triethylamine (0.57 mL) was added, followed by the dropwise addition of TrocCl (0.282 mL, 2.05 mmol). The deep purple solution was stirred and allowed to warm-up to RT over 2 h. The solvent was evaporated, the residue taken into EtOAc (30 mL), washed with 5% aqueous $NaHCO_3$ (2×20 mL) and brine (20 mL), dried over anhydrous $MgSO_4$, and the solvent evaporated to dryness. The residue was purified by flash chromatography (using TLC grade silica gel and a solvent gradient from 30% to 60% EtOAc in hexane) to give the desired product 18-6 as a beige amorphous solid (459 mg, 60% yield).

Step 6:

To a stirred solution of above Troc-protected aniline derivative 18-6 (100 mg, 0.27 mmol) in $CH_2Cl_2$ (1 mL), pyridine (0.032 mL, 0.4 mmol) followed by Fmoc-Cl (80 mg, 0.31 mmol) were added. The reaction mixture was stirred at RT for 2 h. The mixture was diluted with EtOAc (30 mL), the suspension was washed with 5% aqueous $NaHCO_3$ (2×10 mL), dried over anhydrous $MgSO_4$ and evaporated to dryness. The residue was purified by flash chromatography (using TLC grade silica gel and eluting with a solvent gradient from 20% to 30% EtOAc in hexane) to give two samples of the desired Fmoc-protected product 18-7; 47 mg of very pure product and 100 mg of slightly lower purity.

Step 7:

The doubly protected (Troc- and Fmoc-protected) trianinile derivative 18-7 (100 mg, ~0.17 mmol) was dissolved in THF (1 mL) and acetic acid (0.25 mL) followed by freshly activated zinc (20.0 mg, 0.31 mmol) were added. The reaction mixture was stirred vigorously at RT under nitrogen for 2 h. The evolution of reaction was monitored by HPLC and after 2 h only ~30% conversion was observed, therefore, more zinc (15 mg) was added and stirring was continued at 60° C. for 4 h. The reaction mixture was diluted with EtOAc (30 mL), filtered over Celite and the filtrate was cooled in an ice bath and washed with 5% aqueous $NaHCO_3$ (20 mL); care must be taken to prevent build-up of excessive pressure. The organic layer was washed with brine, dried over anhydrous $MgSO_4$, and the solvent was evaporated to give the mono-protected intermediate 4-amino-2-(9H-fluoren-9-ylmethoxycarbonylamino)-5-(methylamino)benzoic acid methyl ester 18-8 as a white crystalline solid (68 mg, 96% yield).

Compound 18-8 was converted into the corresponding Fmoc-protected amine intermediates of general formula III in Scheme 1 following the procedures of Examples 3 or 7, and further elaborated to Fmoc-protected inhibitors of general formula Ic above, using the procedure of Example 4. These Fmoc-protected inhibitors of general formula Ic, or appropriate Fmoc-protected amine intermediates in their synthesis, may also be converted to Fmoc-protected inhibitors of general formula Id above, using the procedures of steps 1, 2 and 3 of Example 8. In both cases, removal of the Fmoc protecting group may be carried out by treatment with piperidine, as is well known to one skilled in the art, and saponification of the ester group may be carried out under basic conditions (following protocols well known to those skilled in the art) to give inhibitors such as compounds 1032 (Table 1) and 3060 (Table 3). The free amine moiety of these inhibitors can be further reacted with reagents commonly known to those skilled in the art, such as isopropyl chloroformate and the like, to form inhibitors such as compound 1033 (Table 1).

Example 19

2-(5-Bromopyrimidin-2-yl)-3-cyclopentyl-1-methyl-1H-indole-6-carboxylic Acid

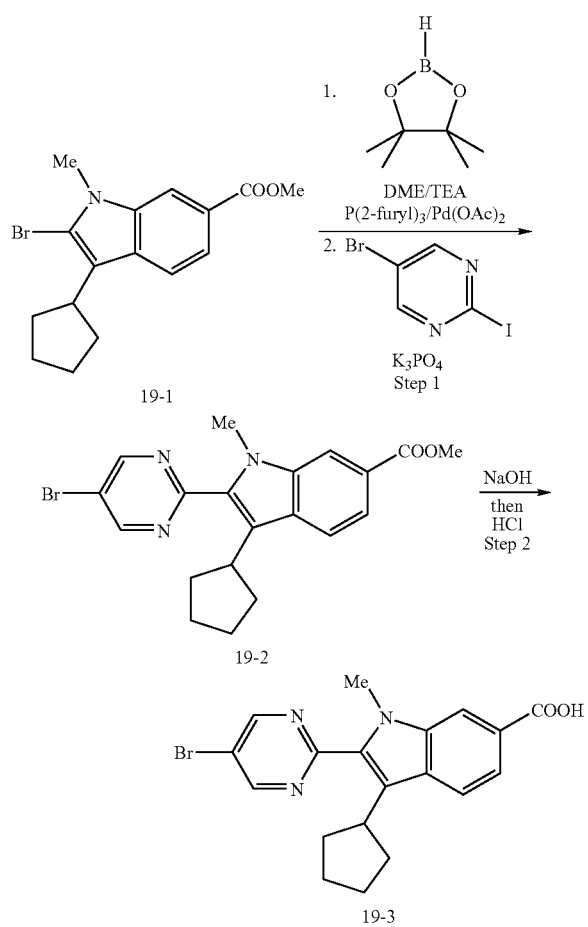

Step 1:

The bromoindole 19-1 (prepared as described in Example 12 of WO 03/010141) (3.0 g, 8.9 mmol, 1 equiv.) was dissolved in anhydrous DME (20 mL) and tri-(2-furyl)phosphine (260 mg, 1.1 mmol, 0.12 equiv.), triethylamine (3.0 mL, 21.5 mmol, 2.4 equiv.) and Pd(OAc)$_2$ (65 mg, 0.28 mmol, 0.03 equiv.) were added. The mixture was purged by bubbling Ar through it for 10 min and pinacolborane (4,4,5,5-tetramethyl-1,3,2-dioxaborolane; 3.0 mL, 20 mmol, 2.2 equiv.) was added by syringe. The resulting dark brown mixture was stirred at 68° C. for 16 h under an argon atmosphere. The reaction mixture was then cooled to RT and the 5-bromo-2-iodopyrimidine (3.0 g, 10.5 mmol, 1.18 equiv.) was added as a solid, followed by careful, slow addition of a cooled suspension of K$_3$PO$_4$ (10.5 g, 47.1 mmol, 5.4 equiv.) in water (7 mL). Alternatively, the addition of K$_3$PO$_4$ may precede the addition of 5-bromo-2-iodopyrimidine. The dark brown reaction mixture was then heated to 80° C. under argon for 24 h. The reaction mixture was cooled to RT and poured into 10% aqueous NaCl (100 mL). The brown suspension was extracted with EtOAc (150 mL). The extract was washed with water (2×50 mL) and brine (100 mL), dried and concentrated to 50 mL. Cooling 2 h in the fridge gave a beige precipitate that was collected by filtration, washed with a small amount of EtOAc and dried. The filtrate was concentrated under vacuum and the residue was slurried in acetone (20 mL), heated to boiling and cooled in the fridge overnight. The solid was filtered and the combined solids were further purified by chromatography using CHCl$_3$ as solvent to give the desired indole ester 19-2 as a beige solid in 77% yield.

Step 2:

The ester 19-2 (300 mg, 0.72 mmol) was suspended in DMSO (10 mL) and the suspension warmed gently to dissolve the solid. The slightly cloudy yellow solution was cooled and stirred while 2.5 N NaOH (2.0 mL, 5.0 mmol, 8.6 equiv.) was added and stirring was continued for 4 h at RT. The mixture was slowly poured into 0.5 N HCl (200 mL). The yellow precipitate was collected by filtration, washed with water and dried to give compound 19-3 (273 mg, 94% yield, 100% homogeneity).

Example 20

3-Cyclopentyl-1,2-dimethyl-6-indolecarboxylic Acid

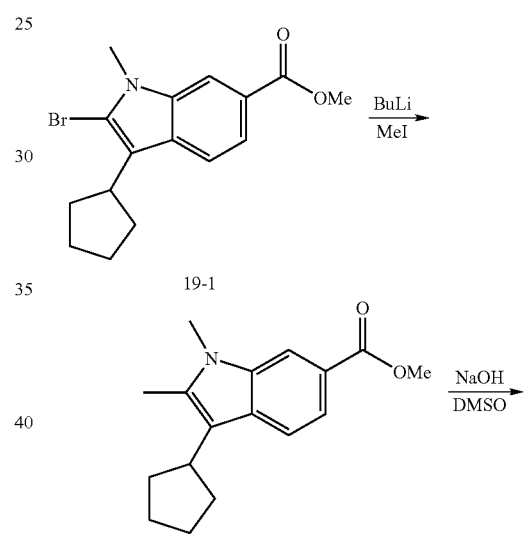

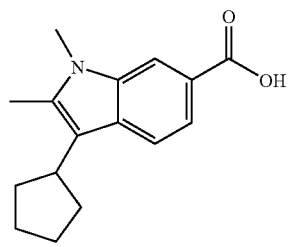

The 2-bromoindole derivative 19-1 (1.009 g, 3.00 mmol, prepared as described in Example 12 of WO 03/010141) was dissolved in anhydrous THF (25 mL) under an argon atmosphere and the solution cooled to −78° C. n-BuLi (2.0 M in hexane, 1.60 mL, 3.20 mmol) was added dropwise and the mixture stirred for 15 min. MeI (0.37 mL, 2.00 mmol) was added and stirring was continued for an additional 30 min. The reaction mixture was then warmed up to RT and volatiles removed under reduced pressure. The residue was dissolved in TBME (100 mL) and the solution washed with brine (2×25 mL). The extract was dried (MgSO₄), concentrated under reduced pressure and the residue purified by flash chromatography using 0-15% EtOAc in hexane as eluent. The desired 2-methylindole derivative 20-1 was obtained as a waxy solid (0.658 g, 80% yield): MS-ES m/z 272.1 (MH⁺). The methyl ester 20-1 was saponified in the usual way (NaOH/DMSO) to give the corresponding carboxylic acid 20-2 in 96% yield: MS-ES m/z 258.1 (MH⁺).

Example 21

3-Cyclopentyl-2-ethenyl-1-methyl-6-indolecarboxylic Acid

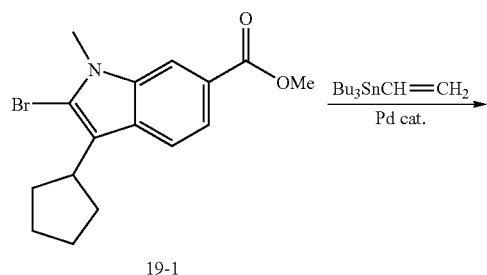

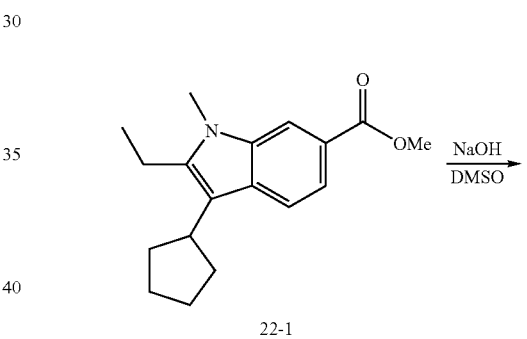

through a small pad of silica gel using THF for washings. The filtrate was concentrated under reduced pressure and the residue purified by flash chromatography using 5-15% EtOAc in hexane as eluent. The desired 2-vinylindole ester 21-1 was obtained as a brownish solid (2.92 g, 69% yield): MS-ES m/z 284.1 (MH⁺). The methyl ester 21-1 was saponified in the usual way (NaOH/DMSO) to give the corresponding carboxylic acid 21-2 in 93% yield: MS-ES m/z 270.1 (MH⁺).

Example 22

3-Cyclopentyl-2-ethyl-1-methyl-6-indolecarboxylic Acid

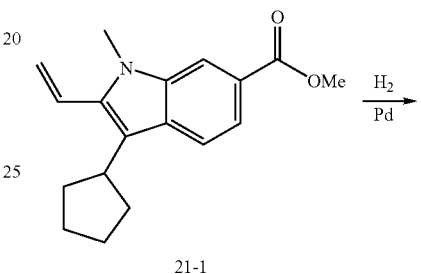

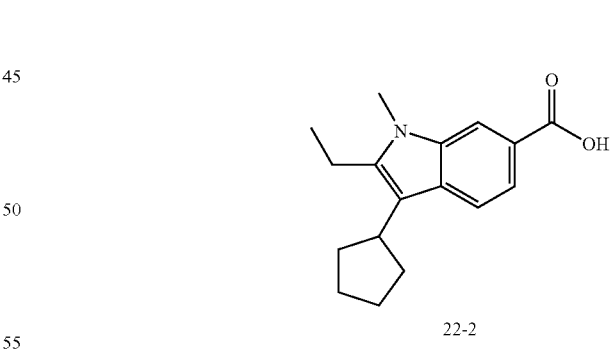

The 2-bromoindole 19-1 (prepared as described in Example 12 of WO 03/010141) (5.000 g, 14.87 mmol) was dissolved in dry dioxane (50 mL) and vinyltributyltin (4.82 mL, 16.50 mmol) was added. The solution was degassed by bubbling N₂ through for 15 min. Bis(triphenylphosphine) palladium(II) chloride (0.350 g, 0.50 mmol) was added and the mixture heated to 100° C. overnight under a nitrogen atmosphere. Additional catalyst (0.350 g, 0.50 mmol) was added and heating resumed for an additional 48 h, at which point TLC analysis indicated the reaction was almost complete. The reaction mixture was cooled to RT and filtered The 2-vinylindole ester 21-1 (Example 21) (0.250 g, 0.88 mmol) was dissolved in MeOH (15 mL) and the solution hydrogenated (1 atm H₂ gas) over 10% Pd(OH)₂/C (50 mg) for 18 h. The catalyst was then removed by filtration and the filtrate evaporated under reduced pressure to give crude ester 22-1. The residue was dissolved in DMSO and saponified with NaOH in the usual manner to give the desired 2-ethylindole derivative 22-2 as a white solid (0.211 g, 88% yield): MS-ES m/z 272.1 (MH⁺).

Example 23

3-Cyclopentyl-2-(2-propenyl)-1-methyl-6-indolecarboxylic Acid

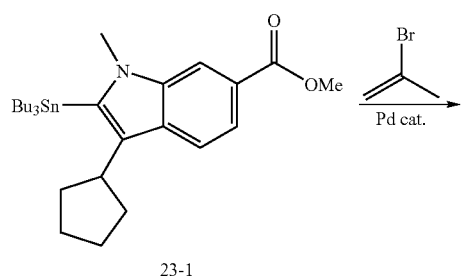

23-1

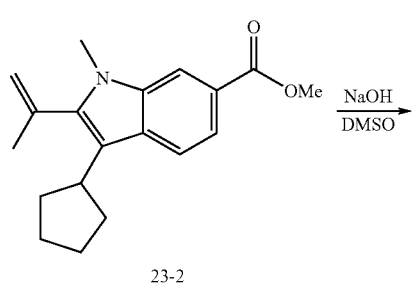

23-2

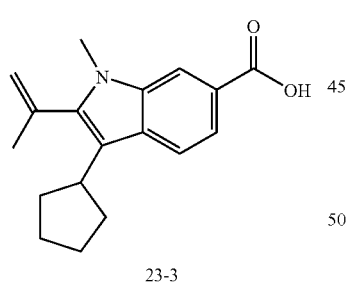

23-3

The 2-stannylindole 23-1 (1.280 g, 2.34 mmol; prepared using methods described in WO 03/010141), triphenylphosphine (0.065 g, 0.25 mmol), CuI (0.045 g, 0.24 mmol), LiCl (0.200 g, 4.72 mmol) and 2-bromopropene (0.444 mL, 5.00 mmol) were dissolved in DMF (6 mL) and the suspension degassed by bubbling Ar for 20 min. $Pd_2(dba)_3$ (0.035 g, 0.034 mmol) was added and after degassing for an additional 10 min, the reaction mixture was heated to 100° C. overnight. The suspension was then diluted with TBME (100 mL) and washed with brine (2×25 mL). The extract was dried ($MgSO_4$) and concentrated under reduced pressure to give a residue that was purified by flash chromatography using 5-10% EtOAc in hexane as eluent. The desired 2-(2-propenyl)indole 23-2 was obtained as beige solid (0.57 g, 81% yield): MS-ES m/z 298.1 ($MH^+$). The methyl ester 23-2 was saponified in the usual way (NaOH/DMSO) to give the corresponding carboxylic acid 23-3 in 96% yield: MS-ESm/z 284.1 ($MH^+$).

Example 24

3-Cyclopentyl-2-isopropyl-1-methyl-6-indole Carboxylic Acid

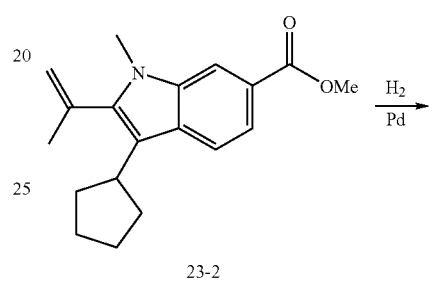

23-2

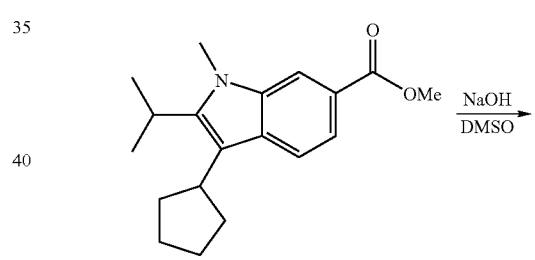

24-1

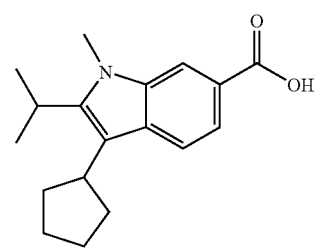

24-2

Following a similar procedure to that described in Example 22 for the 2-ethyl analog, the 2-isopropylindole derivative 24-2 was obtained as a white solid (88% yield): MS-ES m/z 286.1 ($MH^+$).

Example 25

3-Cyclopentyl-2-cyclopropyl-1-methyl-6-indolecarboxylic Acid

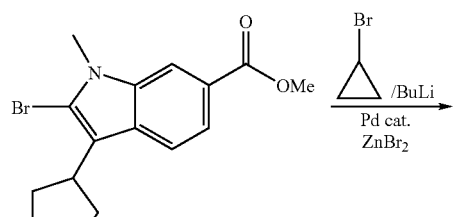

19-1

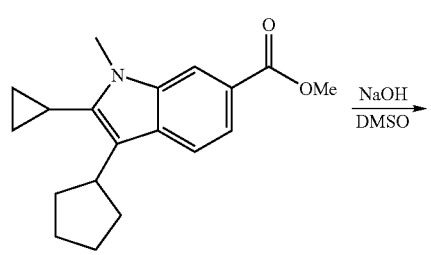

25-1

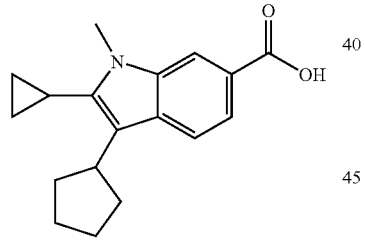

25-2

Cyclopropyl bromide (0.471 g, 3.90 mmol) was dissolved in anhydrous THF (20 mL) and the solution cooled to −78° C. under an Ar atmosphere. nBuLi (1.0 M in hexane, 3.60 mL, 3.60 mmol) was added and the mixture stirred for 15 min. ZnBr$_2$ (0.878 g, 3.90 mmol) in THF (15 mL) was then added, the mixture allowed to warm up to RT and the reaction stirred for 15 min. The 2-bromoindole 19-1 (prepared as described in Example 12 of WO 03/010141) (1.009 g, 3.00 mmol) in THF (15 mL) was added followed by tetrakis(triphenylphosphine) palladium(0) (0.289 g, 0.25 mmol). The mixture was stirred 24 h at reflux, at which point starting material was still present, but the reaction was quenched by addition of AcOH (2 mL). Volatiles were removed under reduced pressure and the residue taken up in TBME (100 mL). The extract was washed with saturated aqueous NaHCO$_3$ and dried (MgSO$_4$). Evaporation under reduced pressure gave a residue that was purified by flash chromatography using 0-15% EtOAc in hexane as eluents to give the desired 2-cyclopropylindole ester 25-1 as a light green solid (0.540 g, 60% yield): MS-ES m/z 298.1 (MH$^+$). The methyl ester 25-1 was saponified in the usual way (NaOH/DMSO) to give the corresponding carboxylic acid 25-2 in 80% yield: MS-ES m/z 284.1 (MH$^+$).

Example 26

3-Cyclopentyl-1-methyl-2-(1-pyrazolyl)-6-indolecarboxylic Acid

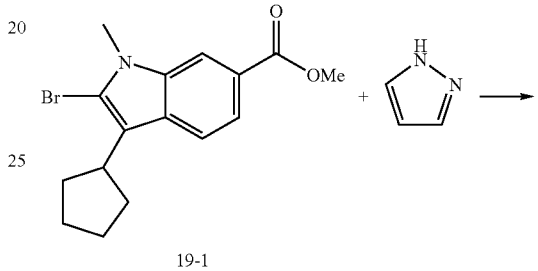

19-1

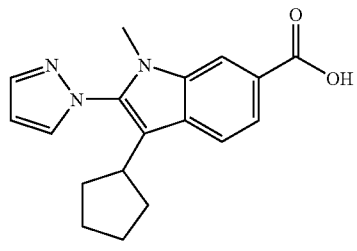

26-1

The 2-bromoindole 19-1 (prepared as described in Example 12 of WO 03/010141) (1.00 g, 2.97 mmol) and pyrazole (2.00 g, 20.4 mmol, 9.9 equiv.) were charged in a sealed tube and the mixture heated to 160° C. for 72 h. The reaction mixture was then cooled to RT and charged on a flash chromatography column. The product was eluted with 40-100% EtOAc in hexane as eluents. The recovered material (1.60 g) which was contaminated with pyrazole, was dissolved in a mixture of THF/MeOH/water and basified with 1N NaOH. Organics were then evaporated under reduced pressure and the residue treated with conc. HCl to precipitate the desired 2-pyrazolylindole carboxylic acid 26-1 (0.400 g, 43% yield).

Analogs containing other N-linked heterocyclic substituents at C-2 of the indole ring were prepared in a similar fashion, starting with nitrogen-based heterocycles such as imidazoles and triazoles.

Example 27

(E)-3-[2-(1-Aminocyclobutyl)-3-methyl-3H-benzoimidazol-5-yl]acrylic acid methyl ester

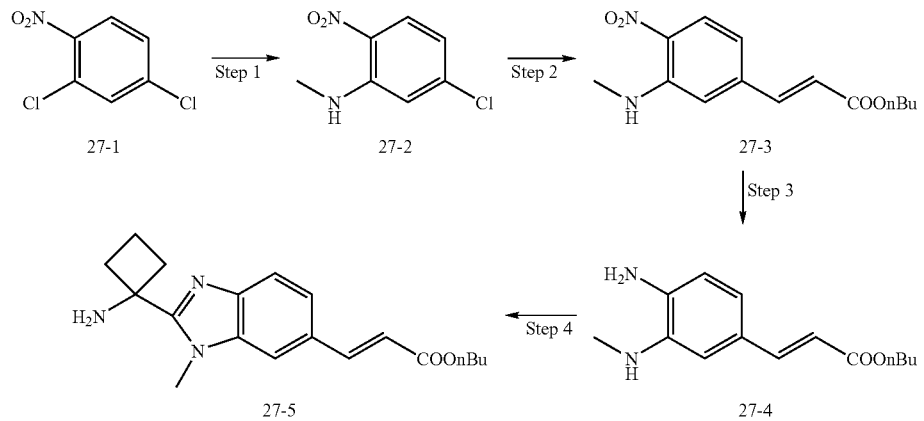

Step 1:

2,4-Dichloronitrobenzene (27-1) (61 g, 0.32 mol), triethylamine (68 mL, 0.48 mol), and 2.0 M methylamine in THF (500 mL, 1.0 mol) were mixed in a 3-L round bottom flask equipped with a Graham condenser under argon pressure. The solution was then heated at 40° C. with stirring and a white solid started to form ($Et_3NH^+Cl^-$). After heating for ~6 hrs, TLC (in 20% ethyl acetate in hexane) showed that the reaction was ~60% complete. Another two equivalents of the methylamine solution in THF (330 mL) was added and the mixture was heated at 40° C. with stirring for another 16 hours. TLC showed that all starting material was consumed. The reaction mixture was allowed to cool down to room temperature and the white solid was removed by filtration and washed thoroughly with THF. The filtrate was concentrated under reduced pressure and re-dissolved in 800 mL of dichloromethane, washed with water and brine, and dried over $Na_2SO_4$. The solvents were removed in vacuo to give compound 27-2 as an orange solid (59.5 g, quantitative), which was pure enough to use in next step.

Step 2:

To a dry pressure tube was added compound 27-2 (2.88 g, 15 mmol), $Pd_2(dba)_3$ (414 mg, 0.45 mmol), P(t-Bu)$_3$ (0.1 M solution in dioxane, 18 mL, 1.8 mmol), and N,N-dicyclohexylmethylamine (3.6 mL, 16.5 mmol) under argon atmosphere. n-Butyl acrylate (2.4 mL, 16.5 mmol) was degassed with argon for 35 minutes before being added to the mixture. The tube was then sealed and the mixture was heated at 110° C. with stirring over the weekend. The reaction was cooled to ambient temperature and diluted with ethyl acetate (200 mL). The solid residue was removed by filtration of the mixture through a silica gel pad and it was washed with ethyl acetate (700 mL). The filtrate was concentrated in vacuo and co-evaporated with hexane three times. The red solid was then stirred with hexanes (40 mL) at 60° C. The mixture was cooled to 0° C. for 15 minutes and the red solid was collected by filtration and washed with hexanes, and was further dried under high vacuum (3.4 g, 81% yield). The product 27-3 was about 90% pure by NMR. Additional product can be obtained from the filtrate by purification on flash column.

Step 3:

Compound 27-3 was converted to compound 27-4 using the method of Example 11, step 5.

Step 4:

Compound 27-4 was converted to compound 27-5 using the method of Example 3.

Example 28

(E)-3-[2-(1-Aminocyclobutyl)-7-chloro-3-methyl-3H-benzimidazol-5-yl]acrylic acid methyl ester

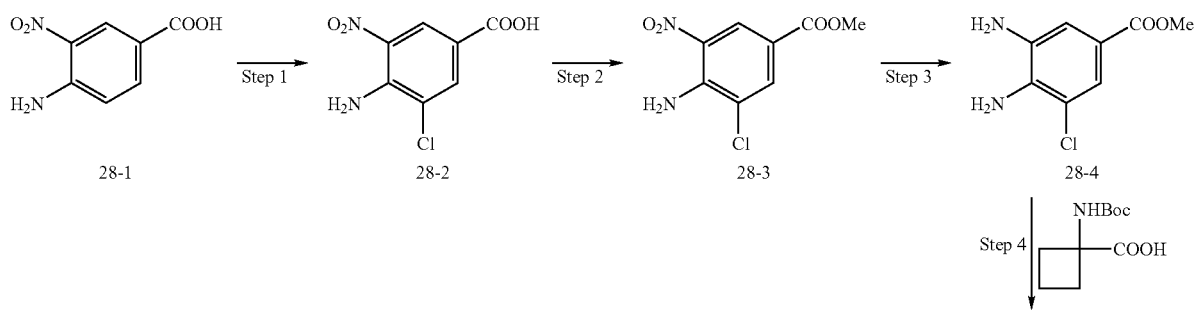

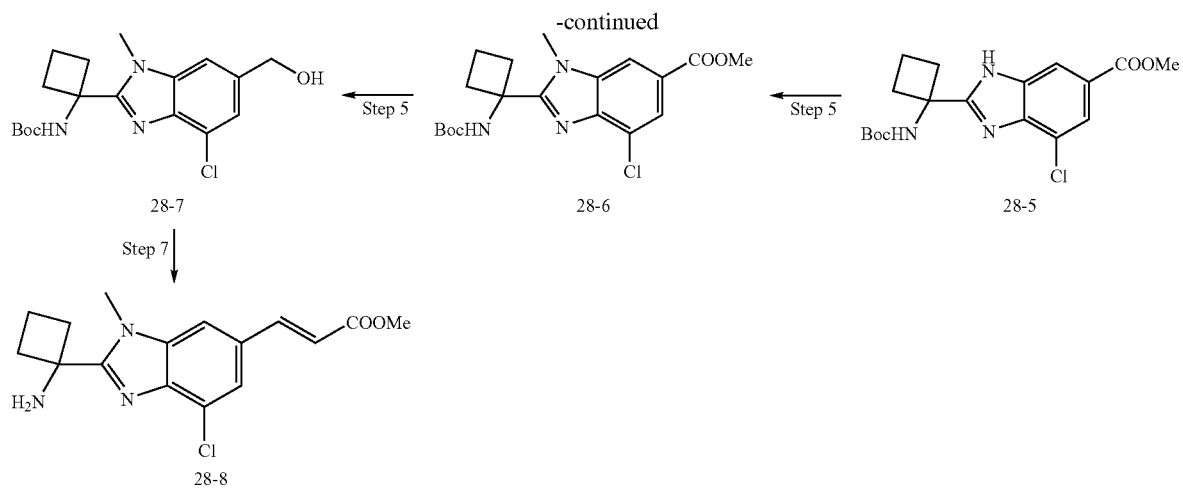

Step 1:

4-Amino-3-nitrobenzoic acid 28-1 (15.00 g, 82 mmol) was dissolved in AcOH (200 mL) and sulfuryl chloride (6.62 mL, 82 mmol) was added. The mixture was stirred for 2 h at RT, after which additional sulfuryl chloride (1.5 mL) was added to complete the reaction. After stirring for an additional 1 h at RT, the reaction mixture was poured over ice and the precipitated solid collected by filtration. The product 28-2 was washed with water, air dried and used directly in the next step.

Step 2:

The crude product 28-2 was dissolved in MeOH (300 mL) and conc. $H_2SO_4$ (1 mL) was added. The mixture was refluxed for 2 days after which point the conversion was ~75% complete. Volatiles were removed under reduced pressure and the residue was partitioned between EtOAc and water. The mixture was basified by slow addition of saturated aqueous $Na_2CO_3$ and the organic phase separated. The extract was washed with brine, dried ($Na_2SO_4$) and concentrated to give 28-3 as a beige solid (12.32 g) that was used directly in the next step.

Step 3:

The nitroaniline 28-3 (11.32 g, 49 mmol), sodium hydrosulfite (35.54 g, 204 mmol) and $NaHCO_3$ (17.15 g, 204 mmol) were dissolved in 3:2 EtOH-water (600 mL). The orange mixture was stirred for 20 h at RT. EtOH was then removed under reduced pressure and the product extracted with EtOAc. The extract was washed with water and brine, dried ($Na_2SO_4$) and evaporated to give compound 28-4 a brown solid (4.60 g, 46% yield) that was used without purification in the next step.

Step 4:

The diamine 28-4 (1.00 g, 5.0 mmol), N-Boc-1-aminocyclobutanecarboxylic acid (1.07 g, 5.0 mmol), HATU (2.20 g, 5.8 mmol) and $Et_3N$ (2.10 mL, 15.0 mmol) were dissolved in DMF (30 mL) and the mixture stirred for 2 days at RT. The reaction mixture was poured onto ice and the precipitated solid collected by filtration. The material was washed with water, dissolved in EtOAc and the extract washed with brine. The solution was then dried ($Na_2SO_4$) and concentrated under reduced pressure. The residue was dissolved in AcOH and heated to 80° C. for 3 h. HPLC analysis indicated complete conversion to the desired benzimidazole derivative. AcOH was removed under reduced pressure, the residue taken up in EtOAc and the solution washed with aqueous $NaHCO_3$ and brine. After drying ($MgSO_4$), removal of solvent gave compound 28-5 as an orange solid (563 mg) that was used directly in the next step.

Step 5:

The benzimidazole 28-5 (1.63 g, 4.29 mmol) and $K_2CO_3$ (2.96 g, 21.45 mmol) were suspended in DMF (10 mL) and iodomethane (0.27 mL, 4.30 mmol) was added. The mixture was stirred for 3 h at RT. The reaction mixture was then poured over ice and the precipitated solid was collected by filtration. The material was washed with water, dissolved in EtOAc, and the solution washed twice with 5% aqueous citric acid and brine. After drying ($MgSO_4$) and removal of volatiles under reduced pressure, compound 28-6 was obtained as a brown solid (1.44 g) that was used directly in the next step.

Step 6:

The methyl ester 28-6 (1.22 g, 3.10 mmol) was dissolved in THF (30 mL) and $LiBH_4$ (0.243 g, 11.14 mmol) was added in small portions at RT. The mixture was then stirred at 40° C. for 16 h. Since conversion was still not complete, additional $LiBH_4$ (0.100 g, 4.6 mmol) was added and the mixture stirred for an additional 3 h at 70° C. The reaction mixture was cooled to RT and the residue diluted with EtOAc. Water was carefully added and the organic phase separated. The extract was washed with water and brine, and dried ($MgSO_4$). The crude alcohol 28-7 (961 mg) was combined with other batches and purified by flash chromatography.

Step 7:

Purified alcohol 28-7 from above (0.450 g, 1.02 mmol) was dissolved in DCM (20 mL) and Dess-Martin periodinane (0.551 g, 1.30 mmol) was added. The mixture was stirred for 2 h at RT. (Carbethoxymethylene)triphenylphosphorane (0.550 g, 1.58 mmol) was then added and the mixture was refluxed for 20 h. Volatiles were then removed under reduced pressure and the residue dissolved in 1:1 TFA-DCM to effect removal of the Boc protecting group. After stirring for 1 h at RT, volatiles were removed under reduced pressure and the residue was partitioned between EtOAc and 1 N HCl. The aqueous phase containing the product was separated, neutralized with 2M $Na_2CO_3$ and extracted 2× with EtOAc. The extract was dried ($Na_2SO_4$) and concentrated to give compound 28-8 as a white foam (212 mg) that was purified by flash chromatography using 80-100% EtOAc in hexane as eluents. The desired benzimidazole fragment was obtained as a white solid (66 mg).

Example 29

5-[2-(1-Aminocyclobutyl)-3-methyl-3H-benzoimidazol-5-yl]-3H-[1,3,4]oxadiazol-2-one

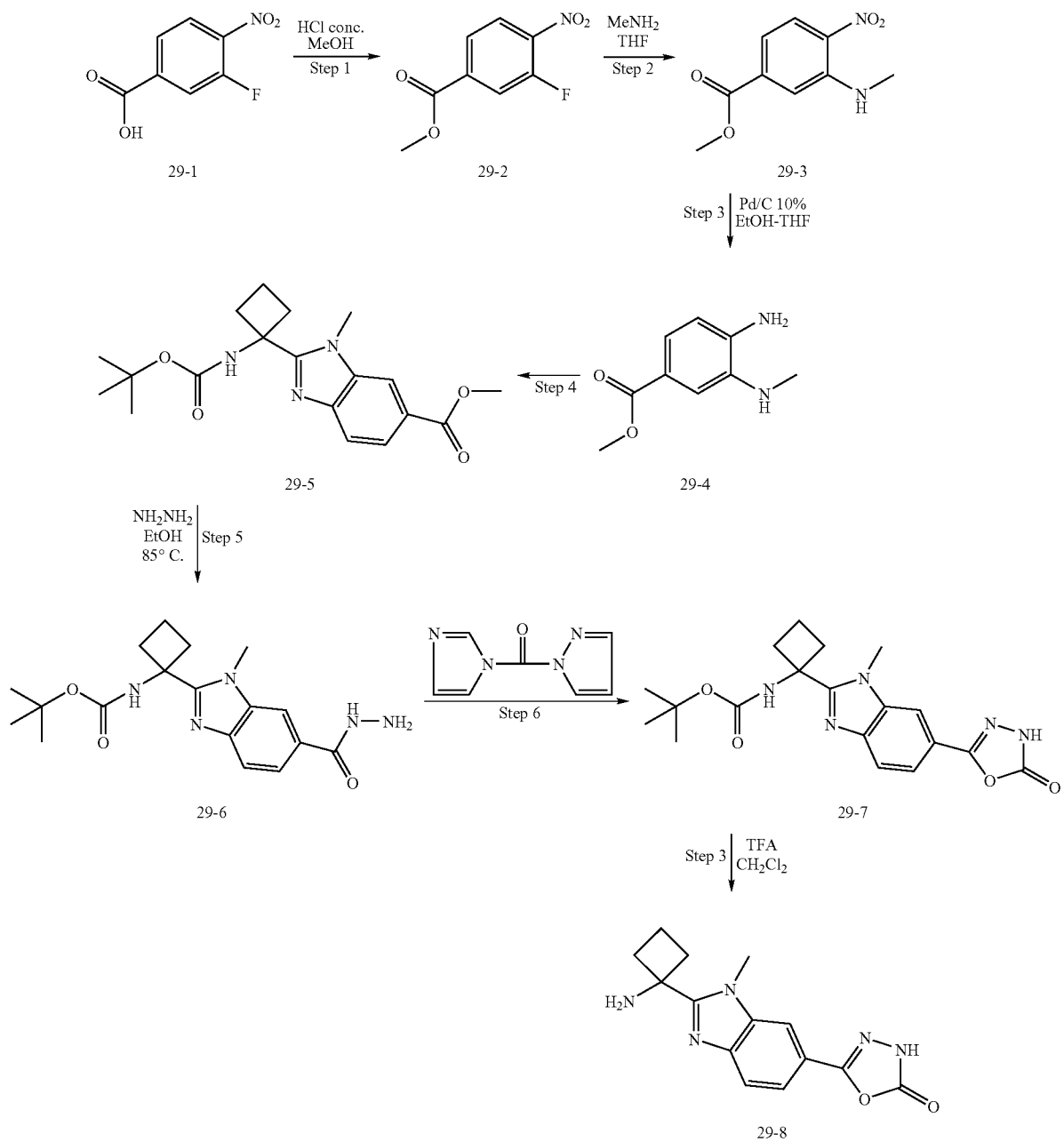

Step 1:

10N HCl (2 mL) was added to a solution of 3-fluoro-4-nitro-benzoic acid (29-1) (10 g, 54.0 mmol) in 300 mL of MeOH and the solution was refluxed for 15 h. The mixture was then concentrated, the residue was diluted with EtOAc, and the organic phase was washed with 2× water and saturated aqueous NaHCO₃, dried (MgSO₄), filtered and evaporated to give 10.45 g (97% yield) of compound 29-2 as a white solid. The compound was used as such for the next reaction.

Step 2:

Methylamine (80 mL of a 2N solution in THF) was added dropwise to a solution of compound 29-2 (10 g, 50.2 mmol) in 100 mL THF at 0° C. The mixture was further stirred at 0° C. for 20 min., then at room temperature for 15 h. The volatiles were then evaporated, and the residue was diluted with EtOAc, and the organic phase was washed with 2× water, saturated aqueous NaHCO₃, dried (MgSO₄), filtered and evaporated to give 10.21 g (96% yield) of compound 29-3 as an orange solid. The compound was used as such for the next reaction.

Step 3:

Palladium (10% on charcoal, 1 g) was added to a solution of compound 29-3 (10 g, 47.6 mmol) in 400 mL of a 1/1 mixture of THF-absolute EtOH. The mixture was stirred under hydrogen atmosphere for 16 h, then the solution was filtered to remove the catalyst and concentrated to give 8.5 g (99% yield) of compound 29-4 as an off-white solid. The compound was used as such for the next reaction.

Step 4:

Compound 29-4 was converted to compound 29-5 using the method of Example 7.

Step 5:

A mixture of compound 29-5 (730 mg, 2.03 mmol) and hydrazine monohydrate (500 µL, 10.3 mmol) in 5 mL ethanol was heated in a screw-cap vial at 85° C. for 72 h. The solution was then concentrated, diluted with $CH_2Cl_2$ and the organic layer was washed with water. The organic layer was dried ($Na_2SO_4$), filtered, and evaporated to yield 642 mg (88%) of compound 29-6 as a grey-white solid that was used as such in the following step.

Step 6:

Triethylamine (190 µL, 1.36 mmol) was added to a solution of compound 29-6 (350 mg, 0.97 mmol) and 1,1'-Carbonyl diimidazole (190 mg, 1.17 mmol) in THF (5 mL). The mixture was stirred at room temperature for 15 h. Volatiles were removed, and the residue was diluted with EtOAc, washed with water, brine, and the organic layer was dried ($Na_2SO_4$), filtered and evaporated to yield 318 mg (85% yield) of compound 29-7 as a waxy white solid that was used as such in the next step.

Step 7:

TFA (3 mL) was added dropwise to a suspension of compound 29-7 (150 mg, 0.39 mmol) in dichloromethane (10 mL) and the resulting solution was stirred for 1 h. The volatiles were evaporated to yield 150 mg (quant. yield) of the trifluoroacetate salt of the desired compound 29-8 as a beige solid.

Example 30

5-[2-(1-Aminocyclobutyl)-3-methyl-3H-benzimidazol-5-yl]-3-methyl-3H-1,3,4-oxadiazol-2-one

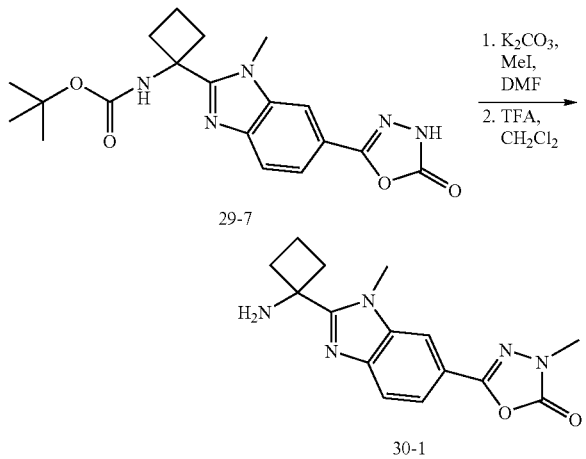

Potassium carbonate (32 mg, 0.23 mmol) was added to a solution of compound 29.7 (80 mg, 0.21 mmol) in DMF (1 mL). The suspension was stirred at room temperature for 15 min. Iodomethane (12.5 µL, 0.2 mmol) was then added and the mixture was stirred for 3 h at room temperature. The mixture was diluted with EtOAc, washed with water (3×), brine, then the organic phase was dried ($MgSO_4$), filtered and evaporated to yield 67 mg (81% yield) of a beige solid. Treatment with TFA as described in Example 29, step 7 gave 57 mg (quant. yield) of the trifluoroacetate salt of the desired compound 30-1 as a beige solid. Compound 30-1 may be coupled to indole intermediates of general formula II to give compounds of formula I, using the procedures of Examples 4 and 34, step 1.

Example 31

5-[2-(1-Aminocyclobutyl)-3-methyl-3H-benzimidazol-5-yl]-2-methyl-2H-pyrazol-3-ol

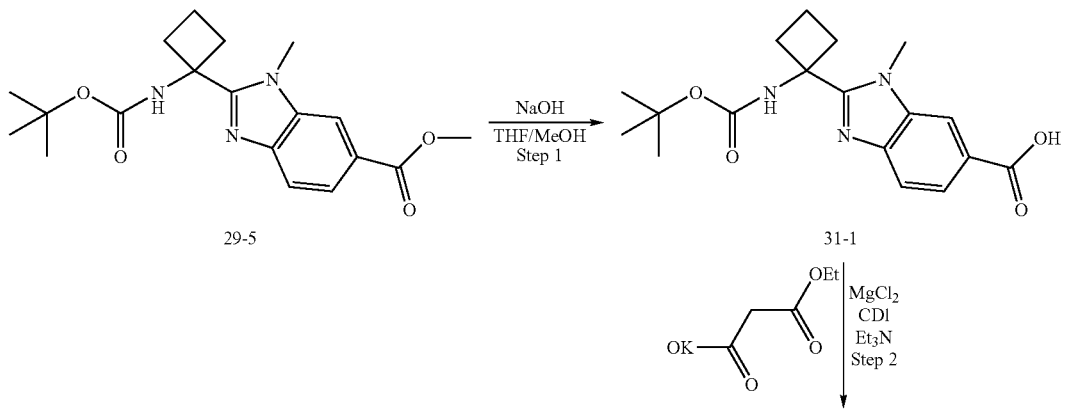

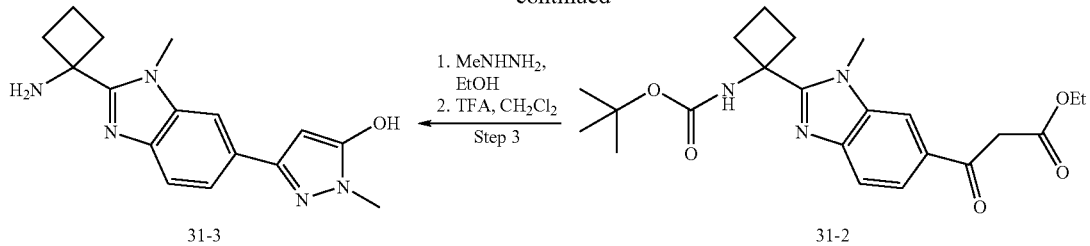

Step 1:

NaOH (10N, 11 mL, 110 mmol) was added to a solution of compound 29-5 (5.0 g, 13.9 mmol) in a 3:2:1 mixture of THF, MeOH and water (180 mL) and the solution was stirred overnight at room temperature. The mixture was then concentrated, the pH was adjusted to 4 using 1N HCl, and the mixture was extracted with EtOAc. The organic layer was washed with brine, dried (MgSO$_4$), filtered and evaporated to give compound 31-1 (3.94 g, 82% yield) as a white solid. The compound was used as such for the next reaction.

Step 2:

1,1'-carbonyldiimidazole (702 mg, 4.33 mmol) was added to a solution of compound 31-1 (1 g, 2.90 mmol) in THF (24 mL). The solution was stirred for 15 h and was then added dropwise to a solution of the malonate anion (prepared via the addition of Et$_3$N (0.81 mL, 5.80 mmol) and MgCl$_2$ (690 mg, 7.25 mmol) to a solution of potassium monoethylmalonate (1 g, 5.96 mmol) in acetonitrile (10 mL) followed by stirring at room temperature for 2.5 h) at 0° C. The resulting mixture was then warmed slowly to room temperature and stirred for a total of 48 h. The mixture was concentrated and toluene was added. The mixture was cooled to 10-15° C. and hydrolyzed slowly via the addition of 1M HCl until the pH reached 3-4. The layers were then separated and the organic layer was diluted with EtOAc, washed with water, dried and evaporated to give a yellow oil. The product was purified by flash chromatography (Eluent: Hexane:AcOEt 4:6 to give 885 mg (74% yield) of compound 31-2 as a white solid.

Step 3:

Methylhydrazine (29 µL, 0.55 mmol) was added to a solution of compound 31-2 (100 mg, 0.24 mmol) in EtOH (2.5 mL). The mixture was stirred at 80° C. for 15 hrs. The mixture was then concentrated and water was added, followed by the addition of 1N HCl to adjust the pH to 6-7. The aqueous layer was extracted 3 times with EtOAc, and the organic phase was dried (MgSO$_4$) and concentrated to give 94 mg (98% yield) of a pale yellow solid. Treatment with TFA in dichloromethane as described in Example 29, step 7, gave 93 mg (quant. yield) of the trifluoroacetate salt of compound 31-3.

Compound 31-3 may be coupled to indole intermediates of general formula II to give compounds of formula I, using the procedures of Examples 4 and 34, step 1.

Example 32

5-[2-(1-Aminocyclobutyl)-3-methyl-3H-benzimidazol-5-yl]-3H-1,3,4-thiadiazol-2-one

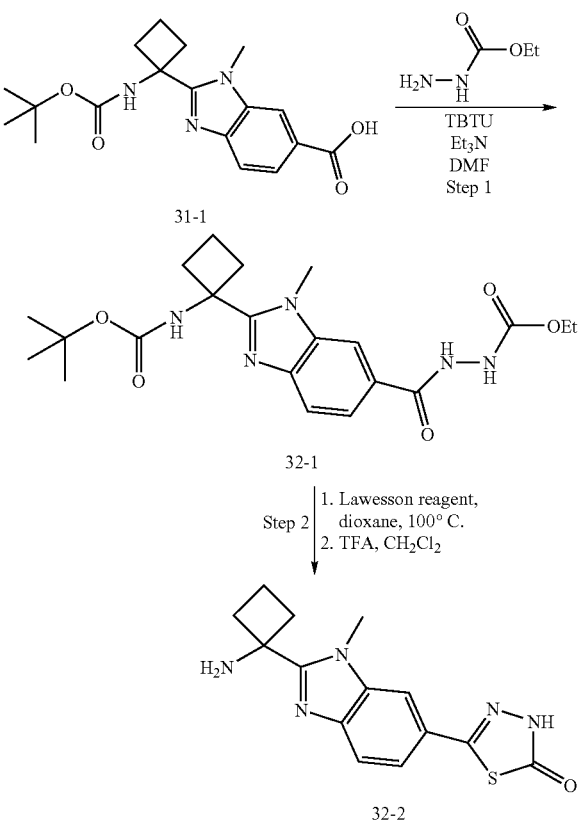

Step 1:

TBTU (380 mg, 1.18 mmol) and triethylamine (380 µL, 3802.73 mmol) were added to a solution of compound 31-1 (350 mg, 1.01 mmol) and ethyl carbazate (120 mg, 1.15 mmol) in DMF (5 mL). The mixture was stirred for 15 h at room temperature and then diluted with EtOAc. The resulting organic suspension was washed with 2× water and 1×NaHCO$_3$(aq.) sat. THF was then added to the organic layer to obtain a solution that was dried (MgSO$_4$), filtered and concentrated. The residue was triturated with EtOAc to give 290 mg (66%) of compound 32-1 as a beige solid. The compound was used as such for the next reaction.

Step 2:

Lawesson Reagent (70 mg, 0.17 mmol) was added to a solution of compound 32-1 (150 mg, 0.35 mmol) in dioxane (10 mL) at 100° C. The resulting mixture was stirred at 100° C. for 8 h. and then 140° C. for 4 h. The mixture was then cooled to 100° C., and an additional portion of Lawesson Reagent (70 mg, 0.17 mmol) was added. The solution was then heated at 100° C. for 15 h. The mixture was concentrated to dryness, and the solid residue was triturated with EtOAc, and filtered. The resulting beige solid (100 mg) was treated with TFA as described in Example 29, step 7, to give 93 mg of the trifluoroacetate salt of compound 32-2.

Compound 32-2 may be coupled to indole intermediates of general formula II to give compounds of formula I, using the procedures of Examples 4 and 34, step 1.

Example 33

[1-(1-Methyl-6-pyrimidin-2-yl-1H-benzoimidazol-2-yl)cyclobutyl]carbamic Acid tert-butyl Ester and concentrated to give a mixture of compounds 33-3 and 33-4 as an orange solid (4.8 g), which was used as is in the next step.

Step 3:

Reduction of the nitro compound 33-3 with $Na_2S_2O_4$/$K_2CO_3$ was carried out using the method described in Example 11, step 5. Compound 33-5 (1.5 g, ~20% yield over the 3 steps) was isolated from the reaction mixture after column chromatography, using a solvent gradient of EtOAc in hexanes from 17% to 25%.

Step 4:

The dianiline 33-5 was converted to compound 33-6, using the method described in Example 7.

Step 5:

Argon was bubbled through a mixture of compound 33-6 (300 mg, 0.79 mmol), lithium chloride (67 mg, 1.6 mmol), $PPh_3$ (31 mg, 0.12 mmol) and 2-tributylstannanylpyrimidine (365 mg, 0.99 mmol) in DMF (6.0 mL) for 15 minutes. $Pd(PPh_3)_4$ (91 mg, 0.079 mmol) and CuI (15 mg, 0.079

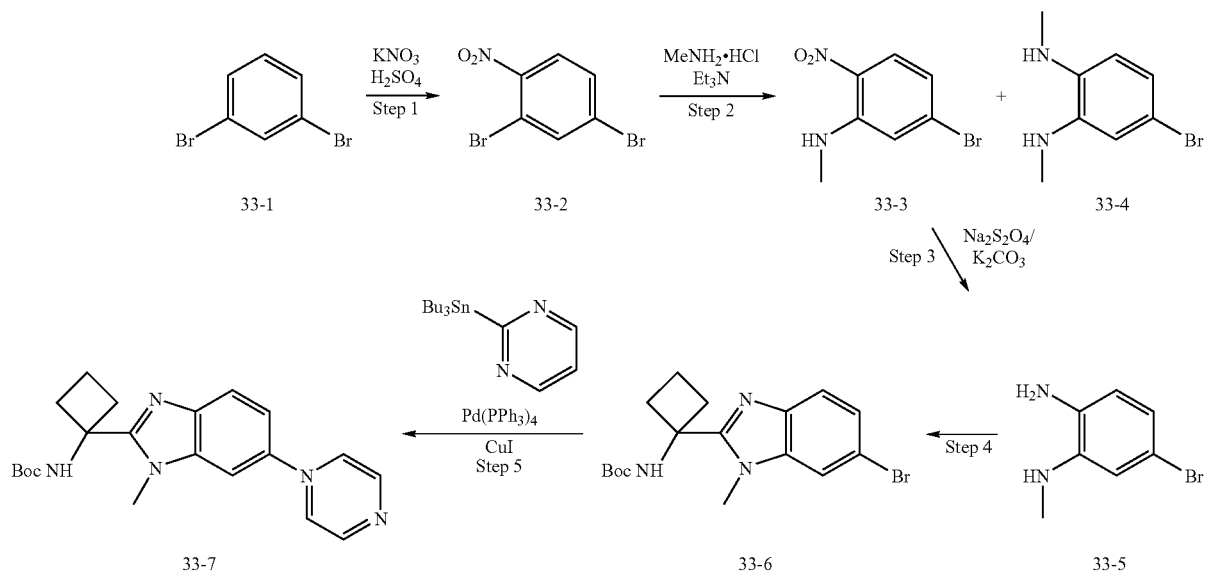

mmol) were added and the mixture was heated at 100° C. for 24 h. The mixture was diluted with EtOAc and the organic phase was washed with water and brine, then dried ($MgSO_4$) and concentrated to give a yellow oil which was purified by flash chromatography (hexane:EtOAc 3:7 to 2:8) to give compound 33-7 as a yellow solid (100 mg, 24%).

Compound 33-7 may be deprotected using standard conditions as described in Example 29, step 7, and the resulting amine coupled to indole intermediates of general formula II to give compounds of formula I, using the procedures of Examples 4 and 34, step 1.

It will be apparent to one skilled in the art that the preparation of analogous intermediates bearing similar heterocyclic or aromatic moieties can be carried out using this procedure or modifications thereof. Alternatively, the coupling reaction of Step 5 may be carried out using the conditions typical of the well-known Suzuki reaction (A. Suzuki, Pure Appl. Chem. (1994) 66, 213; N. Miyaura and A. Suzuki, Chem. Rev. (1995) 95, 2457.).

Step 1:

Commercially available 1,3-dibromobenzene 33-1 (4.1 mL, 33.9 mmol) was dissolved in concentrated sulfuric acid (35 mL) which was cooled in an ice-bath. Potassium nitrate (3.4 g, 33.9 mmol) was added slowly (in small portions) so as to maintain the internal reaction temperature below 10° C. The reaction mixture was stirred for an additional 30 min and then poured into 1 L of ice. The yellow precipitate formed (33-2) was filtered and washed with water, dried under reduced pressure and used directly in the following step.

Step 2:

A mixture of compound 33-2 (6.3 g, 22.4 mmol) and methylamine hydrochloride (3.0 g, 44.8 mmol) in DMF (50 mL) and cooled to 0° C. Triethylamine (9.4 mL, 67 mmol) was added and the mixture was allowed to stir at RT for 3.5 h, then heated at 70° C. overnight. The mixture was poured into water and the resulting precipitate was filtered. The filtrate was extracted with EtOAc (3×) and the extract was washed with water (3×) and saturated NaCl, dried ($MgSO_4$), filtered

Example 34

(E)-3-[2-(1-{[2-(5-Bromopyrimidin-2-yl)-3-cyclopentyl-1-methyl-1H-indole-6-carbonyl]-amino}-cyclobutyl)-3-methyl-3H-benzoimidazol-5-yl]-acrylic Acid

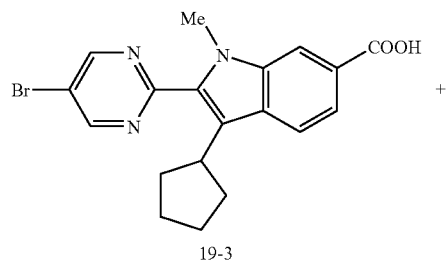

19-3

+

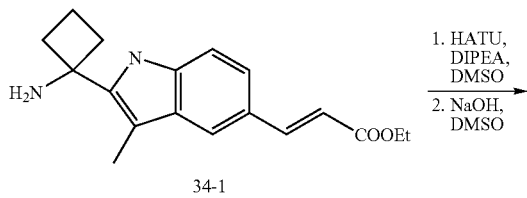

34-1

1. HATU, DIPEA, DMSO
2. NaOH, DMSO

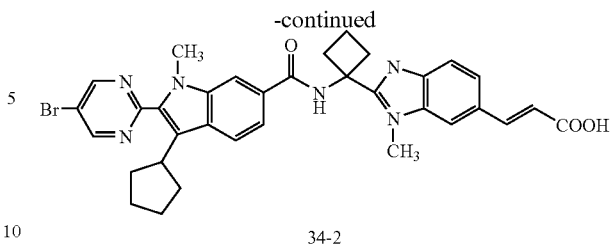

34-2

Compound 19-3 (Example 19) and compound 34-1 (prepared from compound 10-2 using the procedure of Example 3) were coupled using the method of Example 4 to give compound 34-2 (compound 3085, Table 3) as a dark yellow solid (9.3%).

$^1$H NMR (400 MHz, DMSO-$d_6$), δ 1.63 (bs, 2H), 1.80-1.95 (m, 6H), 1.95-2.10 (m, 2H), 2.70 (ddd, J=9.3 & 10.6 Hz, 2H), 2.99 (m, 2H), 3.65-3.75 (m, 1H), 3.76 (s, 3H), 3.85 (s, 3H), 6.54 (d, J=15.6 Hz, 1H), 7.52 (d, J=8.4 Hz, 1H), 7.59 (d, J=8.4 Hz, 1H), 7.64 (d, J=8.2 Hz, 1H), 7.70 (d, J=15.9 Hz, 1H), 7.74 (d, J=8.4 Hz, 1H), 7.86 (s, 1H), 8.12 (s, 1H), 9.18 (s, 2H), 9.20 (s, 1H), 12.25 (s, 1H).

Example 35

3-Cyclopentyl-1-methyl-2-pyridin-2-yl-1H-indole-6-carboxylic acid {1-[1-methyl-6-(5-oxo-4,5-dihydro-1,3,4-oxadiazol-2-yl)-1H-benzimidazol-2-yl]-cyclobutyl}-amide

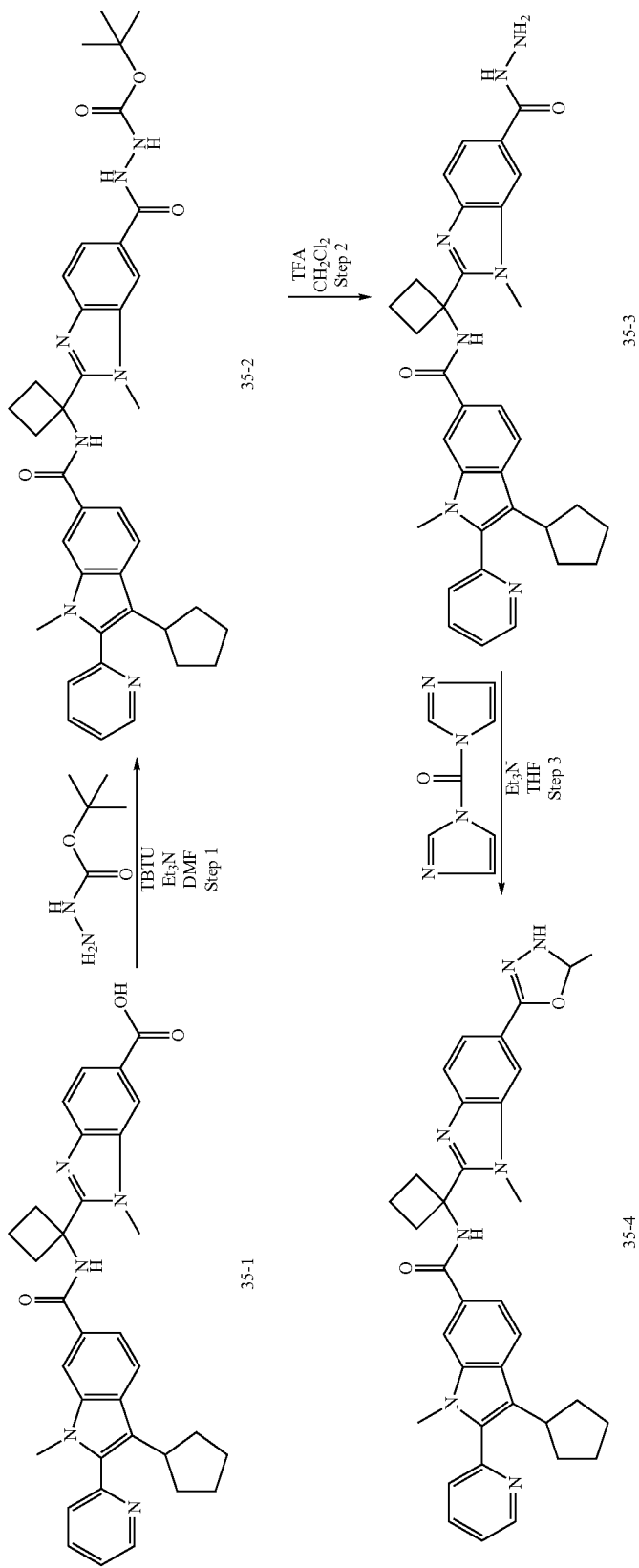

Step 1:

TBTU (350 mg, 1.09 mmol) and triethylamine (380 mL, 2.73 mmol) were added to a solution of compound 35-1 (compound 1025, Table 1) (487 mg, 0.89 mmol) and tert-butyl carbazate (130 mg, 0.98 mmol) in DMF (8 mL). The mixture was stirred for 2 h at room temperature and then diluted with EtOAc. The resulting organic suspension was washed with 2× water and 1× saturated aqueous NaHCO₃. THF was then added to the organic layer and the resulting solution was dried (MgSO₄), filtered and concentrated. The residue was triturated with EtOAc to give 421 mg (72%) of compound 35-2 as a beige solid. The compound was used as such for the next reaction.

isolate compound 35-4 (compound 1128, Table 1) as a yellow amorphous solid in >95% homogeneity (29 mg, 39% yield).

¹H NMR (400 MHz, DMSO): δ 1.54-1.68 (m, 2H), 1.79-1.93 (m, 6H), 1.94-2.05 (m, 1H), 2.09-2.21 (m, 1H), 2.75-2.85 (m, 2H), 3.05-3.25 (m, 3H), 3.69 (s, 3H), 3.90 (s, 3H), 7.49 (m, 1H), 7.57-7.72 (m, 3H), 7.82-7.92 (m, 2H), 7.94-8.02 (m, 1H), 8.06-8.15 (m, 2H), 8.78 (d, J=3.9 Hz, 1H), 9.45 (s, 1H), 12.62 (s, 1H).

Example 36

3-Cyclopentyl-1-methyl-2-pyridin-2-yl-1H-indole-6-carboxylic Acid {1-[6-(5-amino-1,3,4-oxadiazol-2-yl)-1-methyl-1H-benzimidazol-2-yl]cyclobutyl}amide

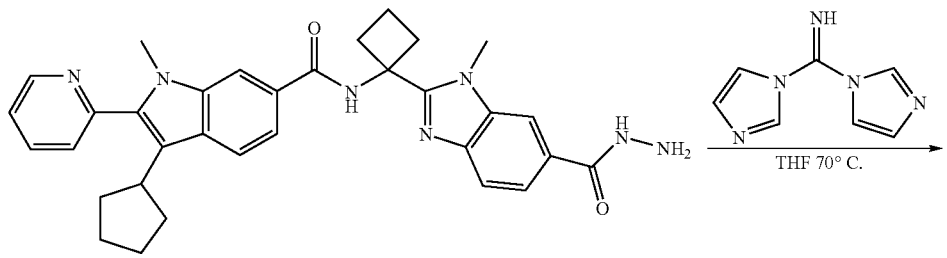

35-3

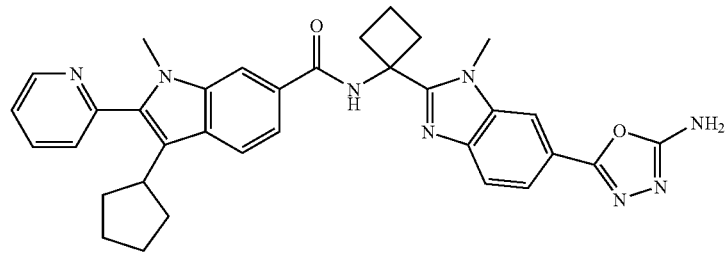

36-1

Step 2:

TFA (3 mL) was added dropwise to a solution of compound 35-2 (200 mg, 0.3 mmol) in dichloromethane (3 mL) and the resulting solution was stirred for 2 h. The volatiles were evaporated to yield 170 mg (quant. yield) of the trifluoroacetate salt of compound 35-3 which was used without further purification.

Step 3:

1,1'-Carbonyl diimidazole (25 mg, 0.15 mmol) was added in one portion to a solution of compound 35-3 (100 mg, 0.13 mmol) and triethylamine (80 μL, 0.57 mmol) in 2 mL THF, and the resulting solution was stirred at room temperature for 4 h. The mixture was then concentrated under reduced pressure, diluted with 4 mL DMSO, and directly purified on a reversed phase C₁₈, semi-preparative HPLC column (using a solvent gradient from 5% H₂O in MeCN to 100% MeCN) to C-(Di-imidazol-1-yl)-methyleneamine (25 mg, 0.16 mmol) was added in a single portion to a solution of compound 35-3 (Example 35) (80 mg, 0.14 mmol) in THF (4 mL). The resulting solution was heated to 70° C. for 16 h, after which time a white precipitate was observed. The reaction was then concentrated under reduced pressure, dissolved in 4 mL DMSO and directly purified on a reversed phase C18, semi-preparative HPLC column (using a solvent gradient from 5% H₂O in MeCN to 100% MeCN) to isolate compound 36-1 (compound 1129, Table 1) as a yellow amorphous solid in >95% homogeneity (19 mg, 23% yield).

¹H NMR (400 MHz, DMSO): δ 1.54-1.67 (m, 2H), 1.79-1.94 (m, 6H), 1.95-2.06 (m, 1H), 2.11-2.23 (m, 1H), 2.74-2.84 (m, 2H), 3.19-3.05 (m, 3H), 3.69 (s, 3H), 3.91 (s, 3H), 7.49 (dd, J=1.8 & 5.7 Hz, 1H), 7.59-7.71 (m, 3H), 7.86-7.92 (m, 2H) 7.96-8.01 (m, 1H), 8.06-8.10 (m, 1H), 8.10 (s, 1H), 8.78 (d, J=4.3 Hz, 1H), 9.51 (s, 1H).

Example 37

3-Cyclopentyl-1-methyl-2-pyridin-2-yl-1H-indole-6-carboxylic Acid [1-(1-methyl-6-1,3,4-oxadiazol-2-yl-1H-benzimidazol-2-yl)cyclobutyl]amide

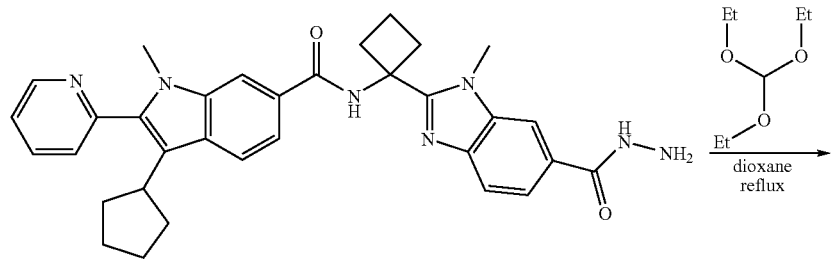

A suspension of compound 35-3 (Example 27) (50 mg, 0.09 mmol) and triethylorthoformate (1 mL, 6 mmol) in dioxane (3 mL) was heated at reflux for 18 h. The resulting almost clear solution was evaporated to dryness, and the residue was dissolved in DMSO (1 mL) and purified on a reversed phase $C_{18}$, semi-preparative HPLC column (using a solvent gradient from 5% $H_2O$ in MeCN to 100% MeCN) to isolate compound 37-1 (compound 1130, Table 1) as a yellow amorphous solid in >95% homogeneity (27 mg, 53% yield).

$^1$H NMR (400 MHz, DMSO): δ 1.55-1.68 (m, 2H), 1.79-1.93 (m, 6H), 1.95-2.04 (m, 1H), 2.12-2.20 (m, 1H), 2.82-2.74 (m, 2H), 3.15-3.05 (m, 3H), 3.69 (s, 3H), 3.92 (s, 3H), 7.49 (dd, J=2.2 & 5.3 Hz, 1H), 7.56-7.73 (m, 3H), 7.93-8.05 (m, 3H), 8.11 (s, 1H), 8.33 (s, 1H), 8.79 (d, J=4.3 Hz, 1H), 9.37 (s, 1H), 9.44 (s, 1H).

Example 38

3-Cyclopentyl-2-(5-fluoro-pyridin-2-yl)-1-methyl-1H-indole-6-carboxylic acid {1-[1-methyl-6-(5-oxo-4,5-dihydro-1,3,4-oxadiazol-2-yl)-1H-benzimidazol-2-yl]-cyclobutyl}-amide

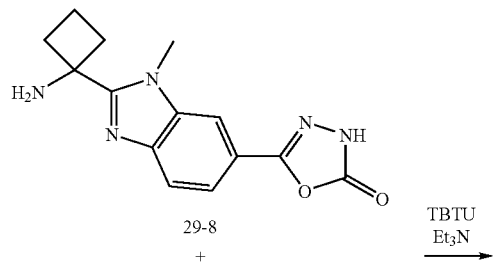

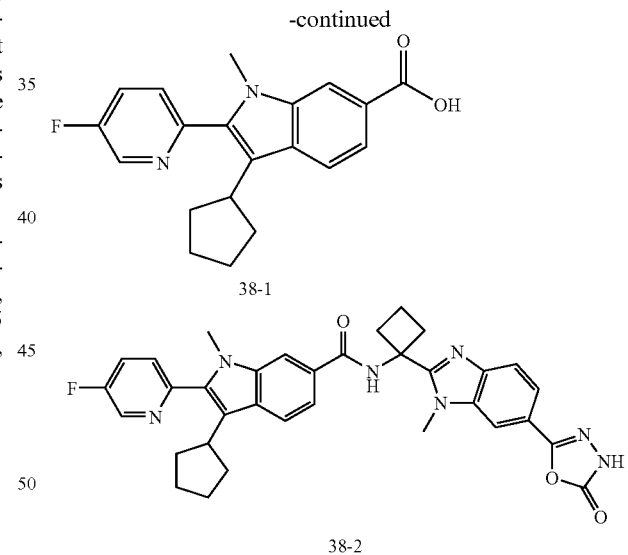

TBTU (45 mg, 0.14 mmol) and triethylamine (49 mL, 0.35 mmol) were added to a solution of compound 38-1 (prepared using procedures described in WO 03/010141) (45 mg, 0.13 mmol) and compound 29-8 (Example 29) (45 mg, 0.11 mmol) in DMF. The solution was stirred for 15 hrs and directly purified on a reversed phase $C_{18}$, semi-preparative HPLC column (using a solvent gradient from 5% $H_2O$ in MeCN to 100% MeCN) to isolate compound 38-2 (compound 1143, Table 1) as a yellow amorphous solid in >95% homogeneity (23 mg, 34% yield).

$^1$H NMR (400 MHz, DMSO): δ 1.54-1.68 (m, 2H), 1.79-1.93 (m, 6H), 1.93-2.04 (m, 1H), 2.07-2.20 (m, 1H), 2.72-2.82 (m, 2H), 3.00-3.15 (m, 3H), 3.67 (s, 3H), 3.89 (s, 3H), 7.57-7.72 (m, 3H), 7.79-7.95 (m, 3H), 8.10 (s, 2H), 8.80 (d, J=2.9 Hz, 1H), 9.45 (s, 1H), 12.63 (s, 1H).

Example 39

Inhibition of NS5B RNA Dependent RNA Polymerase Activity

The compounds of the invention were tested for inhibitory activity against the hepatitis C virus RNA dependent polymerase (NS5B), according to protocol described in WO 03/010141.

Example 40

Specificity of NS5B RNA Dependent RNA Polymerase Inhibition

The compounds of the invention were tested for inhibitory activity against polio virus RNA dependent RNA polymerase in the format that is described for the HCV polymerase, with the exception that poliovirus polymerase was used in place of the HCV NS5B polymerase, as is described in WO 03/010141. The compounds were also profiled for inhibition of the calf thymus DNA dependent RNA polymerase II in a previously described assay format (McKercher et al., 2004 Nucleic Acids Res. 32: 422-431).

Example 41

Cell-Based Luciferase Reporter HCV RNA Replication Assay

Cell Culture

Huh-7 cells with a stable subgenomic HCV replicon that encodes a modified luciferase reporter gene (expressed as a luciferase-FMDV2A-neomycin phosphotransferase fusion gene) were established as previously described (Lohman et al., 1999. Science 285: 110-113; Vroljik et al., 2003 J. Virol Methods 110:201-209.), with the exception that replicon cells were selected with 0.25 mg/mL G418. The amount of luciferase expressed by selected cells directly correlates with the level of HCV replication. These cells, designated as MP-1 cells, are maintained in Dulbecco's Modified Earle Medium (DMEM) supplemented with 10% FBS and 0.25 mg/mL neomycin (standard medium). The cells are passaged by trypsinization and frozen in 90% FBS/10% DMSO. During the assay, DMEM medium supplemented with 10% FBS, containing 0.5% DMSO and lacking neomycin, was used (Assay medium). The day of the assay, MP-1 cells were trypsinized and diluted to 100 000 cells/mL in assay medium. 100 µL is distributed into each well of a black 96-well ViewPlate™ (Packard). The plate was then incubated at 37° C. with 5% $CO_2$ for two hours.

Reagents and Materials:

| Product | Company | Catalog # | Storage |
|---|---|---|---|
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Geneticin (G418) | Gibco-BRL | 10131-027 | −20° C./4° C. |
| Trypsin-EDTA | Gibco-BRL | 25300-054 | −20° C./4° C. |
| ViewPlate ™-96, Black | Packard | 6005182 | RT |

-continued

| Product | Company | Catalog # | Storage |
|---|---|---|---|
| Backing tape, Black | Packard | 6005189 | RT |
| PVDF 0.22 µm Filter Unit | Millipore | SLGV025LS | RT |
| Deep-Well Titer Plate Polypropylene | Beckman | 267007 | RT |

Preparation of Test Compound:

The test compound in 100% DMSO was first diluted in assay medium to a final DMSO concentration of 0.5%. The solution was sonicated for 15 min and filtered through a 0.22 µM Millipore Filter unit. Into column 3 of a Polypropylene Deep-Well Titer Plate, the appropriate volume is transferred into assay medium to obtain the starting concentration (2×) to be tested. In columns 2 and 4 to 12, add 200 µL of assay medium (containing 0.5% DMSO). Serial dilutions (1/2) are prepared by transferring 200 µL from column 3 to column 4, then from column 4 to column 5, serially through to column 11. Columns 2 and 12 are the no inhibition controls.

Addition of Test Compound to Cells:

A volume of 100 µL from each well of the compound dilution plate was transferred to a corresponding well of the Cell Plate (Two columns will be used as the "No inhibition control"; ten [10] columns are used for the dose response). The cell culture plate was incubated at 37° C. with 5% $CO_2$ for 72 hours.

Luciferase Assay:

Following the 72 h incubation period, the medium was aspirated from the 96-well assay plate and a volume of 100 µL of 1× Glo Lysis Buffer (Promega) previously warmed to room temperature was added to each well. The plate was incubated at room temperature for 10 min with occasional shaking. A black tape was put at the bottom of the plate. 100 µL of Bright-Glo luciferase substrate (Promega) previously warmed to room temperature was added to each well followed by gentle mixing. The luminescence was determined on a Packard Topcount instrument using the Data Mode Luminescence (CPS) with a count delay of 1 min and a count time of 2 sec.

| Product | Company | Catalog # | Storage |
|---|---|---|---|
| Glo Lysis Buffer | Promega | E266A | 4° C. |
| Bright-Glo Luciferase Assay System | Promega | E2620 | −20° C. |

The luminescence determination (CPS) in each well of the culture plate was a measure of the amount of HCV RNA replication in the presence of various concentrations of inhibitor. The % inhibition was calculated with the following equation:

% inhibition=100−[CPS (inhibitor)/CPS (control)×100]

A non-linear curve fit with the Hill model was applied to the inhibition-concentration data, and the 50% effective concentration ($EC_{50}$) was calculated by the use of SAS software (Statistical Software; SAS Institute, Inc. Cary, N.C.).

Tables of Compounds

All compounds listed in Tables 1 to 4 below were found to have unexpectedly good activity in the cell-based HCV RNA replication assay described in Example 41.

Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

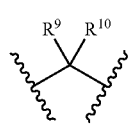

wherein $R^2$, $R^3$, $R^5$, $R^6$, $R^9$, and $R^{10}$ are given in the table.

| Cpd. # | $R^2$ | $R^3$ | $R^5$ | $R^6$ | $R^9\ R^{10}$ | $t_R$ (min) | MS $(M+H)^+$ |
|---|---|---|---|---|---|---|---|
| 1001 | 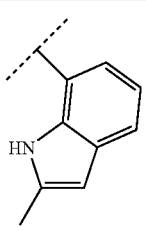 | 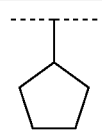 | H | 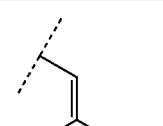 | 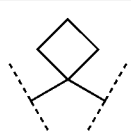 | 6.6 | 640.3 |
| 1002 | 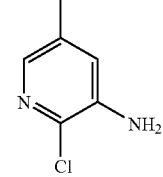 | 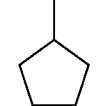 | H | 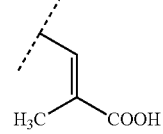 | 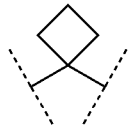 | 5.2 | 638.2 |
| 1003 | 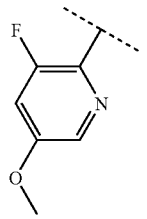 | 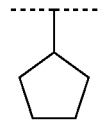 | H | 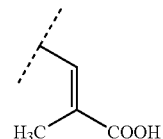 | 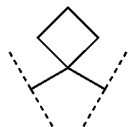 | 5.3 | 636.2 |
| 1004 | 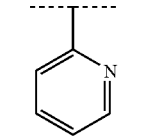 | 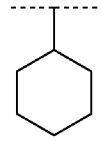 | 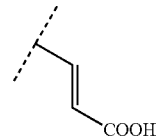 | H | 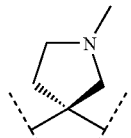 | 5.1 | 617.3 |
| 1005 | 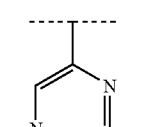 | 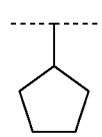 | 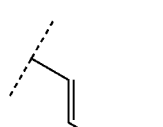 | H | 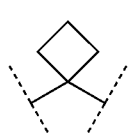 | 5.5 | 574.3 |

TABLE 1-continued
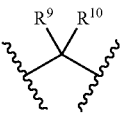
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1006 | 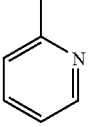 | 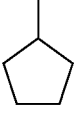 | 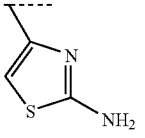 | H | 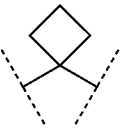 | 4.6 | 602.3 |
| 1007 | 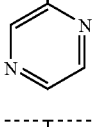 |  | 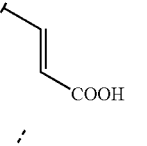 | H |  | 5.6 | 590.4 |
| 1008 | 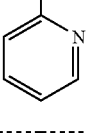 | 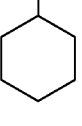 | 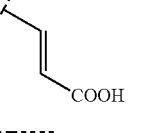 | H | 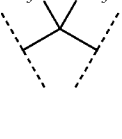 | 5.0 | 576.3 |
| 1009 | 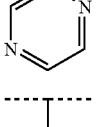 | 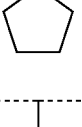 | 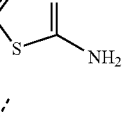 | H | 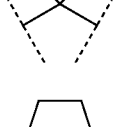 | 5.1 | 603.3 |
| 1010 | 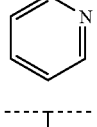 | 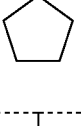 | 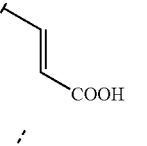 | H | 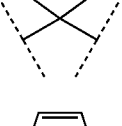 | 4.9 | 588.3 |
| 1011 | 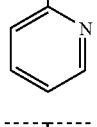 | 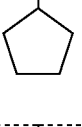 | 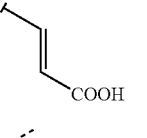 | H |  | 4.8 | 586.3 |
| 1012 | 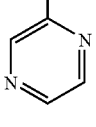 | 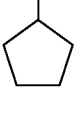 | 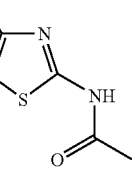 | H | 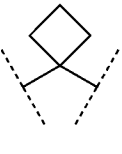 | 5.7 | 645.2 |
| 1013 | 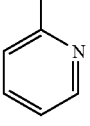 | 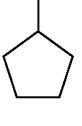 | H | 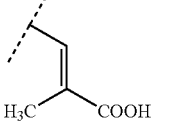 | 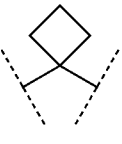 | 4.9 | 588.3 |

TABLE 1-continued
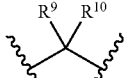
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1014 | 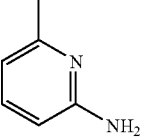 |  | 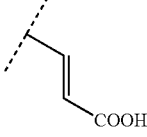 | H | 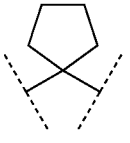 | 4.6 | 603.3 |
| 1015 | 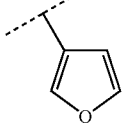 |  | 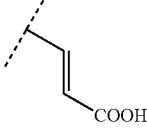 | H | 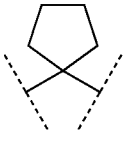 | 6.5 | 577.2 |
| 1016 | 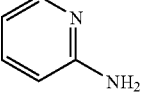 |  | 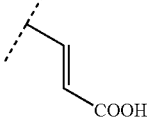 | H | 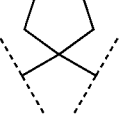 | 4.5 | 601.3 |
| 1017 | 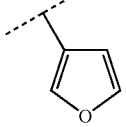 |  | 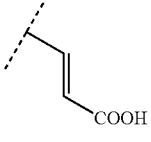 | H | 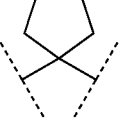 | 6.4 | 575.3 |
| 1018 | 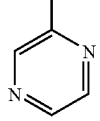 |  | 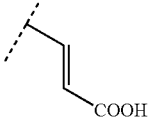 | H | 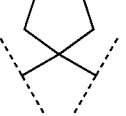 | 5.5 | 587.2 |
| 1019 | 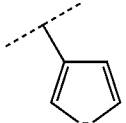 |  | 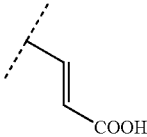 | H | 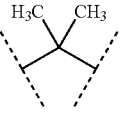 | 6.2 | 551.2 |
| 1020 | 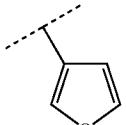 |  | H | 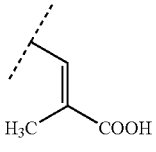 | 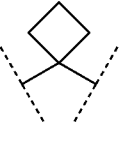 | 6.0 | 577.2 |
| 1021 | 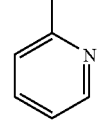 |  | H | 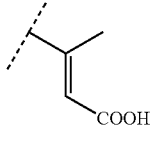 | 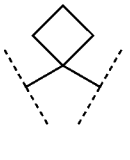 | 4.7 | 588.3 |

TABLE 1-continued wherein R², R³, R⁵, R⁶, R⁹, and R¹⁰ are given in the table.

| Cpd. # | R² | R³ | R⁵ | R⁶ | R⁹ R¹⁰ | $t_R$ (min) | MS (M + H)⁺ |
|---|---|---|---|---|---|---|---|
| 1022 | 2-pyridyl | cyclopentyl | H | CH=C(CH₃)-CH=CH-COOH | spiro[3.3]heptyl | 4.8 | 588.3 |
| 1023 | 2-pyridyl | cyclohexyl | H | CH₂-CH=CH-COOH | N-methyl-pyrrolidinyl-spiro | 4.7 | 617.4 |
| 1024 | 2-pyridyl | cyclopentyl | H | N-imidazolyl | spiro[3.3]heptyl | 4.0 | 570.3 |
| 1025 | 2-pyridyl | cyclopentyl | H | COOH | spiro[3.3]heptyl | 4.4 | 548.2 |
| 1026 | 5-Cl-2-pyridyl | cyclopentyl | CH₂-CH=CH-COOH | H | spiro[4.4]nonyl | 6.4 | 621.3 |
| 1027 | 5-Cl-2-pyridyl | cyclopentyl | H | CH=C(CH₃)-COOH | spiro[3.3]heptyl | 6.1 | 622.3 |
| 1028 | 5-F-2-pyridyl | cyclopentyl | H | CH=C(CH₃)-COOH | spiro[3.3]heptyl | 5.8 | 606.3 |

TABLE 1-continued
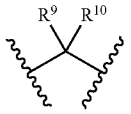
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1029 | 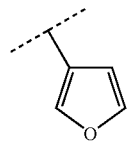 | 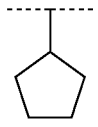 | COOH | 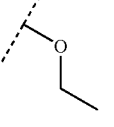 | 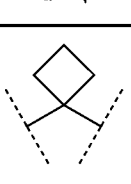 | 6.0 | 581.2 |
| 1030 | 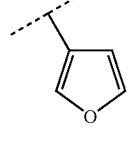 | 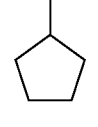 | COOH | H | 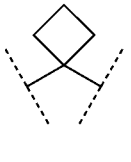 | 5.9 | 537.3 |
| 1031 | 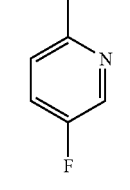 | 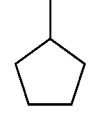 | COOH | H | 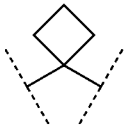 | 5.5 | 566.3 |
| 1032 | 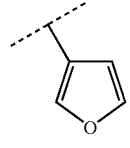 | 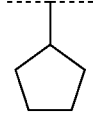 | NH₂ | COOH | 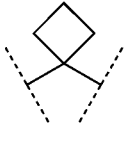 | 6.3 | 552.2 |
| 1033 | 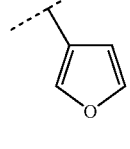 | 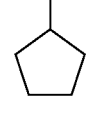 | 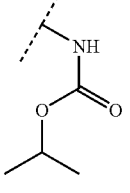 | COOH | 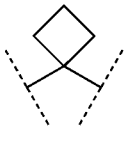 | 7.2 | 638.3 |
| 1034 | 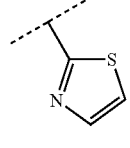 | 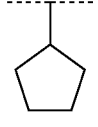 | H | 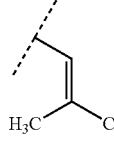 | 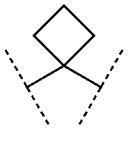 | 5.3 | 594.2 |
| 1035 | 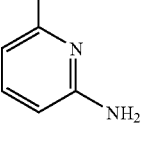 | 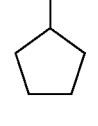 | H | 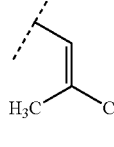 | 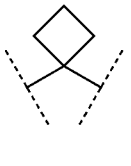 | 4.2 | 603.3 |

TABLE 1-continued
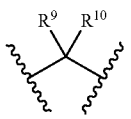
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS $(M+H)^+$ |
|---|---|---|---|---|---|---|---|
| 1036 | 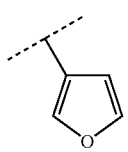 | 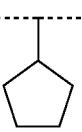 | COOH | CH₃ | 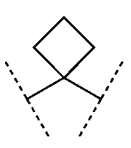 | 5.9 | 551.3 |
| 1037 | 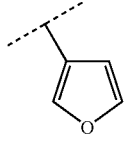 | 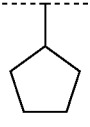 | —OCH₃ | COOH | 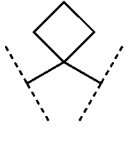 | 6.3 | 567.3 |
| 1038 | 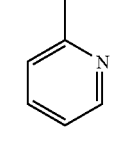 | 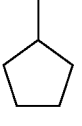 | H | 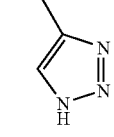 | 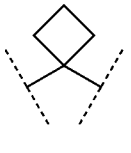 | 4.4 | 571.2 |
| 1039 | 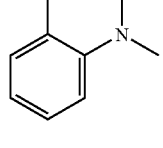 | 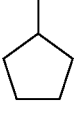 | H | 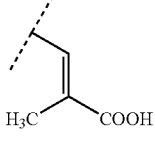 | 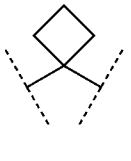 | 5.0 | 630.3 |
| 1040 | 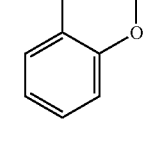 | 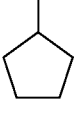 | H | 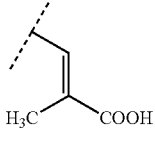 | 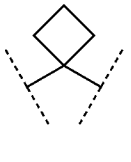 | 6.0 | 617.2 |
| 1041 | 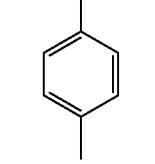 | 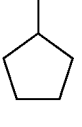 | H | 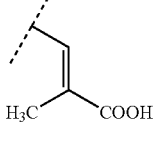 | 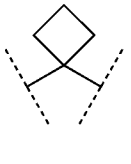 | 6.4 | 601.2 |
| 1042 | 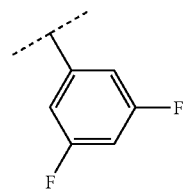 | 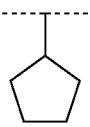 | H | 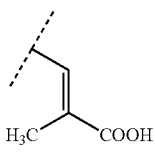 | 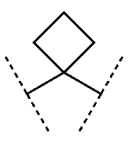 | 6.2 | 623.2 |

TABLE 1-continued wherein R², R³, R⁵, R⁶, R⁹, and R¹⁰ are given in the table.

| Cpd. # | R² | R³ | R⁵ | R⁶ | R⁹ R¹⁰ | $t_R$ (min) | MS (M + H)⁺ |
|---|---|---|---|---|---|---|---|
| 1043 | 4-carbamoylphenyl | cyclopentyl | H | (E)-2-methyl-3-yl-acrylic acid | spiro[3.3]heptane | 4.5 | 630.3 |
| 1044 | 4-methoxyphenyl | cyclopentyl | H | (E)-2-methyl-3-yl-acrylic acid | spiro[3.3]heptane | 6.0 | 617.2 |
| 1045 | 4-aminophenyl | cyclopentyl | H | (E)-2-methyl-3-yl-acrylic acid | spiro[3.3]heptane | 4.1 | 602.2 |
| 1046 | 3-methoxyphenyl | cyclopentyl | H | (E)-2-methyl-3-yl-acrylic acid | spiro[3.3]heptane | 6.0 | 617.2 |
| 1047 | 2,6-dimethylpyridin-3-yl | cyclopentyl | H | (E)-2-methyl-3-yl-acrylic acid | spiro[3.3]heptane | 3.6 | 616.3 |
| 1048 | benzo[d][1,3]dioxol-5-yl | cyclopentyl | H | (E)-2-methyl-3-yl-acrylic acid | spiro[3.3]heptane | 6.0 | 631.2 |

TABLE 1-continued
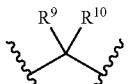
wherein R², R³, R⁵, R⁶, R⁹, and R¹⁰ are given in the table.
| Cpd. # | R² | R³ | R⁵ | R⁶ | R⁹ R¹⁰ 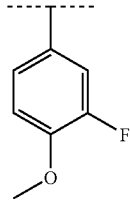 | $t_R$ (min) | MS $(M+H)^+$ |
|---|---|---|---|---|---|---|---|
| 1049 | 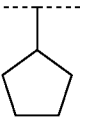 | 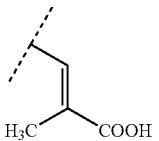 | H | 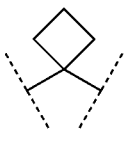 | 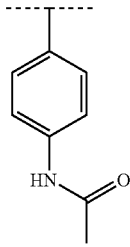 | 6.0 | 635.2 |
| 1050 | 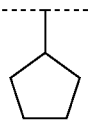 | 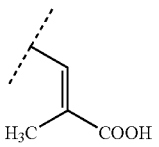 | H | 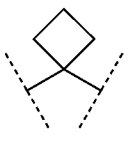 | 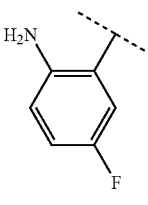 | 4.9 | 644.2 |
| 1051 | 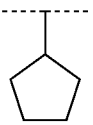 | 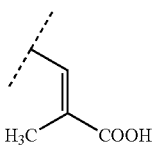 | H | 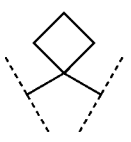 | 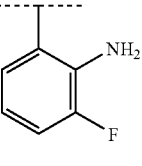 | 5.5 | 620.2 |
| 1052 |  | 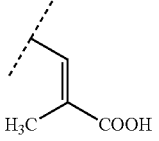 | H | 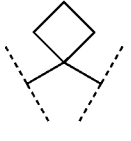 | 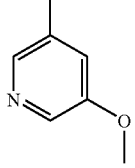 | 5.8 | 620.2 |
| 1053 | 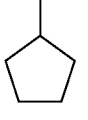 | 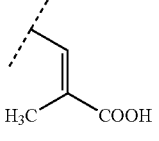 | H | 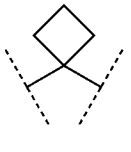 | 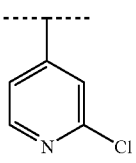 | 4.2 | 618.2 |
| 1054 | 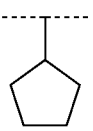 | 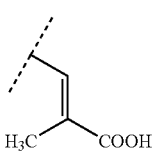 | H | 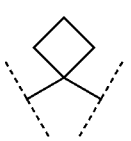 | | 5.6 | 622.2 |

TABLE 1-continued
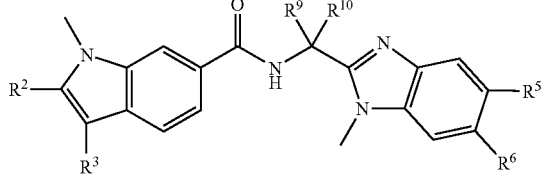
wherein $R^2$, $R^3$, $R^5$, $R^6$, $R^9$, and $R^{10}$ are given in the table.
| Cpd. # | $R^2$ | $R^3$ | $R^5$ | $R^6$ | $R^9$ $R^{10}$ | $t_R$ (min) | MS $(M + H)^+$ |
|---|---|---|---|---|---|---|---|
| 1055 |  | 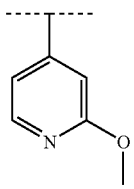 | H | 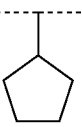 | 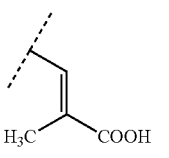 | 5.3 | 618.2 |
| 1056 | 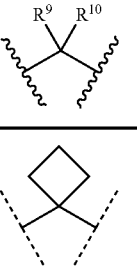 | 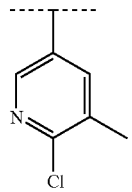 | H | 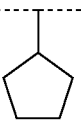 | 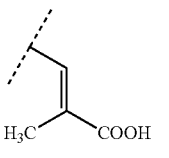 | 5.9 | 636.2 |
| 1057 | 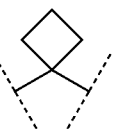 | 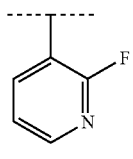 | H | 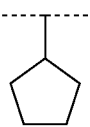 | 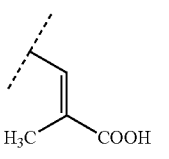 | 5.2 | 606.2 |
| 1058 | 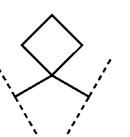 | 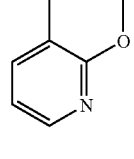 | H | 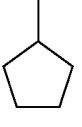 | 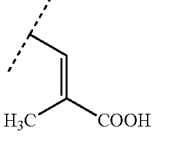 | 5.6 | 618.2 |
| 1059 | 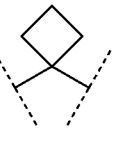 | 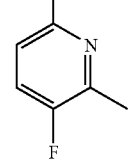 | H | 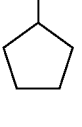 | 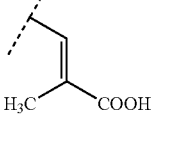 | 5.6 | 620.2 |
| 1060 | 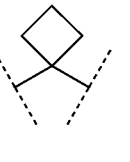 | 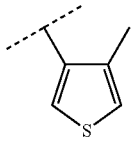 | H | 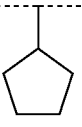 | 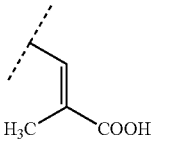 | 6.2 | 607.2 |
| 1061 | 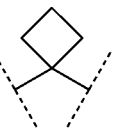 | 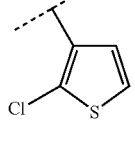 | H | 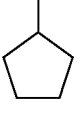 | 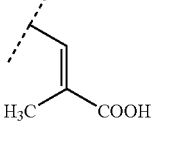 | 6.2 | 627.2 |

TABLE 1-continued
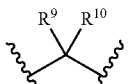
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1062 | 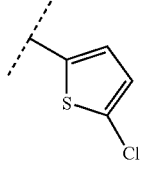 | 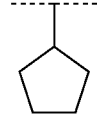 | H | 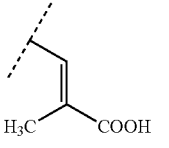 | 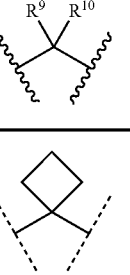 | 6.6 | 627.1 |
| 1063 | 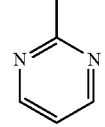 | 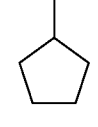 | H | 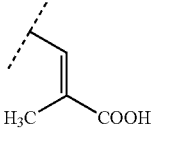 | 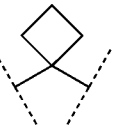 | 4.7 | 589.2 |
| 1064 | 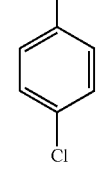 | 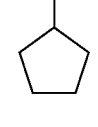 | H | 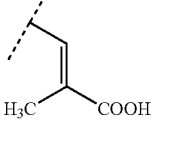 | 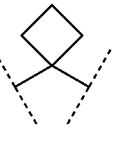 | 6.5 | 621.2 |
| 1065 | 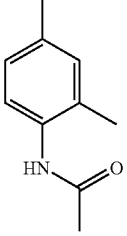 | 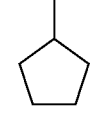 | H | 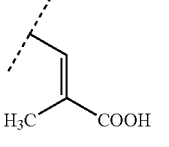 | 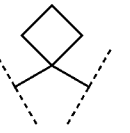 | 4.9 | 658.3 |
| 1066 | 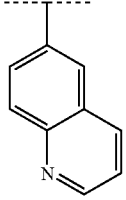 | 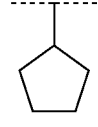 | H | 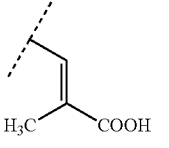 | 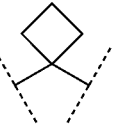 | 4.2 | 638.2 |
| 1067 | 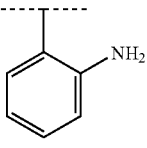 | 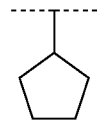 | H | 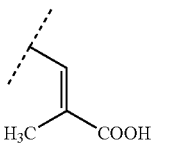 | 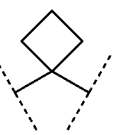 | 5.4 | 602.2 |

TABLE 1-continued
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1068 | 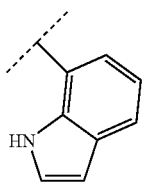 | 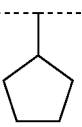 | H | 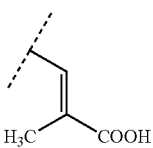 | 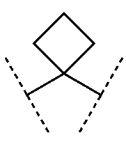 | 6.2 | 626.2 |
| 1069 | 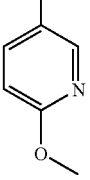 | 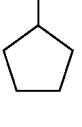 | H | 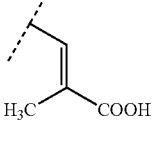 | 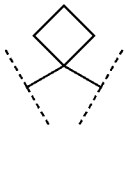 | 5.6 | 618.2 |
| 1070 | 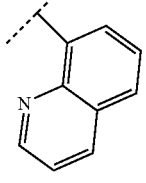 | 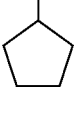 | H | 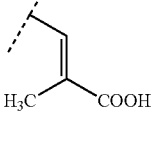 | 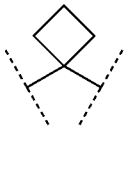 | 4.7 | 638.2 |
| 1071 | 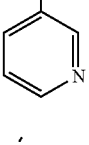 |  | H | 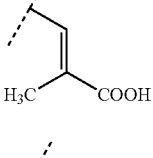 | 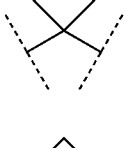 | 3.8 | 588.2 |
| 1072 | 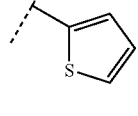 |  | H | 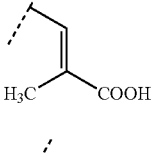 | 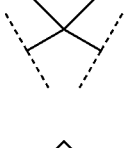 | 5.9 | 593.2 |
| 1073 | 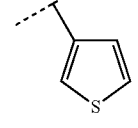 |  | H | 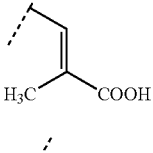 | 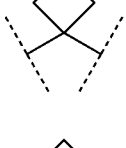 | 6.0 | 593.2 |
| 1074 | 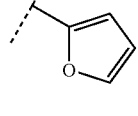 | 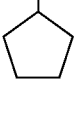 | H | 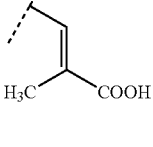 | 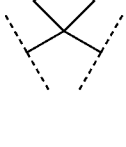 | 5.7 | 577.2 |

TABLE 1-continued

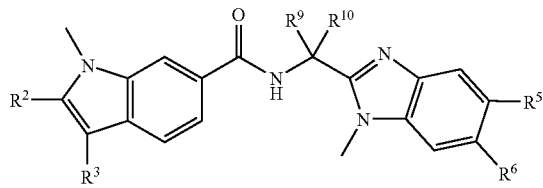

wherein $R^2$, $R^3$, $R^5$, $R^6$, $R^9$, and $R^{10}$ are given in the table.

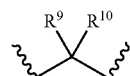

| Cpd. # | $R^2$ | $R^3$ | $R^5$ | $R^6$ | $R^9\ R^{10}$ | $t_R$ (min) | MS $(M+H)^+$ |
|---|---|---|---|---|---|---|---|
| 1075 | phenyl | cyclopentyl | H | $H_3C$-C=C-COOH | cyclobutyl | 6.0 | 587.2 |
| 1076 | 2-chloropyridin-5-yl | cyclopentyl | H | $H_3C$-C=C-COOH | cyclobutyl | 5.7 | 622.2 |
| 1077 | 4-fluoro-3-methylphenyl | cyclopentyl | H | $H_3C$-C=C-COOH | cyclobutyl | 6.5 | 619.2 |
| 1078 | 3-fluoro-4-methylphenyl | cyclopentyl | H | $H_3C$-C=C-COOH | cyclobutyl | 6.4 | 619.2 |
| 1079 | imidazo[1,2-a]pyridin-3-yl | cyclopentyl | H | $H_3C$-C=C-COOH | cyclobutyl | 3.6 | 627.2 |
| 1080 | 2-fluoro-5-methylbenzyl | cyclopentyl | H | $H_3C$-C=C-COOH | cyclobutyl | 6.3 | 619.2 |

TABLE 1-continued wherein $R^2$, $R^3$, $R^5$, $R^6$, $R^9$, and $R^{10}$ are given in the table.

| Cpd. # | $R^2$ | $R^3$ | $R^5$ | $R^6$ | $R^9$ $R^{10}$ | $t_R$ (min) | MS $(M+H)^+$ |
|---|---|---|---|---|---|---|---|
| 1081 | 2-F, 4-methylphenyl | cyclopentyl | H | CH₃C=CHCOOH | cyclobutyl(spiro) | 6.3 | 619.2 |
| 1082 | 2-OMe, 5-F phenyl | cyclopentyl | H | CH₃C=CHCOOH | cyclobutyl(spiro) | 6.0 | 635.2 |
| 1083 | 2-OMe, 4,5-diF phenyl | cyclopentyl | H | CH₃C=CHCOOH | cyclobutyl(spiro) | 6.2 | 653.2 |
| 1084 | 2,5-diF, 4-OMe phenyl | cyclopentyl | H | CH₃C=CHCOOH | cyclobutyl(spiro) | 6.0 | 653.2 |
| 1085 | 2,6-diF, 4-OMe phenyl | cyclopentyl | H | CH₃C=CHCOOH | cyclobutyl(spiro) | 6.0 | 653.2 |
| 1086 | 2-F, 4-OMe phenyl | cyclopentyl | H | CH₃C=CHCOOH | cyclobutyl(spiro) | 6.1 | 635.2 |

TABLE 1-continued
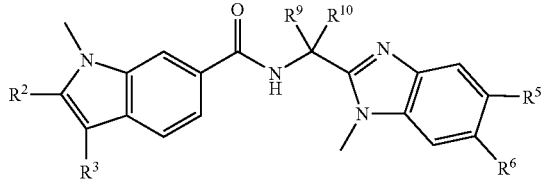
wherein R², R³, R⁵, R⁶, R⁹, and R¹⁰ are given in the table.
| Cpd. # | R² | R³ | R⁵ | R⁶ | 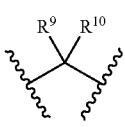 R⁹ R¹⁰ | $t_R$ (min) | MS (M + H)⁺ |
|---|---|---|---|---|---|---|---|
| 1087 | 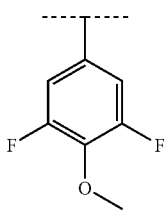 | 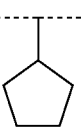 | H | 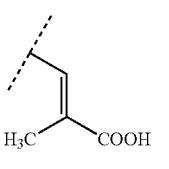 | 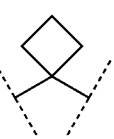 | 6.2 | 653.2 |
| 1088 | 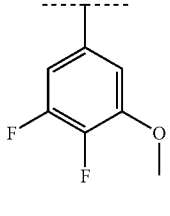 | 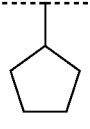 | H | 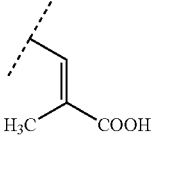 | 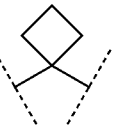 | 6.3 | 653.2 |
| 1089 | 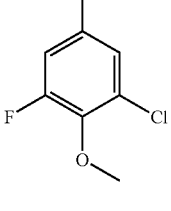 | 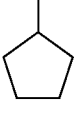 | H | 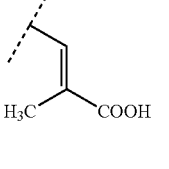 | 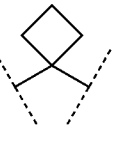 | 6.5 | 669.2 |
| 1090 | 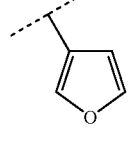 | 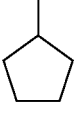 | COOH | —OCH₃ |  | 5.7 | 567.1 |
| 1091 | 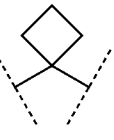 | 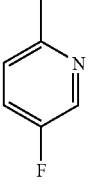 | —OCH₃ | 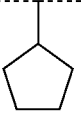 |  | 6.3 | 636.3 |
| 1092 | 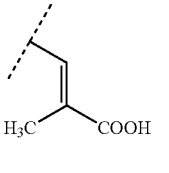 | 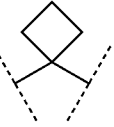 | H | 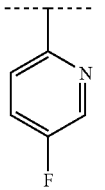 | 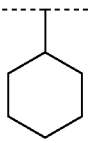 | 5.9 | 620.3 |

TABLE 1-continued
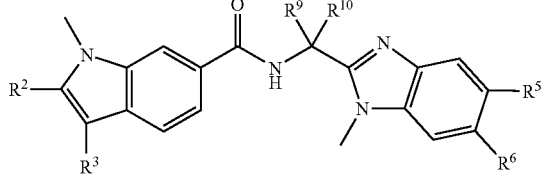
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1093 |  | 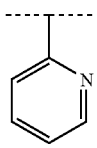 | H | 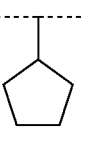 | 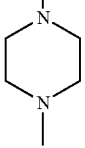 | 3.8 | 602.3 |
| 1094 |  | 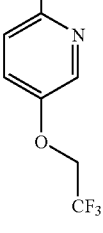 | H | 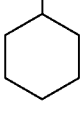 | 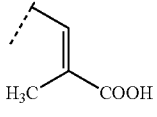 | 6.2 | 700.3 |
| 1095 |  | 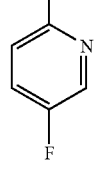 | H | 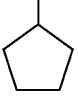 | 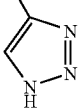 | 5.9 | 589.3 |
| 1096 |  | 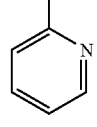 | H |  | 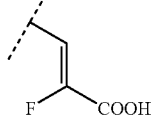 | 4.5 | 592.3 |
| 1097 | 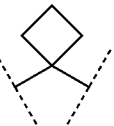 | 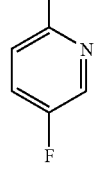 | CH₃ |  | 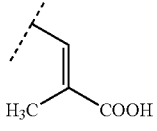 | 5.7 | 620.3 |
| 1098 |  | 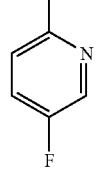 | H |  | 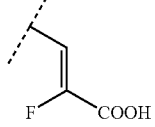 | 6.2 | 610.3 |

TABLE 1-continued

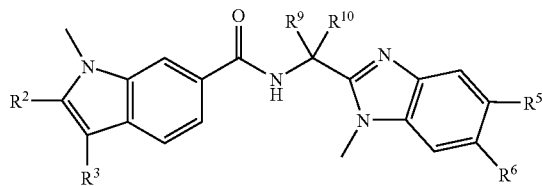

wherein R², R³, R⁵, R⁶, R⁹, and R¹⁰ are given in the table.

| Cpd. # | R² | R³ | R⁵ | R⁶ | R⁹ R¹⁰ | $t_R$ (min) | MS (M + H)⁺ |
|---|---|---|---|---|---|---|---|
| 1099 | 3-(2-hydroxypyridyl) | cyclopentyl | H | CH₃-C(=CH-)-COOH | cyclobutylidene | 5.4 | 604.3 |
| 1100 | 5-bromopyrimidin-2-yl | cyclopentyl | H | CH₃-C(=CH-)-COOH | cyclobutylidene | 5.9 | 667.2 |
| 1101 | 3-(2-methoxypyridyl) | cyclopentyl | H | -CH=CH-COOH | cyclobutylidene | 5.4 | 604.3 |
| 1102 | 5-fluoropyridin-2-yl | cyclopentyl | H | 2-aminothiazol-4-yl | cyclopentylidene | 5.9 | 632.4 |
| 1103 | 5-fluoropyridin-2-yl | cyclopentyl | H | CH₃CH₂-C(=CH-)-COOH | cyclobutylidene | 5.7 | 620.3 |
| 1104 | 5-fluoropyridin-2-yl | cyclopentyl | H | 4-methylpiperazin-1-yl | cyclobutylidene | 4.8 | 620.2 |
| 1105 | 6-aminopyridin-2-yl | cyclopentyl | H | CH₃-C(=CH-)-COOH | C(CH₃)₂ | 4.3 | 591.3 |

TABLE 1-continued
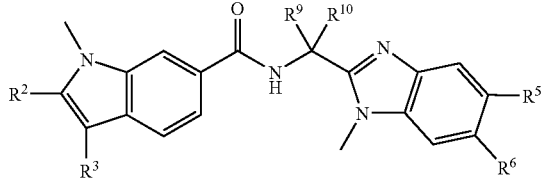
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1106 | 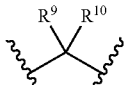 | 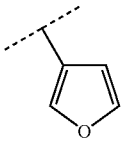 | H | 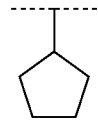 | 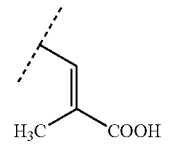 | 6.0 | 565.2 |
| 1107 | 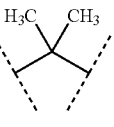 | 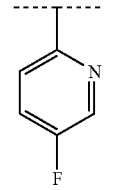 | H | 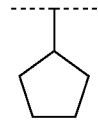 | 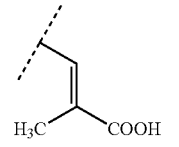 | 5.7 | 594.3 |
| 1108 | 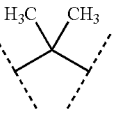 | 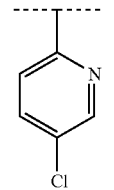 | H | 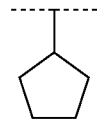 | 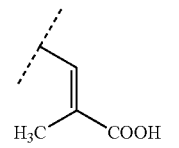 | 6.0 | 610.2 |
| 1109 | 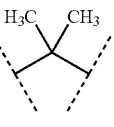 | 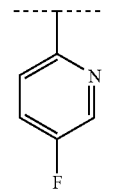 | H | 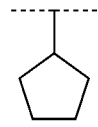 | 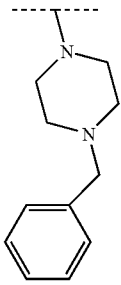 | 5.1 | 696.3 |
| 1110 | 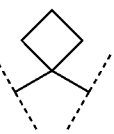 | 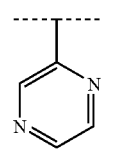 | H | 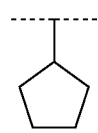 | 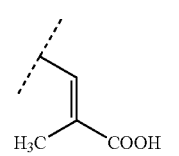 | 5.0 | 589.2 |
| 1111 | CH₃ | 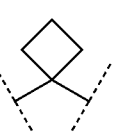 | H | 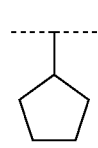 | 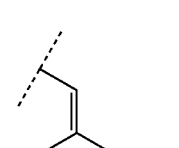 | 6.1 | 525.3 |

TABLE 1-continued
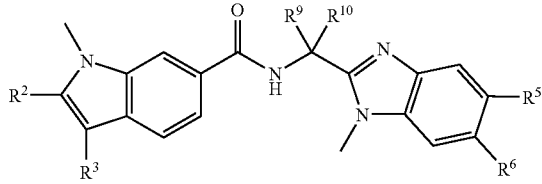
wherein R², R³, R⁵, R⁶, R⁹, and R¹⁰ are given in the table.
| Cpd. # | R² | R³ | R⁵ | R⁶ | R⁹ R¹⁰ | t$_R$ (min) | MS (M + H)⁺ |
|---|---|---|---|---|---|---|---|
| 1112 | 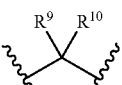 |  | H | 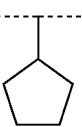 | 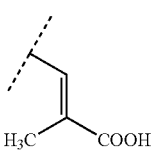 | 6.4 | 539.3 |
| 1113 | 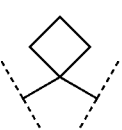 | 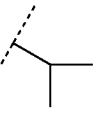 | H | 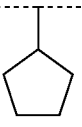 | 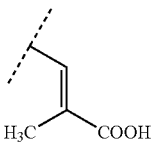 | 6.6 | 553.3 |
| 1114 | Br | 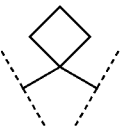 | H | 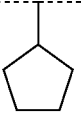 | 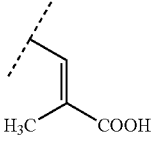 | 5.8 | 589.2 591.2 |
| 1115 | 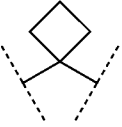 | 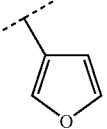 | H | 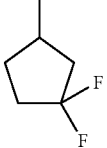 | 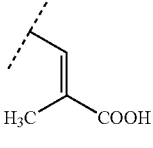 | 5.4 | 613.3 |
| 1116 | 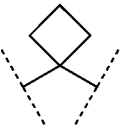 | 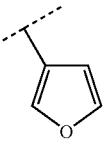 | H | 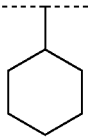 | 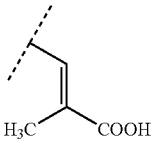 | 6.0 | 591.3 |
| 1117 | Br | 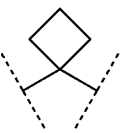 | H | 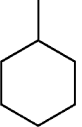 | 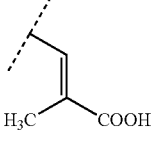 | 6.1 | 605.2 603.2 |
| 1118 | 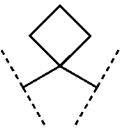 | 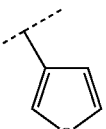 | H | 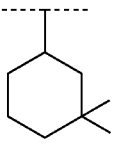 | 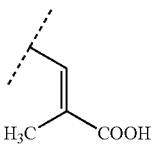 | 5.6 | 627.3 |

TABLE 1-continued
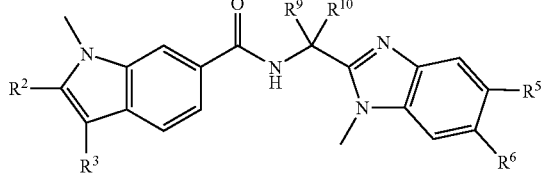
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 1119 | 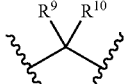 | 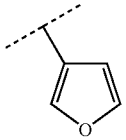 | H | 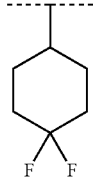 | 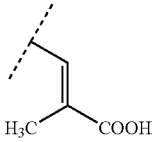 | 5.6 | 627.4 |
| 1120 | 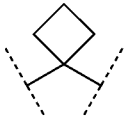 | 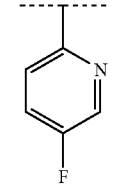 | H | 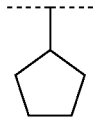 | 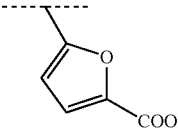 | 5.5 | 632.3 |
| 1121 | 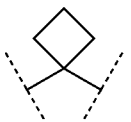 | 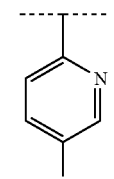 | H | 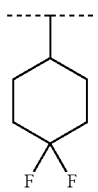 | 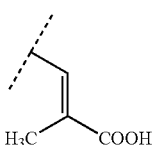 | 5.3 | 656.4 |
| 1122 | 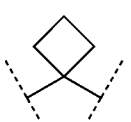 | 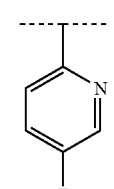 | H | 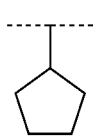 | 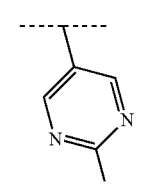 | 5.0 | 615.3 |
| 1123 | CH₃ | 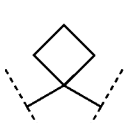 | H | 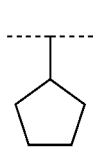 | 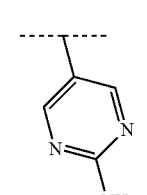 | 5.0 | 534.3 |
| 1124 |  | 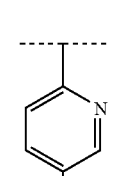 | H | 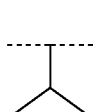 | 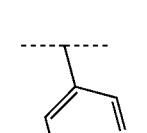 | 5.4 | 600.3 |

TABLE 1-continued
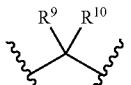
wherein R², R³, R⁵, R⁶, R⁹, and R¹⁰ are given in the table.
| Cpd. # | R² | R³ | R⁵ | R⁶ | R⁹ R¹⁰ | t_R (min) | MS (M + H)⁺ |
|---|---|---|---|---|---|---|---|
| 1125 | 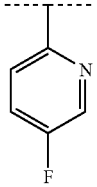 | 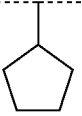 | H | 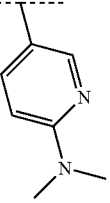 | 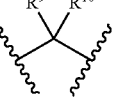 | 5.9 | 642.3 |
| 1126 | 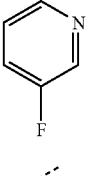 |  | H | 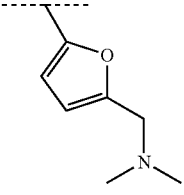 | 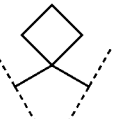 | 4.9 | 645.3 |
| 1127 | 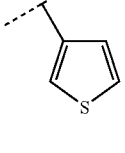 | 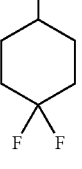 | H | 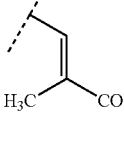 |  | 5.7 | 643.2 |
| 1128 | 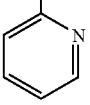 | 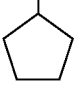 | H | 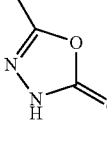 |  | 4.7 | 588.3 |
| 1129 | 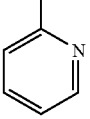 | 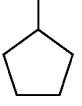 | H | 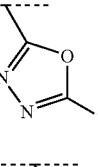 | 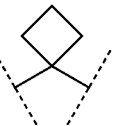 | 4.4 | 587.3 |
| 1130 | 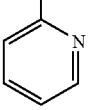 | 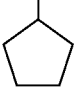 | H | 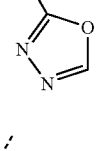 |  | 4.6 | 572.3 |
| 1131 | 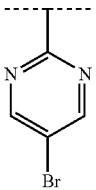 | 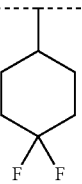 | H | 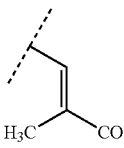 | 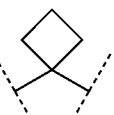 | 5.7 | 719.2 |

TABLE 1-continued
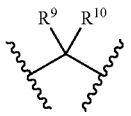
wherein $R^2$, $R^3$, $R^5$, $R^6$, $R^9$, and $R^{10}$ are given in the table.
| Cpd. # | $R^2$ | $R^3$ | $R^5$ | $R^6$ | $R^9$ $R^{10}$ | $t_R$ (min) | MS $(M+H)^+$ |
|---|---|---|---|---|---|---|---|
| 1132 | 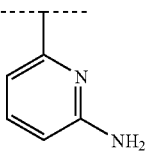 |  | H | 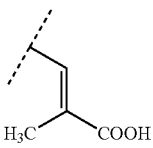 | 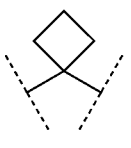 | 4.0 | 653.3 |
| 1133 | 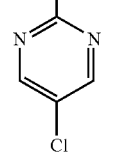 |  | H | 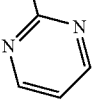 |  | 6.6 | 618.2 |
| 1134 | 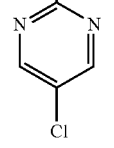 |  | H | 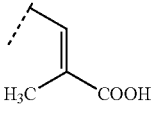 |  | 6.4 | 623.3 |
| 1135 | 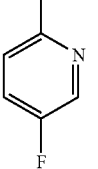 | 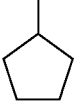 | H | 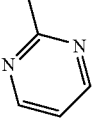 | 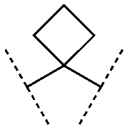 | 6.3 | 600.4 |
| 1136 | 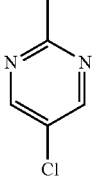 | 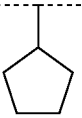 | H | 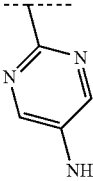 | 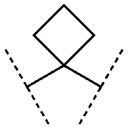 | 5.2 | 632.4 |
| 1137 | 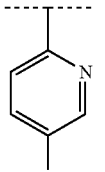 | 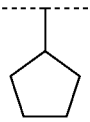 | H | 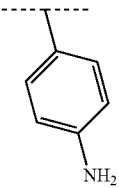 | 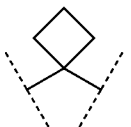 | 4.9 | 613.4 |

TABLE 1-continued
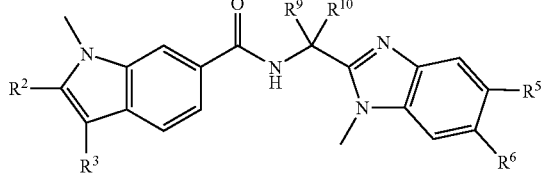
wherein $R^2$, $R^3$, $R^5$, $R^6$, $R^9$, and $R^{10}$ are given in the table.
| Cpd. # | $R^2$ | $R^3$ | $R^5$ | $R^6$ | $R^9$ $R^{10}$ | $t_R$ (min) | MS $(M+H)^+$ |
|---|---|---|---|---|---|---|---|
| 1138 | 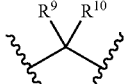 | 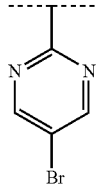 | H | 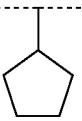 | 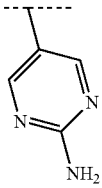 | 5.3 | 676.3 678.3 |
| 1139 |  | 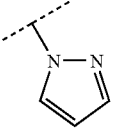 | H | 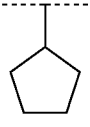 | 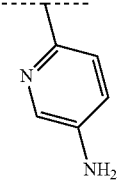 | 5.0 | 585.5 |
| 1140 | 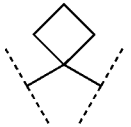 | 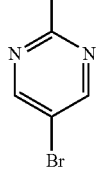 | H | 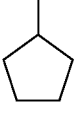 | 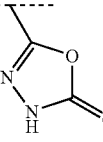 | 6.3 | 667.3 669.3 |
| 1141 | 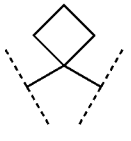 | 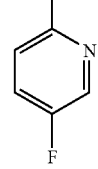 | H | 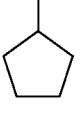 | 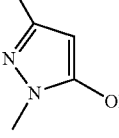 | 5.7 | 618.5 |
| 1142 | 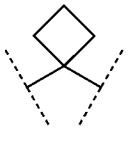 | 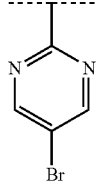 | H | 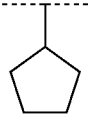 | 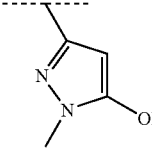 | 6.1 | 679.4 681.4 |
| 1143 | 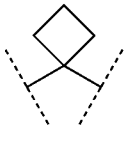 | 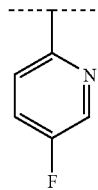 | H | 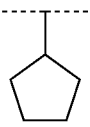 | 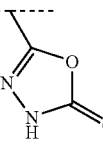 | 5.8 | 606.4 |

TABLE 1-continued
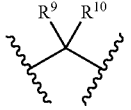
wherein R², R³, R⁵, R⁶, R⁹, and R¹⁰ are given in the table.
| Cpd. # | R² | R³ | R⁵ | R⁶ | R⁹ R¹⁰ | t$_R$ (min) | MS (M + H)⁺ |
|---|---|---|---|---|---|---|---|
| 1144 | 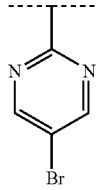 | 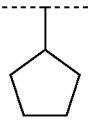 | H | 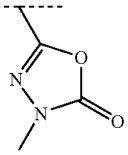 | 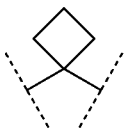 | 6.5 | 681.4 683.4 |
| 1145 | 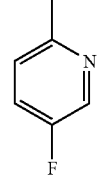 | 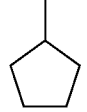 | H | 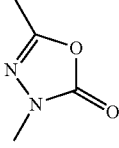 | 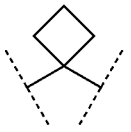 | 6.1 | 620.5 |
| 1146 | 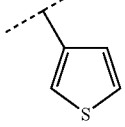 | 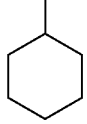 | H | 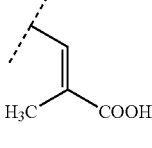 | 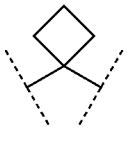 | 7.0 | 607.5 |
| 1147 | 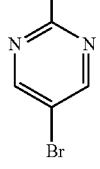 |  | H | 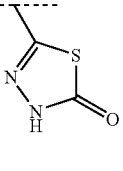 | 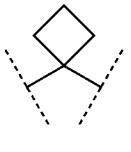 | 6.4 | 683.3 685.3 |
| 1148 | 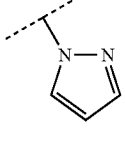 |  | H | 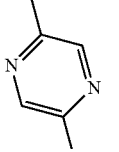 | 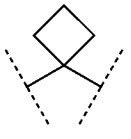 | 5.2 | 586.4 |
| 1149 | 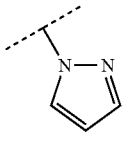 |  | H | 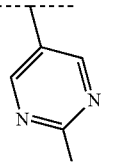 | 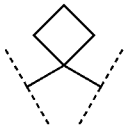 | 5.4 | 586.4 |

TABLE 1-continued
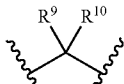
wherein R², R³, R⁵, R⁶, R⁹, and R¹⁰ are given in the table.
| Cpd. # | R² | R³ | R⁵ | R⁶ | 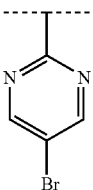 | $t_R$ (min) | MS (M + H)⁺ |
|---|---|---|---|---|---|---|---|
| 1150 | 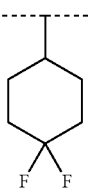 | 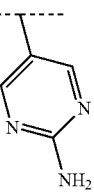 | H | 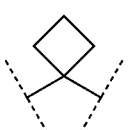 | 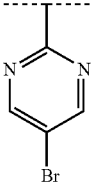 | 5.8 | 726.3<br>728.3 |
| 1151 | 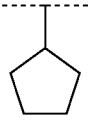 | 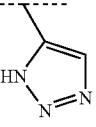 | H | 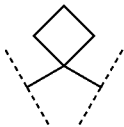 | 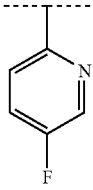 | 6.4 | 650.0<br>652.0 |
| 1152 | 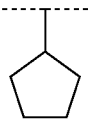 | 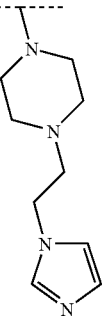 | H | 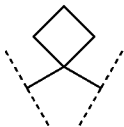 | 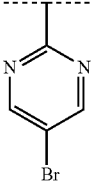 | 4.8 | 700.2 |
| 1153 | 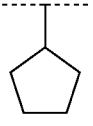 | 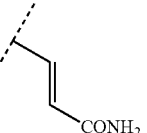 | H | 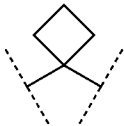 | | 6.1 | 654.2 |

TABLE 2
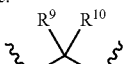
wherein R², R³, R⁵, R⁶, R⁹, and R¹⁰ are given in the table.
| Cpd. # | R² | R³ | R⁵ | R⁶ |  | $t_R$ (min) | MS (M + H)⁺ |
|---|---|---|---|---|---|---|---|
| 2001 |  | 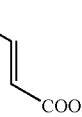 | 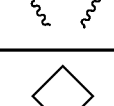 | H |  | 4.3 | 574.3 |
| 2002 |  | 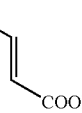 | 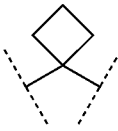 | H |  | 6.2 | 563.1 |
| 2003 |  | 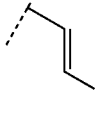 | H | 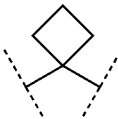 |  | 6.5 | 563.2 |
| 2004 |  | 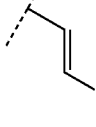 | H | 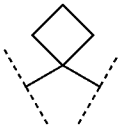 |  | 4.2 | 574.3 |
| 2005 |  |  | H |  |  | 6.1 | 575.3 |
| 2006 |  | 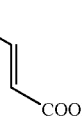 |  | H |  | 6.2 | 575.3 |
| 2007 |  | 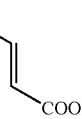 | 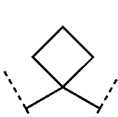 | H |  | 4.5 | 588.4 |
| 2008 |  | 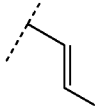 | H |  |  | 4.5 | 588.4 |

TABLE 2-continued
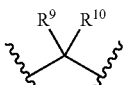
wherein R², R³, R⁵, R⁶, R⁹, and R¹⁰ are given in the table.
| Cpd. # | R² | R³ | R⁵ | R⁶ | R⁹ R¹⁰ | $t_R$ (min) | MS (M + H)⁺ |
|---|---|---|---|---|---|---|---|
| 2009 | 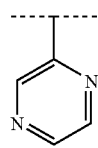 | 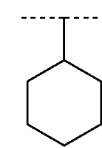 | H | 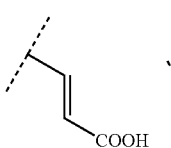 | 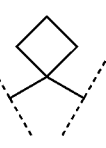 | 5.3 | 589.4 |
| 2010 | 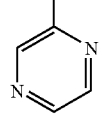 | 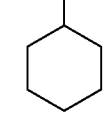 | 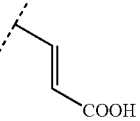 | H | 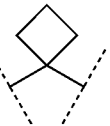 | 5.4 | 589.4 |
| 2011 | 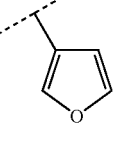 | 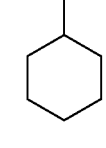 | H | 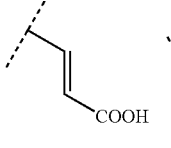 |  | 6.2 | 577.4 |
| 2012 | 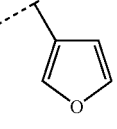 | 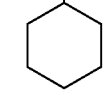 | 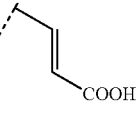 | H | 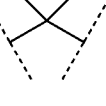 | 6.2 | 577.4 |
| 2013 | 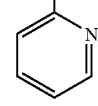 | 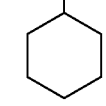 | H | 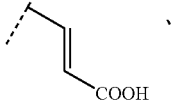 | 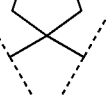 | 4.6 | 600.3 |
| 2014 | 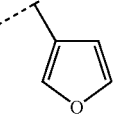 | 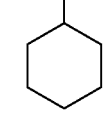 | H | 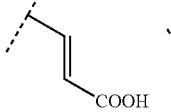 | 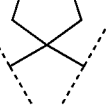 | 6.2 | 589.3 |
| 2015 | 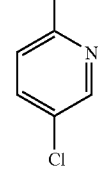 | 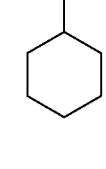 | H | 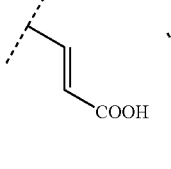 |  | 6.4 | 622.3 |

TABLE 2-continued
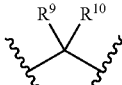
wherein R², R³, R⁵, R⁶, R⁹, and R¹⁰ are given in the table.
| Cpd. # | R² | R³ | R⁵ | R⁶ | 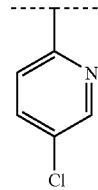 | t_R (min) | MS (M + H)⁺ |
|---|---|---|---|---|---|---|---|
| 2016 | 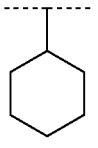 | 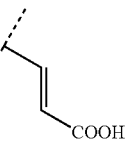 | 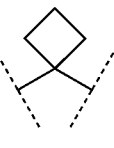 | H | 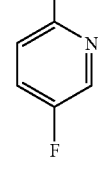 | 6.4 | 622.3 |
| 2017 | 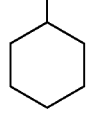 | 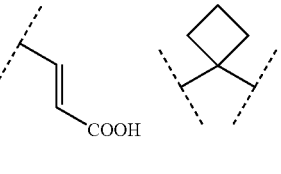 | H | 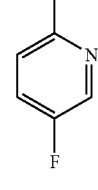 | 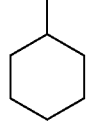 | 5.6 | 606.3 |
| 2018 | 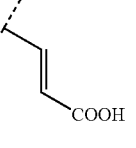 | 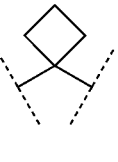 | 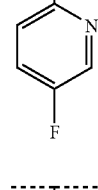 | H | 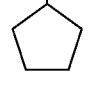 | 6.0 | 606.3 |
| 2019 | 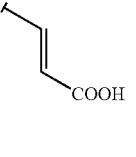 | 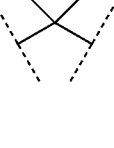 | 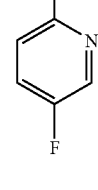 | H | 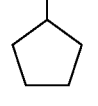 | 5.5 | 592.3 |
| 2020 | 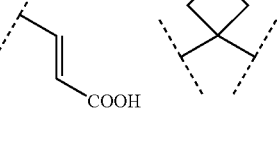 | 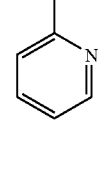 | H | 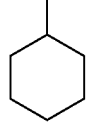 | 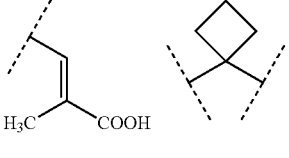 | 5.4 | 592.3 |
| 2021 | | | H | | | 4.5 | 602.3 |

TABLE 2-continued
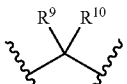
wherein R², R³, R⁵, R⁶, R⁹, and R¹⁰ are given in the table.
| Cpd. # | R² | R³ | R⁵ | R⁶ | $\begin{matrix} R^9 \ R^{10} \\ \end{matrix}$ | $t_R$ (min) | MS (M + H)⁺ |
|---|---|---|---|---|---|---|---|
| 2022 | 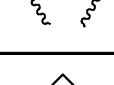 | 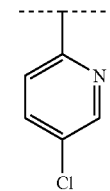 | H | 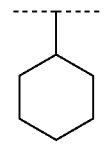 | 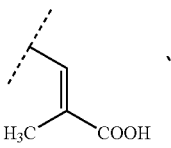 | 6.2 | 636.3 |
| 2023 | 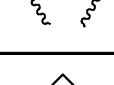 | 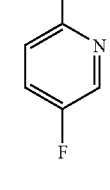 | H | 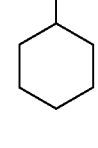 | 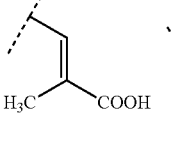 | 5.9 | 620.3 |
| 2024 |  | 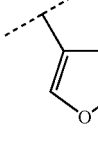 | H | 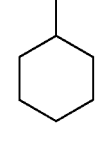 | 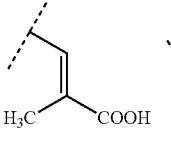 | 6.1 | 591.2 |
| 2025 |  | 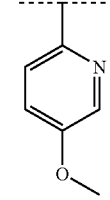 | H | 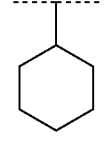 | 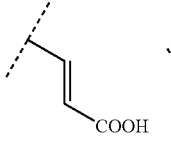 | 5.0 | 618.3 |
| 2026 |  | 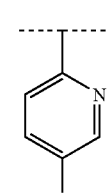 | 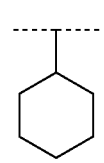 | CH₃ |  | 5.9 | 620.3 |
| 2027 | 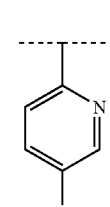 | 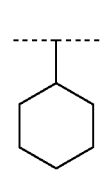 | H | 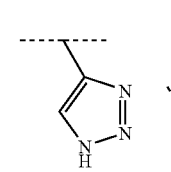 |  | 6.0 | 603.3 |

TABLE 2-continued

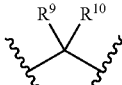

wherein R², R³, R⁵, R⁶, R⁹, and R¹⁰ are given in the table.

| Cpd. # | R² | R³ | R⁵ | R⁶ | R⁹ R¹⁰ | $t_R$ (min) | MS $(M+H)^+$ |
|---|---|---|---|---|---|---|---|
| 2028 | 2-pyridyl | cyclohexyl | CH₃ | CH=CH-COOH | cyclobutylidene | 4.5 | 602.3 |
| 2029 | 5-fluoro-2-pyridyl | cyclohexyl | CH₃ | CH=CH-COOH | cyclobutylidene | 5.7 | 620.3 |
| 2030 | 4-methoxy-2-pyrimidinyl | cyclohexyl | H | CH=CH-COOH | cyclobutylidene | 5.8 | 619.3 |
| 2031 | 5-fluoro-2-pyridyl | cyclohexyl | CH₃ | CH=C(CH₃)-COOH | cyclobutylidene | 5.8 | 634.4 |
| 2032 | 5-fluoro-2-pyridyl | cyclohexyl | H | CH=CH-COOH | cyclopentylidene | 6.3 | 618.3 |
| 2033 | 5-fluoro-2-pyridyl | cyclohexyl | H | CH=CF-COOH | cyclobutylidene | 6.4 | 624.4 |

TABLE 2-continued
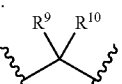
wherein R², R³, R⁵, R⁶, R⁹, and R¹⁰ are given in the table.
| Cpd. # | R² | R³ | R⁵ | R⁶ | 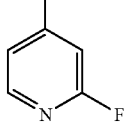 R⁹ R¹⁰ | $t_R$ (min) | MS (M + H)⁺ |
|---|---|---|---|---|---|---|---|
| 2034 | 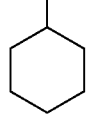 | 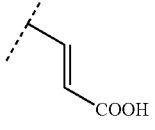 | H | 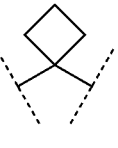 | 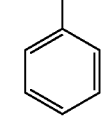 | 5.2 | 606.3 |
| 2035 | 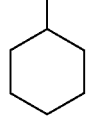 | 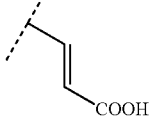 | H | 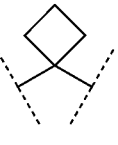 | 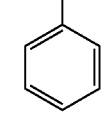 | 6.1 | 587.3 |
| 2036 | 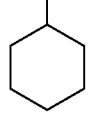 | 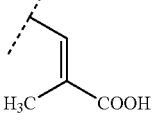 | H | 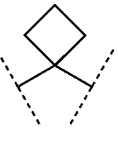 | 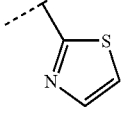 | 6.3 | 601.3 |
| 2037 | 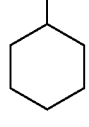 | 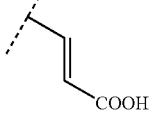 | H |  | 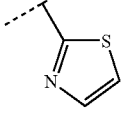 | 5.2 | 594.3 |
| 2038 | 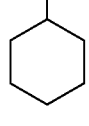 | 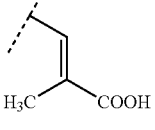 | H |  | 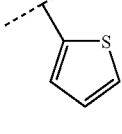 | 5.4 | 608.3 |
| 2039 |  | 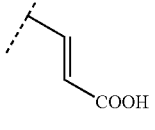 | H | 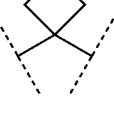 | 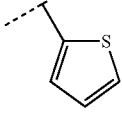 | 6.0 | 593.3 |
| 2040 | 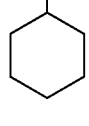 | 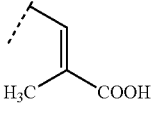 | H | 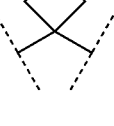 | 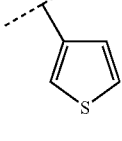 | 6.2 | 607.3 |
| 2041 |  | 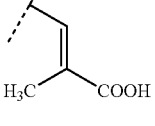 | H | 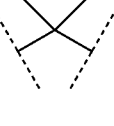 | | 6.1 | 607.3 |

TABLE 2-continued
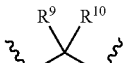
wherein R², R³, R⁵, R⁶, R⁹, and R¹⁰ are given in the table.
| Cpd. # | R² | R³ | R⁵ | R⁶ | 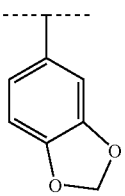 | $t_R$ (min) | MS (M + H)⁺ |
|---|---|---|---|---|---|---|---|
| 2042 | 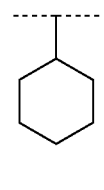 | 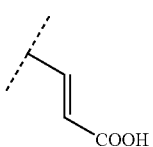 | H | 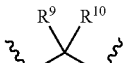 | 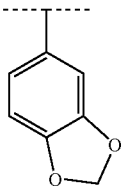 | 5.9 | 631.3 |
| 2043 | 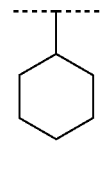 | 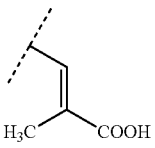 | H |  | 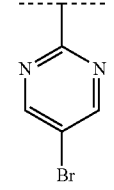 | 6.1 | 645.3 |
| 2044 | 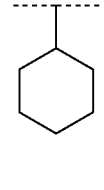 | 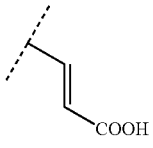 | H |  | 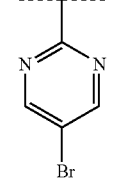 | 5.8 | 667.2 |
| 2045 | 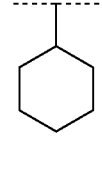 | 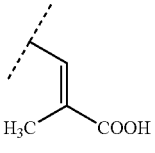 | H | 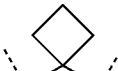 | 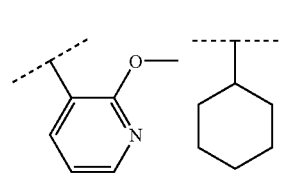 | 6.0 | 681.2 |
| 2046 | 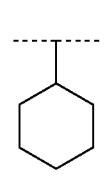 | 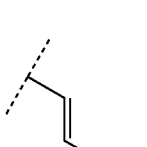 | H |  | 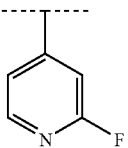 | 5.5 | 618.3 |
| 2047 | 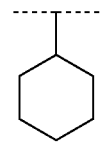 | 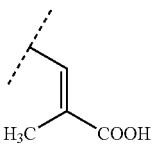 | H |  | | 5.4 | 620.3 |

TABLE 2-continued
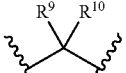
wherein R², R³, R⁵, R⁶, R⁹, and R¹⁰ are given in the table.
| Cpd. # | R² | R³ | R⁵ | R⁶ | 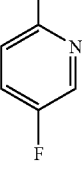 R⁹ R¹⁰ | t_R (min) | MS (M + H)⁺ |
|---|---|---|---|---|---|---|---|
| 2048 | 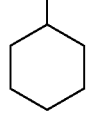 | 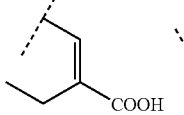 | H | 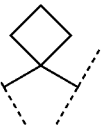 | 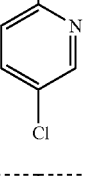 | 5.9 | 634.3 |
| 2049 | 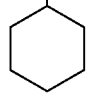 | 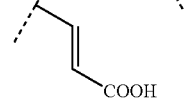 | H |  | 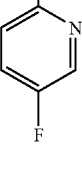 | 6.2 | 610.3 612.3 |
| 2050 | 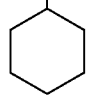 | 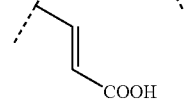 | H |  | 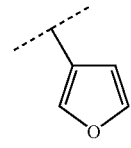 | 5.7 | 594.3 |
| 2051 | 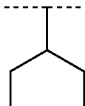 | 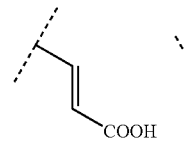 | H | 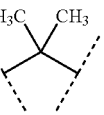 | 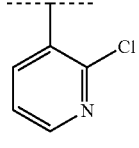 | 6.0 | 565.3 |
| 2052 | 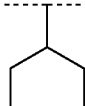 | 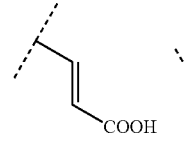 | H | 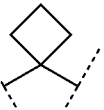 | 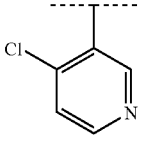 | 4.0 | 622.3 |
| 2053 | 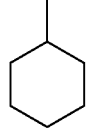 | 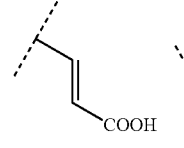 | H | 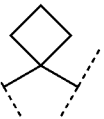 | 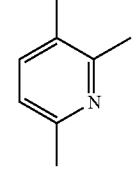 | 3.8 | 622.3 |
| 2054 | 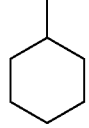 | 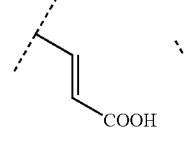 | H | 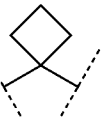 | | 2.8 | 616.3 |

TABLE 2-continued

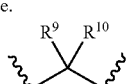

wherein R², R³, R⁵, R⁶, R⁹, and R¹⁰ are given in the table.

| Cpd. # | R² | R³ | R⁵ | R⁶ | R⁹ R¹⁰ | $t_R$ (min) | MS (M + H)⁺ |
|---|---|---|---|---|---|---|---|
| 2055 | 2-amino-5-fluoropyridin-3-yl | cyclohexyl | H | (E)-3-carboxyprop-1-en-1-yl | cyclobutylidene | 3.2 | 621.3 |
| 2056 | 2-fluoro-5-methylpyridin-3-yl | cyclohexyl | H | (E)-3-carboxyprop-1-en-1-yl | cyclobutylidene | 4.2 | 620.4 |
| 2057 | 4-fluoro-5-methylpyridin-3-yl | cyclohexyl | H | (E)-3-carboxyprop-1-en-1-yl | cyclobutylidene | 4.0 | 620.4 |
| 2058 | furan-3-yl | cyclopentyl | H | (E)-3-carboxyprop-1-en-1-yl | C(CH₃)₂ | 5.7 | 551.1 |
| 2059 | 5-fluoropyridin-2-yl | cyclohexyl | H | (E)-3-carboxy-2-methylprop-1-en-1-yl | C(CH₃)₂ | 5.9 | 608.3 |
| 2060 | 2-fluoropyridin-3-yl | cyclohexyl | H | (E)-3-carboxyprop-1-en-1-yl | cyclobutylidene | 5.2 | 606.2 |
| 2061 | 5-fluoropyridin-2-yl | cyclopentyl | H | (E)-3-carboxy-2-methylprop-1-en-1-yl | cyclobutylidene | 5.6 | 606.2 |

TABLE 2-continued
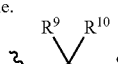
wherein R², R³, R⁵, R⁶, R⁹, and R¹⁰ are given in the table.
| Cpd. # | R² | R³ | R⁵ | R⁶ | 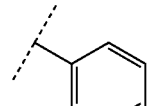 | $t_R$ (min) | MS (M + H)⁺ |
|---|---|---|---|---|---|---|---|
| 2062 | 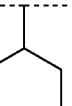 | 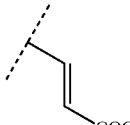 | H | 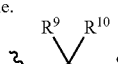 | 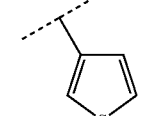 | 6.4 | 575.3 |
| 2063 | 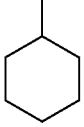 |  | H | 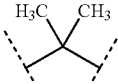 | 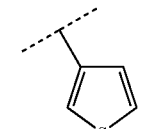 | 6.3 | 581.3 |
| 2064 | 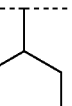 | 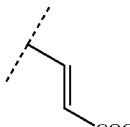 | H |  | 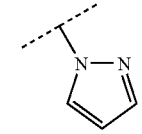 | 6.0 | 593.3 |
| 2065 | 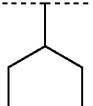 |  | H |  | 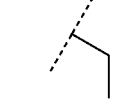 | 5.8 | 577.3 |
| 2066 | 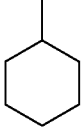 |  | H |  | 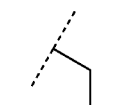 | 6.4 | 539.3 |
| 2067 | 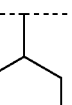 |  | H |  | 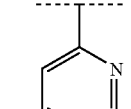 | 6.7 | 553.3 |
| 2068 | 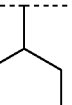 | 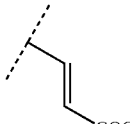 | H |  | 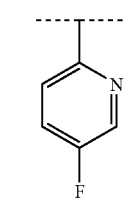 | 4.6 | 574.3 |
| 2069 | 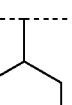 | 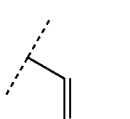 | H |  | | 6.2 | 592.3 |

TABLE 2-continued wherein R², R³, R⁵, R⁶, R⁹, and R¹⁰ are given in the table.

| Cpd. # | R² | R³ | R⁵ | R⁶ | R⁹ R¹⁰ | $t_R$ (min) | MS (M + H)⁺ |
|---|---|---|---|---|---|---|---|
| 2070 | 5-fluoropyridin-2-yl | cyclopentyl | H | CH=CH-COOH | cyclopropylidene | 5.9 | 578.3 |
| 2071 | 5-fluoropyridin-2-yl | cyclopentyl | —OCH₃ | CH=CH-COOH | cyclobutylidene | 6.0 | 622.3 |
| 2072 | 5-fluoropyridin-2-yl | cyclohexyl | —OCH₃ | CH=CH-COOH | cyclobutylidene | 6.3 | 636.4 |
| 2073 | 1-methylpyrazol-4-yl | cyclohexyl | H | CH=CH-COOH | cyclobutylidene | 5.6 | 591.3 |
| 2074 | 5-chloropyrimidin-2-yl | cyclohexyl | H | CH=CH-COOH | cyclobutylidene | 6.5 | 623.4 625.4 |

16.7
12.3

TABLE 3 wherein R², R⁴, R⁵, R⁸, R⁹, and R¹⁰ are given in the table.

| Cpd. # | R² | R⁴ | R⁵ | R⁸ | R⁹, R¹⁰ | $t_R$ (min) | MS $(M+H)^+$ |
|---|---|---|---|---|---|---|---|
| 3001 | pyrazin-2-yl | H | H | cyclobutylmethyl | spirocyclopentyl | 5.8 | 629.3 |
| 3002 | quinoxalin-2-yl | H | H | CH₃ | spirocyclobutyl | 5.4 | 625.4 |
| 3003 | pyridin-2-yl | H | H | CH₃ | spirocyclobutyl | 4.9 | 574.3 |
| 3004 | pyrazin-2-yl | H | H | CH₃ | spirocyclobutyl | 5.2 | 575.2 |
| 3005 | pyridin-2-yl | H | H | ethyl | spirocyclobutyl | 5.0 | 588.3 |
| 3006 | pyridin-2-yl | H | H | isopropyl | spirocyclobutyl | 4.9 | 602.2 |
| 3007 | pyridin-2-yl | H | H | CH₃ | C(CH₃)₂ | 4.7 | 562.4 |

TABLE 3-continued
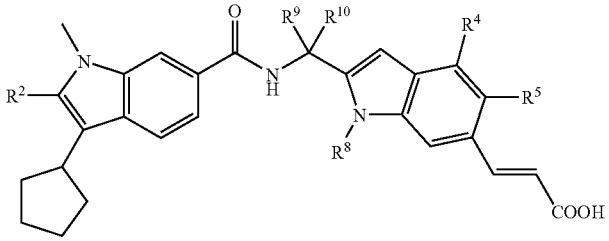
wherein R², R⁴, R⁵, R⁸, R⁹, and R¹⁰ are given in the table.
| Cpd. # | R² | R⁴ | R⁵ | R⁸ | R⁹ R¹⁰ 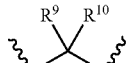 | $t_R$ (min) | MS (M + H)⁺ |
|---|---|---|---|---|---|---|---|
| 3008 | 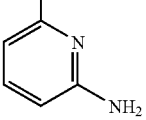 | H | H | CH₃ | 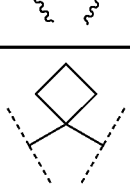 | 4.2 | 589.2 |
| 3009 | 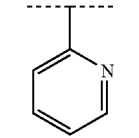 | H | H | CH₃ | 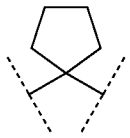 | 4.9 | 588.4 |
| 3010 | 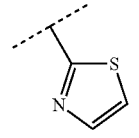 | H | H | CH₃ | 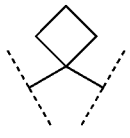 | 5.1 | 580.2 |
| 3011 | 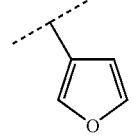 | H | H | CH₃ | 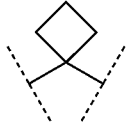 | 6.0 | 563.2 |
| 3012 | 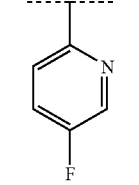 | H | H | CH₃ | 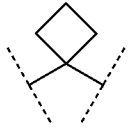 | 5.6 | 592.2 |
| 3013 | 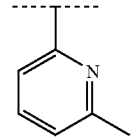 | H | H | CH₃ | 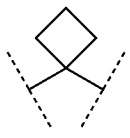 | 4.4 | 588.3 |
| 3014 | 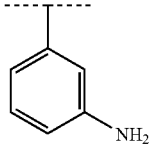 | H | H | CH₃ | 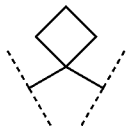 | 4.6 | 588.3 |

TABLE 3-continued

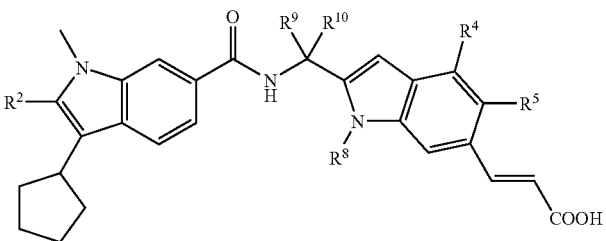

wherein R², R⁴, R⁵, R⁸, R⁹, and R¹⁰ are given in the table.

| Cpd. # | R² | R⁴ | R⁵ | R⁸ | R⁹ R¹⁰ | $t_R$ (min) | MS $(M+H)^+$ |
|---|---|---|---|---|---|---|---|
| 3015 | 5-methylpyridin-2-yl | H | H | CH₃ | spiro-cyclobutyl | 4.8 | 588.3 |
| 3016 | 6-methylpyridin-3-yl | H | H | CH₃ | spiro-cyclobutyl | 4.2 | 588.3 |
| 3017 | pyrazin-2-yl | H | H | CH₃ | spiro-cyclopentyl | 5.5 | 589.2 |
| 3018 | 6-aminopyridin-2-yl | H | H | CH₃ | H₃C  CH₃ | 4.2 | 577.2 |
| 3019 | furan-3-ylmethyl | H | H | CH₃ | H₃C  CH₃ | 6.1 | 551.2 |
| 3020 | furan-3-ylmethyl | H | H | CH₃ | spiro-cyclopentyl | 6.3 | 577.2 |
| 3021 | pyridin-2-ylmethyl | H | H | CH₃ | spiro-cyclopentenyl | 4.7 | 586.2 |

TABLE 3-continued

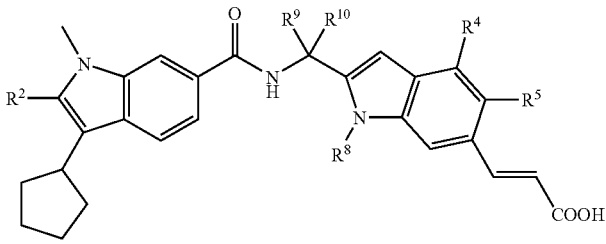

wherein R², R⁴, R⁵, R⁸, R⁹, and R¹⁰ are given in the table.

| Cpd. # | R² | R⁴ | R⁵ | R⁸ | R⁹ R¹⁰ | $t_R$ (min) | MS $(M+H)^+$ |
|---|---|---|---|---|---|---|---|
| 3022 | pyrazin-2-yl | H | H | CH₃ | cyclopentane spiro | 5.4 | 587.2 |
| 3023 | furan-3-yl | H | H | CH₃ | cyclopentane spiro | 6.3 | 575.3 |
| 3024 | pyridin-2-yl | H | H | CH₃ | 1,3-dioxane spiro | 4.6 | 606.2 |
| 3025 | pyridin-2-yl | H | H | CH₂-cyclobutyl | cyclobutane spiro | 5.1 | 614.2 |
| 3026 | pyridin-2-yl | H | H | CH₂CH₂CH₂F | cyclobutane spiro | 4.9 | 606.2 |
| 3027 | pyridin-2-yl | H | H | CH₂CH₂CH₂OCH₃ | cyclobutane spiro | 5.0 | 618.2 |
| 3028 | pyridin-2-yl | H | H | CH₂-cyclopropyl | cyclobutane spiro | 5.2 | 614.2 |

TABLE 3-continued

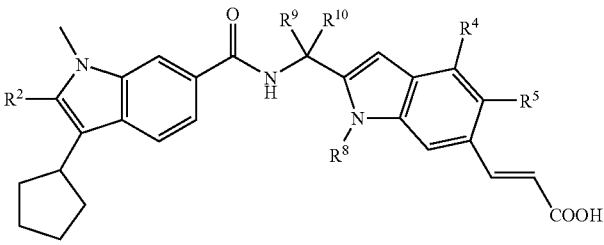

wherein R², R⁴, R⁵, R⁸, R⁹, and R¹⁰ are given in the table.

| Cpd. # | R² | R⁴ | R⁵ | R⁸ | R⁹ R¹⁰ | $t_R$ (min) | MS $(M+H)^+$ |
|---|---|---|---|---|---|---|---|
| 3029 | pyrazinyl | H | H | -CH₂-cyclobutyl | cyclobutylidene | 5.7 | 615.2 |
| 3030 | pyrazinyl | H | H | isobutyl | cyclobutylidene | 5.5 | 603.2 |
| 3031 | pyrazinyl | H | H | n-propyl | cyclobutylidene | 5.4 | 589.2 |
| 3032 | pyrazinyl | H | H | -CH₂-cyclopropyl | cyclobutylidene | 5.7 | 615.2 |
| 3033 | pyrazinyl | H | H | n-propyl | cyclopentylidene | 5.5 | 603.3 |
| 3034 | furan-3-yl | H | H | -CH₂-cyclobutyl | cyclobutylidene | 6.7 | 603.3 |
| 3035 | furan-3-yl | H | H | isobutyl | cyclobutylidene | 6.5 | 591.3 |

TABLE 3-continued
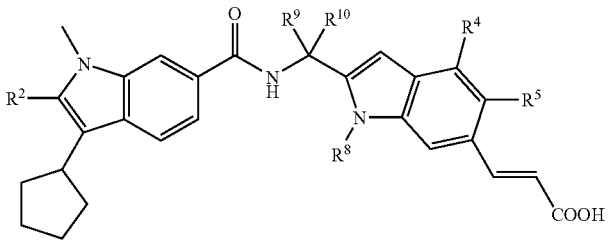
wherein R², R⁴, R⁵, R⁸, R⁹, and R¹⁰ are given in the table.
| Cpd. # | R² | R⁴ | R⁵ | R⁸ | R⁹ R¹⁰ | $t_R$ (min) | MS $(M+H)^+$ |
|---|---|---|---|---|---|---|---|
| 3036 | 3-furyl | H | H | -CH₂CF₃ | cyclobutyl | 7.2 | 631.2 |
| 3037 | 3-furyl | H | H | -CH₂CH(CH₃)₂ | cyclobutyl | 6.8 | 605.3 |
| 3038 | 3-furyl | H | H | -CH₂CH₂CH₂F | cyclobutyl | 6.4 | 595.2 |
| 3039 | 3-furyl | H | H | -CH₂CH₂OCH₃ | cyclobutyl | 6.4 | 607.2 |
| 3040 | 3-furyl | H | H | -CH₂CH₂CH(CH₃)₂ | cyclobutyl | 7.0 | 619.3 |
| 3041 | 3-furyl | H | H | -CH₂CH₃ | cyclobutyl | 6.4 | 577.2 |
| 3042 | 3-furyl | H | H | -CH₂-cyclopropyl | cyclobutyl | 6.6 | 603.3 |

TABLE 3-continued

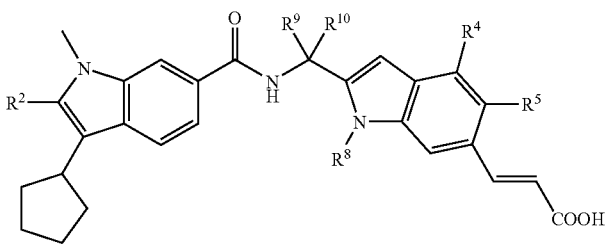

wherein R², R⁴, R⁵, R⁸, R⁹, and R¹⁰ are given in the table.

| Cpd. # | R² | R⁴ | R⁵ | R⁸ | R⁹ R¹⁰ | $t_R$ (min) | MS $(M+H)^+$ |
|---|---|---|---|---|---|---|---|
| 3043 | 2-pyridyl | H | H | cyclobutylmethyl | cyclopentylidene | 5.4 | 628.3 |
| 3044 | 2-pyridyl | H | H | 3-fluoropropyl | cyclopentylidene | 5.1 | 620.3 |
| 3045 | 2-pyridyl | H | H | propyl | cyclopentylidene | 5.1 | 602.3 |
| 3046 | 3-furyl | H | H | CH₃ | N-methylpyrrolidinyl | 5.7 | 592.3 |
| 3047 | 3-furyl | H | H | propyl | cyclopentenyl | 6.4 | 589.3 |
| 3048 | 3-furyl | H | H | 3-methoxypropyl | cyclopentenyl | 6.3 | 619.3 |
| 3049 | 3-furyl | H | H | 3-fluoropropyl | cyclopentenyl | 6.4 | 607.3 |

TABLE 3-continued

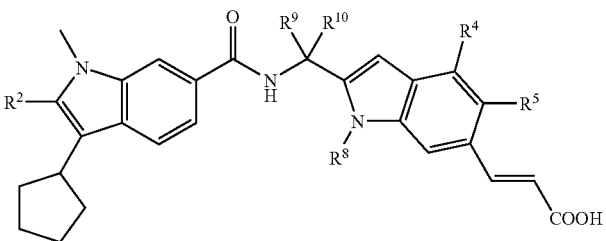

wherein $R^2$, $R^4$, $R^5$, $R^8$, $R^9$, and $R^{10}$ are given in the table.

| Cpd. # | $R^2$ | $R^4$ | $R^5$ | $R^8$ | $R^9$ $R^{10}$ | $t_R$ (min) | MS $(M+H)^+$ |
|---|---|---|---|---|---|---|---|
| 3050 | 2-pyridyl | H | H | CH$_3$ | N-methyl azaspiro | 4.4 | 603.3 |
| 3051 | pyrazinyl | H | —OCH$_3$ | CH$_3$ | spirocyclobutane | 5.3 | 605.3 |
| 3052 | 3-furyl | H | H | CH$_3$ | piperidine spiro NH | 5.7 | 592.3 |
| 3053 | acetamido-thiazolyl | H | H | CH$_3$ | spirocyclobutane | 5.5 | 637.3 |
| 3054 | 5-Cl-2-pyridyl | H | H | CH$_3$ | cyclopentene spiro | 6.4 | 620.3 |
| 3055 | 5-Cl-2-pyridyl | H | H | CH$_3$ | spirocyclobutane | 6.3 | 608.3 |

TABLE 3-continued
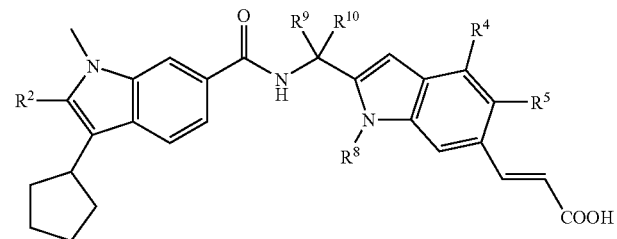
wherein $R^2$, $R^4$, $R^5$, $R^8$, $R^9$, and $R^{10}$ are given in the table.
| Cpd. # | $R^2$ | $R^4$ | $R^5$ | $R^8$ | $R^9$ $R^{10}$ | $t_R$ (min) | MS $(M+H)^+$ |
|---|---|---|---|---|---|---|---|
| 3056 | Br | H | H | CH$_3$ | | 6.2 | 577.1 |
| 3057 | 5-F-pyridin-2-yl | H | H | CH$_3$ | | 5.9 | 604.3 |
| 3058 | 6-methoxy-pyridin-2-yl | H | H | CH$_3$ | | 6.9 | 604.3 |
| 3059 | pyridin-4-yl | H | H | CH$_3$ | | 4.0 | 574.3 |
| 3060 | furan-3-yl | H | —NH$_2$ | CH$_3$ | | 6.3 | 578.3 |
| 3061 | pyridin-3-yl | H | H | CH$_3$ | | 4.2 | 574.3 |
| 3062 | 6-methoxy-pyridin-3-yl | H | H | CH$_3$ | | 5.9 | 604.2 |

TABLE 3-continued

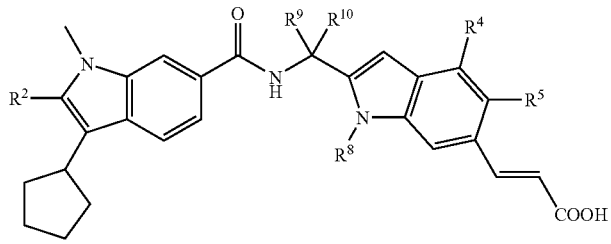

wherein $R^2$, $R^4$, $R^5$, $R^8$, $R^9$, and $R^{10}$ are given in the table.

| Cpd. # | $R^2$ | $R^4$ | $R^5$ | $R^8$ | $R^9 \quad R^{10}$ | $t_R$ (min) | MS $(M+H)^+$ |
|---|---|---|---|---|---|---|---|
| 3063 | 3-thienyl | H | H | CH$_3$ | bicyclobutyl | 6.2 | 579.3 |
| 3064 | 2-amino-thiazol-4-yl | H | H | CH$_3$ | bicyclobutyl | 4.2 | 595.2 |
| 3065 | 2-methyl-thiazol-4-yl | H | H | CH$_3$ | bicyclobutyl | 5.6 | 594.2 |
| 3066 | 2-(2,2,2-trifluoroethylamino)-thiazol-4-yl | H | H | CH$_3$ | bicyclobutyl | 5.9 | 677.2 |
| 3067 | 2-thienyl | H | H | CH$_3$ | bicyclobutyl | 5.9 | 579.2 |
| 3068 | 3-furyl | H | —OCH$_3$ | CH$_3$ | bicyclobutyl | 6.6 | 593.3 |
| 3069 | 2-pyridyl | H | —OCH$_3$ | CH$_3$ | bicyclobutyl | 5.0 | 604.3 |

TABLE 3-continued
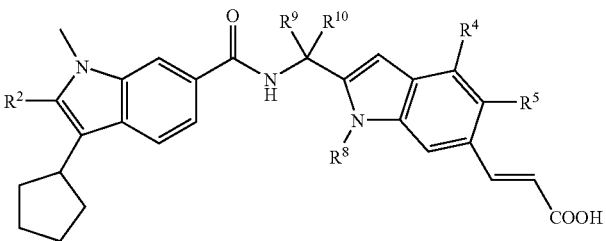
wherein R², R⁴, R⁵, R⁸, R⁹, and R¹⁰ are given in the table.
| Cpd. # | R² | R⁴ | R⁵ | R⁸ | R⁹ R¹⁰ | $t_R$ (min) | MS (M + H)⁺ |
|---|---|---|---|---|---|---|---|
| 3070 | thiazole-pyridin-3-yl | H | H | CH₃ | spirocyclobutyl | 5.1 | 657.2 |
| 3071 | thiazole-pyridin-4-yl | H | H | CH₃ | spirocyclobutyl | 4.7 | 657.1 |
| 3072 | thiazole-pyrimidin-5-yl | H | H | CH₃ | spirocyclobutyl | 6.1 | 658.1 |
| 3073 | thiazole-furan-2-yl | H | H | CH₃ | spirocyclobutyl | 6.5 | 646.1 |

TABLE 3-continued
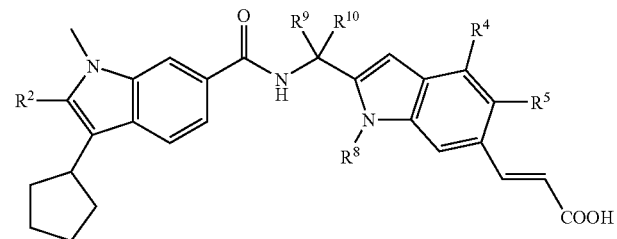
wherein $R^2$, $R^4$, $R^5$, $R^8$, $R^9$, and $R^{10}$ are given in the table.
| Cpd. # | $R^2$ | $R^4$ | $R^5$ | $R^8$ | $R^9 \quad R^{10}$ | $t_R$ (min) | MS $(M+H)^+$ |
|---|---|---|---|---|---|---|---|
| 3074 | thiazole-NH-pyridin-2-yl | H | H | CH₃ | cyclobutyl | 5.2 | 672.2 |
| 3075 | thiazole-NH-pyridin-3-yl | H | H | CH₃ | cyclobutyl | 4.8 | 672.2 |
| 3076 | thiazole-NH-pyridin-4-yl | H | H | CH₃ | cyclobutyl | 4.7 | 672.2 |
| 3077 | thiazole-NH-CH₂CH₂-OCH₃ | H | H | CH₃ | cyclobutyl | 4.6 | 653.3 |

TABLE 3-continued

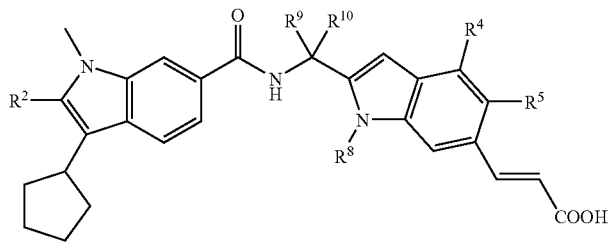

wherein R², R⁴, R⁵, R⁸, R⁹, and R¹⁰ are given in the table.

| Cpd. # | R² | R⁴ | R⁵ | R⁸ | $R^9 \underset{\lambda}{\times} R^{10}$ | $t_R$ (min) | MS (M + H)⁺ |
|---|---|---|---|---|---|---|---|
| 3078 | 5-fluoropyridin-2-yl | H | —OCH₃ | CH₃ | spirocyclobutyl | 6.2 | 622.2 |
| 3079 | 4-methoxypyrimidin-2-yl | H | H | CH₃ | spirocyclobutyl | 5.8 | 605.3 |
| 3080 | pyridin-2-yl | H | CH₃ | CH₃ | spirocyclobutyl | 4.6 | 588.3 |
| 3081 | 5-fluoropyridin-2-yl | H | CH₃ | CH₃ | spirocyclobutyl | 5.6 | 606.3 |
| 3082 | phenyl | H | H | CH₃ | spirocyclobutyl | 6.0 | 573.3 |
| 3083 | 2-fluoropyridin-3-yl | H | H | CH₃ | spirocyclobutyl | 5.2 | 592.3 |

TABLE 3-continued
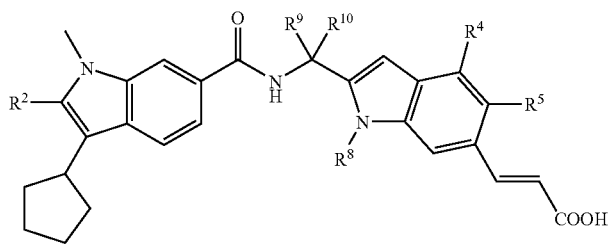
wherein R², R⁴, R⁵, R⁸, R⁹, and R¹⁰ are given in the table.
| Cpd. # | R² | R⁴ | R⁵ | R⁸ | R⁹ R¹⁰ | $t_R$ (min) | MS $(M+H)^+$ |
|---|---|---|---|---|---|---|---|
| 3084 | benzo[1,3]dioxol-5-yl | H | H | CH₃ | spirocyclobutane | 5.9 | 617.3 |
| 3085 | 5-bromopyrimidin-2-yl | H | H | CH₃ | spirocyclobutane | 5.7 | 653.2 |
| 3086 | 6-methoxypyridazin-3-yl | H | H | CH₃ | spirocyclobutane | 5.3 | 605.3 |
| 3087 | 5-chloropyridin-2-yl | H | H | CH₃ | H₃C  CH₃ | 6.0 | 596.3 |
| 3088 | 5-fluoropyridin-2-yl | H | H | CH₃ | H₃C  CH₃ | 5.6 | 580.2 |
| 3089 | CH₃ | H | H | CH₃ | spirocyclobutane | 6.0 | 511.2 |

TABLE 3-continued wherein R², R⁴, R⁵, R⁸, R⁹, and R¹⁰ are given in the table.

| Cpd. # | R² | R⁴ | R⁵ | R⁸ | R⁹ R¹⁰ | $t_R$ (min) | MS (M + H)⁺ |
|---|---|---|---|---|---|---|---|
| 3090 | vinyl | H | H | CH₃ | bicyclobutane | 6.3 | 523.2 |
| 3091 | ethyl | H | H | CH₃ | bicyclobutane | 6.4 | 525.2 |
| 3092 | isopropenyl | H | H | CH₃ | bicyclobutane | 6.6 | 537.2 |
| 3093 | isobutyl | H | H | CH₃ | bicyclobutane | 6.6 | 539.2 |
| 3094 | 2-hydroxypyridin-6-yl | H | H | CH₃ | bicyclobutane | 5.0 | 590.2 |
| 3095 | 6-hydroxypyridin-3-yl | H | H | CH₃ | bicyclobutane | 4.8 | 590.2 |
| 3096 | Cl | H | H | CH₃ | bicyclobutane | 6.0 | 531.1, 533.1 |

TABLE 3-continued wherein R², R⁴, R⁵, R⁸, R⁹, and R¹⁰ are given in the table.

| Cpd. # | R² | R⁴ | R⁵ | R⁸ | R⁹ R¹⁰ | $t_R$ (min) | MS (M + H)⁺ |
|---|---|---|---|---|---|---|---|
| 3097 | —C≡CH | H | H | CH₃ | cyclobutyl | 5.8 | 521.1 |
| 3098 | —C≡N | H | H | CH₃ | cyclobutyl | 5.5 | 522.1 |
| 3099 | phenyl | H | H | CH₃ | H₃C CH₃ | 6.3 | 561.3 |
| 3100 | benzodioxole | H | H | CH₃ | H₃C CH₃ | 6.2 | 605.3 |
| 3101 | 3-thienyl | H | H | CH₃ | H₃C CH₃ | 6.2 | 567.2 |
| 3102 | 2-thienyl | H | H | CH₃ | H₃C CH₃ | 6.3 | 567.2 |
| 3103 | pyrazolyl | H | H | CH₃ | cyclobutyl | 5.6 | 563.3 |

TABLE 3-continued

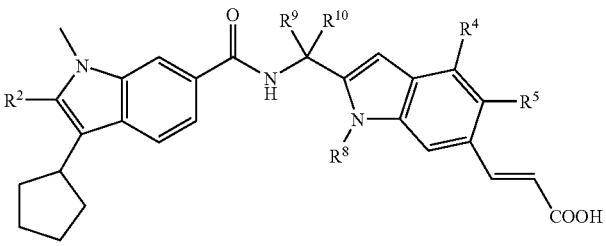

wherein R², R⁴, R⁵, R⁸, R⁹, and R¹⁰ are given in the table.

| Cpd. # | R² | R⁴ | R⁵ | R⁸ | $\begin{array}{c} R^9 \quad R^{10} \\ \end{array}$ | $t_R$ (min) | MS $(M + H)^+$ |
|---|---|---|---|---|---|---|---|
| 3104 | (3-tetrahydrofuranyl) | H | H | CH₃ | (bicyclobutyl) | 5.4 | 567.3 |
| 3105 | (2-aminopyrimidin-4-yl) | H | H | CH₃ | (bicyclobutyl) | 4.5 | 590.3 |
| 3106 | (benzothiophen-6-yl) | H | H | CH₃ | (bicyclobutyl) | 6.2 | 629.3 |
| 3107 | (2-(pyrrol-1-yl)phenyl) | H | H | CH₃ | (bicyclobutyl) | 6.2 | 638.4 |
| 3108 | (4-(pyrrol-1-yl)phenyl) | H | H | CH₃ | (bicyclobutyl) | 6.4 | 638.4 |
| 3109 | (4-ethoxypyrimidin-2-yl) | H | H | CH₃ | (bicyclobutyl) | 5.4 | 619.4 |

TABLE 3-continued wherein R², R⁴, R⁵, R⁸, R⁹, and R¹⁰ are given in the table.

| Cpd. # | R² | R⁴ | R⁵ | R⁸ | R⁹ R¹⁰ | $t_R$ (min) | MS (M + H)⁺ |
|---|---|---|---|---|---|---|---|
| 3110 | 5-amino-pyridin-2-yl | H | H | CH₃ | spiro-cyclobutyl | 3.4 | — |
| 3111 | 2,2-dimethyl-2,3-dihydrobenzofuran-7-yl | H | H | CH₃ | spiro-cyclobutyl | 6.3 | 643.4 |
| 3112 | 2-methylbenzothiazol-5-yl | H | H | CH₃ | spiro-cyclobutyl | 5.7 | 644.4 |
| 3113 | 2-(morpholin-4-yl)phenyl | H | H | CH₃ | spiro-cyclobutyl | 5.4 | 658.4 |
| 3114 | 3-(morpholin-4-yl)phenyl | H | H | CH₃ | spiro-cyclobutyl | 5.4 | 658.5 |
| 3115 | 1H-pyrazol-3-yl | H | H | CH₃ | spiro-cyclobutyl | 5.3 | 563.3 |

TABLE 3-continued
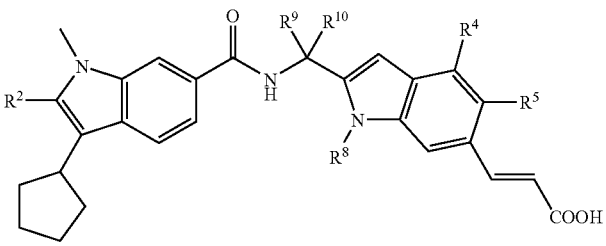
wherein $R^2$, $R^4$, $R^5$, $R^8$, $R^9$, and $R^{10}$ are given in the table.
| Cpd. # | $R^2$ | $R^4$ | $R^5$ | $R^8$ | $R^9$ $R^{10}$ | $t_R$ (min) | MS $(M+H)^+$ |
|---|---|---|---|---|---|---|---|
| 3116 | n-butyl | H | H | CH₃ | cyclobutyl | 6.6 | 539.3 |
| 3117 | 2-pyridyl | H | H | CH₃ | cyclopropyl | 5.6 | 560.3 |
| 3118 | cyclopropyl | H | H | CH₃ | cyclobutyl | 6.4 | 537.3 |
| 3119 | 5-fluoro-2-pyridyl | H | H | CH₃ | cyclopropyl | 6.1 | 578.2 |
| 3120 | 3-furyl | H | H | CH₃ | cyclopropyl | 6.4 | 549.2 |
| 3121 | 2-pyrazinyl | H | H | CH₃ | cyclopropyl | 5.4 | 561.3 |
| 3122 | 6-amino-2-pyridyl | H | H | CH₃ | cyclopropyl | 4.4 | 575.3 |

TABLE 3-continued
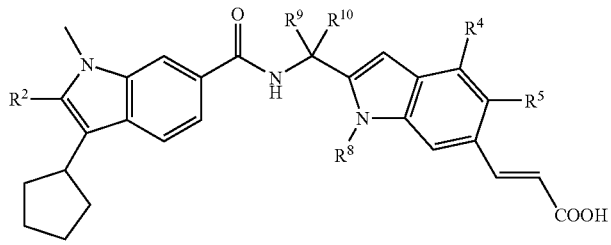
wherein $R^2$, $R^4$, $R^5$, $R^8$, $R^9$, and $R^{10}$ are given in the table.
| Cpd. # | $R^2$ | $R^4$ | $R^5$ | $R^8$ | $R^9$ $R^{10}$ | $t_R$ (min) | MS $(M + H)^+$ |
|---|---|---|---|---|---|---|---|
| 3123 | ![2-pyridyl-5-Cl] | H | H | CH$_3$ | cyclopropyl | 6.5 | 594.2 596.2 |
| 3124 | ![5-Br-pyrimidin-2-yl] | H | —OCH$_3$ | CH$_3$ | cyclobutyl | 6.6 | 683.3 685.3 |
| 3125 | ![4-methylpyrazol-1-yl] | H | H | CH$_3$ | cyclobutyl | 5.8 | 577.3 |
| 3126 | ![5-Cl-pyrimidin-2-yl] | H | H | CH$_3$ | cyclobutyl | 6.2 | 609.2 |
| 3127 | ![5-Cl-pyrimidin-2-yl] | H | —OCH$_3$ | CH$_3$ | cyclobutyl | 6.5 | 639.3 |

TABLE 3-continued
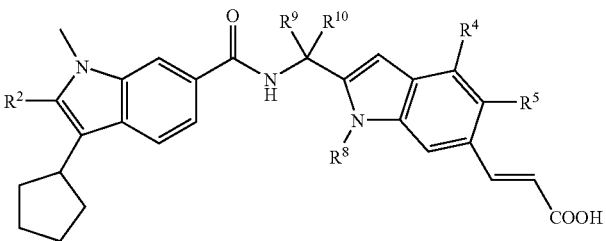
wherein R², R⁴, R⁵, R⁸, R⁹, and R¹⁰ are given in the table.
| Cpd. # | R² | R⁴ | R⁵ | R⁸ | R⁹ R¹⁰ | $t_R$ (min) | MS (M + H)⁺ |
|---|---|---|---|---|---|---|---|
| 3128 | 1-methylpyrazol-4-yl | H | H | CH₃ | spiro-cyclobutane | 5.6 | 577.3 |
| 3129 | 5-methoxypyrimidin-2-yl | H | H | CH₃ | spiro-cyclobutane | 5.7 | 605.4 |
| 3130 | pyridin-2-yl | Cl | H | CH₃ | spiro-cyclobutane | 5.4 | 608.3 610.3 |
| 3131 | 5-bromopyrimidin-2-yl | Cl | H | CH₃ | spiro-cyclobutane | 7.1 | 689.3 687.6 |
| 3132 | pyrimidin-5-yl | H | H | CH₃ | spiro-cyclobutane | 5.2 | 575.3 |

TABLE 4

Structure with R¹, R², R³, R⁵, R⁶, R⁹, R¹⁰ substituents on an indole-carboxamide-benzimidazole scaffold.

wherein R¹, R², R³, R⁵, R⁶, R⁹, and R¹⁰ are given in the table.

| Cpd. # | R¹ | R² | R³ | R⁵ | R⁶ | R⁹/R¹⁰ | t_R (min) | MS (MH)⁺ |
|---|---|---|---|---|---|---|---|---|
| 4001 | CH₃ | 2-pyridyl | cyclopentyl | -CH=CH-COOH | H | spirocyclobutyl | 4.7 | 574.3 |
| 4002 | CH₃ | 6-amino-2-pyridyl | cyclopentyl | -CH=CH-COOH | H | spirocyclobutyl | 4.4 | 589.4 |
| 4003 | CH₃ | pyrazinyl | cyclopentyl | -CH=CH-COOH | H | spirocyclobutyl | 5.4 | 575.4 |
| 4004 | CH₃ | 2-pyridyl | cyclohexyl | H | -CH=CH-COOH | spirocyclobutyl | 5.4 | 588.3 |
| 4005 | CH₃ | pyrazinyl | cyclohexyl | H | -CH=CH-COOH | spirocyclobutyl | 5.8 | 589.3 |
| 4006 | CH₃ | 3-furyl | cyclopentyl | -CH=CH-COOH | H | spirocyclobutyl | 3.3 | 563.1 |
| 4007 | sec-butyl | 3-furyl | cyclohexyl | -CH=CH-COOH | H | spirocyclobutyl | 6.6 | 591.4 |
| 4008 | H | 3-furyl | cyclohexyl | H | -CH=CH-COOH | spirocyclobutyl | 6.1 | 563.3 |

TABLE 4-continued
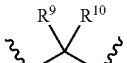
wherein R¹, R², R³, R⁵, R⁶, R⁹, and R¹⁰ are given in the table.
| Cpd. # | R¹ | R² | R³ | R⁵ | R⁶ | 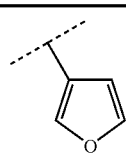 | $t_R$ (min) | MS (MH)⁺ |
|---|---|---|---|---|---|---|---|---|
| 4009 | H | 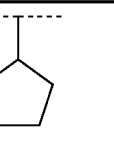 | 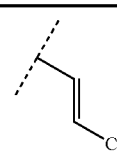 | H | 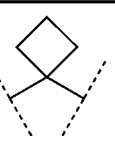 | 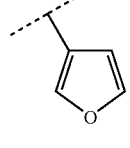 | 5.9 | 549.3 |
| 4010 | H | 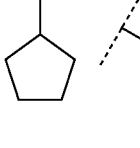 |  | 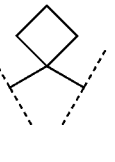 | H | 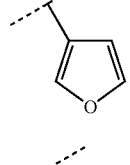 | 5.8 | 549.3 |
| 4011 | CH₃ | 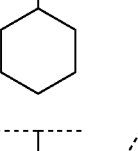 | 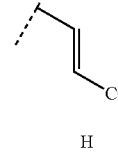 | H |  | 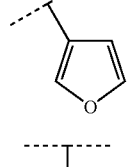 | 6.4 | 577.4 |
| 4012 | CH₃ | 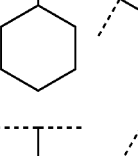 | 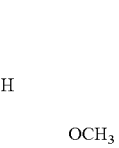 | 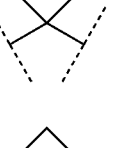 | H | 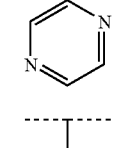 | 6.5 | 577.4 |
| 4013 | CH₃ | 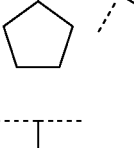 | 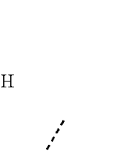 | 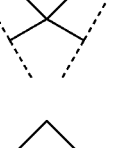 | OCH₃ | 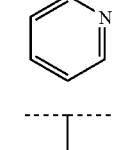 | 5.4 | 605.3 |
| 4014 | H | 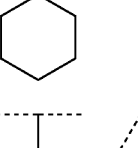 | 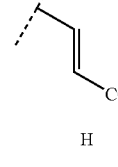 | H | 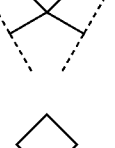 | 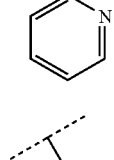 | 4.8 | 574.3 |
| 4015 | H | 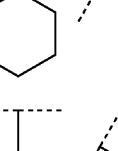 | 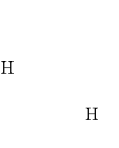 | 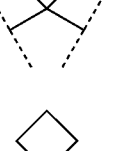 | H | 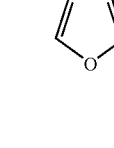 | 4.9 | 574.3 |
| 4016 | H | 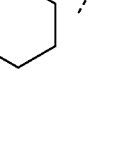 |  |  | H | | 6.2 | 561.3 |

TABLE 4-continued
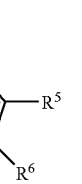
wherein R[1], R[2], R[3], R[5], R[6], R[9], and R[10] are given in the table.
| Cpd. # | R[1] | R[2] | R[3] | R[5] | R[6] | R[9] R[10] | $t_R$ (min) | MS (MH)+ |
|---|---|---|---|---|---|---|---|---|
| 4017 | H | 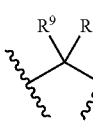 |  | H |  | 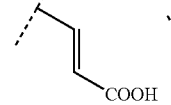 | 4.4 | 560.3 |
| 4018 | H |  |  |  | H |  | 4.5 | 560.3 |
| 4019 | CH[3] |  | 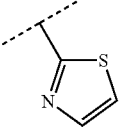 |  | H |  | 5.6 | 580.2 |
| 4020 | CH[3] |  | 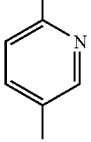 |  | H | 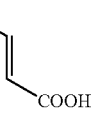 | 6.3 | 608.2 |
| 4021 | CH[3] |  | 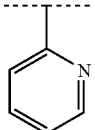 | H |  | 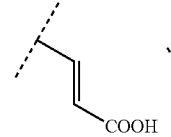 | 6.5 | 622.3 |
| 4022 | CH[3] |  | 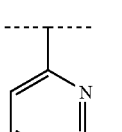 |  | H |  | 7.0 | 604.3 |
| 4023 | CH[3] |  | 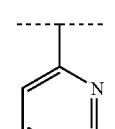 |  | 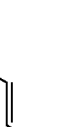 | 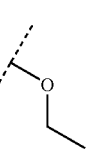 | 5.1 | 618.3 |

TABLE 4-continued
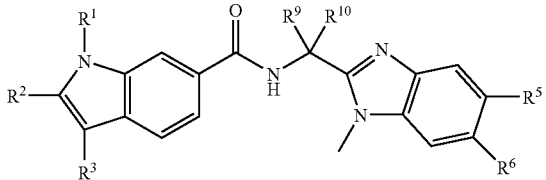
wherein R¹, R², R³, R⁵, R⁶, R⁹, and R¹⁰ are given in the table.
| Cpd. # | R¹ | R² | R³ | R⁵ | R⁶ | 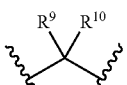 | $t_R$ (min) | MS (MH)⁺ |
|---|---|---|---|---|---|---|---|---|
| 4024 | CH₃ | 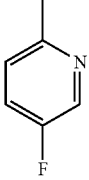 |  | 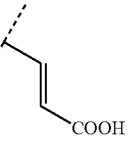 | 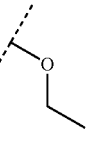 |  | 6.1 | 636.3 |
| 4025 | CH₃ | 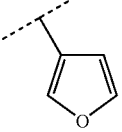 |  | 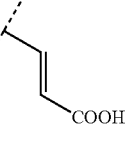 | 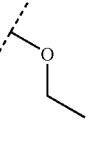 |  | 6.3 | 607.3 |
| 4026 | CH₃ | 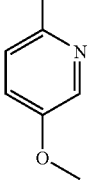 |  | 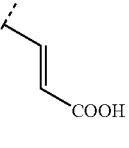 | H |  | 6.0 | 604.3 |
| 4027 | CH₃ | 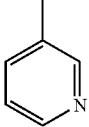 |  | 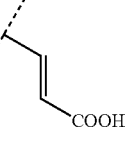 | H |  | 4.2 | 574.3 |
| 4028 | CH₃ | 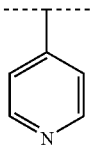 |  | 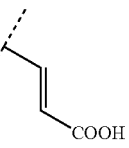 | H | 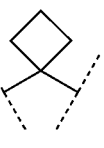 | 4.1 | 574.3 |
| 4029 | CH₃ | 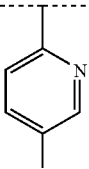 |  | 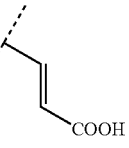 | CH₃ | 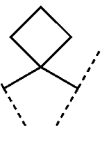 | 5.8 | 606.3 |

TABLE 4-continued wherein R¹, R², R³, R⁵, R⁶, R⁹, and R¹⁰ are given in the table.

| Cpd. # | R¹ | R² | R³ | R⁵ | R⁶ | R⁹ R¹⁰ | $t_R$ (min) | MS (MH)⁺ |
|---|---|---|---|---|---|---|---|---|
| 4030 | CH₃ | 5-fluoropyridin-2-yl | cyclohexyl | H | CH=CH-CH₂-COOH | cyclobutylidene | 5.7 | 606.4 |
| 4031 | CH₃ | pyridin-4-yl | 3,3-difluorocyclopentyl | H | CH=CH-CH₂-COOH | cyclobutylidene | 3.8 | 610.3 |
| 4032 | CH₃ | furan-3-ylmethyl | 3,3-difluorocyclopentyl | H | CH=CH-CH₂-COOH | cyclobutylidene | 5.4 | 599.3 |
| 4033 | H | Br | cyclohexyl | H | CH=CH-CH₂-COOH | cyclobutylidene | 6.1 | 575.2 / 577.2 |
| 4034 | CH₃ | 5-fluoropyridin-2-yl | 4,4-difluorocyclohexyl | H | CH=CH-CH₂-COOH | cyclobutylidene | 5.2 | 642.3 |
| 4035 | H | 5-fluoropyridin-2-yl | cyclohexyl | H | CH=CH-CH₂-COOH | cyclobutylidene | 6.4 | 592.3 |

TABLE 4-continued
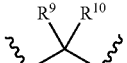
wherein R¹, R², R³, R⁵, R⁶, R⁹, and R¹⁰ are given in the table.
| Cpd. # | R¹ | R² | R³ | R⁵ | R⁶ | R⁹ R¹⁰ | $t_R$ (min) | MS (MH)⁺ |
|---|---|---|---|---|---|---|---|---|
| 4036 | H | 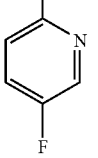 | 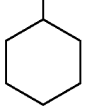 | H | 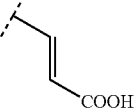 |  | 6.4 | 578.2 |
| 4037 | CH₃ | 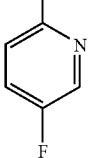 | 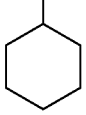 | H | 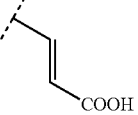 |  | 6.3 | 592.2 |
| 4038 | CH₃ | 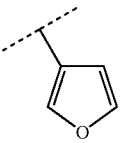 | 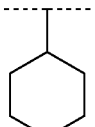 | H | 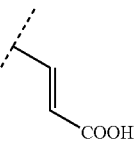 | 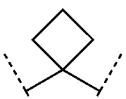 | 5.4 | 613.2 |
| 4039 | CH₃ | 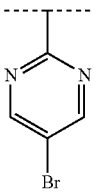 | 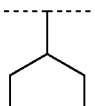 | H | 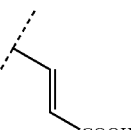 | 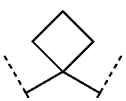 | 6.7 | 667.2 669.2 |
| 4040 | CH₃ | 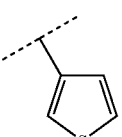 | 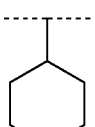 | H | 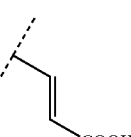 |  | 5.6 | 629.3 |
| 4041 | CH₃ | 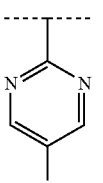 | 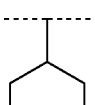 | H | 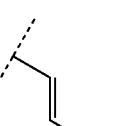 |  | 6.2 | 703.3 |

TABLE 4-continued
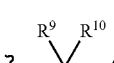
wherein $R^1$, $R^2$, $R^3$, $R^5$, $R^6$, $R^9$, and $R^{10}$ are given in the table.
| Cpd. # | $R^1$ | $R^2$ | $R^3$ | $R^5$ | $R^6$ | $R^9\phantom{X}R^{10}$ | $t_R$ (min) | MS $(MH)^+$ |
|---|---|---|---|---|---|---|---|---|
| 4042 | $CH_3$ | 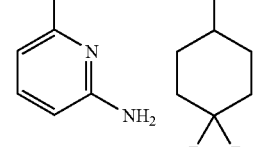 |  | H | 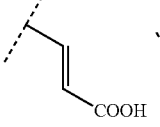 |  | 3.9 | 639.3 |
| 4043 | $CH_3$ | 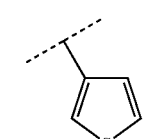 | 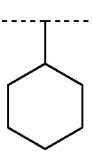 | H | 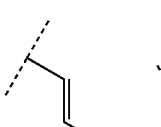 | 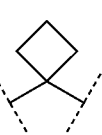 | 6.9 | 593.4 |
| 4044 | $CH_3$ | 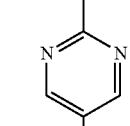 | 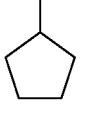 |  | H |  | 6.4 | 609.4 |
What is claimed is:
1. A compound selected from:
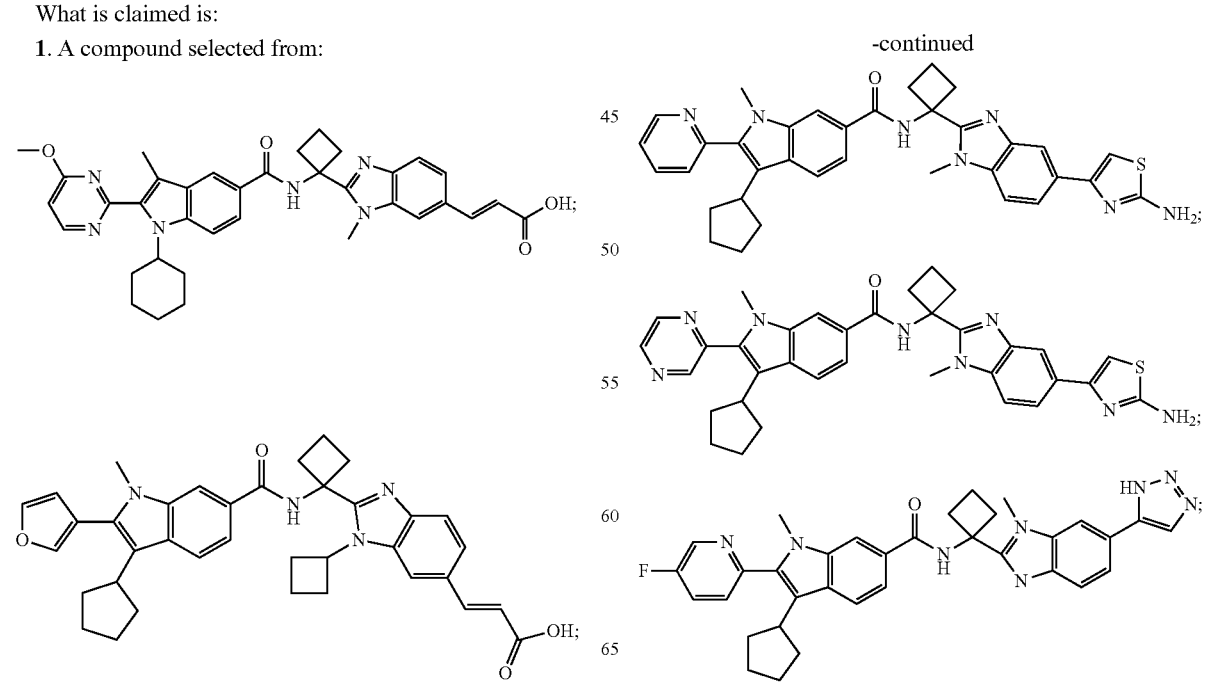

-continued
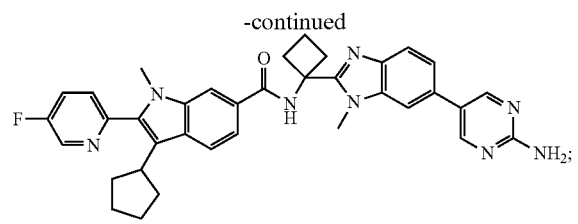
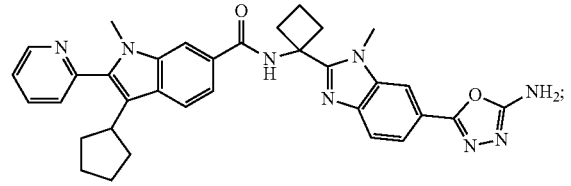
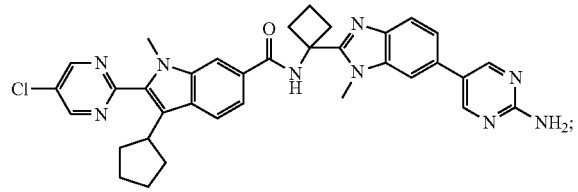
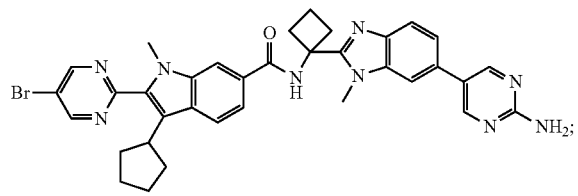
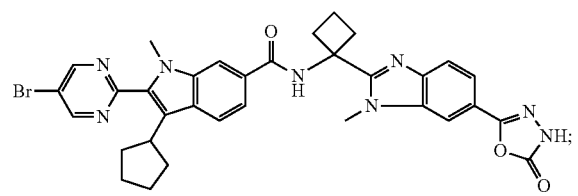
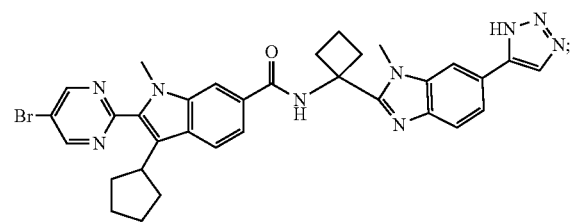
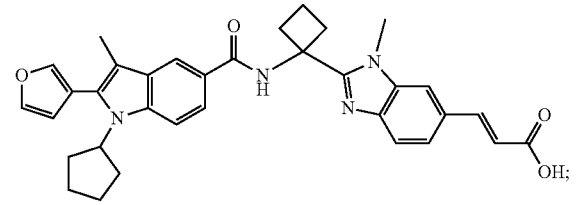
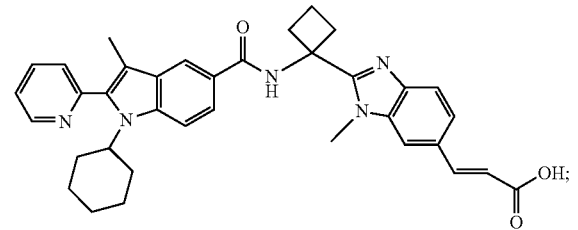
-continued
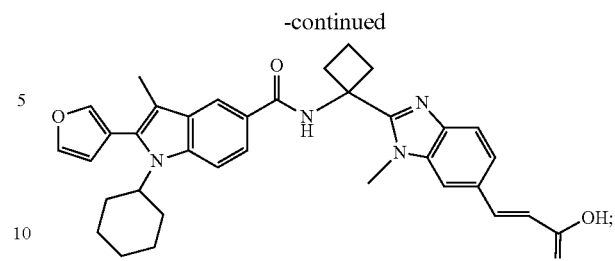
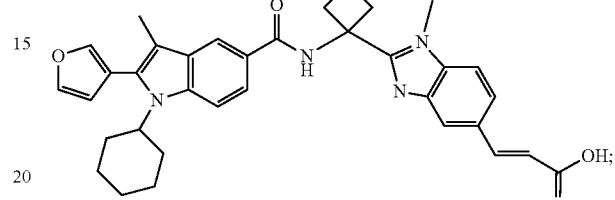
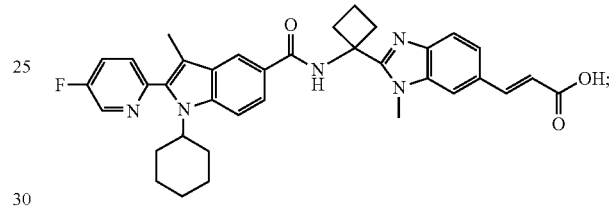
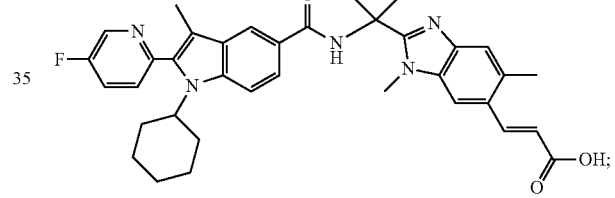
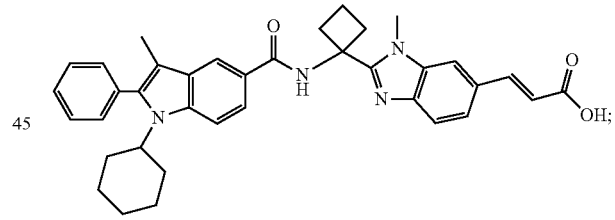
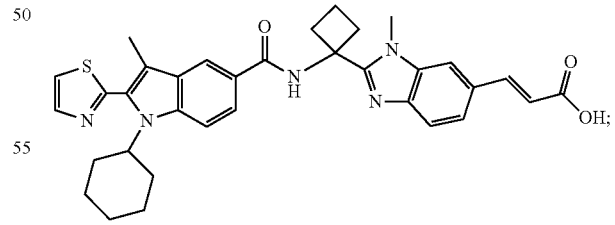
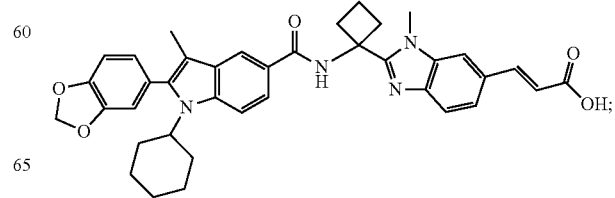

-continued
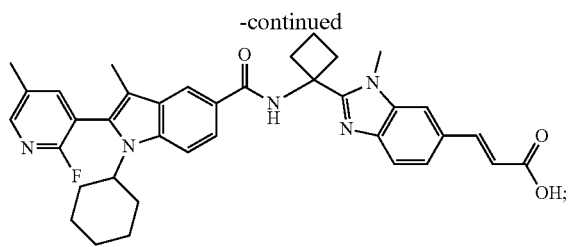
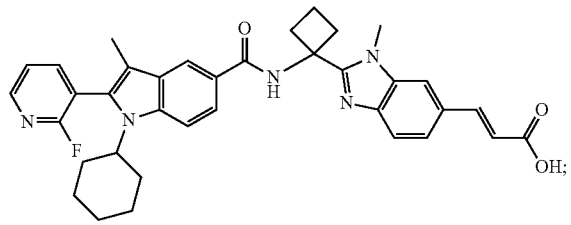
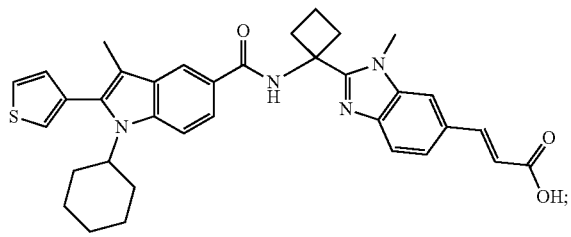
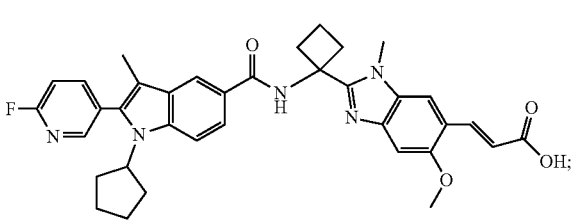
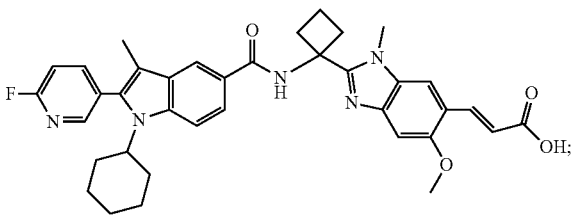
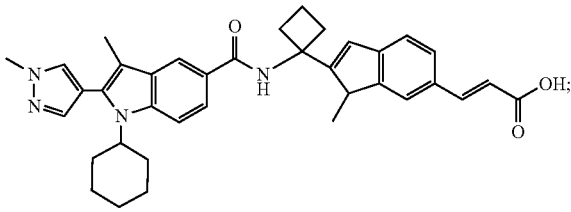
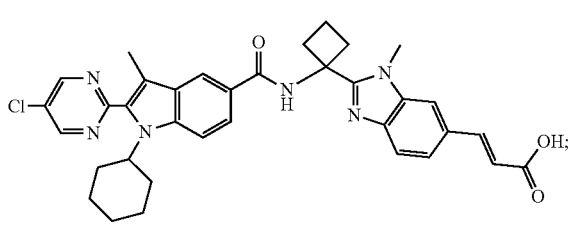
-continued
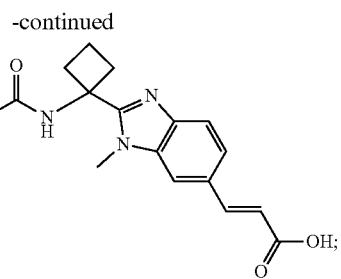
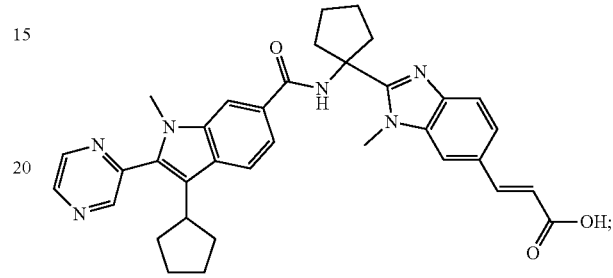
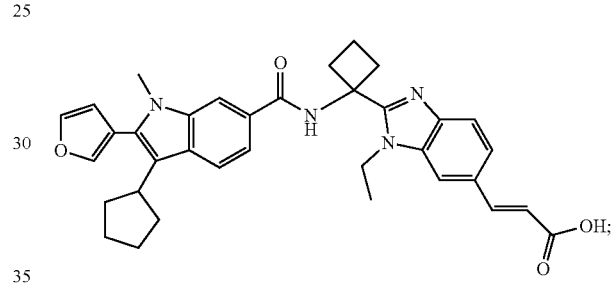
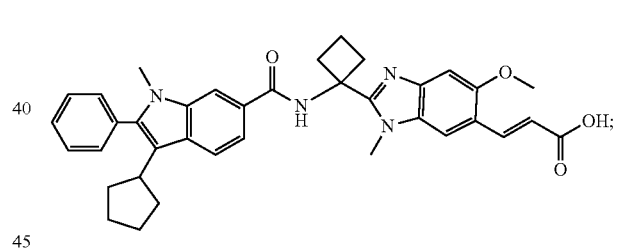
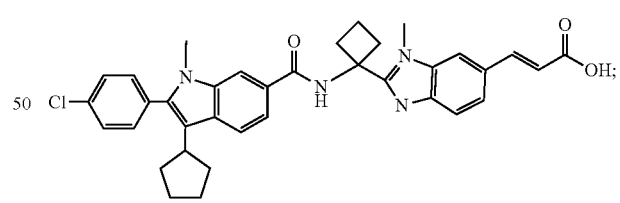
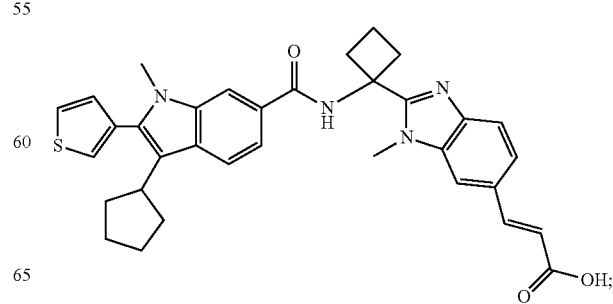

243
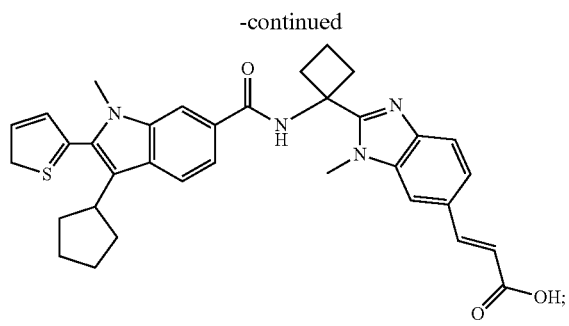
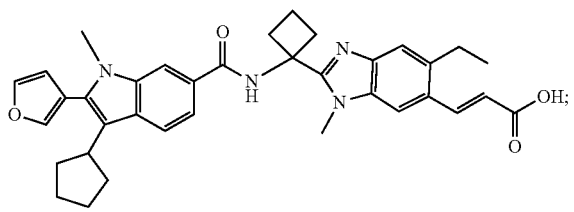
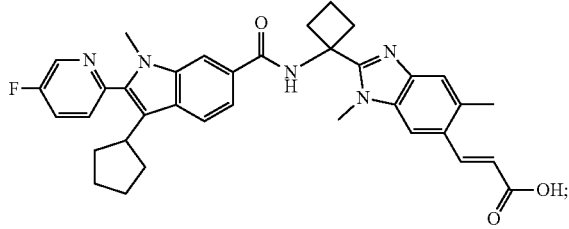
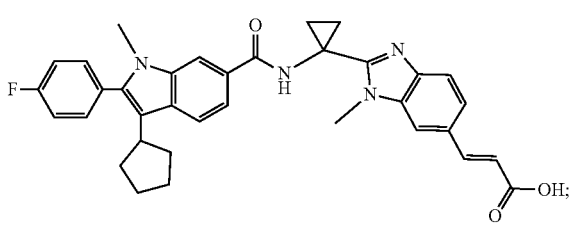
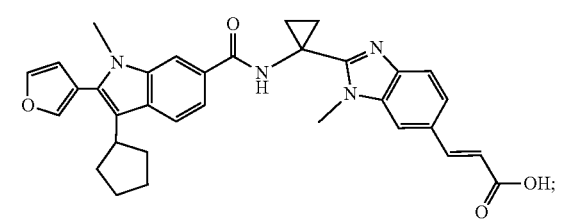
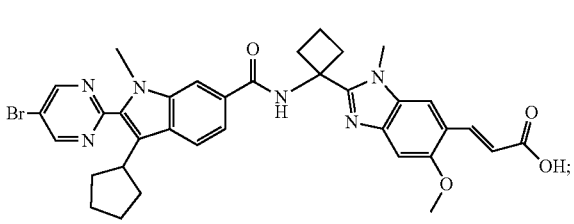
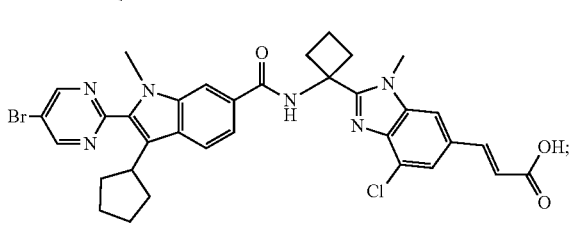
244
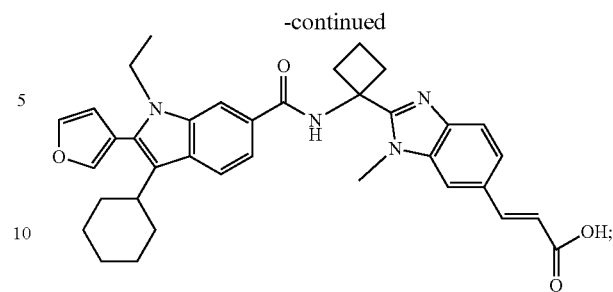
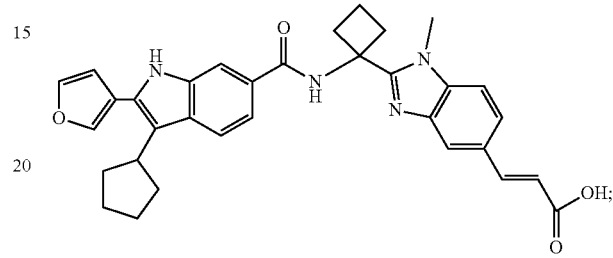
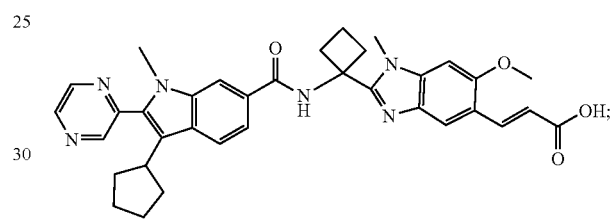
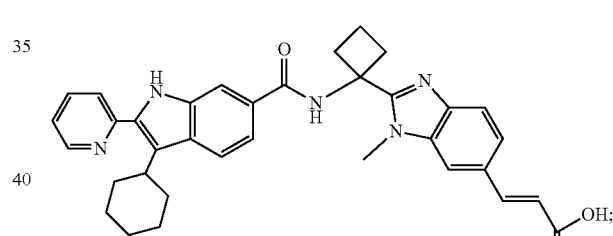
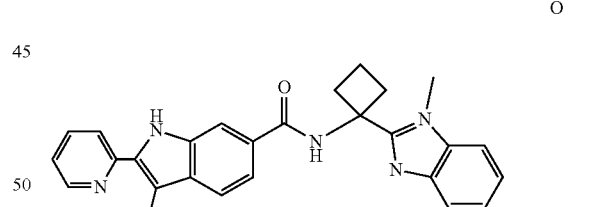
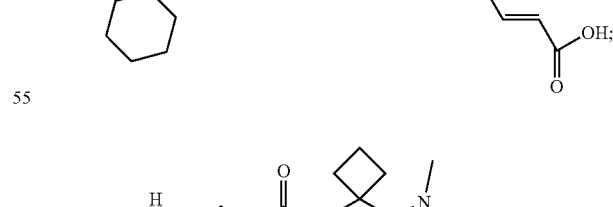
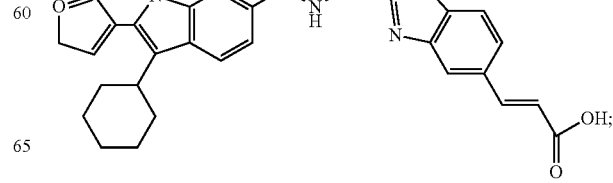

245
-continued
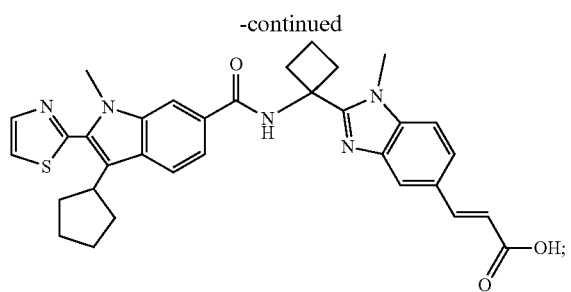
246
-continued
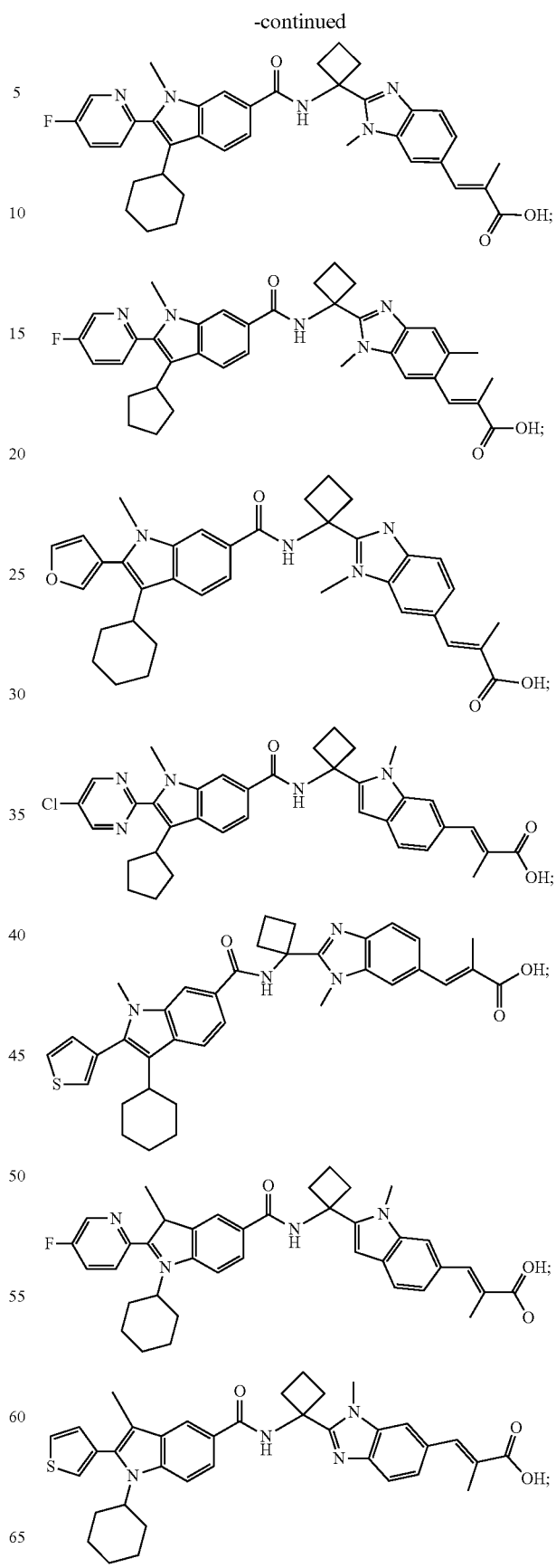

247
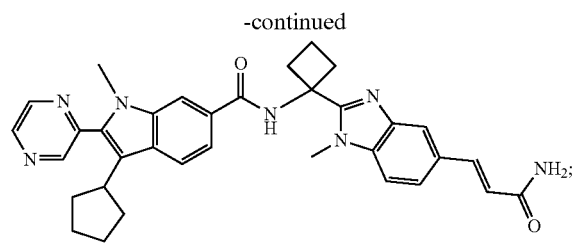
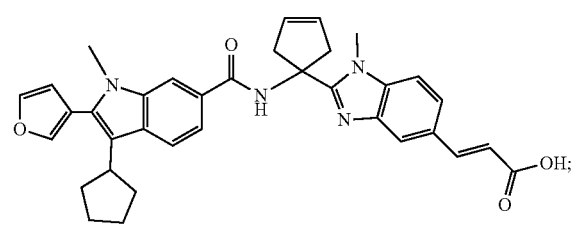
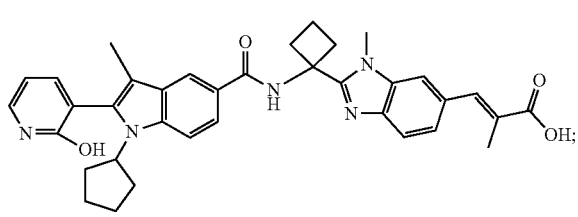
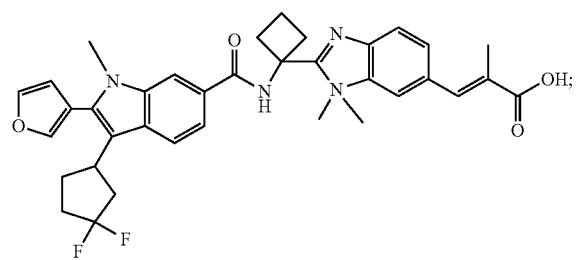
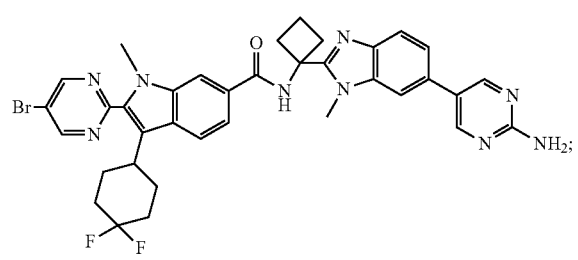
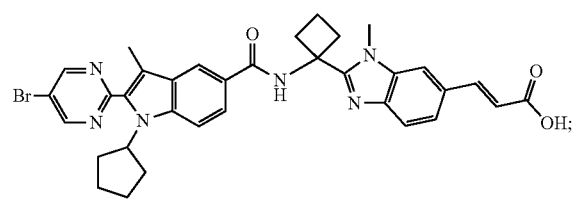
248
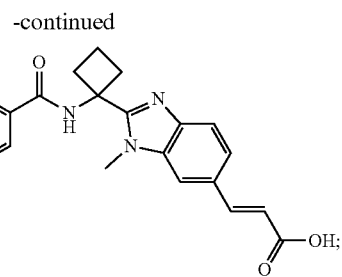
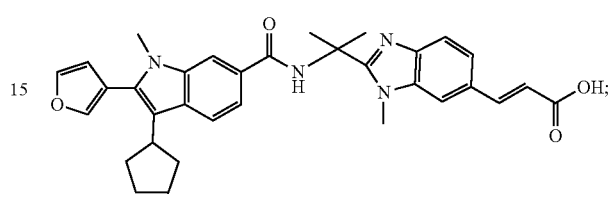
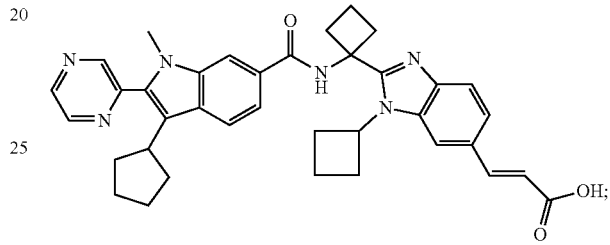
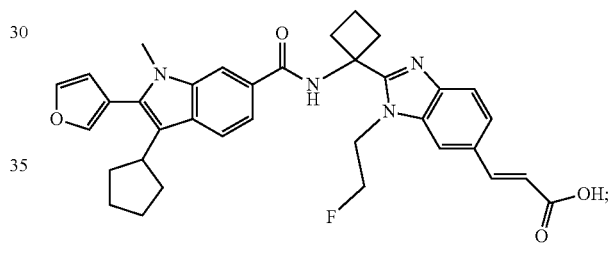
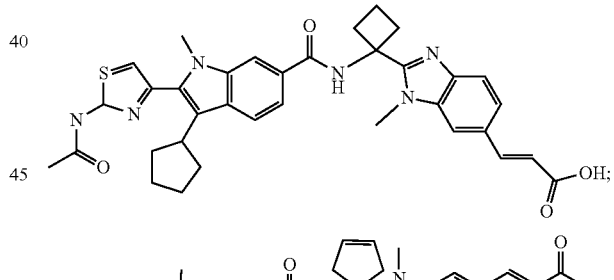
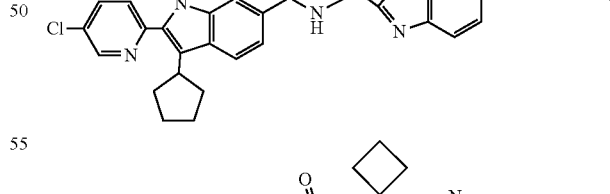

-continued

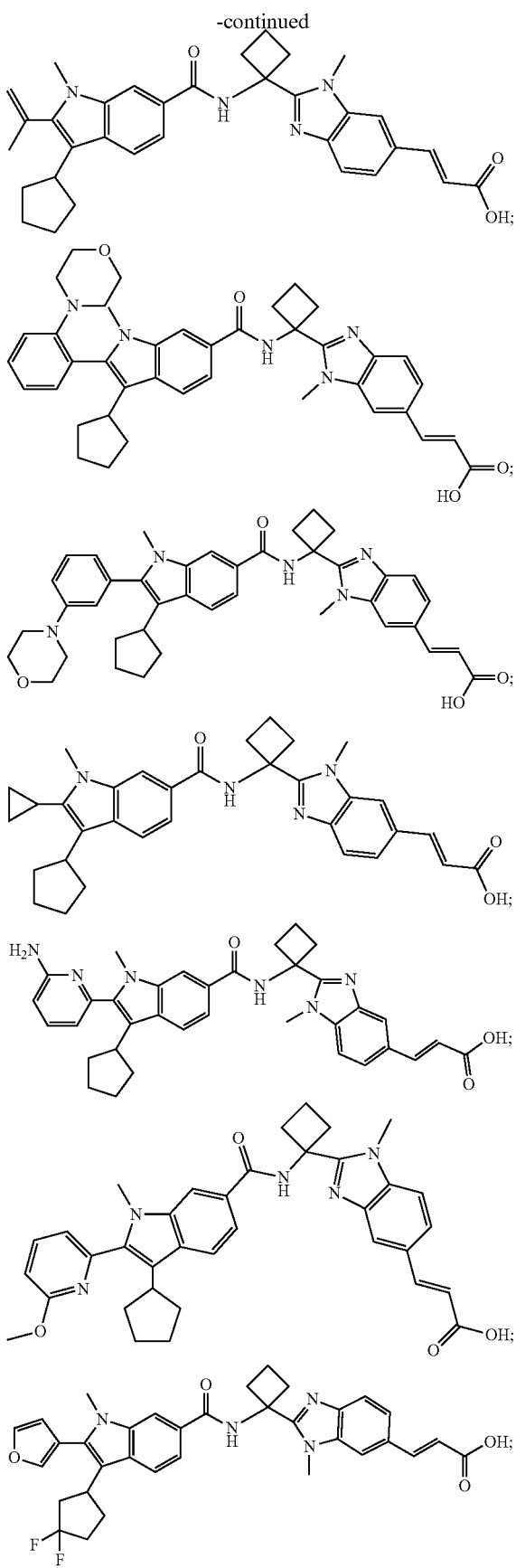

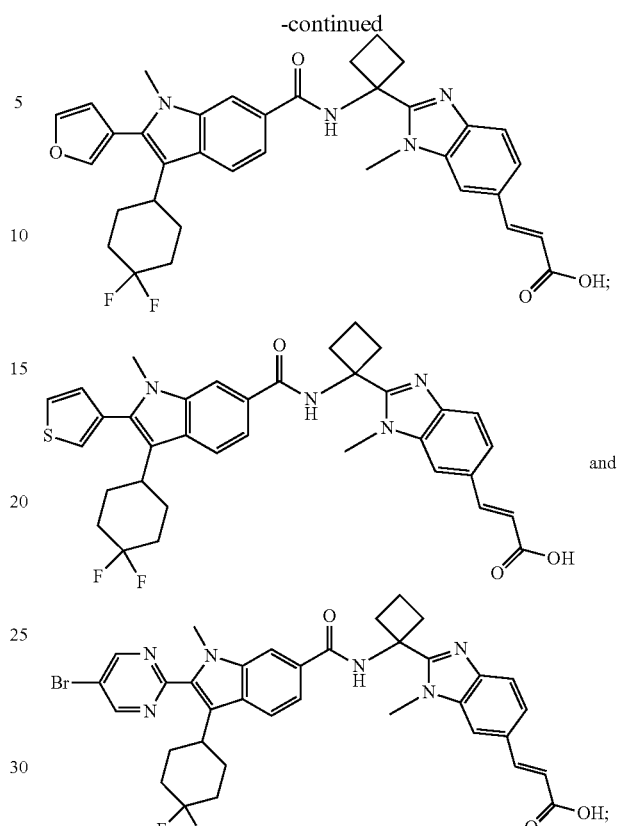

or a pharmaceutically acceptable salt thereof.

2. A pharmaceutical composition for the treatment of HCV infection, comprising an effective amount of a compound according to claim 1, or a pharmaceutically acceptable salt thereof, and a pharmaceutically acceptable carrier.

3. The composition according to claim 2 further comprising a therapeutically effective amount of one or more antiviral agents.

4. The composition according to claim 3, wherein said antiviral agent is selected from: ribavirin and amantadine.

5. The composition according to claim 3 wherein the antiviral agent is an other anti-HCV agent.

6. The pharmaceutical composition according to claim 5, wherein the other anti-HCV agent is an immunomodulatory agent selected from α-, β-, δ-γ-, τ- and ω-interferon and pegylated forms thereof.

7. The composition according to claim 5, wherein the other anti-HCV agent is another inhibitor of HCV polymerase.

8. The composition according to claim 5, wherein the other anti-HCV agent is an inhibitor of HCV NS3 protease.

9. The composition according to claim 5, wherein the other anti-HCV agent is an inhibitor of another target in the HCV life cycle.

10. The composition according to claim 9, wherein said inhibitor of another target in the HCV life cycle is selected from an agent that inhibits a target selected from HCV helicase, HCV NS2/3 protease and HCV IRES, and an agent that interferes with the function of an NS5A protein.

11. A method of inhibiting the RNA-dependent RNA polymerase activity of the enzyme NS5B, encoded by HCV, comprising exposing the enzyme NS5B to an effective amount of a compound according to claim 1 under conditions where the RNA-dependent RNA polymerase activity of the enzyme NS5B is inhibited.

12. A method of inhibiting HCV replication, comprising exposing a cell infected with HCV to an effective amount of a compound according to claim 1 under conditions where replication of HCV is inhibited.

13. A method of treating HCV infection in a mammal, comprising administering to the mammal an effective amount of a compound according to claim 1, or a pharmaceutically acceptable salt or ester thereof, or a composition thereof.

14. A method of treating HCV infection in a mammal, comprising administering to the mammal an effective amount of a compound according to claim 1, or a pharmaceutically acceptable salt or ester thereof, or a composition thereof, in combination with another antiviral agent.

15. An article of manufacture comprising
- a composition effective to treat an HCV infection or to inhibit the NS5B polymerase of HCV and
- packaging material comprising a label which indicates that the composition can be used to treat infection by the hepatitis C virus,
- wherein said composition comprises a compound according to claim 1 or a pharmaceutically acceptable salt thereof.

\* \* \* \* \*